United States Patent
Kawakami et al.

(10) Patent No.: US 6,949,332 B2
(45) Date of Patent: Sep. 27, 2005

(54) SILVER HALIDE EMULSION AND METHOD OF PREPARING THE SAME

(75) Inventors: Hiroshi Kawakami, Minami-Ashigara (JP); Mikio Ihama, Minami-Ashigara (JP); Takeshi Suzumoto, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/796,163

(22) Filed: Mar. 10, 2004

(65) Prior Publication Data

US 2005/0032007 A1 Feb. 10, 2005

(30) Foreign Application Priority Data

| Mar. 11, 2003 | (JP) | ......................................... 2003-065480 |
| Mar. 27, 2003 | (JP) | ......................................... 2003-088838 |
| Sep. 10, 2003 | (JP) | ......................................... 2003-318909 |

(51) Int. Cl.$^7$ .............................. G03C 5/18; G03C 5/26; G03C 1/005; G03C 1/494

(52) U.S. Cl. ........................ 430/449; 430/559; 430/570; 430/572; 430/558; 430/546; 430/631; 430/640; 430/642

(58) Field of Search ................................. 430/449, 559, 430/570, 572, 558, 546, 631, 640, 642

(56) References Cited

U.S. PATENT DOCUMENTS

| 6,048,681 A | * | 4/2000 | Suzumoto et al. | ........... 430/570 |
| 6,066,440 A | * | 5/2000 | Araki et al. | ................. 430/640 |
| 6,117,629 A | | 9/2000 | Yamashita et al. | |
| 6,143,486 A | | 11/2000 | Parton et al. | |
| 6,329,133 B1 | | 12/2001 | Andrievsky et al. | |
| 6,620,581 B1 | | 9/2003 | Parton et al. | |
| 2004/0185392 A1 | * | 9/2004 | Suzuki et al. | ................ 430/559 |

FOREIGN PATENT DOCUMENTS

JP            2002-49113 A        2/2002

* cited by examiner

*Primary Examiner*—Geraldine Letscher
(74) *Attorney, Agent, or Firm*—Sughrue Mion, PLLC

(57) ABSTRACT

A silver halide emulsion containing water, dispersion medium comprising modified gelatin whose amino group is chemically modified, and silver halide grains comprising spectrally sensitized silver halide grains each having a multilayer adsorption of dye chromophores on the surface thereof. A method of preparing the silver halide emulsion. A silver halide photosensitive material contains the silver halide emulsion in a light-sensitive silver halide emulsion layer thereof.

9 Claims, No Drawings

SILVER HALIDE EMULSION AND METHOD OF PREPARING THE SAME

CROSS-REFERENCE TO RELATED APPLICATIONS

This application is based upon and claims the benefit of priority from prior Japanese Patent Applications No. 2003-065480, filed Mar. 11, 2003; No. 2003-088838, filed Mar. 27, 2003; and No. 2003-318909, filed Sep. 10, 2003, the entire contents of all of which are incorporated herein by reference.

BACKGROUND OF THE INVENTION

1. Field of the Invention

The present invention relates to a silver halide emulsion and a method of preparing the same. More particularly, the present invention relates to a highly sensitive silver halide emulsion whose fog increase during storage is slight, and a method of preparing such a silver halide emulsion.

2. Description of the Related Art

Strenuous efforts have been exerted to now toward the sensitivity enhancement for silver halide photosensitive materials. In silver halide photographic emulsions, the sensitizing dye adsorbed on the surface of silver halide grains absorbs light having been incident on the photosensitive material and transfers light energy thereof to silver halide grains, thereby exhibiting a photosensitivity. Accordingly, in the spectral sensitization of silver halides, it is contemplated that the enhancement of spectral sensitivity can be attained by realizing adsorption of a large amount of sensitizing dye on silver halide grains so as to increase the light absorption and thus increasing the light energy transferred to silver halides.

Consequently, in recent years, it is common practice to use emulsions wherein the configuration of silver halide grains is tabular so as to have a large surface area per volume. This idea of using tabular grains is common knowledge in the art to which the invention pertains (see, for example, U.S. Pat. No. 4,956,269).

For increasing the surface area of grains, it is needed to reduce the thickness of tabular grains. The reduction of the thickness tends to be disadvantageous from the viewpoint of stability of grain configuration, light scattering and monodispersity of grain size. Thus, the reduction of the thickness would tend to bring about inefficiency inhibiting the sensitivity enhancement. When the grain thickness falls in the region of 0.2 μm or less, there would occur such a situation that the sensitivity enhancement corresponding to an increase of surface area despite the reduction of grain thickness cannot be easily accomplished. The cause thereof would be relevant to the above-mentioned trend.

In the meantime, there has been proposed a concept of increasing the amount of sensitizing dye super-imposed per unit surface area by effecting adsorption in multiple layers (hereinafter referred to as "multilayer adsorption") of a sensitizing dye which has conventionally been adsorbed on silver halide grains in a single layer (see, for example, Jpn. Pat. Appln. KOKAI Publication No. (hereinafter referred to as "JP-A-") 10-239789). In the proposed method, it is not necessary to reduce the grain thickness to an extreme extent, so that it is easy to avoid the aforementioned inefficiency attributed to the deteriorations of stability of grain configuration, light scattering and monodispersity of grain size.

However, it is not an easy task to achieve stable multilayer adsorption of sensitizing dyes and efficient transfer of absorbed light energy to silver halide grains. Thus, a large number of investigations have been made on this matter. In particular, in recent years, the sensitivity enhancement by a multilayer adsorption of a combination of specified cationic dye and anionic dye has been attempted (see, for example, JP-A-2000-89405, and European Patent Publication (hereinafter also referred to as "EP") 0985965A, EP's 1085373A and 1199595A).

In the methods thereof, however, the interaction between the sensitizing dye of the first layer having directly been adsorbed on silver halide grains and the dye layers superimposed on the first layer is so weak that expected sensitivity cannot be realized.

As means for solving this problem, there is disclosed adding of sensitizing dyes in the form of a dispersion containing a surfactant or the form of an oil drop dispersion (see, for example, JP-A-2002-49113). However, even if this means is applied, the level of improvement in the above problem is not satisfactory.

BRIEF SUMMARY OF THE INVENTION

It is an object of the present invention to provide a highly sensitive silver halide emulsion whose fog increase during storage is slight and to provide a method of preparing the emulsion. It is another object of the present invention to accordingly provide a silver halide photosensitive material of high film speed and excellent storability.

As a result of extensive and intensive studies, it has been found that the objects of the present invention can be attained by the following means (1) to (16).

(1) A silver halide emulsion containing water, dispersion medium and silver halide grains wherein the dispersion medium comprising modified gelatin whose amino group is chemically modified, and the silver halide grains comprising spectrally sensitized silver halide grains each having a multilayer adsorption of dye chromophores on the surface thereof.

(2) The silver halide emulsion according to (1) mentioned above wherein a ratio of the modified gelatin to the dispersion medium is 5% or more.

(3) The silver halide emulsion according to (1) or (2) mentioned above wherein the modified gelatin is gelatin to which one carboxyl group (—COOH group) is introduced when one amino acid group thereof is chemically modified, and a chemical modification ratio of the amino groups of the modified gelatin is 5% to 100%.

(4) A method of preparing, in a reaction vessel, the silver halide emulsion according to any one of (1) to (3) mentioned above wherein at least one of the dye chromophores is a cationic dye, and the method comprising adding, to the reaction vessel, the cationic sensitizing dye in the form of water-based dispersion substantially not containing an anionic surfactant.

(5) A method of preparing, in a reaction vessel, the silver halide emulsion according to any one of (1) to (3) mentioned above wherein at least one of the dye chromophores is a cationic dye, and the method comprising adding, to the reaction vessel, the cationic sensitizing dye in the form of water-based dispersion substantially not containing an organic solvent.

(6) A method of preparing, in a reaction vessel, the silver halide emulsion according to any one of (1) to (3) mentioned above wherein at least one of the dye chromophores is a cationic dye, and the method comprising adding, to the reaction vessel, the cationic sensitizing dye in the form of water-based dispersion, and a concentration of the cationic sensitizing dye in the water-based dispersion is 1 wt % or more.

(7) The silver halide emulsion according to (1) mentioned above wherein a variation coefficient of equivalent circle diameters of all the silver halide grains is 40% or less, and 70% or more of the total projected area of the silver halide grains is occupied by the spectrally sensitized silver halide grains each having a multilayer adsorption of dye chromophores on the surface thereof.

(8) The silver halide emulsion according to any one of (1) to (3) mentioned above wherein the average thickness of all the silver halide grains contained in the silver halide emulsion is 0.2 μm or less.

(9) The silver halide emulsion according to any one of (1) to (3), (7) and (8) mentioned above wherein a content of Ca or Mg in the silver halide emulsion is $2 \times 10^{-3}$ mol to $4 \times 10^{-2}$ mol per mol of silver of the silver halide emulsion.

(10) A method of preparing, in a reaction vessel, the silver halide emulsion according to any one of (1) to (3) mentioned above wherein the method comprising adding, to the reaction vessel, the modified gelatin and desalting a silver halide emulsion to which the modified gelatin is added, wherein the adding the modified gelatin is conducted before the desalting.

(11) The method according to any one of (4) to (6) mentioned above wherein a content of the anionic surfactant in the reaction vessel immediately after the completion of adding all the dye chromophores is 0.45 g or less per mole of silver of a silver halide emulsion contained in the reaction vessel.

(12) The method according to any one of (4) to (6) mentioned above wherein the cationic sensitizing dye in the form of water-based dispersion containing an inorganic salt.

(13) The method according to any one of (4) to (6) mentioned above wherein an amount of silver of a silver halide emulsion in the reaction vessel at the time of adding the cationic sensitizing dye is 100 g/kg or more and/or an amount of gelatin of a silver halide emulsion in the reaction vessel at the time of adding the cationic sensitizing dye is 90 g/kg or less.

(14) A silver halide photosensitive material containing, in a light-sensitive silver halide emulsion layer, the silver halide emulsion according to any one of (1) to (3), and (7) to (9).

(15) The silver halide photosensitive material according to (14) mentioned above wherein the photosensitive material containing a compound capable of undergoing a one-electron oxidation to thereby form a one-electron oxidation product capable of releasing further one or more electrons.

(16) The silver halide photosensitive material according to (14) mentioned above wherein the photosensitive material further containing a compound represented by general formula (M) or general formula (U).

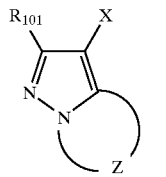
(M)

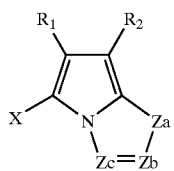
(U)

In the general formula (M), $R_{101}$ represents a hydrogen atom or substituent. Z represents a nonmetallic atom group required to form a 5-membered azole ring containing 2 to 4 nitrogen atoms wherein the azole ring may have a substituent (including a condensed ring). X represents a hydrogen atom or substituent.

In the general formula (U), Za represents —NH— or —CH($R_3$)—, each of Zb and Zc independently represents —C($R_4$)= or —N=. Each of $R_1$, $R_2$ and $R_3$ independently represents an electron-withdrawing group having a Hammett substituent constant σp of 0.2 to 1.0. $R_4$ represents a hydrogen atom or substituent. When there are two or more $R_4$s in the general formula (U), these may be the same or different to each other. X represents a hydrogen atom or substituent.

DETAILED DESCRIPTION OF THE INVENTION

The present invention will be described in detail below.

In the present invention, there is a case in which a dye chromophore is contained as a partial structure of a dye or a case in which a dye as a whole is dye chromophore. A dye containing a dye chromophore is preferably used as a sensitizing dye.

The chromophore used in the present invention will be described in "Chromophore (i)" below.

Chromophore (i)

The terminology "chromophore" used herein means an atomic group which is the main cause of molecular absorption bands as described on page 1052 of Physicochemical Dictionary (5th edition, published by Iwanami Shoten, Publishers in 1998), the disclosure of which is incorporated herein by reference, for example, any atomic group selected from among C=C, N=N and other atomic groups having unsaturated bonds.

Examples thereof include a cyanine dye, styryl dye, hemicyanine dye, merocyanine dye (including zeromethine-merocyanine (simple merocyanine), trinuclear merocyanine dye, tetranuclear merocyanine dye, rhodacyanine dye, complex cyanine dye, complex merocyanine dye, an allopolar dye, an oxonol dye, hemioxonol dye, squarium dye, croconium dye, an azamethine dye, coumarin dye, allylidene dye, anthraquinone dye, triphenylmethane dye, an azo dye, an azomethine dye, spiro compound, metallocene dye, fluorenone dye, fulgide dye, perillene dye, phenazine dye, phenothiazine dye, quinone dye, an indigo dye, diphenylmethane dye, polyene dye, acridine dye, acridinone dye, diphenylamine dye, quinacridone dye, quinophthalone dye, phenoxazine dye, phthaloperillene dye, porphyrin dye, chlorophyll dye, phthalocyanine dye and metal complex dye.

Of these, there can preferably be employed methine chromophores such as a cyanine dye, styryl dye, hemicyanine dye, merocyanine dye, trinuclear merocyanine dye, tetranuclear merocyanine dye, rhodacyanine dye, complex cyanine dye, complex merocyanine dye, allopolar dye, oxonol dye, hemioxonol dye, squarium dye, croconium dye and azamethine dye. More preferred are a cyanine dye, merocyanine dye, trinuclear merocyanine dye, tetranuclear merocyanine dye, rhodacyanine dye and oxonol dye. More preferred are a cyanine dye, merocyanine dye, trinuclear merocyanine dye, tetranuclear merocyanine dye, rhodacyanine dye and oxonol dye. Much more preferred are a cyanine dye, merocyanine dye, rhodacyanine dye and oxonol dye. Especially preferable are a cyanine dye and merocyanine dye. A cyanine dye is most preferred.

Details of these dyes are described in the following "Dye documents (ii)".

Dye Documents (ii)

F. M. Harmer, "Heterocyclic Compounds—Cyanine Dyes and Related Compounds", John Wiley & Sons, New York, London, 1964, D. M. Sturmer, "Heterocyclic Compounds—Special topics in heterocyclic chemistry", chapter 18, section 14, pages 482 to 515, John Wiley & Sons, New York, London, 1977 and "Rodd's Chemistry of Carbon Compounds", 2nd ed. vol.IV, part B, 1977 and 15th chapter, pp. 369–422, Elsevier Science Publishing Company Inc., New York, all the disclosures of which are incorporated herein by reference.

To explain in more detail, those described in Research Disclosure (RD) 17643, pp. 23–24, RD18716, page 648, right column to page 649, right column, RD308119, page 996, right column to page 998, right column, EP 0565096A1, page 65, lines 7–10, all the disclosures of which are incorporated herein by reference, are preferably used. Also the dyes having a partial structure or a hole structure represented by general formulas and specific examples shown in the specifications of U.S. Pat. No. 5,747,236 (especially pages 30–39), U.S. Pat. No. 5,994,051 (especially pages 32–43), U.S. Pat. No. 5,340,694 (especially pages 21–58, provided that in the dyes represented by (XI), (XII) and (XIII), the numbers n12, n15, n17 and n18 are not limited as long as each of these is an integer of 0 or greater (preferably, 4 or less), may be preferably used, the contents described in the pages of the above U.S. Patents are incorporated herein by reference.

Further, those having a partial structure of a hole structure represented by general formulas and specific examples shown in the specification of JP-A's-10-239789, 11-133531, 2000-267216, 2000-275772, 2001-75222, 2001-75247, 2001-75221, 2001-75226, 2001-75223, 2001-255615, 2002-23294, 10-171058, 10-186559, 10-197980, 2000-81678, 2001-5132, 2001-166413, 2002-49113, 64-91134, 10-110107, 10-171058, 10-226758, 10-307358, 10-307359, 10-310715, 2000-231174, 2000-231172, 2000-231173 and 2001-356442, EP's 0985965A, 0985964A, 0985966A, 0985967A, 1085372A, 1085373A, 1172688, 1199595A and 887700A1, and JP-A's-10-239789, 2001-75222 and 10-171058, the entire contents of which are incorporated herein by reference, may also be used preferably.

Next, multilayer adsorption of dye chromophores will be described. In the present invention, the multilayer adsorption of chromophores means adsorption of more than one layer of dye chromophores on silver halide grain surfaces. In another word, the chromophores are laminated.

Specifically, there can be mentioned a method in which a dye is adsorbed on the surface of silver halide grain in an amount of more than the saturated coating amount, or a method in which a compound consisting of a plurality of dye chromophores (so to called a multi-chromophore dye compound or linked dye) (in the compound, it is preferable that the plurality of dye chromophores are not conjugated), is adsorbed on a silver halide grain. Such methods are described in "Multilayer adsorption related patents (iii)" below. Among these, multilayer adsorption is attained by dye chromophores mutually linked by attractive force other than a covalent bond.

Multilayer Adsorption Related Patents (iii)

The publications and specifications of JP-A's-10-239789, 11-133531, 2000-267216, 2000-275772, 2001-75222, 2001-75247, 2001-75221, 2001-75226, 2001-75223, 2001-255615, 2002-23294, 10-171058, 10-186559, 10-197980, 2000-81678, 2001-5132, 2001-166413, 2002-49113, 64-91134, 10-110107, 10-171058, 10-226758, 10-307358, 10-307359, 10-310715, 2000-231174, 2000-231172, 2000-231173, and 2001-356442, and EP's 0985965A, 0985964A, 0985966A, 0985967A, 1085372A, 1085373A, 1172688A, 1199595A and 887700A1, all the contents of which are incorporated herein by reference.

Further, it is preferable to use the techniques described in the publications of JP-A's-10-239789, 2001-75222 and 10-171058, all the contents of which are incorporated herein by reference, in combination.

The expression "adsorption of more than one layer of chromophore on silver halide grain surfaces" used herein means that the adsorption amount of dye chromophore per area is greater than a one-layer saturated coating amount, this one-layer saturated coating amount defined as the saturated adsorption amount per area attained by a dye which exhibits the smallest dye-occupied area on silver halide grain surfaces among the sensitizing dyes added to the emulsion. The number of adsorption layers means the adsorption amount evaluated on the basis of one-layer saturated coating amount. In the case of a multi-chromophore dye compound, the dye-occupied area of unconnected individual dyes can be employed as the basis. The unconnected individual dye, for example, is a dye having one dye chromophore by replacing the liking portion with an alkyl group or alkylsulfonic acid group.

The dye-occupied area can be determined from an adsorption isothermal line showing the relationship between free dye concentration and adsorbed dye amount, and a grain surface area. The adsorption isothermal line can be determined with reference to, for example, A. Herz et al. "Adsorption from Aqueous Solution", Advances in Chemistry Series, No. 17, page 173 (1968).

The adsorption amount of a sensitizing dye onto emulsion grains can be determined by two methods. The one method comprises centrifuging an emulsion having undergone a dye adsorption to thereby separate the emulsion into emulsion grains and a supernatant aqueous solution of gelatin, determining an unadsorbed dye concentration from the measurement of spectral absorption of the supernatant, and subtracting the same from the added dye amount to thereby determine the adsorbed dye amount. The other method comprises depositing emulsion grains, drying the same, dissolving a given weight of the deposit to a silver halide solvent and dye solvent, e.g., a mixture of an aqueous solution of sodium thiosulfate and methanol, and measuring a spectral absorption thereof to thereby determine the adsorbed dye amount. When a plurality of sensitizing dyes are employed, the absorption amount of each dye can be determined by high-performance liquid chromatography or other techniques.

With respect to the method of determining the dye absorption amount by measuring the dye amount in a supernatant, reference can be made to, for example, W. West et al., Journal of Physical Chemistry, vol. 56, page 1054 (1952). However, even unadsorbed dye may be deposited when the addition amount of dye is large, so that an accurate absorption amount may not always be obtained by the method of measuring the dye concentration of the supernatant.

On the other hand, in the method in which the absorption amount of dye is determined by dissolving deposited silver halide grains, the deposition velocity of emulsion grains is overwhelmingly faster, so that grains and deposited dye can easily be separated from each other. Thus, only the amount of dye adsorbed on grains can accurately be determined. Therefore, this method is most reliable as a means for determining the dye absorption amount.

As one method of measuring the surface area of silver halide grains, there can be employed the method wherein a transmission electron micrograph is taken according to the replica method and wherein the configuration and size of each individual grain are measured and calculated. In this method, the thickness of tabular grains is calculated from the length of shadow of the replica. With respect to the method of taking a transmission electron micrograph, reference can be made to, for example, Denshi Kenbikyo Shiryo Gijutsu Shu (Electron Microscope Specimen Technique Collection) edited by the Kanto Branch of the Society of Electron Microscope of Japan and published by Seibundo Shinkosha in 1970 and P. B. Hirsch, "Electron Microscopy of Thin Crystals", Buttwrworths, London (1965).

Reference can be made to the following literatures, for example, for other methods: The Journal of Photographic Science, vol. 14, p.185 (1966) by A. M. Kragin et al., Transactions of the Faraday Society, volume 60, page 1325 (1964) by J. F. Paddy, Journal de Chimie Physique et de Physicochimie biologique, vol. 63, page 1123 (1963) by S. Boyer et al., Journal of Physical Chemistry, vol. 56, page 1054 (1952) by W. West et al., International Coloquium, by E. Klein, edited by H. Sauvenier, and Scientific Photography, by Liege (1959).

Although the area occupied by dyes can be experimentally determined with respect to individual cases by the above-mentioned method, as the molecular occupied area of commonly employed sensitizing dyes is close to approximately 0.8 $nm^2$, it is practical to simply assume that the dye-occupied area is 0.8 $nm^2$ with respect to all dyes and to estimate the approximate number of adsorbed layers.

The adsorption of dye chromophores on silver halide grains is preferably accomplished in the form of at least 1.3 layers, more preferably at least 1.5 layers and most preferably at least 1.7 layers. Although there is no particular upper limit, the number of layers is preferably 10 or less layers, more preferably 5 or less layers and most preferably 3 or less layers.

With respect to the silver halide photographic emulsion of the present invention, it is preferred that ½ or more of the total projected area of silver halide grains be occupied by silver halide grains of 100 or greater light absorption intensity in the use of grains of 500 nm or larger wavelength at the spectral absorption maximum and occupied by silver halide grains of 60 or greater light absorption intensity in the use of grains of less than 500 nm wavelength at the spectral absorption maximum. With respect to grains of 500 nm or larger wavelength at the spectral absorption maximum, the light absorption intensity thereof is preferably 150 or higher, more preferably 170 or higher and most preferably 200 or higher. On the other hand, with respect to grains of less than 500 nm wavelength at the spectral absorption maximum, the light absorption intensity thereof is preferably 90 or higher, more preferably 100 or higher and most preferably 120 or higher. Although there is no particular upper limit, the light absorption intensity is preferably 2000 or less, more preferably 800 or less and most preferably 400 or less.

In the present invention, the light absorption intensity refers to light absorption area intensity per grain surface area realized by a dye. It is defined as an integral value, over wave number ($cm^{-1}$), of optical density Log ($Io/(Io-I)$), wherein Io represents the quantity of light incident on each unit surface area of grains and I represents the quantity of light absorbed by the dye on the surface. The range of integration is from 5000 $cm^{-1}$ to 35,000 $cm^{-1}$.

After measurement of the dye absorption amount, an approximate ratio of grains having multilayer adsorption of dyes may be known by measuring the light absorption intensity of 20 or more grains selected randomly.

An average number of layers of dye absorption of all the grains may be obtained by the measurement of the dye absorption amount. On the other hand, the measurement of light absorption intensity using microscopic spectrophotometry to be described later make it possible to obtain an approximate average of light absorption intensity of each grain. Calculating an approximate ratio of average dye absorption layer number/light absorption intensity, and obtaining a product of the thus calculated value and the light absorption intensity of target grain for the measurement an approximate dye absorption layer number of the target grain for the measurement may be obtained.

From the above, a ratio among the all measured grains of grains having more than one layer of dye absorption may be obtained, which ratio is an approximate ratio of the grains having a multilayer absorption of dyes. The ratio, to the total projected area, of grains having a multilayer absorption of dyes may easily be obtained by parallel measurement of the projected area of the grains which were the target for the measurement of the dye absorption intensity. In the silver halide emulsion of the present invention, the ratio of silver halide grains having a multilayer adsorption of dye chromophores on the surfaces thereof is preferably 70% or more, and more preferably 90% or more of the total projected area.

As one method of measuring the light absorption intensity, there can be mentioned the method of using a microscopic spectrophotometer. The microscopic spectrophotometer is a device capable of measuring an absorption spectrum of minute area, whereby a transmission spectrum and reflectance spectrum of each grain can be measured. From the measurements of both spectra absorption spectrum may be obtained. With respect to the measurement of an absorption spectrum of each grain by the microscopic spectrophotometry, reference can be made to the report of Yamashita et al. (page 15 of Abstracts of Papers presented before the 1996 Annual Meeting of the Society of Photographic Science and Technology of Japan). The absorption intensity per grain can be determined from the absorption spectrum. Because the light transmitted through grains is absorbed by two surfaces, i.e., upper surface and lower surface, so, the absorption intensity per grain surface area can be determined as ½ of the absorption intensity per grain obtained in the above manner. At that time, although the interval for absorption spectrum integration is from 5000 $cm^{-1}$ to 35,000 $cm^{-1}$ in view of the definition of light absorption intensity, experimentally, it is satisfactory to integrate over an interval including about 500 $cm^{-1}$ after and before the interval of absorption by sensitizing dye.

The light absorption intensity is a value unequivocally determined from the oscillator strength and number of adsorbed molecules per area with respect to the sensitizing dye. If, with respect to the sensitizing dye, the oscillator strength, dye adsorption amount and grain surface area are measured, these can be converted into the light absorption intensity.

The oscillator strength of sensitizing dye can be experimentally determined as a value proportional to the absorption area intensity (optical density×cm$^{-1}$) of sensitizing dye solution, so that the light absorption intensity can be calculated within an error of about 10% by the formula:

light absorption intensity·0.156×A×B/C wherein A represents the absorption area intensity per M of dye (optical density×cm$^{-1}$), B represents the adsorption amount of sensitizing dye (mol/mol Ag) and C represents the grain surface area C (m$^2$/mol Ag).

Calculation of the light absorption intensity through this formula gives substantially the same value as the integral value, over wave number (cm$^{-1}$), of light absorption intensity (Log (Io/(Io−I))) measured in accordance with the aforementioned definition.

In the present invention, in the use of ordinary dyes having one dye chromophore, the first-layer dye refers to a dye which is adjacent to silver halide grains and adsorbed inside thereon. The dye of the second layer or the rest of the layers refers to a dye which although being adsorbed on silver halide grains in the aforementioned measurement of adsorption amount, is not directly adsorbed on silver halide grains and arranged outside adjacent to the first-layer dye. When the dye compound has multiple chromophores, the first-layer dye refers to a dye chromophore which is adjacent to silver halide grains and adsorbed inside thereon. The dye of the second layer or the rest of the layers refers to a dye chromophore which is arranged outside adjacent to the inside dye chromophore.

In the present invention, the wavelength at maximum absorption of the dye of the second layer or the rest of the layers is preferably equal to or smaller than that of the dye of the first layer. The spacing between these wavelengths is preferably in the range of 0 to 50 nm, more preferably 0 to 30 nm, and most preferably 0 to 20 nm.

In the present invention, the reduction potentials and oxidation potentials of the dye of the first layer and the dye of the second layer or the rest of the layers are not limited. In particular, however, the reduction potential of the dye of the first layer is preferably noble to the value of the reduction potential of the dye of the second layer or the rest of the layers minus 0.2 V, more preferably noble to the value of the reduction potential of the dye of the second layer or the rest of the layers minus 0.1 V, and most preferably noble to the reduction potential of the dye of the second layer or the rest of the layers.

The measuring of reduction potential or oxidation potential, although various methods can be employed, is preferably carried out by phase discrimination type second higher harmonic alternating current polarography, in which accurate measurements can be obtained. The method of measuring potentials by the above phase discrimination type second higher harmonic alternating current polarography is described in Journal of Imaging Science, vol. 30, page 27 (1986).

It is preferred that the dye of the second layer or the rest of the layers be luminescent in gelatin dry films. With respect to the type of luminescent dye, one having a skeletal structure of dye for use for dye laser is preferred. This type of luminescent dye is described in order in, for example, Mitsuo Maeda, Laser Kenkyu (Study of Laser), vol. 8, pages 694, 803 and 958 (1980) and vol. 9, page 85 (1981) and "Dye Lasers" written by F. Sehaefer, Springer (1973), the entire contents of which are incorporated herein by reference.

The luminescent yield of the dye limited to that of the second layer in gelatin dry films is preferably 0.05 or higher, more preferably 0.1 or higher, still more preferably 0.2 or higher and most preferably 0.5 or higher.

When there occurs an energy transfer from the dye of the second layer or the rest of the layers to the dye of the first layer according to nonequilibrium excitation energy transfer mechanism, it is preferred that the life of excitation in gelatin dry films of only the dye of the second layer be prolonged. In this instance, the luminescent yield of the particular dye of the second layer may be high or low. The life of fluorescence in gelatin dry films of only the dye of the second layer is preferably 10 ps or greater, more preferably 40 ps or greater, and still more preferably 160 ps or greater. The life of fluorescence of the dye of the second layer or the rest of the layers, although there is no particular upper limit, is preferably 1 ms or less.

It is preferred that the overlapping of the luminescence of the dye of the second layer or the rest of the layers and the absorption of the dye of the first layer be extensive. Assuming that the emission spectrum of the dye of the second layer or the rest of the layers is l(ν) and the absorption spectrum of the dye of the first layer is a(ν), the product thereof, l(ν)·a(ν), is preferably 0.001 or greater, more preferably 0.01 or greater, still more preferably 0.1 or greater, and most preferably 0.5 or greater. Herein, ν represents wave number (cm$^{-1}$), and with respect to each of these spectra, the spectral area has been normalized to 1.

The energy transfer efficiency associated with the transfer of excitation energy of the dye of the second layer or the rest of the layers to the dye of the first layer is preferably 10% or greater, more preferably 30% or greater, still more preferably 60% or greater, and most preferably 90% or greater. Herein, the terminology "excitation energy of the dye of the second layer or the rest of the layers" means the energy possessed by the dye being in the excited state resulting from the absorption of light energy by the dye of the second layer or the rest of the layers. It is assumed that the transfer of the excitation energy possessed by a certain molecule to another molecule occurs through the excited electron transfer mechanism, energy transfer mechanism of Forster Model, energy transfer mechanism of Dextor Model, etc. In the multilayer adsorption system under the present study as well, it is preferred that the conditions for inducing efficient transfer of excitation energy that can be anticipated according to the above mechanisms be satisfied. It is more preferred that the conditions for inducing the energy transfer mechanism of Forster Model be satisfied. For enhancing the efficiency of energy transfer of Forster Model, it is effective to lower the refractive index in the vicinity of emulsion grain surfaces.

The efficiency of energy transfer from the dye of the second layer or the rest of the layers to the dye of the first layer can be determined through an analysis of rate of fluorescence decay with respect to the dye of the second layer and a dynamics analysis of light excited state with respect to the rate of fluorescence rise of the dye of the first layer, etc.

Further, the efficiency of energy transfer from the dye of the second layer or the rest of the layers to the dye of the first layer can also be determined as the ratio of efficiency of spectral sensitization at excitation of the dye of the second layer or the rest of the layers/efficiency of spectral sensitization at excitation of the dye of the first layer.

In the present invention, it is preferred that the adsorbed dye of the first layer form a J-aggregate. Although the dye of the second layer or the rest of the layers may be adsorbed in monomeric form or may form a short wavelength aggregate such as H-aggregate, it is especially preferred that the dye form a J-aggregate and be adsorbed. The J-aggregate is preferred from the viewpoint of high light absorption coefficient and absorption sharpness, and accordingly it is extremely useful in the spectral sensitization at common monolayer absorption. Having such spectral characteristics is extremely preferable with respect to the dye of the second layer or the rest of the layers as well. Moreover, the J-aggregate exhibits high fluorescence yield and small Stokes shift, so that it is desirable in the transfer of light energy absorbed by the dye of the second layer or the rest of the layers to the dye of the first layer which has close light absorption wavelength according to the Forster Model energy transfer mechanism.

The spacing between largest wavelength and smallest wavelength exhibiting 50% of the maximum of spectral absorptivity (Amax) by sensitizing dye with respect to an emulsion containing silver halide photographic emulsion grains of 60 or greater, or 100 or greater light absorption intensity is preferably 120 nm or less, more preferably 100 nm or less. The spacing between largest wavelength and smallest wavelength exhibiting 50% of the maximum of spectral sensitivity (Smax) is preferably 120 nm or less, more preferably 100 nm or less.

Similarly, the spacing between largest wavelength and smallest wavelength exhibiting 80% of each of Amax and Smax is preferably 20 nm or greater and is preferably 100 nm or less, more preferably 80 nm or less and most preferably 50 nm or less.

Further similarly, the spacing between largest wavelength and smallest wavelength exhibiting 20% of each of Amax and Smax is preferably 180 nm or less, more preferably 150 nm or less, still more preferably 120 nm or less and most preferably 100 nm or less.

The largest wavelength exhibiting a spectral absorptivity of 50% of Amax or Smax is preferably in the range of 460 to 510 nm, or 560 to 610 nm, or 640 to 730 nm.

Assuming that A1max represents a wavelength exhibiting the maximum of spectral absorptivity attributed to the dye chromophore of the first layer of silver halide grains while A2max represents a wavelength exhibiting the maximum of spectral absorptivity attributed to the dye chromophore of the second layer or the rest of the layers, each of A1max and A2max is preferably in the range of 400 to 500 nm, or 500 to 600 nm, or 600 to 700 nm, or 700 to 1000 nm.

Furthermore, assuming that S1max represents a wavelength exhibiting the maximum of spectral sensitivity attributed to the dye chromophore of the first layer of silver halide grains while S2max represents a wavelength exhibiting the maximum of spectral sensitivity attributed to the dye chromophore of the second layer or the rest of the layers, each of S1max and S2max is preferably in the range of 400 to 500 nm, or 500 to 600 nm, or 600 to 700 nm, or 700 to 1000 nm.

The multilayer adsorption of dye chromophores with the use of intermolecular force will be described below. This multilayer adsorption refers to multilayer adsorption of dye chromophores on the surface of silver halide grains which has been accomplished by mutual bonding of dye chromophores through attractive force other than a covalent bonding.

Although the attractive force other than covalent bonding is not particularly limited, there can be mentioned, for example, van der Waals' force (in specifically divided expression, consisting of orientation force acting between permanent dipole and permanent dipole, induction force acting between permanent dipole and induced dipole and dispersion force acting between temporary dipole and induced dipole), charge transfer (CT) force, Coulomb's force (electrostatic force), hydrophobic bond force, hydrogen bond force, coordinate bond force, etc. These bonding forces can be used either individually or in arbitrary combination.

Of these, van der Waals' force, charge transfer force, Coulomb's force, hydrophobic bond force and hydrogen bond force are preferred; van der Waals' force, Coulomb's force and hydrogen bond force are more preferred; and van der Waals' force and Coulomb's force are most preferred.

The terminology "mutually bonded" means that dye chromophores are placed under restraint by these attractive forces. In the description by another expression, the energy of attractive force (namely, adsorption energy ($\Delta G$)) is preferably 15 kJ/mol or greater, more preferably 20 kJ/mol or greater, and most preferably 40 kJ/mol or greater. The energy of attractive force, although there is no particular upper limit, is preferably 5000 kJ/mol or less, more preferably 1000 kJ/mol or less.

In particular, there can be preferably employed, for example, the method of JP-A-10-239789 in which use is made of a dye having an aromatic group, or joint use is made of an anionic sensitizing dye and a cationic sensitizing dye having an aromatic group; the method of JP-A-10-171058 in which use is made of a dye having a polyvalent charge; the method of JP-A-10-186559 in which use is made of a dye having a hydrophobic group; the method of JP-A-10-197980 in which use is made of a dye having a coordinate bond group; the method of JP-A-2001-5132 in which use is made of a dye having a trinuclear basic nucleus; the method of JP-A-2001-13614 in which use is made of a dye having a specified hydrophilicity or hydrophobicity; the method of JP-A-2001-75220 in which use is made of a dye of specified intramolecular basicity; the method of JP-A-2001-75221 in which use is made of a specified dye other than a cyanine dye; the method of JP-A-2001-152038 in which use is made of a dye having an acid dissociative group of specified pKa value; the methods of JP-A's-2001-166413, 2001-323180 and 2001-337409 in which use is made of dyes having a specified hydrogen bond group; the method of JP-A-2001-209143 in which use is made of a dye having a specified fluorescence quantum yield; the method of JP-A-2001-264913 in which use is made of a specified decolorable dye; the method of JP-A-2001-343720 in which use is made of a dye contained in a gel matrix; the method of JP-A-2002-23294 in which use is made of a specified infrared dye; the method of JP-A-2002-99053 in which use is made of a dye having a specified potential; or the methods of EP's 0985964, 0985965, 0985966, 0985967, 1085372, 1085373, 1172688 and 1199595 in which use is made of specified cationic sensitizing dyes.

Now, the multilayer adsorption of dye chromophores by means of Coulomb's force which is especially preferably employed in the present invention will be further described.

In the multilayer adsorption of dye chromophores by means of Coulomb's force, use is made of a cationic sensitizing dye in combination with an anionic sensitizing dye. The cationic sensitizing dye refers to a sensitizing dye wherein the whole charge of dye chromophores excluding counter ions is positive. The anionic sensitizing dye refers to a sensitizing dye wherein the whole charge of dye chromophores excluding counter ions is negative.

Although the addition sequence and addition amounts of cationic sensitizing dye and anionic sensitizing dye can be arbitrarily chosen, it is preferred that in the sensitizing dyes of the first layer (sensitizing dyes directly adsorbed on silver halide grains), an anionic sensitizing dye occupy 60% or more, especially 70% or more of the saturated coating amount.

The addition form of cationic sensitizing dye is an important factor in the multilayer adsorption of dye chromophores by means of Coulomb's force and thus will be described below.

Specific examples of cationic sensitizing dyes which can be employed in the present invention will be shown below, which however in no way limit the scope of the present invention.

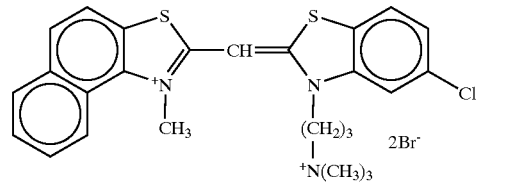

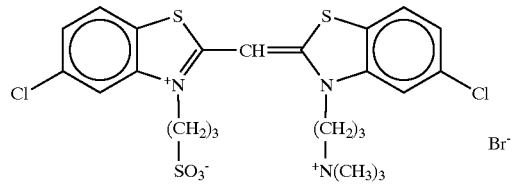

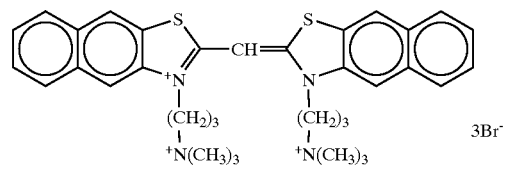

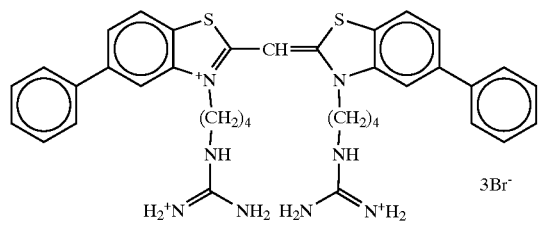

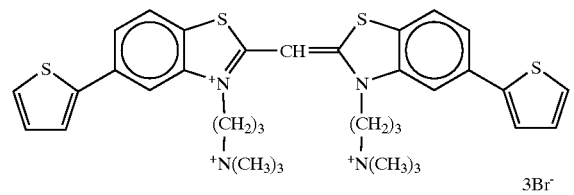

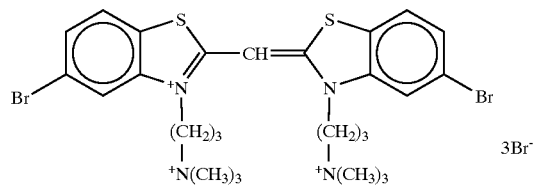

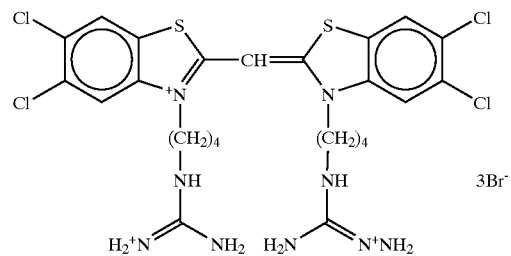

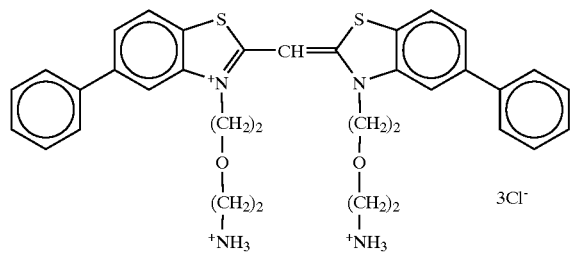

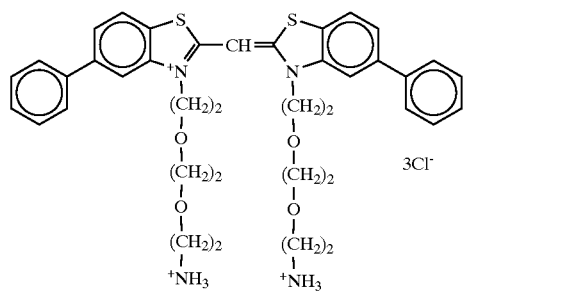

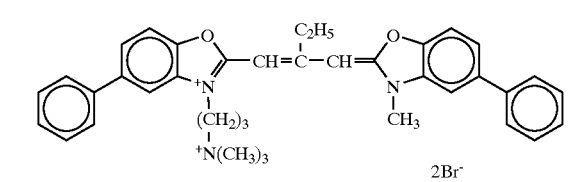

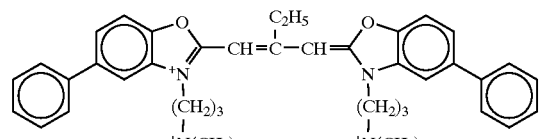

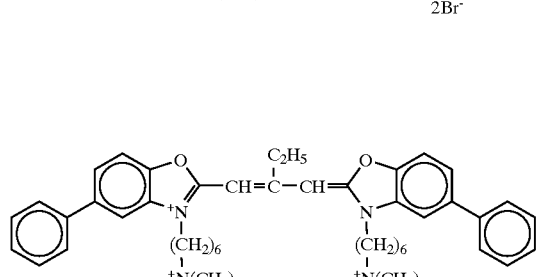

-continued
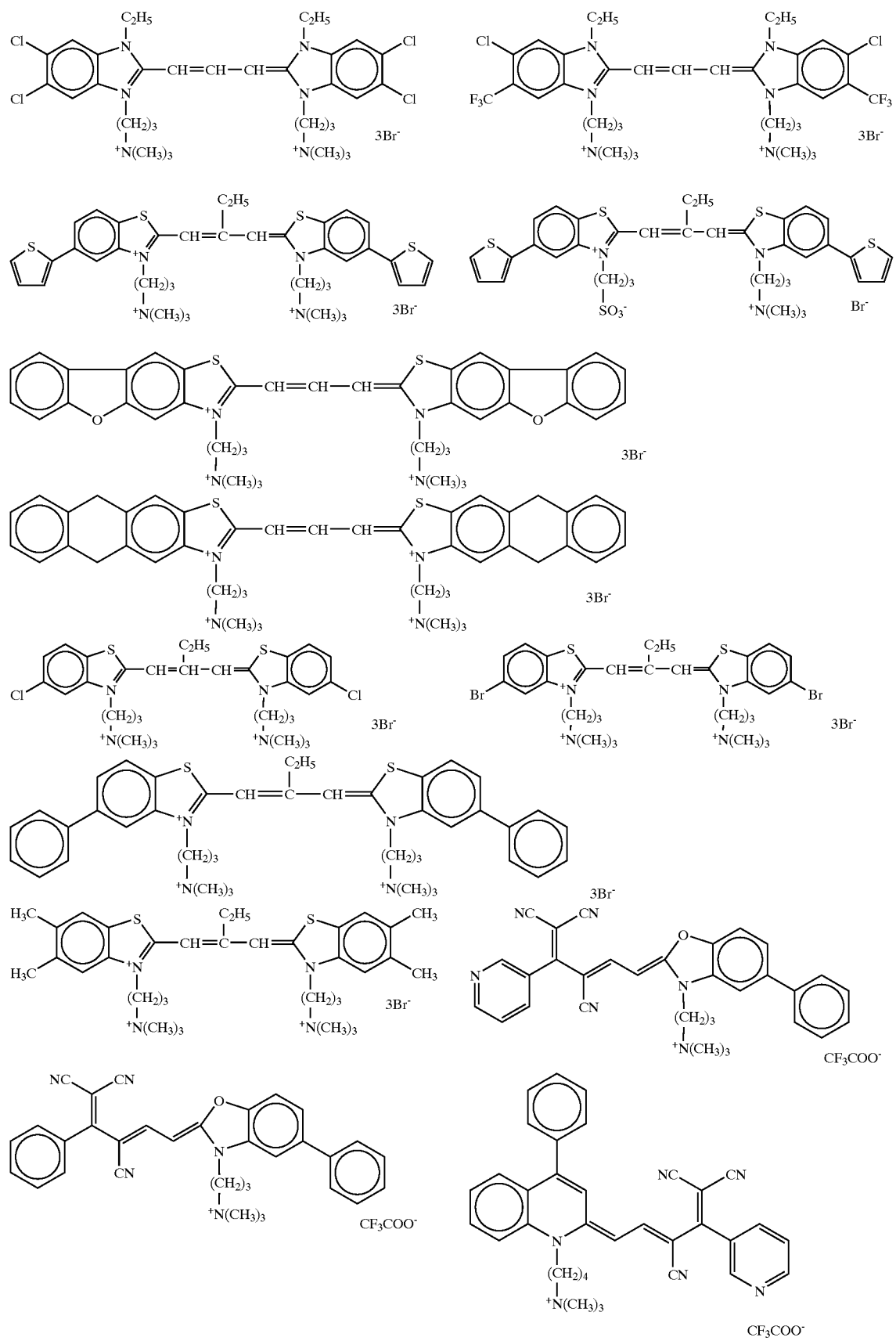

The cationic sensitizing dye for use in the present invention is preferably a cyanine dye.

In the present invention, it is recommended to add cationic sensitizing dyes in the form of a water-based dispersion not containing the following anionic surfactant and/or organic solvent. Preferably, cationic sensitizing dyes are added in the form of a water-based dispersion containing an inorganic salt. The concentration of cationic sensitizing dye in such a water-based dispersion is preferably 0.5 wt % or more, more preferably 1 wt % or more. When a sensitizing dye is added in the form of a water-based dispersion, multilayer adsorption of cationic sensitizing dye on silver halide grains would successfully occur, thereby enabling stable production of an emulsion involving a multilayer adsorption of sensitizing dyes.

In the present invention, preferably, a cationic sensitizing dye which is substantially insoluble in water is added in the form of a solid dispersion obtained by mechanically pulverizing the cationic sensitizing dye into fine particles with an average diameter of 30 μm or less, preferably 20 μm or less and more preferably 10 μm or less and dispersing the fine particles in water. It is preferred that the distribution of average diameters be narrow and monodispersed. The expression "substantially insoluble in water" means that the solubility in water is 0.2 wt % or below. The diameter of fine particles dispersed in water can be measured through an optical microscope or from a pattern obtained by diffraction scattering of beams emitted from a laser source which is attributed to fine particles. In the mechanical pulverization of sensitizing dyes in water, various dispersers can be effectively used. For example, use can be made of a high-speed agitator, a ball mill, a sand mill, a colloid mill, an attritor, an ultrasonic disperser, etc. In the mechanical pulverization, it is recommended in the present invention to perform dispersion substantially without the use of any anionic surfactants as described later. The expression "substantially without the use" means that the concentration of surfactants is 0.1 wt % or less. The concentration of surfactants is preferably 0.01 wt % or less, most preferably nil. Further, in the mechanical pulverization, substantially any organic solvent is not used in the present invention. The expression "substantially any organic solvent is not used" means that the concentration of organic solvent is 10 wt % or less. The concentration of organic solvent is preferably 1 wt % or less, most preferably nil. The temperature at which cationic sensitizing dyes are dispersed in water is preferably in the range of 20 to 80° C., more preferably 40 to 60° C. The dispersion of cationic sensitizing dye, for imparting antisetting properties, can be mixed with a water soluble polymer and stored or refrigerated at, for example, 30° C. or below for a prolonged period of time.

Use can be made of, for example, a gelatin derivative, a graft polymer of gelatin with another polymer, a protein, such as albumin and casein; a cellulose derivative, such as hydroxyethylcellulose, carboxymethylcellulose, and cellulose sulfate ester; sodium alginate, a saccharide derivative, such as a starch derivative; and many synthetic hydrophilic polymers, including homopolymers and copolymers, such as a polyvinyl alcohol, polyvinyl alcohol partial acetal, poly-N-vinylpyrrolidone, polyacrylic acid, polymethacrylic acid, polyacrylamide, a polyvinylimidazole and a polyvinylpyrazole. Lime-processed gelatin, as well as acid-processed gelatin, enzyme-treated gelatin such as those described in Bull. Soc. Sci. Photo. Japan, Np. 16, p.30 (1966), the entire contents of which is incorporated herein by reference. Also, a hydrolysis product or enzymatic decomposition product of gelatin may be used.

Gelatin is preferably employed in the present invention. This water soluble polymer may be added in the form of an aqueous solution or a solid. In the addition of such water soluble polymer, known antiseptic agents can be used according to necessity. The concentration of the water soluble polymer for use as a dispersion medium in water is preferably 0.5% by weight or more, more preferably in the range of 1 to 10% by weight. The thus prepared sensitizing dye dispersion can be stably stored for long, for example, one month or more, by simply cooling the same without the need to effect drying.

Since cationic sensitizing dyes must be dispersed in high concentration by the above methods in the present invention, it is extremely effective to add an inorganic salt to the dispersion. With respect to the addition of inorganic salts to the dispersion, reference can be made to the description of JP-A-11-52507. Sodium nitrate, potassium nitrate, sodium sulfate, potassium sulfate, sodium phosphate, potassium phosphate, sodium carbonate, potassium carbonate, sodium borate and potassium borate are especially effective as such inorganic salts. The addition of these inorganic salts enables controlling the viscosity increase at the preparation of high-concentration water base dye dispersion and the viscosity increase thereof after the preparation. The addition amount of inorganic salts is preferably 0.5 wt % or more based on water solvent. Further, the addition amount is preferably ½ weight or more per the weight of dispersed dye, more preferably equal weight or more. Moreover, in the present invention, the selection of counter ion of cationic sensitizing dye is important from the viewpoint of obtaining a high-concentration water-based dispersion.

The adjusting of pH value is important in the preparation of cationic sensitizing dye water-based dispersion according to the present invention. The pH value is appropriately selected within the range of 2 to 10 in accordance with the viscosity and particle size of the dispersion.

In the present invention, the water-based dispersion of cationic sensitizing dye can be added at any time during the preparation of silver halide emulsion. Preferably, the dye of the first layer is added during chemical sensitization or therebefore. The dye of the second layer, the dye of the third layer and so on as constituents of the multilayer adsorption are preferably added during chemical sensitization or thereafter but before coating operation. In particular, it is preferred that the dye of the first layer be added during grain formation, after grain formation but before desalting, after desalting but before chemical sensitization, or during chemical sensitization. The dye of the second layer is preferably added during chemical sensitization, after chemical sensitization or before coating operation. In the addition of cationic sensitizing dye water-based dispersion, it may be added instantaneously, or may be added slowly over a period of 30 sec to 10 min. In the addition, the agitation of the system must be performed efficiently, and the lower the viscosity of the system, the greater the suitability.

In the present invention, upon the addition of a water-based dispersion of cationic sensitizing dye, the amount of silver of the silver halide emulsion is preferably 100 g/kg or more, more preferably in the range of 120 to 200 g/kg. Herein, the amount of silver of the silver halide emulsion refers to the weight of silver atoms contained in 1 kg of the emulsion. When the amount of silver is too small, the multilayer adsorption of sensitizing dyes would become difficult due to unbalanced equilibrium against the medium. On the other hand, when the amount of silver is extremely large, coagulation of emulsion grains would unfavorably occur at the time of multilayer adsorption. Moreover, in the present invention, upon the addition of a water-based dispersion of cationic sensitizing dye, the amount of gelatin of the silver halide emulsion is preferably 90 g/kg or less, more preferably in the range of 70 to 30 g/kg. Herein, the amount of gelatin of the silver halide emulsion refers to the weight of gelatin, including the chemically modified gelatin to be described later, contained in 1 kg of the emulsion. When the amount of gelatin is too large, the multilayer adsorption of sensitizing dyes would tend to become difficult due to competitive adsorption with gelatin. On the other hand, when the amount of gelatin is extremely small, coagulation of emulsion grains would unfavorably occur at the time of multilayer adsorption.

Other conditions of the silver halide emulsion upon the addition of a water-based dispersion of cationic sensitizing dye can fundamentally be selected from conventional relevant ranges. Preferably, the pH value of silver halide emulsion is in the range of 5 to 7, and the pAg value thereof is in the range of 7 to 12.

The multilayer adsorption through adsorption of a compound comprised of multiple dye chromophores onto silver halide grains will be described below. The compound is a dye containing multiple dye chromophores.

With respect to this compound, the multiple dye chromophores, although can be linked to each other through covalent bonds or coordinate bonds, are preferably linked to each other through covalent bonds. (With respect to coordinate bonds, each thereof can be regarded as coordinate bond force being one of the aforementioned intermolecular forces described in (iii)) mentioned above. Further, with respect to the compound, the covalent bonds or coordinate bonds may be those formed in advance or those formed in the course of preparation of silver halide photosensitive material (for example, in silver halide emulsion). With respect to the latter method, use can be made of, for example, the method of JP-A-2000-81678. Carrying out bond formation in advance is preferred.

In each multichromophore dye compound, the number of dye chromophores, although not limited as long as it is at least two, is preferably in the range of 2 to 7, more preferably 2 to 5, still more preferably 2 or 3, and most preferably 2. The multiple dye chromophores may be identical with or different from each other. Although the type of dye chromophore is not limited, there can preferably be mentioned dye chromophores set forth in "Chromophore (i)" above. Preferred dye chromophores are also the same. In particular, those of the following general formulae (QA), (QB), (QC) and (QD) described later are preferred.

As examples of the multiple chromophore dye compound, for example, the multiple chromophore dyes linked by a methine chain as disclosed in the publication of JP-A-9-265144, the multiple chromophore dyes in which oxonol dyestuffs are lined as disclosed in the publication of JP-A-10-226758, the specific multiple chromophore dyes having benzimidazole nuclei and etc as described in the publications of JP-A's-10-110107, 10-307358, 10-307359 and 10-310715, the multiple chromophore dyes linked with a specific group as disclosed in the publications of JP-A's-9-265143, 2000-231172, 2000-231173, 2002-55406, 2002-82403, 2002-82404 and 2002-82405, the multiple chromophore dyes produced in an emulsion using a dye having a reactive group as described in the publication of JP-A-2000-81678, the specific multiple chromophore dyes having a specific benzoxazole nuclei as described in the publication of JP-A-2000-231174, the multiple chromophore dye having a specific characteristic or dissociative group as described in the publication of JP-A-2001-311015, the multiple chromophore dyes having a specific characteristic as described in the publication of JP-A-2001-356442, the multiple chromophore dyes having a specific merocyanine as described in the publication of JP-A-2002-90927, and the multiple chromophore dyes having a specific dissociative group as described in the publications of JP-A's-2002-90928 and 2002-90929, can be mentioned.

The compounds represented by the following general formula (Q) are preferable as the multiple chromophore dye compounds used in the present invention.

In this formula, each of Da and Db represents a dye chromophore. La represents a connecting group. Sa is an integer of 1 to 4. qa represents an integer of 1 to 5. Each of ra and rb independently is an integer of 1 to 100. Mb represents a charge-balancing counter ion. mb represents a number required for neutralizing molecular charge.

The general formula (Q) indicates that the dye chromophores can be connected to each other through any arbitrary connecting form.

Although the dye chromophores represented by Da and Db are not limited, there can be mentioned those as described in "Chromophore (i)" above, and preferred dye chromophores are the same.

It is preferred that at least one of Da's be selected from among cyanine and merocyanine dye chromophores. It is more preferred that at least one of Da's be selected from among cyanine dye chromophores. Da and Db, although may be identical with or different from each other, are preferably different from each other.

In the present invention, when the compound of the general formula (Q) is adsorbed on silver halide grains, it is preferred that Da be adsorbed on silver halides while Db is not directly adsorbed on silver halides. That is, it is preferred that the strength of adsorption of ([—La—]Sa[Db]qa) onto silver halide grains be less than that of Da.

As apparent from the above, Da is preferably a dye moiety which is adsorptive onto silver halide grains. In this connection, the adsorption may be accomplished by either physical adsorption or chemical adsorption.

It is preferred that Db exhibits low adsorptivity onto silver halide grains and be a luminescent dye. With respect to the type of luminescent dye, one having a skeletal structure of dye for use in dye laser is preferred. Such a dye is described in order in, for example, Mitsuo Maeda, Laser Kenkyu (Study of Laser), vol. 8, pages 694, 803 and 958 (1980) and vol. 9, page 85 (1981) and "Dye Lasers" written by F. Sehaefer, Springer (1973), the entire contents of which are incorporated herein by reference.

Further, the wavelength at absorption maximum of Da in silver halide photosensitive materials is preferably larger than that of ([—La—]Sa[Db]qa). Still further, the light emission of ([—La—]Sa[Db]qa) preferably overlaps the absorption of Da. Moreover, Da preferably forms a J-aggregate. From the viewpoint that the connected dye of the general formula (I) exhibits absorption and spectral sensitivity within the given range of wavelength, it is preferred that ([—La—]Sa[Db]qa) also form a J-aggregate.

Although the reduction potentials and oxidation potentials of Da and ([—La—]Sa[Db]qa) are not limited, it is preferred that the reduction potential of Da be noble to the value of reduction potential of ([—La—]Sa[Db]qa) minus 0.2 V.

La represents a connecting group (preferably, divalent connecting group). The connecting groups represented by La include a single bond (also referred to as "simple direct bond"). These connecting groups preferably consist of a single bond, or an atom or atomic group involving at least one of carbon, nitrogen, sulfur and oxygen atoms. Preferred examples of such connecting groups include a single bond and a connecting group having 0 to 100 carbon atoms, preferably 1 to 20 carbon atoms, constituted of one or a combination of two or more of an alkylene group (e.g., methylene, ethylene, trimethylene, tetramethylene or pentamethylene), arylene group (e.g., phenylene or naphthylene), alkenylene group (e.g., ethenylene or propenylene), alkynylene group (e.g., ethynylene or propynylene), amido group, ester group, sulfoamido group, sulfonic ester group, ureido group, sulfonyl group, sulfinyl group, thioether group, ether group, carbonyl group, —N(Va)— (wherein Va represents a hydrogen atom or a monovalent substituent) and heterocyclic divalent group (e.g., 6-chloro-1,3,5-triazine-2,4-diyl, pyrimidine-2,4-diyl or quinoxaline-2,3-diyl).

These connecting groups may have a substituent. Further, these connecting groups may contain a ring (aromatic or nonaromatic hydrocarbon ring, or heterocycle).

More preferred examples of such connecting groups include a single bond and a divalent connecting group having 1 to 10 carbon atoms constituted of one or a combination of two or more of an alkylene group having 1 to 10 carbon atoms (e.g., methylene, ethylene, trimethylene, tetramethylene or pentamethylene), arylene group having 6 to 10 carbon atoms (e.g., phenylene or naphthylene), alkenylene group having 2 to 10 carbon atoms (e.g., ethenylene or propenylene), alkynylene group having 2 to 10 carbon atoms (e.g., ethynylene or propynylene), ether group, amido group, ester group, sulfoamido group and sulfonic ester group. These may be substituted with the aforementioned W.

La is a connecting group wherein energy transfer or electron transfer may be carried out by through-bond interactions. Although the through-bond interactions include tunnel interaction, super-exchange interaction, etc., the through-bond interaction based on super-exchange interaction is preferred thereamong. The through-bond interaction and super-exchange interaction are those defined in Chem. Rev., vol. 96, pp. 1960–1963, written by Shammai Speiser (1996). As connecting groups capable of energy transfer or electron transfer through such interactions, there can preferably be mentioned those described in Chem. Rev., vol. 96, pp. 1967–1969, written by Shammai Speiser (1996), the entire contents of which are incorporated by reference.

Sa is an integer of 1 to 4. When Sa is 2 or greater, it is meant that Da and Db are connected to each other through 2 or more connecting groups. Sa is preferably 1 or 2, more preferably 1. When Sa is 2 or greater, two or more La's contained may be the same connecting groups or different from each other.

qa is an integer of 1 to 5, preferably 1 or 2, and more preferably 1. Each of ra and rb is an integer of 1 to 100, preferably an integer of 1 to 5, more preferably 1 or 2, and most preferably 1. When qa, ra and rb are 2 or greater, two or more Da's and Db's, La's, and Sa's and qa's contained may be the same dye chromophores or different to each other, may be the same connecting groups or different to each other, and may be the same numbers or different to each other, respectively.

In the compounds of the general formula (Q), additional dye chromophores may be substituted. In the general formula (Q), it is preferred that the whole thereof have a charge of −1 or less, and more preferred that the whole charge be −1.

As the dye chromophores for use in the present invention, there can be mentioned those as described in "Chromophore (i)" above. Preferred examples thereof are also the same. In the expression by general formula, methine dye chromophores of the following general formula (QA), (QB), (QC) or (QD) are most preferred.

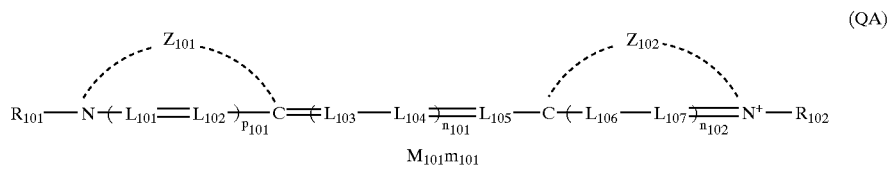

(QA)

In the formula (QA), each of $L_{101}$, $L_{102}$, $L_{103}$, $L_{104}$, $L_{105}$, $L_{106}$ and $L_{107}$ represents a methine group. Each of $P_{101}$ and $P_{102}$ is 0 or 1. $n_{101}$ is 0, 1, 2, 3 or 4. Each of $Z_{101}$ and $Z_{102}$ represents an atomic group required for forming a nitrogen-containing heterocycle, provided that the ring may have condensed rings and may have substituents. $M_{101}$ represents a charge-balancing counter ion, and $m_{101}$ represents a number of 0 or greater required for neutralizing molecular charge. Each of $R_{101}$ and $R_{102}$ represents a hydrogen atom, alkyl group, aryl group or heterocyclic group.

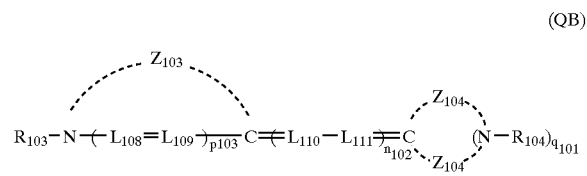

(QB)

In the formula (QB), each of $L_{108}$, $L_{109}$, $L_{110}$ and $L_{111}$ represents a methine group. $p_{103}$ is 0 or 1. $q_{101}$ is 0 or 1. $n_{102}$ is 0, 1, 2, 3 or 4. $Z_{103}$ represents an atomic group required for forming a nitrogen-containing heterocycle. $Z_{104}$ and $Z_{104}'$ represent atomic groups required for forming a ring or a noncyclic acid terminal in cooperation with (N—$R_{104}$) $q_{101}$. Provided that each of the rings formed by $Z_{103}$ and by $Z_{104}$ and $Z_{104}'$ may have a ring fused thereto by condensation and may have a substituent. $M_{102}$ represents a charge-balancing counter ion, and $m_{102}$ represents a number of 0 or greater required for neutralizing molecular charge. Each of $R_{103}$ and $R_{104}$ represents a hydrogen atom, alkyl group, aryl group or heterocyclic group.

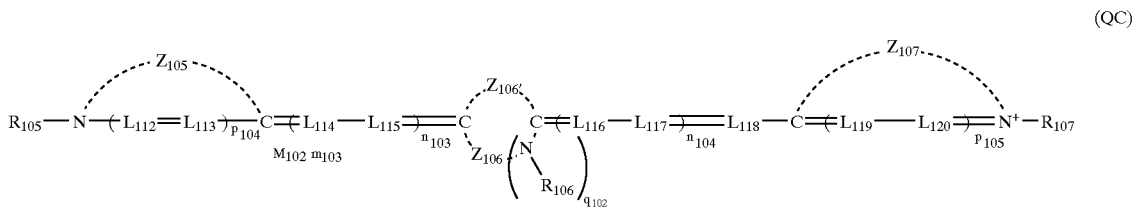

(QC)

In the formula (QC), each of $L_{112}$, $L_{113}$, $L_{114}$, $L_{115}$, $L_{116}$, $L_{117}$, $L_{118}$, $L_{119}$ and $L_{120}$ represents a methine group. Each of $p_{104}$ and $p_{105}$ is 0 or 1. $q_{102}$ is 0 or 1. Each of $n_{103}$ and $n_{104}$ is 0, 1, 2, 3 or 4. $Z_{105}$ and $Z_{107}$ represent atomic groups required for forming a nitrogen-containing heterocycle. $Z_{106}$ and $Z_{106}'$ represent atomic groups required for forming a ring in cooperation with $(N-R_{106})q_{102}$. Provided that each of the rings formed by $Z_{105}$ and by $Z_{106}$ and $Z_{106}'$, and by $Z_{107}$ may have a ring fused thereto by condensation and may have a substituent. $M_{103}$ represents a charge-balancing counter ion, and $m_{103}$ represents a number of 0 or greater required for neutralizing molecular charge. Each of $R_{105}$, $R_{106}$ and $R_{107}$ represents a hydrogen atom, alkyl group, aryl group or heterocyclic group.

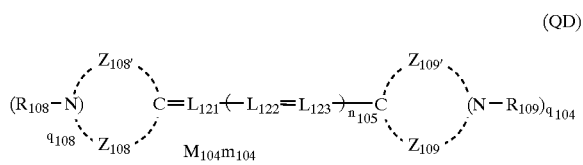

(QD)

In the formula (QD), each of $L_{121}$, $L_{122}$ and $L_{123}$ represents a methine group. Each of $q_{103}$ and $q_{104}$ is 0 or 1. $n_{105}$ is 0, 1, 2, 3 or 4. $Z_{108}$ and $Z_{108}'$ represent atomic groups required for forming a ring or a noncyclic acid terminal in cooperation with $(N-R_{108})q_{103}$. $Z_{109}$ and $Z_{109}'$ represent atomic groups required for forming a ring or a noncyclic acid terminal in cooperation with $(N-R_{109})q_{104}$. Provided that each of the rings formed by $Z_{108}$ and $Z_{108}'$ and by $Z_{109}$ and $Z_{109}'$ may have a ring fused thereto by condensation and may have a substituent. $M_{104}$ represents a charge-balancing counter ion, and $m_{104}$ represents a number of 0 or greater required for neutralizing molecular charge. Each of $R_{108}$ and $R_{109}$ represents a hydrogen atom, alkyl group, aryl group or heterocyclic group.

The dye chromophores represented by the general formulae (QA), (QB), (QC) and (QD) will be described in detail below.

Each of $Z_{101}$, $Z_{102}$, $Z_{103}$, $Z_{105}$ and $Z_{107}$ represents an atomic group required for forming a nitrogen-containing heterocycle, preferably a 5- or 6-membered nitrogen-containing heterocycle. Provided that these may have a ring fused thereto by condensation or may have a substituent, to which rings may be condensed. The rings may be aromatic or nonaromatic rings, or may be hydrocarbon or heterocyclic rings. Aromatic rings are preferred. For example, there can be mentioned hydrocarbon aromatic rings, such as benzene and naphthalene rings, and heteroaromatic rings, such as pyrazine and thiophene rings.

As the nitrogen-containing heterocycle, there can be mentioned, for example, a thiazoline nucleus, thiazole nucleus, benzothiazole nucleus, oxazoline nucleus, oxazole nucleus, benzoxazole nucleus, selenazoline nucleus, selenazole nucleus, benzoselenazole nucleus, tetrazoline nucleus, tetrazole nucleus, benzotetrazole nucleus, 3,3-dialkylindolenine nucleus (e.g., 3,3-dimethylindolenine), imidazoline nucleus, imidazole nucleus, benzimidazole nucleus, pyrroline nucleus, 2-pyridine nucleus, 4-pyridine nucleus, 2-quinoline nucleus, 4-quinoline nucleus, 1-isoquinoline nucleus, 3-isoquinoline nucleus, imidazo[4,5-b]quinoxaline nucleus, oxadiazole nucleus, thiadiazole nucleus, pyrazole nucleus, tetrazole nucleus, pyrimidine nucleus or the like. As preferred examples thereof, there can be mentioned a benzothiazole nucleus, benzoxazole nucleus, 3,3-dialkylindolenine nucleus (e.g., 3,3-dimethylindolenine), benzimidazole nucleus, 2-pyridine nucleus, 4-pyridine nucleus, 2-quinoline nucleus, 4-quinoline nucleus, 1-isoquinoline nucleus and 3-isoquinoline nucleus.

These may have substituents bonded by substitution and have condensed rings. Preferred substituents and condensed rings are an alkyl group, aryl group, alkoxy group, halogen atom, condensed aromatic ring, sulfo group, carboxyl group and hydroxyl group.

As specific examples of the heterocycles formed by $Z_{101}$, $Z_{102}$, $Z_{103}$, $Z_{105}$ and $Z_{107}$, there can be mentioned those as given on columns 23 and 24 of U.S. Pat. No. 5,340,694, the entire contents of which are incorporated herein by reference, as examples of $Z_{11}$, $Z_{12}$, $Z_{13}$, $Z_{14}$ and $Z_{16}$.

When the dye chromophore represented by the general formula (QA), (QB) or (QC) is the dye chromophore of the first layer, as $Z_{101}$, $Z_{102}$, $Z_{103}$, $Z_{105}$ and $Z_{107}$, there can preferably be mentioned a benzothiazole nucleus, benzoxazole nucleus, 3,3-dialkylindolenine nucleus (e.g., 3,3-dimethylindolenine) or benzimidazole nucleus. More preferably, there can be mentioned a benzoxazole nucleus, benzothiazole nucleus or benzimidazole nucleus. Most preferably, there can be mentioned a benzoxazole nucleus or benzothiazole nucleus. The substituents provided on these nuclei are preferably a halogen atom, aromatic group and condensed aromatic ring.

When the dye chromophore represented by the general formula (QA), (QB) or (QC) is the dye chromophore of the second layer or the rest of the layers, as $Z_{101}$, $Z_{102}$, $Z_{103}$, $Z_{105}$ and $Z_{107}$, there can preferably be mentioned a benzothiazole nucleus, benzoxazole nucleus, 3,3-dialkylindolenine nucleus (e.g., 3,3-dimethylindolenine) or benzimidazole nucleus. More preferably, there can be mentioned a benzoxazole nucleus, benzothiazole nucleus or benzimidazole nucleus. Most preferably, there can be mentioned a benzoxazole nucleus or benzothiazole nucleus. The substituents W provided on these nuclei are preferably a halogen atom, aromatic group, condensed aromatic ring and acid group.

The acid group will now be described. The acid group refers to a group having a dissociative proton.

As examples thereof, there can be mentioned a sulfo group, carboxyl group, sulfato group, —$CONHSO_2$— group (sulfonylcarbamoyl group or carbonylsulfamoyl group), —CONHCO— group (carbonylcarbamoyl group), —$SO_2NHSO_2$— group (sulfonylsulfamoyl group), sulfonamido group, sulfamoyl group, phosphato group, phosphono group, boric acid group, phenolic hydroxyl, etc., from which proton is dissociated depending on the pKa thereof and the environmental pH. For example, proton dissociative acid groups from which proton can be dissociated at a proportion of 90% or higher when the pH is in the range of 5 to 11 are preferred.

A sulfo group, carboxyl group, —CONHSO$_2$— group, —CONHCO— group and —SO$_2$NHSO$_2$— group are more preferred. A sulfo group and carboxyl group are still more preferred. A sulfo group is most preferred.

$Z_{104}$ and $Z_{104}'$ and $(N-R_{104})q_{101}$, also $Z_{108}$ and $Z_{108}'$ and $(N-R_{108})q_{103}$ and further $Z_{109}$ and $Z_{109}'$ and $(N-R_{109})q_{104}$ represent atomic groups required for, through combination thereof, forming a ring or a noncyclic acid terminal. The type of ring, although not limited, is preferably a heterocycle (more preferably 5- or 6-membered heterocycle), still more preferably an acid nucleus. The acid nucleus and noncyclic acid terminal will now be described. The acid nucleus and noncyclic acid terminal may take the form of acid nucleus and noncyclic acid terminal of any common merocyanine dye. In preferred forms, $Z_{104}$, $Z_{108}$ and $Z_{109}$ are thiocarbonyls (including thioester, thiocarbamoyl and the like) represented by —(C=S)—, carbonyls (including ester, carbamoyl and the like) represented by —(C=O)—, sulfonyls (including sulfonic ester, sulfamoyl and the like) represented by —(SO$_2$)—, sulfinyls represented by —(S=O)— and cyanos. More preferably, $Z_{104}$, $Z_{108}$ and $Z_{109}$ are thiocarbonyls and carbonyls. $Z_{104}'$, $Z_{108}'$ and $Z_{109}'$ represent the remaining atomic groups required for forming the acid nucleus and noncyclic acid terminal. When the noncyclic acid terminal is formed, $Z_{104}'$, $Z_{108}'$ and $Z_{109}'$ are preferably thiocarbonyls, carbonyls, sulfonyls, sulfinyls, cyanos or the like. Furthermore, use can be made of a structure having an exomethylene resulting from substitution of the carbonyl or thiocarbonyl forming the above acid nucleus or noncyclic acid terminal at an active methylene position of active methylene compound as a raw material for the acid nucleus or noncyclic acid terminal, or a structure resulting from repetition of the above structure. The substitution of an acid nucleus with an acid nucleus results in the formation of dyes of trinuclear merocyanine, tetranuclear merocyanine, etc., and the substitution of an acid terminal with an acid terminal results in, for example, one having dicyanomethylene and cyano at its terminals.

Each of $q_{101}$, $q_{103}$ and $q_{104}$ is 0 or 1, preferably 1.

The acid nucleus and noncyclic acid terminal mentioned herein are described on, for example, pages 197 to 200 of The Theory of the Photographic Process, 4th ed. by James, Macmillan, 1977, the contents described in the pages of which are incorporated herein by reference. Herein, the noncyclic acid terminal refers to an acid, namely, electron-accepting terminal which does not form any ring. As the acid nucleus and noncyclic acid terminal, there can be mentioned, for example, those described in the publications and specifications of U.S. Pat. Nos. 3,567,719, 3,575,869, 3,804,634, 3,837,862, 4,002,480 and 4,925,777, JP-A-3-167546, and U.S. Pat. Nos. 5,994,051 and 5,747,236, the entire contents of which are incorporated by reference.

The acid nucleus is preferred when a heterocycle (preferably a 5 or 6-membered nitrogen-containing heterocycle) consisting of carbon, nitrogen and/or chalcogen (typically, oxygen, sulfur, selenium and tellurium) atoms is formed, and is more preferred when a 5 or 6-membered nitrogen-containing heterocycle consisting of carbon, nitrogen and/or chalcogen (typically, oxygen, sulfur, selenium and tellurium) atoms is formed. For example, there can be mentioned the following acid nuclei:

2-pyrazolin-5-one, pyrazolidine-3,5-dione, imidazolin-5-one, hydantoin, 2 or 4-thiohydantoin, 2-iminoxazolidin-4-one, 2-oxazolin-5-one, 2-thioxazolidine-2,5-dione, 2-thioxazoline-2,4-dione, isoxazolin-5-one, 2-thiazolin-4-one, thiazolidin-4-one, thiazolidine-2,4-dione, rhodanine, thiazolidine-2,4-dithione, isorhodanine, indane-1,3-dione, thiophen-3-one, thiophen-3-one-l,1-dioxide, indolin-2-one, indolin-3-one, 2-oxoindazolinium, 3-oxoindazolinium, 5,7-dioxo-6,7-dihydrothiazolo[3,2-a]pyrimidine, cyclohexane-1,3-dione, 3,4-dihydroisoquinolin-4-one, 1,3-dioxane-4,6-dione, barbituric acid, 2-thiobarbituric acid, chroman-2,4-dione, indazolin-2-one, pyrido[1,2-a]pyrimidine-1,3-dione, pyrazolo[1,5-b]quinazolone, pyrazolo[1,5-a]benzimidazole, pyrazolopyridone, 1,2,3,4-tetrahydroquinoline-2,4-dione, 3-oxo-2,3-dihydrobenzo[d]thiophene-1,1-dioxide, and 3-dicyanomethine-2,3-dihydrobenzo[d]thiophene-1,1-dioxide nuclei.

These acid nuclei and noncyclic acid terminals may have rings fused thereto by condensation and may have substituents.

As preferred acid nuclei, there can be mentioned hydantoin, 2 or 4-thiohydantoin, 2-oxazolin-5-one, 2-thioxazoline-2,4-dione, thiazolidine-2,4-dione, rhodanine, thiazolidine-2,4-dithione, barbituric acid and 2-thiobarbituric acid. As more preferred acid nuclei, there can be mentioned hydantoin, 2 or 4-thiohydantoin, 2-oxazolin-5-one, rhodanine, barbituric acid and 2-thiobarbituric acid.

When the dye chromophore represented by the general formula (QB) or (QD) is the dye chromophore of the first layer, the most preferred acid nuclei are 2 or 4-thiohydantoin, 2-oxazolin-5-one and rhodanine.

When the dye chromophore represented by the general formula (QB) or (QD) is the dye chromophore of the second layer or the rest of the layers, the most preferred acid nucleus is barbituric acid.

Rings formed by $Z_{106}$ and $Z_{106}'$ and $(N-R_{106})q_{102}$, although not limited, are preferably heterocycles (more preferably 5- or 6-membered heterocycles), and can be the same as described above with respect to the rings of $Z_{104}$ and $Z_{104}'$ and $(N-R_{104})q_{101}$, etc. As preferred rings, there can be mentioned those obtained by removing an oxo group or a thioxo group from the acid nuclei described above with respect to the rings of $Z_{104}$ and $Z_{104}'$ and $(N-R_{104})q_{101}$, etc.

As more preferred rings, there can be mentioned those obtained by removing an oxo group or a thioxo group from the acid nuclei listed above as specific examples with respect to the rings of $Z_{104}$ and $Z_{104}'$ and $(N-R_{104})q_{101}$, etc. As still more preferred rings, there can be mentioned those obtained by removing an oxo group or a thioxo group from hydantoin, 2 or 4-thiohydantoin, 2-oxazolin-5-one, 2-thioxazoline-2,4-dione, thiazolidine-2,4-dione, rhodanine, thiazolidine-2,4-dithione, barbituric acid and 2-thiobarbituric acid. As even still more preferred rings, there can be mentioned those obtained by removing an oxo group or a thioxo group from hydantoin, 2 or 4-thiohydantoin, 2-oxazolin-5-one, rhodanine, barbituric acid and 2-thiobarbituric acid. As most preferred heterocycles, there can be mentioned those obtained by removing an oxo group or a thioxo group from 2 or 4-thiohydantoin, 2-oxazolin-5-one and rhodanine.

$q_{102}$ is 0 or 1, preferably 1.

Each of $R_{101}$, $R_{102}$, $R_{103}$, $R_{104}$, $R_{105}$, $R_{106}$, $R_{107}$, $R_{108}$ and $R_{109}$ independently represents a hydrogen atom, alkyl group, aryl group or heterocyclic group, and preferably represents an alkyl group, aryl group or heterocyclic group. Examples of the alkyl, aryl and heterocyclic groups represented by $R_{101}$ to $R_{109}$ include an unsubstituted alkyl group preferably having 1 to 18, more preferably 1 to 7, and most preferably 1 to 4 carbon atoms (e.g., methyl, ethyl, propyl, isopropyl, butyl, isobutyl, hexyl, octyl, dodecyl or octadecyl); substituted alkyl group preferably having 1 to 18, more preferably 1 to 7, and most preferably 1 to 4 carbon atoms {in particular, alkyls having the aforementioned acid groups are preferred, preferably an aralkyl group (e.g., benzyl, 2-phenylethyl, 2-(4-biphenyl)ethyl, 2-sulfobenzyl, 4-sulfobenzyl, 4-sulfophenetyl, 4-phosphobenzyl or 4-carboxybenzyl), unsaturated hydrocarbon group (e.g., allyl or vinyl, namely, herein alkenyl and alkynyl are comprehended in the substituted alkyls), hydroxyalkyl group (e.g., 2-hydroxyethyl or 3-hydroxypropyl), carboxyalkyl group (e.g., 2-carboxyethyl, 3-carboxypropyl, 4-carboxybutyl or carboxymethyl), alkoxyalkyl group (e.g., 2-methoxyethyl, 2-(2-methoxyethoxy)ethyl or 3-sulfopropoxyethoxyethyl), aryloxyalkyl group (e.g., 2-phenoxyethyl, 2-(4-biphenyloxy)ethyl, 2-(l-naphthoxy)ethyl, 2-(4-sulfophenoxy)ethyl or 2-(2-phosphophenoxy)ethyl), alkoxycarbonylalkyl group (e.g., ethoxycarbonylmethyl or 2-benzyloxycarbonylethyl), aryloxycarbonylalkyl group (e.g., 3-phenoxycarbonylpropyl or 3-sulfophenoxycarbonylpropyl), acyloxyalkyl group (e.g., 2-acetyloxyethyl), acylalkyl group (e.g., 2-acetylethyl), carbamoylalkyl group (e.g., 2-morpholinocarbonylethyl), sulfamoylalkyl group (e.g., N,N-dimethylsulfamoylmethyl), sulfoalkyl group (e.g., 2-sulfoethyl, 3-sulfopropyl, 3-sulfobutyl, 4-sulfobutyl, 2-[3-sulfopropoxy]ethyl, 2-hydroxy-3-sulfopropyl, 3-phenyl-3-sulfopropyl, 4-phenyl-4-sulfobutyl or 3-(2-pyridyl)-3-sulfopropyl), sulfoalkenyl group, sulfatoalkyl group (e.g., 2-sulfatoethyl, 3-sulfatopropyl or 4-sulfatobutyl), heterocycle-substituted alkyl group (e.g., 2-(pyrrolidin-2-on-1-yl)ethyl, 2-(2-pyridyl)ethyl, tetrahydrofurfuryl or 3-pyridiniopropyl), alkylsulfonylcarbamoylalkyl group (e.g., methanesulfonylcarbamoylmethyl), acylcarbamoylalkyl group (e.g., acetylcarbamoylmethyl), acylsulfamoylalkyl group (e.g., acetylsulfamoylmethyl), alkylsulfonylsulfamoylalkyl group (e.g., methanesulfonylsulfamoylmethyl), ammonioalkyl group (e.g., 3-(trimethylammonio)propyl or 3-ammoniopropyl), aminoalkyl group (e.g., 3-aminopropyl, 3-(dimethylamino)propyl or 4-(methylamino)butyl) or guanidinoalkyl group (e.g., 4-guanidinobutyl)); substituent or unsubstituted aryl group preferably having 6 to 20, more preferably 6 to 10, and most preferably 6 to 8 carbon atoms (e.g., phenyl, 1-naphthyl, p-mehtoxyphenyl, p-methylphenyl, p-chlorophenyl, biphenyl, 4-sulfophenyl or 4-sulfonaphthyl); and substituted or unsubstituted heterocyclic group preferably having 1 to 20, more preferably 3 to 10, and most preferably 4 to 8 carbon atoms (e.g., 2-furyl, 2-thienyl, 2-pyridyl, 3-pyrazolyl, 3-isoxazolyl, 3-isothiazolyl, 2-imidazolyl, 2-oxazolyl, 2-thiazolyl, 2-pyridazyl, 2-pyrimidyl, 3-pyrazyl, 2-(1,3,5-triazolyl), 3-(1,2,4-triazolyl), 5-tetrazolyl, 5-methyl-2-thienyl, 4-methoxy-2-pyridyl or 4-sulfo-2-pyridyl).

When the dye chromophore represented by the general formula (QA), (QB), (QC) or (QD) is the dye chromophore of the first layer, the substituent represented by each of $R_{101}$ to $R_{109}$ is preferably an unsubstituted or substituted alkyl group. The substituted alkyl group is preferably an alkyl having the aforementioned acid group. The acid group is preferably a sulfo group, carboxyl group, —$CONHSO_2$— group, —CONHCO— group or —$SO_2NHSO_2$— group; more preferably a sulfo group or a carboxyl group; and most preferably a sulfo group.

When the dye chromophore represented by the general formula (QA), (QB), (QC) or (QD) is the dye chromophore of the second layer or the rest of the layers, the substituent represented by each of $R_{101}$ to $R_{109}$ is preferably an unsubstituted or substituted alkyl; more preferably an alkyl group substituted with a sulfo group, carboxyl group, —$CONHSO_2$— group, —CONHCO— group or —$SO_2NHSO_2$— group, ammonioalkyl group, aminoalkyl group or guanidinoalkyl group; and most preferably an alkyl group substituted with a sulfo group or ammonioalkyl group.

Each of $L_{101}$, $L_{102}$, $L_{103}$, $L_{104}$, $L_{105}$, $L_{106}$, $L_{107}$, $L_{108}$, $L_{109}$, $L_{110}$, $L_{111}$, $L_{112}$, $L_{113}$, $L_{114}$, $L_{115}$, $L_{116}$, $L_{117}$, $L_{118}$, $L_{119}$, $L_{120}$, $L_{121}$, $L_{122}$ and $L_{123}$ independently represents a methine group. The methine groups represented by $L_{101}$ to $L_{123}$ may have substituents, which can be those mentioned above as W. As such substituents, there can be mentioned, for example, a substituted or unsubstituted alkyl group having 1 to 15 carbon atoms, preferably 1 to 10 carbon atoms and more preferably 1 to 5 carbon atoms (e.g., methyl, ethyl or 2-carboxyethyl), substituted or unsubstituted aryl group having 6 to 20 carbon atoms, preferably 6 to 15 carbon atoms and more preferably 6 to 10 carbon atoms (e.g., phenyl or o-carboxyphenyl), substituted or unsubstituted heterocyclic group having 3 to 20 carbon atoms, preferably 4 to 15 carbon atoms and more preferably 6 to 10 carbon atoms (e.g., N,N-dimethylbarbituric acid group), halogen atom (e.g., chlorine, bromine, iodine or fluorine), alkoxy group having 1 to 15 carbon atoms, preferably 1 to 10 carbon atoms and more preferably 1 to 5 carbon atoms (e.g., methoxy or ethoxy), amino group having 0 to 15 carbon atoms, preferably 2 to 10 carbon atoms and more preferably 4 to 10 carbon atoms (e.g., methylamino, N,N-dimethylamino, N-methyl-N-phenylamino or N-methylpiperadino), alkylthio group having 1 to 15 carbon atoms, preferably 1 to 10 carbon atoms and more preferably 1 to 5 carbon atoms (e.g., methylthio or ethylthio), and arylthio group having 6 to 20 carbon atoms, preferably 6 to 12 carbon atoms and more preferably 6 to 10 carbon atoms (e.g., phenylthio or p-methylphenylthio). These may form rings in cooperation with other methine groups, or can form rings in cooperation with $Z_{101}$ to $Z_{109}$, $R_{101}$ to $R_{109}$ and Ra.

$L_{101}$, $L_{102}$, $L_{106}$, $L_{107}$, $L_{108}$, $L_{109}$, $L_{112}$, $L_{113}$, $L_{119}$ and $L_{120}$ preferably represent unsubstituted methine groups.

Each of $n_{101}$, $n_{102}$, $n_{103}$, $n_{104}$ and $n_{105}$ is independently 0, 1, 2, 3 or 4, preferably 0, 1, 2 or 3, more preferably 0, 1 or 2, and most preferably 0 or 1. When $n_{101}$ to $n_{105}$ are 2 or greater, methine groups are repeated, which are, however, not needed to be identical with each other.

Each of $p_{101}$, $p_{102}$, p103, $p_{104}$ and $p_{105}$ is independently 0 or 1, preferably 0.

$M_{101}$, $M_{102}$, $M_{103}$, $M_{104}$ and Mb, when required for neutralizing the ionic charge of dye, are included in the formulae in order to indicate the presence of cations or anions. As representative cations, there can be mentioned inorganic cations such as proton ($H^+$), alkali metal ions (e.g., sodium ion, potassium ion and lithium ion) and alkaline earth metal ions (e.g., calcium ion); and organic ions such as ammonium ions (e.g., ammonium ion, tetraalkylammonium ion, triethylammonium ion, pyridinium ion, ethylpyridinium ion and 1,8-diazabicyclo[5,4,0]-7-undecenium ion). The anions can be inorganic anions or organic anions. As such, there can be mentioned halide anions (e.g., fluoride ion, chloride ion and iodide ion), substituted arylsulfonate ions (e.g., p-toluenesulfonate ion and p-chlorobenzenesulfonate ion), aryldisulfonate ions (e.g., 1,3-benzenedisulfonate ion, 1,5-naphthalenedisulfonate ion and 2,6-naphthalenedisulfonate ion), alkylsulfate ions (e.g., methylsulfate ion), sulfate ion, thiocyanate ion, perchlorate ion, tetrafluoroborate ion, picrate ion, acetate ion and trifluoromethanesulfonate ion. Further, use can be made of ionic polymers and other dyes having charges opposite to those of dyes. $CO_2^-$ and $SO_3^-$, when having a proton as a counter ion, can be indicated as $CO_2H$ and $SO_3H$, respectively.

Each of $m_{101}$, $m_{102}$, $m_{103}$, $m_{104}$ and mb is a number of 0 or greater required to balance a charge, preferably a number of 0 to 4, and more preferably a number of 0 to 1. When an intramolecular salt is formed, each thereof is 0.

In the silver halide emulsion comprised of silver halide grains having dye chromophores adsorbed in multilayer form according to the present invention, dyes described in "Multilayer adsorption related patents (iii)" above can be used as those constituting the multilayer adsorption.

$D_1$, La and $D_2$ described in JP-A-2002-169251, the entire contents of which is incorporated herein by reference, can preferably be used as Da, La and Db of the general formula (Q), respectively.

These dyes may be synthesized based on the methods described in "Heterocyclic Compounds—Cyanine Dyes and Related Compounds" by F. M. Harmer, John Wiley & Sons, New York, London (1964); "Heterocyclic Compounds—Special topics in heterocyclic chemistry" by D. M. Sturmer, Chapter 18, Clause 14, pp.482–515, John Wiley & Sons, New York, London (1977); and "Rodd's Chemistry of Carbon Compounds" 2nd ed. Vol. IV, Part B (1977) and Chapter 15, pp.369–422, Elsevier Science Publishing Company Inc.

In the silver halide emulsion comprised of silver halide grains having dye chromophores adsorbed in multilayer form according to the present invention, the dyes are not limited to those described above as constituting the multilayer adsorption, and other dyes can be used individually or in combination therewith. As preferably employed dyes, there can be mentioned, for example, a cyanine dye, merocyanine dye, rhodacyanine dye, trinuclear merocyanine dye, tetranuclear merocyanine dye, allopolar dye, hemicyanine dye and styryl dye. A cyanine dye, a merocyanine dye and rhodacyanine dye are more preferred. A cyanine dye is most preferred. Details of these dyes are described in the aforementioned "Dye documents (ii)".

These sensitizing dyes to be used in combination may be used alone or two or more may be used in combination. A combination of sensitizing dyes is often used for the purpose of supersensitization. The representative examples of combinations are disclosed in U.S. Pat. Nos. 2,688,545, 2,977,229, 3,397,060, 3,522,052, 3,527,641, 3,617,293, 3,628,964, 3,666,480, 3,672,898, 3,679,428, 3,303,377, 3,769,301, 3,814,609, 3,837,862 and 4,026,707, British Patents 1,344,281 and 1,507,803, JP-B's-43-49336 and 53–12375, and JP-A's-52-110618 and 52-109925, all the disclosures of which are incorporated herein by reference.

Dyes which themselves do not have a spectral sensitizing function or substances which substantially do not absorb visible rays but show supersensitization can be incorporated into an emulsion with sensitizing dyes.

Supersensitizers preferably used in spectral sensitization in the present invention (e.g., pyrimidylamino compounds, triazinylamino compounds, azolium compounds, aminostyryl compounds, aromatic organic acid-formaldehyde condensation products, azaindene compounds, cadmium salts) and the combination of supersensitizers with sensitizing dyes are disclosed, e.g., in U.S. Pat. Nos. 3,511,664, 3,615,613, 3,615,632, 3,615,641, 4,596,767, 4,945,038, 4,965,182, 2,933,390, 3,635,721, 3,743,510, 3,617,295, and 3,635,721, and the using methods disclosed in these patents are also preferably used.

The time of addition of the dyes and sensitizing dyes of the present invention (and other sensitizing dyes and supersensitizers) to the silver halide emulsions for use in the present invention may be at any stage of the preparation of the emulsion recognized as useful hitherto. For example, the dyes and sensitizing dyes may be added at any stage if it is before coating of the emulsion, i.e., at the time of a step for forming silver halide grains and/or before desalting, during desalting step and/or after desalting and before beginning of chemical ripening, as disclosed in U.S. Pat. Nos. 2,735,766, 3,628,960, 4,183,756 and 4,225,666, JP-A's-58-184142 and 60-196749, or immediately before or during chemical ripening, after chemical ripening and before coating as disclosed in JP-A-58-113920. Also, as disclosed in U.S. Pat. No. 4,225,666 and JP-A-58-7629, these sensitizing dyes can be used as a single compound alone or in combination with a compound having a different structure, and they can be divided and added separately, e.g., one part of them is added during grain formation step and the remaining is added during chemical ripening or after completion of chemical ripening, alternatively one part is added prior to chemical ripening or during ripening stage and the remaining after completion of chemical ripening. The kinds of compounds added separately and the combinations of compounds may be varied.

The addition amount of the dye and sensitizing dyes of the present invention (and other sensitizing dyes and supersensitizers) for use in the present invention varies depending on the shape and the size of silver halide grains and the amount may be any one, but it is preferably from $1\times10^{-8}$ to 1 mol per mol of silver halide, more preferably from $1\times10^{-6}$ to $1\times10^{-2}$ mol per mol of silver halide. For example, in the case where the silver halide grain size is 0.2 to 1.3 $\mu$m, the addition amount is preferably from $2\times10^{-6}$ to $3.5\times10^{-3}$ mol per mol of silver halide, and more preferably from $7.5\times10^{-6}$ to $1.5\times10^{-3}$ mol per mol of silver halide.

Provided that when multilayer adsorption of dye chromophores is conducted, such an amount that is necessary to do so are required.

The dispersion medium contained in the silver halide emulsion of the present invention will be described below. The dispersion medium commonly employed in silver halide emulsions is gelatin. In the silver halide emulsion of the present invention, use can be made of not only gelatin per se but also a variety of synthetic hydrophilic polymeric materials including gelatin derivatives, graft polymers from gelatin and other polymers, and proteins such as albumin and casein; cellulose derivatives such as hydroxyethylcellulose, carboxymethylcellulose and cellulose sulfate, sodium alginate, and sugar derivatives such as starch derivatives; and homo- or copolymers such as polyvinyl alcohol, partially acetalized polyvinyl alcohol, poly-N-vinylpyrrolidone, polyacrylic acid, polymethacrylic acid, polyacrylamide, polyvinylimidazole and polyvinylpyrazole. Provided that an amino-modified gelatin must be contained as part of the dispersion medium. The advantages of the present invention can be exerted by the use of an amino-modified gelatin in a ratio of at least 1%, preferably 5% or more and more preferably 10% or more based on the total weight of the dispersion medium. However, since the ratio of amino-modified gelatin required for the exertion of the advantages of the present invention may vary depending on the conditions of emulsion production, it is preferred to appropriately regulate the addition amount of amino-modified gelatin. Further, since the enhancement of the advantages of the present invention realized by ratio increase is slight in the region wherein the ratio of amino-modified gelatin is 20% or higher, the necessity of having to attain a ratio of 20% or higher is low.

The amino-modified gelatin for use in the silver halide emulsion of the present invention will be described below.

As the —$NH_2$ group of gelatin, there can be mentioned not only the amino groups as end groups of gelatin molecule and amino groups of lysine residue, hydroxylysine residue, histidine residue and arginine residue but also when the argininie residue is converted to ornithine residue, amino thereof. Further, there can be mentioned impurity groups such as adenine and guanine residues. The chemical modification of —$NH_2$ group refers to adding a reactive agent to gelatin and inducing reaction with the amino group so as to form a covalent bond or effect deamination. That is, it is meant that a primary amino (—$NH_2$) is converted to a secondary amino (—NH—), a tertiary amino or a deamination product.

In particular, the chemical modification can be accomplished by adding, for example, an acid anhydride (e.g., maleic anhydride, o-phthalic anhydride, succinic anhydride, isatoic anhydride or benzoic anhydride), an acid halide (e.g., R—COX, R—$SO_2$X, R—O—COX or phenyl-COCl), a compound having an aldehyde group (e.g., R—CHO), a compound having an epoxy group, a deaminating agent (e.g., $HNO_2$ or deaminase), an active ester compound (e.g., sulfonic ester, p-nitrophenyl acetate, isopropenyl acetate, methyl o-chlorobenzoate or p-nitrophenyl benzoate), an isocyanate compound (e.g., aryl isocyanate), active halogen compounds [for example, an aryl halide (e.g., benzyl bromide, biphenylhalomethanes, benzoylhalomethanes, phenylbenzoylhalomethanes or 1-fluoro-2,4-dinitrobenzene), a β-ketohalide, an α-haloaliphatic acid, a β-halonitrile or a chloride derivative of (s-triazine, pyrimidine, pyridazine, pyrazine, pyridazone, quinoxaline, quinazoline, phthalazine, benzoxazole, benzothiazole or benzimidazole)], a carbamoylating agent (e.g., cyanate or nitrourea), a compound having an acrylic active double bond group (e.g., maleimide, acrylamine, acrylamide, acrylonitrile, methyl methacrylate, vinyl sulfone, vinyl sulfonate, ester, sulfonamide, styrene/vinylpyridine, allylamine, butadiene, isoprene or chloroprene), a sultone (e.g., butane sultone or propane sultone), a guanidinating agent (e.g., o-methylisourea) or a carboxylazide and thereafter inducing reaction with amino.

In the chemical modification, agents capable of predominantly reacting with the —$NH_2$ group of gelatin are preferred to agents which also react with the —OH and —COOH groups of gelatin so as to form a covalent bond. The terminology "predominantly" refers to 60% or more, preferably 80 to 100% and more preferably 95 to 100%. It is preferred that the reaction product be in a form substantially not containing groups resulting from substitution of oxygen of ether or ketone group with chalcogen atom, such as —S— and thione group. The terminology "substantially not containing" refers to 10% or less, preferably 0 to 3% based on the number of chemically modified groups. Accordingly, out of the above compounds, an acid anhydride, sultone, compound having an active double bond group, carbamoylating agent, active halogen compound, isocyanate compound, active ester compound, compound having an aldehyde group and deaminating agent are preferred. A mode wherein the chemical modification would substantially not be accompanied by crosslinking of gelatin molecules is preferred. The expression "substantially not be accompanied" preferably refers to 10% or less, more preferably 0 to 3% based on the chemically modified groups.

In particular, a chemical modification such that one to three —COOH groups are introduced at every modification of one —$NH_2$ group is preferred. A chemical modification such that one —COOH group is introduced at every modification of one —$NH_2$ group is more preferred. As the agent for use in chemical modification, when one —COOH group is introduced per —$NH_2$ group, there can be mentioned succinic anhydride, phthalic anhydride or maleic anhydride. When two —COOH groups are introduced, there can be mentioned trimellitic anhydride. When three —COOH groups are introduced, there can be mentioned pyromellitic anhydride.

Specifically, phthalated gelatin obtained by chemical modification of the —$NH_2$ group with phthalic anhydride is preferred from the viewpoint that not only are the advantages of the present invention conspicuous but also it can stably be produced on an industrial scale.

With respect to the details of chemical modification agents, method of chemical modification for gelatin and other related matter, reference can be made to the publication and specifications of JP-A's-4-226449 and 50-3329 and U.S. Pat. Nos. 2,525,753, 2,614,928, 2,614,929, 2,763,639, 2,594,293 and 3,132,945 and the descriptions of Glue and Gelatin, edited by Yoshihiro Abiko, chapter 11, Gelatin Manufacturers Association of Japan (1987) and The Science and Technology of Gelatin, edited by Ward et al., chapter 7, Academic Press (1977).

With respect to the chemically modified gelatin of the present invention, the chemical modification % of amino is essentially 15% or higher, preferably 50% or higher, more preferably 70% or higher and most preferably 90% or higher.

The chemically modified gelatin of the present invention has a methionine content of, although not particularly limited, preferably 30 μmol/g or higher, more preferably 35 μmol/g or higher.

With respect to the molecular weight of the chemically modified gelatin, the average molecular weight is preferably in the range of 10 thousand to 200 thousand, more preferably 18 thousand to 150 thousand.

The chemical modification % of —$NH_2$ group of chemically modified gelatin can be determined in the following manner. Nonmodified gelatin and modified gelatin are prepared, and the numbers of —$NH_2$ groups thereof are measured and designated e1 and e2, respectively. The chemical modification % can be calculated by the use of the formula: 100×(e1−e2)/e1. In the determination of e1 and e2, there can be mentioned methods wherein use is made of infrared absorption intensity ascribed to —$NH_2$ group, NMR signal intensity of relevant proton, color reaction, fluorescent reaction, etc. With respect to the details thereof, reference can be made to the description of Handbook on Analytical Chemistry, Organic Edition-2, Maruzen Co., Ltd. (1991). Further, there can be mentioned quantitative determination methods, such as change of gelatin titration curves and formol titrimetry. With respect to the details thereof, reference can be made to the description of The Science and Technology of Gelatin, chapter 15, Academic Press (1977).

The methionine content of gelatin can be determined by a method wherein gelatin is completely decomposed into amino acids according to an alkali hydrolysis process and analyzed with the use of an amino acid analyzer and thereafter the amount of methionine relative to the amount of glycine is determined. With respect to the details thereof, reference can be made to the description of JP-A-7-311428.

In the present invention, the timing of addition of amino-modified gelatin is not particularly limited. Although generally the addition is effected during the formation of silver halide grains, just before desalting or during re-dispersion after desalting, it is preferred with respect to gelatin chemically modified so that one —COOH group is introduced at every modification of —NH$_2$ group that the addition be effected before desalting (specifically, at latest before the initiation of desalting).

The silver halide grains contained in the silver halide emulsion of the present invention is composed of silver iodobromide, silver bromide or silver chloroiodobromide. The silver chloride content is preferably 8 mol % or less, more preferably 3 mol % or less, or 0 mol %. The silver iodide content is preferably 20 mol % or less since the variation coefficient of the equivalent circle diameter distribution of all the silver halide grain is preferably 40% or less. The lowering of the variation coefficient of the distribution of equivalent circular diameter can be facilitated by lowering the silver iodide content. Attention should be made especially for the tabular grain emulsion since the dependency of the variation coefficient on the silver iodide content is large. In more detail, the variation coefficient of the equivalent circle diameter distribution is more preferably 25% or less, and the silver iodide content is more preferably 10 mol % or less.

The configuration of the grain is preferably tabular grain, and the present invention is preferably applied to an emulsion comprising thin tabular grains having an average grain thickness of 0.2 μm or less. The grain thickness and equivalent circle diameter of tabular grain are easily obtained by shooting a photograph with transmission electron micrograph. The thickness is calculated from the length of replica shadow, while the equivalent circle diameter is calculated from the projected area of the grain. The equivalent circle diameter indicates the diameter of a circle having the same area as the grain projected area. A ratio, in a tabular grain, of equivalent circle diameter to thickness is called an aspect ratio.

The configuration of tabular grains of the present invention is generally hexagonal. The terminology "hexagonal configuration" means that the shape of the principal plane of tabular grains is hexagonal, the neighboring side ratio (maximum side length/minimum side length) thereof being 2 or less. The neighboring side ratio is preferably 1.6 or less, more preferably 1.2 or less. That the lower limit thereof is 1.0 is needless to mention. In the grains of high aspect ratio, especially, triangular tabular grains are increased in the tabular grains. The triangular tabular grains are produced when the Ostwald ripening has excessively been advanced. From the viewpoint of obtaining substantially hexagonal tabular grains, it is preferred that the period of this ripening be minimized. For this purpose, it is requisite to endeavor to raise the tabular grain ratio by nucleation. It is preferred that one or both of an aqueous silver ion solution and an aqueous bromide ion solution contain gelatin for the purpose of raising the probability of occurrence of hexagonal tabular grains at the time of adding silver ions and bromide ions to a reaction mixture according to the double jet technique, as described in JP-A-63-11928 by Saito.

The hexagonal tabular grains for use in the present invention are formed through the steps of nucleation, Ostwald ripening and growth. Although all of these steps are important for suppressing the spread of grain size distribution, especial attention should be paid so as to prevent the spread of size distribution at the first nucleation step because the spread of size distribution brought about in a previous step cannot be narrowed by an ensuing step. What is important in the nucleation step is the relationship between the temperature of reaction mixture and the period of nucleation comprising adding silver ions and bromide ions to a reaction mixture according to the double jet technique and producing precipitates. JP-A-63-92942 by Saito describes that it is preferred that the temperature of the reaction mixture at the time of nucleation be in the range of from 20 to 45° C. for realizing a monodispersity enhancement. Further, JP-A-2-222940 by Zola et al describes that the suitable temperature at nucleation is 60° C. or below.

In order to obtain monodispersed tabular grains having large aspect ratios, there is a case in which gelatin is additionally added during grain formation. At this time, gelatin to be used is preferably chemically modified gelatin described above. Gelatin to which carboxyl groups are newly introduced when amino groups are chemically modified, and trimellitated gelatin and succinated gelatin may be especially preferably use.

The gelatin is preferably added before a growth step, and more preferably added immediately after nucleation.

The addition amount is preferable 60%, more preferably 80%, and especially preferably 90% of the weight of all the dispersion medium during the grain formation.

It is preferable for the tabular grain emulsion to have an inner structure with regard to silver iodide distribution. In this case, the structure of the silver iodide distribution may be a double structure, triple structure, quadruple or higher structure.

In the present invention, the tabular grains have dislocation lines. The dislocation lines of the tabular grains can be observed by the direct method using a transmission electron microscope at low temperatures as described in, for example, J. F. Hamilton, Phot. Sci. Eng., 11, 57 (1967) and T. Shiozawa, J. Soc. Phot. Sci. Japan, 3, 5, 213 (1972). Illustratively, silver halide grains are harvested from the emulsion with the care that the grains are not pressurized with such a force that dislocation lines occur on the grains, are put on a mesh for electron microscope observation and, while cooling the specimen so as to prevent damaging (printout, etc.) by electron beams, are observed by the transmission method. The greater the thickness of the above grains, the more difficult the transmission of electron beams. Therefore, the use of an electron microscope of high voltage type (at least 200 kV on the grains of 0.25 μm in thickness) is preferred for ensuring clearer observation. The thus obtained photograph of grains enables determining the position and number of dislocation lines in each grain viewed in the direction perpendicular to the principal planes.

In the emulsion of the present invention the number of dislocation lines of the tabular grains is preferably at least 10 per grain on the average and more preferably at least 20 per grain on the average. When dislocation lines are densely present or when dislocation lines are observed in the state of crossing each other, it happens that the number of dislocation lines per grain cannot accurately be counted. However, in this instance as well, rough counting on the order of, for example, 10, 20 or 30 dislocation lines can be effected, so that a clear distinction can be made from the presence of only a few dislocation lines. The average number of dislocation lines per grain is determined by counting the number of dislocation lines of each of at least 100 grains and calculating a number average thereof. There are instances when hundreds of dislocation lines are observed.

Dislocation lines can be introduced in, for example, the vicinity of the periphery of tabular grains. In this instance, the dislocation is nearly perpendicular to the periphery, and each dislocation line extends from a position corresponding to x% of the distance from the center of tabular grains to the side (periphery) to the periphery. The value of x preferably ranges from 10 to less than 100, more preferably from 30 to less than 99, and most preferably from 50 to less than 98. In this instance, the figure created by binding the positions from which the dislocation lines start is nearly similar to the configuration of the grain. The created figure may be one which is not a complete similar figure but deviated. The dislocation lines of this type are not observed around the center of the grain. The dislocation lines are crystallographically oriented approximately in the (211) direction. However, the dislocation lines often meander and may also cross each other.

Dislocation lines may be positioned either nearly uniformly over the entire zone of the periphery of the tabular grains or local points of the periphery. That is, referring to, for example, hexagonal tabular silver halide grains, dislocation lines may be localized either only in the vicinity of six apexes or only in the vicinity of one of the apexes. Contrarily, dislocation lines can be localized only in the sides excluding the vicinity of six apexes.

Furthermore, dislocation lines may be formed over regions including the centers of two mutually parallel principal planes of tabular grains. In the case where dislocation lines are formed over the entire regions of the principal planes, the dislocation lines may crystallographically be oriented approximately in the (211) direction when viewed in the direction perpendicular to the principal planes, and the formation of the dislocation lines may be effected either in the (110) direction or randomly. Further, the length of each dislocation line may be random, and the dislocation lines may be observed as short lines on the principal planes or as long lines extending to the side (periphery). The dislocation lines may be straight or often meander. In many instances, the dislocation lines cross each other.

The position of dislocation lines may be localized on the periphery, principal planes or local points as mentioned above, or the formation of dislocation lines may be effected on a combination thereof. That is, dislocation lines may be concurrently present on both the periphery and the principal planes.

The introduction of dislocation lines in the tabular grains can be accomplished by disposing a specified phase of high silver iodide content within the grains. In the dislocation line introduction, the phase of high silver iodide content may be provided with discontinuous regions of high silver iodide content. Practically, the phase of high silver iodide content within the grains can be obtained by first preparing base grains, providing them with a phase of high silver iodide content and covering the outside thereof with a phase of silver iodide content lower than that of the phase of high silver iodide content. The silver iodide content of the base tabular grains is lower than that of the phase of high silver iodide content, and is preferably 0 to 20 mol %, more preferably 0 to 15 mol %.

In the present invention, the terminology "phase of high silver iodide content within the grains" refers to a silver halide solid solution containing silver iodide. The silver halide of this solid solution is preferably silver iodide, silver iodobromide or silver chloroiodobromide, more preferably silver iodide or silver iodobromide (the silver iodide content is in the range of 10 to 40 mol % based on the silver halides contained in the phase of high silver iodide content). For selectively causing the phase of high silver iodide content within the grains (hereinafter referred to as "internal high silver iodide phase") to be present on any place of the sides, corners and faces of the base grains, it is desirable to control forming conditions for the base grains, forming conditions for the internal high silver iodide phase and forming conditions for the phase covering the outside thereof. With respect to the forming conditions for the base grains, the pAg (logarithm of inverse number of silver ion concentration), the presence or absence, type and amount of silver halide solvent and the temperature are important factors. Regulating the pAg at base grain growth to 8.5 or less, preferably 8 or less, enables selectively causing the internal high silver iodide phase to be present near the apex or on the face of the base grains in the subsequent step of forming the internal high silver iodide phase.

On the other hand, regulating the pAg at base grain growth to at least 8.5, preferably at least 9, enables causing the internal high silver iodide phase to be present on the side of the base grains in the subsequent step of forming the internal high silver iodide phase. The threshold value of the pAg is changed upward or downward depending on the temperature and the presence or absence, type and amount of silver halide solvent. When, for example, a thiocyanate is used as the silver halide solvent, the threshold value of the pAg is deviated toward a higher value. What is most important as the pAg at growth is the pAg at the termination of growth of base grains. On the other hand, even when the pAg at growth does not satisfy the above value, the selected position of the internal high silver iodide phase can be controlled by carrying out, after the growth of base grains, the regulation to the above pAg and a ripening. Ammonia, an amine compound, a thiourea derivative or a thiocyanate salt is effective as the silver halide solvent. For the formation of the internal high silver iodide phase, use can be made of the so-called conversion methods.

These conversion methods include one in which, during grain formation, halide ions whose salts formed with silver ions exhibit a solubility lower than that of the salts formed with the halide ions that are forming the grains or the vicinity of the surface of the grains occurring at the time of grain formation, are added. In the present invention, it is preferred that the amount of added low-solubility halide ions be at least some value (relating to halogen composition) relative to the surface area of grains occurring at the time of the addition. For example, it is preferred that, during grain formation, KI be added in an amount not smaller than some amount relative to the surface area of silver halide grains occurring at the time of the grain formation. Specifically, it is preferred that an iodide salt be added in an amount of at least $8.2 \times 10^{-5}$ mol/m$^2$.

Preferred process for forming the internal high silver iodide phase comprises adding an aqueous solution of a silver salt simultaneously with the addition of an aqueous solution of halide salts containing an iodide salt.

For example, an aqueous solution of AgNO$_3$ is added simultaneously with the addition of an aqueous solution of KI by the double jet. The addition initiating times and addition completing times of the aqueous solution of KI and the aqueous solution of AgNO$_3$ may be differed from each other, that is, the one may be earlier or later than the other. The addition molar ratio of an aqueous solution of AgNO$_3$ to an aqueous solution of KI is preferably at least 0.1, more preferably at least 0.5, and most preferably at least 1. The total addition molar amount of an aqueous solution of AgNO$_3$ relative to halide ions within the system and added iodide ions may fall in a silver excess region. It is preferred that the pAg exhibited when the aqueous solution of halide containing such iodide ions and the aqueous solution of silver salt are added by the double jet be decreased in accordance with the passage of double jet addition time. The pAg prior to the addition initiation is preferably in the range of 6.5 to 13, more preferably 7.0 to 11. The pAg at the time of addition completion is most preferably in the range of 6.5 to 10.0.

In the performing of the above process, it is preferred that the solubility in the mixture system be as low as possible. Accordingly, the temperature of the mixture system exhibited at the time of formation of the high silver iodide phase is preferably in the range of 30 to 80° C., more preferably 30 to 70° C.

Furthermore, the formation of the internal high silver iodide phase can preferably be performed by adding fine grains of silver iodide, fine grains of silver iodobromide, fine grains of silver chloroiodide or fine grains of silver chloroiodobromide. It is especially preferred that the formation be effected by adding fine grains of silver iodide. Although these fine grains generally have a size of 0.01 to 0.1 $\mu$m, use can also be made of fine grains with a size of not greater than 0.01 $\mu$m, or 0.1 $\mu$m or more. With respect to the process for preparing these fine grains of silver halide, reference can be made to descriptions of JP-A's-1-183417, 2-44335, 1-183644, 1-183645, 2-43534 and 2-43535. The internal high silver iodide phase can be provided by adding these fine grains of silver halide and conducting a ripening. When the fine grains are dissolved by ripening, use can be made of the aforementioned silver halide solvent. It is not needed that all these added fine grains be immediately dissolved and disappear. It is satisfactory if, when the final grains have been completed, they are dissolved and disappear.

The position of the internal high silver iodide phase, as measured from the center of, for example, a hexagon resulting from grain projection, is preferably present in the range of 5 to less than 100 mol %, more preferably 20 to less than 95 mol %, and most preferably 50 to less than 90 mol %, based on the amount of silver of the whole grain. The amount of silver halide forming this internal high silver iodide phase, in terms of the amount of silver, is 50 mol % or less, preferably 20 mol % or less, based on the amount of silver of the whole grain. With respect to the above high silver iodide phase, there are provided recipe values of the production of silver halide emulsion, not values obtained by measuring the halogen composition of final grains according to various analytical methods. The internal high silver iodide phase is often caused to completely disappear in final grains by, for example, recrystallization during the shell covering step, and all the above silver amounts relate to recipe values thereof.

Therefore, although the observation of dislocation lines can be easily performed in the final grains by the above method, the internal silver iodide phase introduced for the introduction of dislocation lines often cannot be confirmed as a clear phase because the boundary silver iodide composition is continuously changed. The halogen composition at each grain part can be determined by a combination of X-ray diffractometry, the EPMA method (also known as the XMA method, in which silver halide grains are scanned by electron beams to thereby detect the silver halide composition), the ESCA method (also known as the XPS method, in which X rays are irradiated and photoelectrons emitted from grain surface are separated into spectra), etc.

The outside phase which covers the internal high silver iodide phase has a silver iodide content lower than that of the internal high silver iodide phase. The silver iodide content of the covering outside phase is preferably in the range of 0 to 30 mol %, more preferably 0 to 20 mol %, and most preferably 0 to 10 mol %, based on the silver halide contained in the covering outside phase.

Although the temperature and pAg employed at the formation of the outside phase which covers the internal high silver iodide phase are arbitrary, the temperature preferably ranges from 30 to 80° C., most preferably from 35 to 70° C., and the pAg preferably ranges from 6.5 to 11.5. The use of the aforementioned silver halide solvent is occasionally preferred, and the most preferred silver halide solvent is a thiocyanate salt.

Another method of introducing dislocation lines in the tabular grains comprises using an iodide ion-releasing agent as described in JP-A-6-11782, which can preferably be employed.

Also, dislocation lines can be introduced by appropriately combining this method of introducing dislocation lines with the aforementioned method of introducing dislocation lines.

The variation coefficient of the intergranular iodine distribution of silver halide grains for use in the present invention is preferably 20% or less, more preferably 15% or less, and much more preferably 10% or less. When the variation coefficient of the iodine content distribution of each silver halide is greater than 20%, unfavorably, a high contrast is not realized and a sensitivity lowering is intense when a pressure is applied.

Any known processes such as the process of adding fine grains as described, for example, in JP-A-1-183417 and the process of using an iodide ion-releasing agent as described in JP-A-2-68538 can be employed either individually or in combination for the production of silver halide grains whose intergranular iodine distribution is narrow for use in the present invention.

The silver halide grains for use in the present invention preferably have a variation coefficient of intergranular iodine distribution of 20% or less. The process described in JP-A-3-213845 can be used as the most suitable process for converting the intergranular iodine distribution to a monodispersion. That is, a monodisperse intergranular iodine distribution can be accomplished by a process in which fine silver halide grains containing silver iodide in an amount of at least 95 mol % are formed by mixing together an aqueous solution of a water soluble silver salt and an aqueous solution of a water soluble halide (containing at least 95 mol % of iodide ions) by means of a mixer provided outside a reactor vessel for crystal growth and, immediately after the formation, fed in the reactor vessel. The terminology "reactor vessel" used herein means the vessel in which the nucleation and/or crystal growth of tabular silver halide grains is carried out.

With respect to the above process of mixer preparation followed by adding procedure and the preparatory means for use therein, the following three techniques can be employed as described in JP-A-3-213845:

(i) immediately after formation of fine grains in a mixer, the fine grains are transferred into a reactor vessel;

(ii) powerful and effective agitation is carried out in the mixer; and (iii) an aqueous solution of protective colloid is injected into the mixer.

The protective colloid used in technique (iii) above may be separately injected in the mixer, or may be incorporated in the aqueous solution of silver halide or the aqueous solution of silver nitrate before the injection in the mixer. The concentration of protective colloid is at least 1% by weight, preferably in the range of 2 to 5% by weight. Examples of polymeric compounds exhibiting a protective colloid function to the silver halide grains for use in the present invention include polyacrylamide polymers, amino polymers, polymers having thioether groups, polyvinyl alcohol, acrylic polymers, hydroxyquinoline having polymers, cellulose, starch, acetal, polyvinylpyrrolidone and ternary polymers. Low-molecular-weight gelatin can preferably be used as the above polymeric compound. The molecular weight of low-molecular-weight gelatin is preferably 30,000 or less, more preferably 10,000 or less.

The grain formation temperature in the preparation of fine silver halide grains is preferably 35° C. or below, more preferably 25° C. or below. The temperature of the reactor vessel in which fine silver halide grains are incorporated is at least 50° C., preferably at least 60° C., and more preferably at least 70° C.

The grain size of fine-size silver halide for use in the present invention can be determined by placing grains on a mesh and making a direct observation through a transmission electron microscope. The size of fine grains of the present invention is 0.3 μm or less, preferably 0.1 μm or less, and more preferably 0.01 μm or less. This fine silver halide may be added simultaneously with the addition of other halide ions and silver ions, or may be separately added. The fine silver halide grains are mixed in an amount of 0.005 to 20 mol %, preferably 0.01 to 10 mol %, based on the total silver halide.

The silver iodide content of each individual grain can be measured by analyzing the composition of each individual grain by means of an X-ray microanalyzer. The terminology "variation coefficient of intergranular iodine distribution" means a value defined by the formula:

variation coefficient=(standard deviation/av·silver iodide content)×100 wherein the standard deviation, specifically the standard deviation of silver iodide content, and the average silver iodide content are obtained by measuring the silver iodide contents of at least 100, preferably at least 200, and more preferably at least 300 emulsion grains. The measuring of the silver iodide content of each individual grain is described in, for example, EP No. 147,868. There are cases in which a correlation exists between the silver iodide content Yi (mol %) of each individual grain and the equivalent spherical diameter Xi (μm) of each individual grain and cases in which no such correlation exists. It is preferred that no correlation exist therebetween. The structure associated with the silver halide composition of grains of the present invention can be identified by, for example, a combination of X-ray diffractometry, the EPMA method (also known as the XMA method, in which silver halide grains are scanned by electron beams to thereby detect the silver halide composition) and the ESCA method (also known as the XPS method, in which X rays are irradiated and photoelectrons emitted from grain surface are separated into spectra). In the measuring of silver iodide content in the present invention, the terminology "grain surface" refers to the region whose depth from surface is about 5 nm, and the terminology "grain internal part" refers to the region other than the above surface. The halogen composition of such a grain surface can generally be measured by the ESCA method.

In the present invention, use can be made of not only the above tabular grains but also regular crystal grains such as cubic, octahedral and tetradecahedral grains and, further, amorphous twinned crystal grains.

In the silver halide emulsion of the present invention, performing washing with water is preferable for desalting. The temperature at which the washing with water is carried out can be selected in accordance with the purpose, and preferably the temperature is selected in the range of 5° C. to 50° C. The pH at which the washing with water is carried out can be selected in accordance with the purpose, and preferably the pH is selected in the range of 2 to 10, and more preferably in the range of 3 to 8. The pAg at which the washing with water is carried out can be selected in accordance with the purpose, and preferably the pAg is selected in the range of 5 to 10. As a method of washing with water, it is possible to select from the noodle washing method, the dialysis method using a semipermeable membrane, the centrifugation method, the coagulation settling method, and the ion exchange method.

In the case of the coagulation settling method, however, it is preferable not to conduct the washing by a method of using an anionic polymer as widely accepted in a general silver halide emulsion. The reason thereof is that in the present invention the multilayer adsorption, as will be described later, of dye chromophores is preferably conducted under the condition where an anionic surfactant, which will be described later, is not present to the utmost. Most of the anionic polymers are within the scope of anionic surfactant to be described later. A part of these polymers remains in the emulsion after washing with water for desalting, thereby cause to decrease the advantage of enhancing speed, which is one of the objects of the present invention.

Preferably used methods of washing with water for desalting are the dialysis method using a diaphragm and the coagulation settling method without using an anionic polymer. These are preferable from the view point that the addition of an anionic polymer at the time of washing with water for desalting is not necessary, and being suited for industrially practical applicability.

In particular, the latter coagulation sedimentation process in which no anionic polymer is used is advantageous over the dialytic process in which a semipermeable membrane is used from the viewpoint that the facilities for desalting washing can be simplified and high reproducibility can be ensured. As a specific example, there can be mentioned a method in which prior to desalting washing, phthalated gelatin is added to an emulsion and thereafter coagulation sedimentation is carried out while maintaining the pH value of the emulsion at 3 to 4. Although the optimum conditions regarding the amount of phthalated gelatin added prior to desalting washing and the pH value at coagulation sedimentation, because depend on the conditions of other factors of emulsion production, cannot be categorically described, it is often preferred that the amount of phthalated gelatin added be such that the proportion of phthalated gelatin to all the dispersion medium of emulsion just after the addition is 5% or more, and that the pH value at coagulation sedimentation fall within the aforementioned range.

The aforementioned anionic surfactant will be described below. As the anionic surfactant with respect to which it is preferred to avoid the presence thereof in the step of multilayer adsorption of dye chromophores or use thereof in the dispersion of cationic sensitizing dyes in the production of silver halide emulsion according to the present invention, there can be mentioned compounds of the following general formula (SAA):

$$(Ra)—(Y)_n \quad\quad\quad (SAA)$$

In the formula, Ra represents a group having at least two carbon atoms; and Y represents —COOM, —SO$_3$M or —P(=O)(OM)$_2$. M represents a cation, such as a hydrogen ion, an alkali metal ion or a quaternary ammonium ion.

Further, as the anionic surfactant with respect to which it is preferred to avoid the presence thereof in the step of multilayer adsorption of dye chromophores or use thereof in the dispersion of cationic sensitizing dyes in the production of silver halide emulsion according to the present invention, there can be mentioned compounds of the following general formula (SAB), general formula (SAC), general formula (SAD), general formula (SAE) and general formula (SAF).

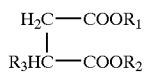
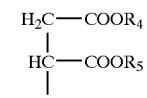

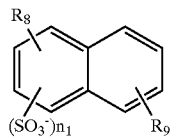

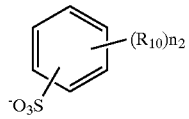
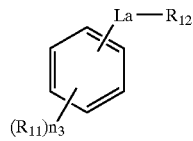

In the formulae, each of $R_1$, $R_2$, $R_4$, $R_5$, $R_6$, $R_8$, $R_9$, $R_{10}$ and $R_{11}$ independently represents a halogen atom (e.g., chlorine atom, bromine atom or iodine atom) or an alkyl group (e.g., methyl, ethyl, propyl, butyl, isobutyl, pentyl, hexyl, octyl, nonyl, decyl or octadecyl) which may be a linear chain or a branched chain. This alkyl group may further be substituted with any substituent, such as a halogen atom (e.g., chlorine atom, bromine atom or iodine atom), an alkyl group (e.g., methyl, ethyl, propyl, butyl, isobutyl, pentyl, hexyl, octyl, nonyl, decyl or octadecyl) or an aryl group (e.g., phenyl or naphthyl).

Each of $R_3$, $R_7$ and $R_{12}$ represents —COOM, —SO$_3$M or —P(=O)(OM)$_2$. M represents a cation, such as a hydrogen ion, an alkali metal ion or a quaternary ammonium ion.

Each of $n_1$, $n_2$ and $n_3$ is an integer of 1 to 3.

La represents any of connecting groups (including a single bond), preferably a connecting group having 0 to 100 carbon atoms, generally 1 to 20 carbon atoms, composed of one or a combination of two or more of a single bond, an alkylene group (generally having 1 to 20 carbon atoms, such as methylene, ethylene, propylene, butylene, pentylene, hexylene or octylene), an arylene group (generally having 6 to 26 carbon atoms, such as phenylene or naphthylene), an alkenylene group (generally having 2 to 20 carbon atoms, such as ethenylene or propenylene), an alkynylene group (generally having 2 to 20 carbon atoms, such as ethynylene or propynylene), an amido group, an ester group, a sulfoamido group, a sulfonic ester group, a ureido group, a sulfonyl group, a sulfinyl group, a thioether group, an ether group, a carbonyl group, —NR$_{51}$— (R$_{51}$ is a hydrogen atom or a monovalent substituent) and a heterylene group (generally having 1 to 26 carbon atoms, such as 6-chloro-1,3,5-triazyl-2,4-diyl or quinoxaline-2,3-diyl).

Specific examples of the anionic surfactants with respect to which it is preferred to avoid the presence thereof in the step of multilayer adsorption of dye chromophores or use thereof in the dispersion of cationic sensitizing dyes will be shown below, which however in no way limit the scope of the present invention.

SA-1
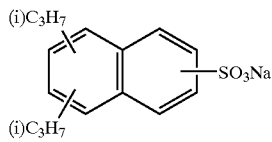

SA-2
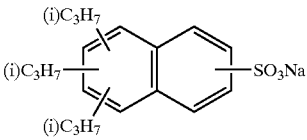

SA-3
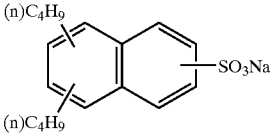

SA-4
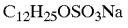
C$_{12}$H$_{25}$OSO$_3$Na

SA-5
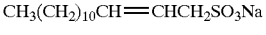
CH$_3$(CH$_2$)$_{10}$CH=CHCH$_2$SO$_3$Na

SA-6
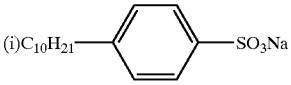

SA-7
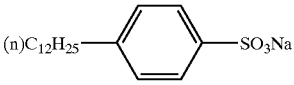

SA-8
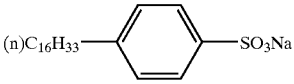

SA-9
C$_{14}$H$_{29}$—(OCH$_2$CH$_2$)$_2$SO$_3$Na

SA-10
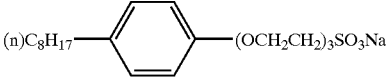

SA-11
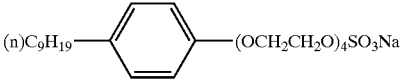

SA-12
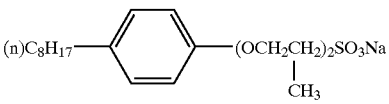

SA-13
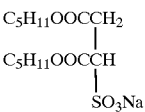

SA-14
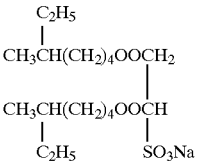

SA-15
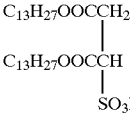

SA-16
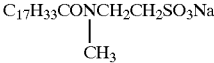

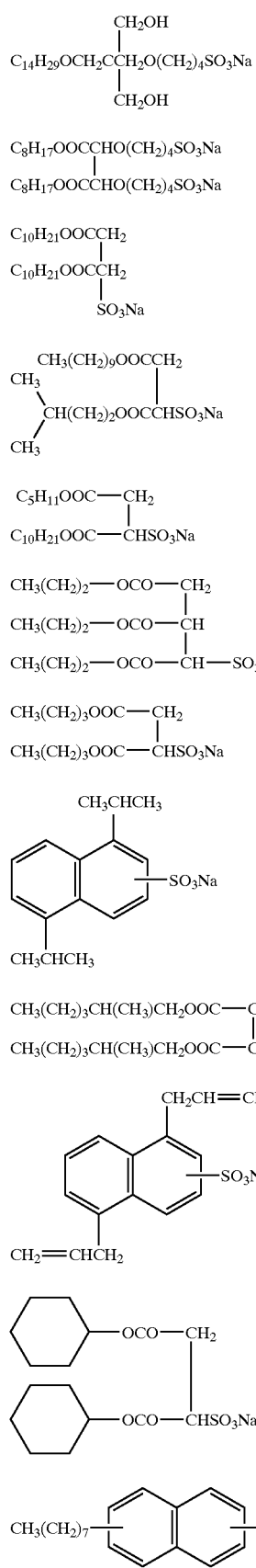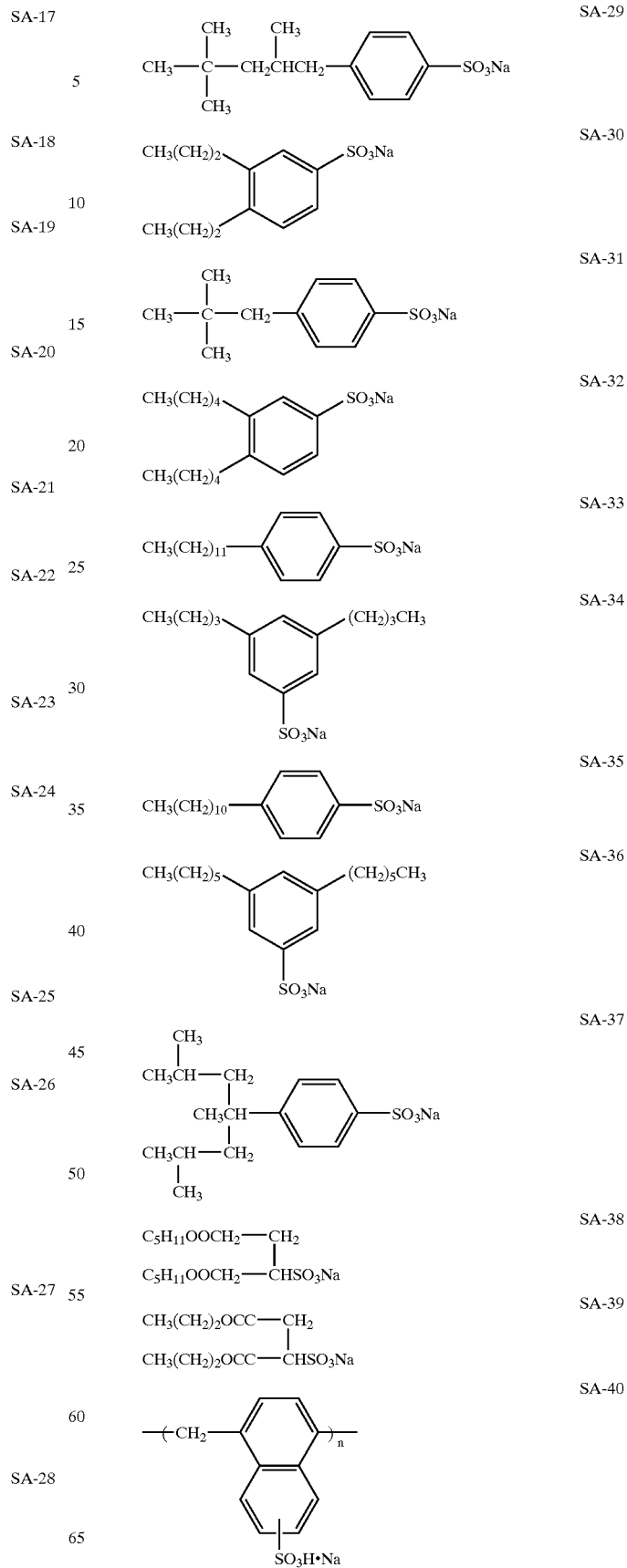

SA-41

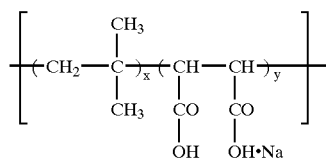

SA-42

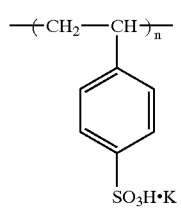

The aforementioned general formula (SAA) comprehends gelatins, peptides and amino acids, which are excluded from the anionic surfactants with respect to which it is preferred to avoid the presence thereof in the step of multilayer adsorption of dye chromophores.

In the emulsion during the multilayer adsorption of dye chromophores, the amount of the above anionic surfactant is preferably 0.45 g or less, more preferably 0.20 g or less per mol of silver halides. This amount, although being variable during the step of multilayer adsorption of dye chromophores, can be represented by the amount exhibited just upon the completion of addition of all the dye chromophores to be contained in the silver halide emulsion of the present invention. It is preferred that the amount of the above anionic surfactant fall within the above range at all times during the step of multilayer adsorption.

In the silver halide emulsion of the present invention at least one of sulfur sensitization, selenium sensitization, tellurium sensitization, gold sensitization, palladium sensitization and noble metal sensitization may be performed during any-step of the preparation procedure of a silver halide emulsion. It is preferable to combine two or more sensitizing methods. Various types of emulsions may be prepared depending on the step at which the chemical sensitization is performed. For examples there are types in which the chemical sensitization nuclei are mounted inside the grain, the chemical sensitization nuclei are mounted at a shallow portion from the grain surface and the chemical sensitization nuclei are made on the grain surface. In the present invention, the place of the chemical sensitization nuclei may be selected depending on the purposes.

Selenium sensitization and/or gold sensitization are preferably performed on the silver halide emulsion of the present invention. Selenium compounds disclosed in hitherto published patents can be used as the selenium sensitizer in the present invention. In the use of labile selenium compound and/or nonlabile selenium compound, generally, it is added to an emulsion and the emulsion is agitated at high temperature, preferably 40° C. or above, for a given period of time. Compounds described in, for example, Jpn. Pat. Appln. KOKOKU Publication No. (hereinafter referred to as JP-B-) 44-15748, JP-B-43-13489, JP-A's-4-25832 and 4-109240 are preferably used as the labile selenium compound.

Specific examples of the labile selenium sensitizers include isoselenocyanates (for example, aliphatic isoselenocyanates such as allyl isoselenocyanate), selenoureas, selenoketones, selenoamides, selenocarboxylic acids (for example, 2-selenopropionic acid and 2-selenobutyric acid), selenoesters, diacyl selenides (for example, bis(3-chloro-2, 6-dimethoxybenzoyl) selenide), selenophosphates, phosphine selenides and colloidal metal selenium.

The labile selenium compounds, although preferred types thereof are as mentioned above, are not limited thereto. It is generally understood by persons of ordinary skill in the art to which the invention pertains that the structure of the labile selenium compound as a photographic emulsion sensitizer is not so important as long as the selenium is labile and that the labile selenium compound plays no other role than having its selenium carried by organic portions of selenium sensitizer molecules and causing it to present in labile form in the emulsion. In the present invention, the labile selenium compounds of this broad concept can be used advantageously.

Compounds described in JP-B's-46-4553, 52-34492 and 52-34491 can be used as the nonlabile selenium compound in the present invention. Examples of the nonlabile selenium compounds include selenious acid, potassium selenocyanate, selenazoles, quaternary selenazole salts, diaryl selenides, diaryl diselenides, dialkyl selenides, dialkyl diselenides, 2-selenazolidinedione, 2-selenoxazolidinethione and derivatives thereof.

These selenium sensitizers are dissolved in water or an organic solvent such as methanol and ethanol or a mixed solvent of these, and added at the time of chemical sensitization. Preferably, the addition is performed prior to the initiation of chemical sensitization. The above selenium sensitizers can be used either individually or in combination. The joint use of an labile selenium compound and a nonlabile selenium compound is preferred.

The addition amount of selenium sensitizer for use in the present invention, although varied depending on the activity of employed selenium sensitizer, the type and size of silver halide, the ripening temperature and time, etc., is preferably in the range of $2 \times 10^{-6}$ to $5 \times 10^{-6}$ mol per mol of silver halide. The temperature of chemical sensitization in the use of a selenium sensitizer is preferably between 40° C. and 80° C. The pAg and pH are arbitrary. For example, with respect to pH, the effect of the present invention can be exerted even if it widely ranges from 4 to 9.

Selenium sensitization is effectively attained in the presence of a silver halide solvent.

Examples of the silver halide solvent usable in the present invention are (a) organic thioethers described in, e.g., U.S. Pat. Nos. 3,271,157, 3,531,289, and 3,574,628, and JP-A's-54-1019 and 54-158917, (b) thiourea derivatives described in, e.g., JP-A's-53-82408, 55-77737, and 55-2982, (c) a silver halide solvent having a thiocarbonyl group sandwiched between an oxygen or sulfur atom and a nitrogen atom described in JP-A-53-144319, (d) imidazoles described in JP-A-54-100717, (e) ammonia, and (f) thiocyanate.

Particularly preferable solvents are thiocyanate, ammonia, and tetramethylthiourea. Although the amount of a solvent used changes in accordance with the type of the solvent, a preferable amount of, e.g., thiocyanate is $1 \times 10^{-4}$ to $1 \times 10^{-2}$ mol per mol of a silver halide.

The oxidation number of gold of the gold sensitizer mentioned above may be either +1 or +3, and gold compounds customarily used as gold sensitizers can be employed. Representative examples thereof include chloroauric acid salts, potassium chloroaurate, auric trichloride, potassium auric thiocyanate, potassium iodoaurate, tetracyanoauric acid, ammonium aurothiocyanate, pyridyltrichlorogold, gold sulfide and gold selenide. The addition amount of gold sensitizer, although varied depending on various conditions, is preferably between $1 \times 10^{-7}$ mol and $5 \times 10^{-5}$ mol per mol of silver halide as a yardstick.

With respect to the emulsion for use in the present invention, it is desired to perform sulfur sensitization in combination for the chemical sensitization. The sulfur sensitization is generally performed by adding a sulfur sensitizer and agitating the emulsion at high temperature, preferably 40° C. or above, for a given period of time.

In the above sulfur sensitization, those known as sulfur sensitizers can be used. For example, use can be made of thiosulfates, allylthiocarbamidothiourea, allyl isothiacyanate, cystine, p-toluenethiosulfonates and rhodanine. Use can also be made of other sulfur sensitizers described in, for example, U.S. Pat. Nos. 1,574,944, 2,410,689, 2,278,947, 2,728,668, 3,501,313 and 3,656,955, West German Patent No. 1,422,869, JP-B-56-24937 and JP-A-55-45016. The addition amount of sulfur sensitizer is satisfactory if it is sufficient to effectively increase the sensitivity of the emulsion. This amount, although varied to a large extent under various conditions such as the pH, temperature and size of silver halide grains, is preferably in the range of $1 \times 10^{-7}$ to $5 \times 10^{-5}$ mol per mol of silver halide.

In the silver halide emulsion of the present invention, it is preferable that a suitable amount of Ca or Mg is contained in the silver halide emulsion of the present invention. By this, the advantage of enhancing speed of the present invention is accelerated, and granularity is also improved. A suitable amount range of Ca or Mg is $2 \times 10^{-3}$ to $4 \times 10^{-2}$ mol per mol of silver halide. When both Ca and Mg coexist, the sum of the both within the range will be fine. When the content of Ca or Mg is lower than the range, and when the content of Ca or Mg is higher than the range, the advantage of enhancing speed of the present invention is not accelerated.

When the content of Ca or Mg is too high, an inorganic salt precipitates or processing blot is likely to arise during the processing of a photosensitive material, so, attention should be made.

The addition of Ca or Mg to an emulsion may be conducted at an arbitrary timing during the preparation process of the silver halide emulsion, but it is preferable for a Ca salt or Mg salt to add during chemical sensitization to adjust the content in the emulsion. The addition of a Ca salt or Mg salt is especially preferable at the time of after a part of all of a dye chromophore is added but before the initiation of chemical sensitization.

Gelatin generally used in the preparation of an emulsion already contains Ca, and the amount thereof is $2 \times 10^{-6}$ to $1 \times 10^{-4}$ mol per mol of gelatin. The calcium content can be adjusted by further adding a Ca salt or Mg salt to the gelatin or by first desalting (decalcificating) the gelatin in accordance with a known method such as washing or ion exchange, if necessary, and then adding a Ca salt or Mg salt. Calcium nitrate and Calcium chloride are preferable as the Ca salt. Magnesium nitrate, magnesium sulfate and magnesium chloride are preferable as the Mg salt.

ICP emission spectral analysis is an example of a method of determining calcium or magnesium.

The silver halide emulsion for use in the present invention can be subjected to a reduction sensitization during the grain formation, or after the grain formation but before the chemical sensitization, during the chemical sensitization or after the chemical sensitization.

The reduction sensitization can be performed by a method selected from among the method in which a reduction sensitizer is added to the silver halide emulsion, the method commonly known as silver ripening in which growth or ripening is carried out in an environment of pAg as low as 1 to 7 and the method commonly known as high-pH ripening in which growth or ripening is carried out in an environment of pH as high as 8 to 11. At least two of these methods can be used in combination.

The above method in which a reduction sensitizer is added is preferred from the viewpoint that the level of reduction sensitization can be finely regulated.

Examples of known reduction sensitizers include stannous salts, ascorbic acid and derivatives thereof, amines and polyamino acids, hydrazine derivatives, formamidinesulfinic acid, silane compounds and borane compounds. In the reduction sensitization employed in the present invention, appropriate one may be selected from among these known reduction sensitizers and used or at least two may be selected and used in combination. Preferred reduction sensitizers are stannous chloride, thiourea dioxide, dimethylaminoborane, ascorbic acid and derivatives thereof. Although the addition amount of reduction sensitizer must be selected because it depends on the emulsion manufacturing conditions, it is preferred that the addition amount range from $10^{-7}$ to $10^{-3}$ mol per mol of silver halide.

Each reduction sensitizer is dissolved in water or any of organic solvents such as alcohols, glycols, ketones, esters and amides and added during the grain growth. Although the reduction sensitizer may be put in a reaction vessel in advance, it is preferred that the addition be effected at an appropriate time during the grain growth. It is also suitable to add in advance the reduction sensitizer to an aqueous solution of a water-soluble silver salt or a water-soluble alkali halide and to precipitate silver halide grains with the use of the resultant aqueous solution. Alternatively, the reduction sensitizer solution may preferably be either divided and added a plurality of times in accordance with the grain growth or continuously added over a prolonged period of time.

An oxidizer capable of oxidizing silver is preferably used during the process of producing the emulsion for use in the present invention. The silver oxidizer is a compound having an effect of acting on metallic silver to thereby convert the same to silver ion. A particularly effective compound is one that converts very fine silver grains, formed as a by-product in the step of forming silver halide grains and the step of chemical sensitization, into silver ions. Each silver ion produced may form a silver salt sparingly soluble in water, such as a silver halide, silver sulfide or silver selenide, or may form a silver salt easily soluble in water, such as silver nitrate. The silver oxidizer may be either an inorganic or an organic substance. Examples of suitable inorganic oxidizers include ozone, hydrogen peroxide and its adducts (e.g., $NaBO_2 \cdot H_2O_2 \cdot 3H_2O$, $2NaCO_3 \cdot 3H_2O_2$, $Na_4P_2O_7 \cdot 2H_2O_2$ and $2Na_2SO_4 \cdot H_2O_2 \cdot 2H_2O$), peroxy acid salts (e.g., $K_2S_2O_8$, $K_2C_2O_6$ and $K_2P_2O_8$), peroxy complex compounds (e.g., $K_2[Ti(O_2)C_2O_4] \cdot 3H_2O$, $4K_2SO_4 \cdot Ti(O_2)OH \cdot SO_4 \cdot 2H_2O$ and $Na_3[VO(O_2)(C_2H_4)_2] \cdot 6H_2O)$, permanganates (e.g., $KMnO_4$), chromates (e.g., $K_2Cr_2O_7$) and other oxyacid salts, halogen elements such as iodine and bromine, perhalogenates (e.g., potassium periodate), salts of high-valence metals (e.g., potassium hexacyanoferrate (II)) and thiosulfonates.

Examples of suitable organic oxidizers include quinones such as p-quinone, organic peroxides such as peracetic acid and perbenzoic acid and active halogen releasing compounds (e.g., N-bromosuccinimide, chloramine T and chloramine B).

Oxidizers preferred in the present invention are inorganic oxidizers selected from among ozone, hydrogen peroxide and its adducts, halogen elements and thiosulfonates and organic oxidizers selected from among quinones.

The use of the silver oxidizer in combination with the above reduction sensitization is preferred. This combined use can be effected by performing the reduction sensitization after the use of the oxidizer or vice versa or by simultaneously performing the reduction sensitization and the use of the oxidizer. These methods can be performed during the step of grain formation or the step of chemical sensitization.

The fogging during aging of the silver halide emulsion for use in the present invention can be improved by adding and dissolving a previously prepared silver iodobromide emulsion at the time of chemical sensitization. Although the timing of the addition is arbitrary as long as it is performed during chemical sensitization, it is preferred that the silver iodobromide emulsion be first added and dissolved and, thereafter, a sensitizing dye and a chemical sensitizer be added in this order. The employed silver iodobromide emulsion has an iodine content lower than the surface iodine content of host grains, which is preferably a pure silver bromide emulsion. This silver iodobromide emulsion, although the size thereof is not limited as long as it is completely dissolvable, preferably has an equivalent spherical diameter of 0.1 $\mu$m or less, more preferably 0.05 $\mu$m or less. Although the addition amount of silver iodobromide emulsion depends on employed host grains, basically, it preferably ranges from 0.005 to 5 mol %, more preferably from 0.1 to 1 mol %, based on the mole of silver.

The emulsion for use in the present invention is preferably doped with hexacyanoiron (II) complex or hexacyanoruthenium complex (hereinafter also referred to simply as "metal complex"). The addition amount of the metal complex is preferably in the range of $10^{-7}$ to $10^{-3}$ mol per mol of silver halide, more preferably $1.0 \times 10^{-5}$ to $5 \times 10^{-4}$ mol per mol of silver halide.

The addition and incorporation of the metal complex for use in the present invention may be performed at any stage through the process of preparing silver halide grains which consists of nucleation, growth, physical ripening and chemical sensitization. Also, the addition and incorporation may be performed in some divisions. However, it is preferred that at least 50% of the total content of metal complex contained in each silver halide grain be contained in layers underlying the outermost surface of silver halide grain where ½ or less of the silver content is present. These layers containing the metal complex may be overlaid with a layer which does not contain any metal complex.

The incorporation of the above metal complex is preferably accomplished by dissolving the metal complex in water or a suitable solvent and directly adding the solution to the reaction mixture during the formation of silver halide grains, or by adding the metal complex solution to the aqueous solution of halide, aqueous solution of silver salt or other solution for preparation of silver halide grains and thereafter conducting grain formation. Alternatively, the incorporation of metal complex is also preferably accomplished by adding silver halide grains in which the metal complex has been introduced in advance, dissolving them and depositing them on other silver halide grains.

With respect to the hydrogen ion concentration of the reaction mixture to which the metal complex is added, the pH value is preferably in the range of 1 to 10, more preferably 3 to 7.

A compound capable of undergoing a one-electron oxidation to thereby form a one-electron oxidation product capable of releasing further one or more electrons to be described later is preferably contained in the silver halide photosensitive material of the present invention. Such compounds indicate those selected from the following type 1 to type 5.

(Type 1)
a compound capable of undergoing a one-electron oxidation to thereby form a one-electron oxidation product thereof, wherein the one-electron oxidation product is capable of releasing further two or more electrons accompanying a subsequent bond cleavage reaction;

(Type 2)
a compound capable of undergoing a one-electron oxidation to thereby form a one-electron oxidation product thereof, wherein the one-electron oxidation product is capable of releasing further one electron accompanying a subsequent bond cleavage reaction, and the compound having, in its molecule, two or more groups adsorptive to silver halide;

(Type 3)
a compound capable of undergoing a one-electron oxidation to thereby form a one-electron oxidation product thereof, wherein the one-electron oxidation product is capable of releasing further one or more electrons after going through a subsequent bond forming reaction;

(Type 4)
a compound capable of undergoing a one-electron oxidation to thereby form a one-electron oxidation product thereof, wherein the one-electron oxidation product is capable of releasing further one or more electrons after going through a subsequent intramolecular ring cleavage reaction; and (Type 5)
a compound represented by X—Y, wherein X represents a reducing group and Y represents a split-off group. The reducing group represented by X is capable of undergoing a one-electron oxidation to thereby form a one-electron oxidation product thereof, from which Y is split accompanying a subsequent cleavage reaction of X—Y bond to thereby form an X radical, the X radical capable of further releasing another electron.

Among the compounds of types 1 and 3–5, preferable compounds are "compounds each having a group adsorptive to silver halide" or "compounds each having a partial structure of a spectral sensitizing dye in the molecule". More preferable compounds are "compounds each having a group adsorptive to silver halide."

The compounds of types 1 to 5 will be described in detail below.

With respect to the compound of type 1, the expression "bond cleavage reaction" specifically refers to the cleavage of a carbon-carbon bond, carbon-silicon bond, carbon-hydrogen bond, carbon-boron bond, carbon-tin bond, or carbon-germanium bond. Cleavage of carbon-hydrogen bond may further accompany the above bond cleavage. The compound of type 1 is a compound capable of undergoing a one-electron oxidation to thereby form a one-electron oxidation product. The one-electron oxidation product only thereafter capable of undergoing a bond cleavage reaction to thereby further release two or more electrons (preferably three or more electrons). In another expression, the one-electron oxidation product of the compound of type 1 is capable of being oxidized with further two or more electrons (preferably three or more electrons).

Among the compounds of type 1, preferable compounds are represented by the general formula (A), general formula (B), general formula (1), general formula (2) or general formula (3):

(A)

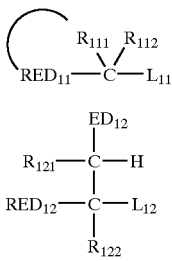

(B)

$$\begin{array}{c} ED_{12} \\ | \\ R_{121}\text{—}C\text{—}H \\ | \\ RED_{12}\text{—}C\text{—}L_{12} \\ | \\ R_{122} \end{array}$$

In the general formula (A), $RED_{11}$, represents a one-electron oxidizable reducing group; $L_{11}$ represents a split-off group. $R_{112}$ represents a hydrogen atom or substituent. $R_{111}$ represents a nonmetallic atomic group capable of forming, together with carbon atom (C) and $RED_{11}$, a specific 5- or 6-membered cyclic structure, wherein the 5- or 6-membered cyclic structure means a tetrahydro form, hexahydro form or octahydro form of a 5- or 6-membered aromatic ring (including an aromatic heterocycle).

In the general formula (B), $RED_{12}$ represents a one-electron oxidizable reducing group; $L_{12}$ represents a split-off group. Each of $R_{121}$ and $R_{122}$ represents a hydrogen atom or substituent.

$ED_{12}$ represents an electron-donating group. In the general formula (B), $R_{121}$ and $RED_{12}$, or $R_{121}$ and $R_{122}$, or $ED_{12}$ and $RED_{12}$ may be bonded with each other to thereby form a cyclic structure.

These compounds are those which, after a one-electron oxidation of the reducing group represented by $RED_{11}$ or $RED_{12}$ of the general formula (A) or general formula (B), can spontaneously split $L_{11}$ or $L_{12}$ through a bond cleavage reaction, namely, cleave the C (carbon atom)— to —$L_{11}$ bond or the C (carbon atom)— to —$L_{12}$ bond to thereby further release two or more electrons, preferably three or more electrons.

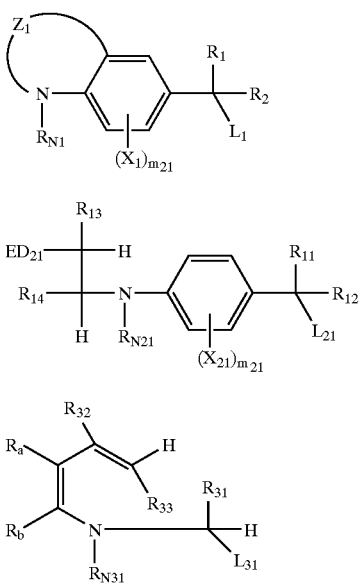

In the general formula (1), $Z_1$ represents an atomic group capable of forming a 6-membered ring together with the nitrogen atom and the two carbon atoms of the benzene ring; each of $R_1$, $R_2$ and $R_{N1}$ represents a hydrogen atom or substituent; $X_1$ represents a group capable of substituting on the benzene ring; $m_1$ is an integer of 0 to 3; and $L_1$ represents a split-off group. In the general formula (2), $ED_{21}$ represents an electron-donating group; each of $R_{11}$, $R_{12}$, $R_{N21}$, $R_{13}$ and $R_{14}$ represents a hydrogen atom or substituent; $X_{21}$ represents a substituent capable of substituting on the benzene ring; $m_{21}$ is an integer of 0 to 3; and $L_{21}$ represents a split-off group. Any two of $R_{N21}$, $R_{13}$, $R_{14}$, $X_{21}$ and $ED_{21}$ may be bonded with each other to thereby form a cyclic structure. In the general formula (3), each of $R_{32}$, $R_{33}$, $R_{31}$, $R_{N31}$, $R_a$ and $R_b$ represents a hydrogen atom or substituent; and $L_{31}$ represents a split-off group. Provided that, when $R_{N31}$ represents a group other than an aryl group, $R_a$ and $R_b$ are bonded to each other to thereby form an aromatic ring.

These compounds are those which, after a one-electron oxidation, can spontaneously split $L_1$, $L_{21}$ or $L_{31}$ through a bond cleavage reaction, namely, cleave the C (carbon atom)— to —$L_1$ bond, the C (carbon atom)— to —$L_{21}$ bond or the C (carbon atom)— to —$L_{31}$ bond to thereby further release two or more electrons, preferably three or more electrons.

First, the compound represented by the general formula (A) will be described in detail below.

In the general formula (A), the reducing group represented by $RED_{11}$ that is capable of being oxidized with one-electron, is a group capable of bonding with $R_{111}$ described later to thereby form a specific ring. The reducing group can be, for example, a divalent group corresponding to a monovalent group, as mentioned below, having one hydrogen atom removed therefrom at a position that is appropriate for cyclization. The monovalent group can be, for example, any of an alkylamino group, arylamino group (e.g., anilino, naphthylamino), heterocyclic amino group (e.g., benzothiazolylamino, pyrrolylamino), alkylthio group, arylthio group (e.g., phenylthio), heterocyclic thio group, alkoxy group, aryloxy group (e.g., phenoxy), heterocyclic oxy group, aryl group (e.g., phenyl, naphthyl, anthranyl) and aromatic or nonaromatic heterocyclic group (for example, 5- to 7-membered monocyclic or condensed heterocycle containing at least one hetero atom selected from the group consisting of a nitrogen atom, sulfur atom, oxygen atom and selenium atom, which heterocycle can be, for example, a tetrahydroquinoline ring, tetrahydroisoquinoline ring, tetrahydroquinoxaline ring, tetrahydroquinazoline ring, indoline ring, indole ring, indazole ring, carbazole ring, phenoxazine ring, phenothiazine ring, benzothiazoline ring, pyrrole ring, imidazole ring, thiazoline ring, piperidine ring, pyrrolidine ring, morpholine ring, benzimidazole ring, benzimidazoline ring, benzoxazoline ring or methylenedioxyphenyl ring) (hereinafter, for simplicity, $RED_{11}$ is referred to as denoting a monovalent group). These groups may each have a substituent.

The substituent can be, for example, any of a halogen atom, alkyl groups (including, e.g., an aralkyl group, cycloalkyl group, active methine group), an alkenyl group, alkynyl group, aryl group, heterocyclic group (the substitution position of the heterocyclic group is not questioned), heterocyclic group containing a quaternated nitrogen atom (e.g., pyridinio, imidazolio, quinolinio or isoquinolinio), acyl group, alkoxycarbonyl group, aryloxycarbonyl group, carbamoyl group, carboxyl group or a salt thereof, sulfonylcarbamoyl group, acylcarbamoyl group, sulfamoylcarbamoyl group, carbazoyl group, oxalyl group, oxamoyl group, cyano group, carbonimidoyl group, thiocarbamoyl group, hydroxyl group, alkoxy groups (including a group containing ethyleneoxy or propyleneoxy repeating units), aryloxy group, heterocyclic oxy group, acyloxy group, alkoxy- or aryloxy-carbonyloxy group, carbamoyloxy group, sulfonyloxy group, amino group, alkyl-, aryl- or heterocyclic-amino group, acylamino group, sulfonamido group, ureido group, thioureido group, imido group, alkoxy- or aryloxy-carbonylamino group, sulfamoylamino group, semicarbazido group, thiosemicarbazido group, hydrazino group, ammonio group, oxamoylamino group, alkyl- or aryl-sulfonylureido group, acylureido group, acylsulfamoylamino group, nitro group, mercapto group, alkyl-, aryl- or heterocyclic-thio group, alkyl- or aryl-sulfonyl group, alkyl- or aryl-sulfinyl group, sulfo group or a salt thereof, sulfamoyl group, acylsulfamoyl group, sulfonylsulfamoyl group or a salt thereof, and group containing a phosphoramide or phosphoric ester structure. These substituents may be further substituted with these substituents.

In the general formula (A), $L_{11}$ represents a split-off group that can be split off through a bond cleavage only after a one-electron oxidation of the reducing group represented by $RED_{11}$. Specifically, $L_{11}$ represents, for example, a carboxyl group or a salt thereof, silyl group, hydrogen atom, triarylboron anion, trialkylstannyl group, trialkylgermyl group or a group of the formula —$CR_{C1}R_{C2}R_{C3}$.

When $L_{11}$ represents a salt of carboxyl group, as a counter ion for forming a salt, there can be mentioned, for example, an alkali metal ion (e.g., $Li^+$, $Na^+$, $K^+$ or $Cs^+$), an alkaline earth metal ion (e.g., $Mg^{2+}$, $Ca^{2+}$ or $Ba^{2+}$), a heavy metal ion (e.g., $Ag^+$ or $Fe^{2+/3+}$), an ammonium ion or a phosphonium ion. When $L_{11}$ represents a silyl group, specifically, the silyl group is, for example, a trialkylsilyl group, an aryldialkylsilyl group or a triarylsilyl group. The alkyl of these groups can be, for example, methyl, ethyl, benzyl or t-butyl. The aryl of these groups can be, for example, phenyl.

When $L_{11}$ represents a triarylboron anion, the aryl thereof is preferably a substituted or unsubstituted phenyl, wherein the substituent can be any of those which may be had by $RED_{11}$. When $L_{11}$ represents a trialkylstannyl group or a trialkylgermyl group, the alkyl thereof is a substituted or unsubstituted linear, branched or cyclic alkyl having 1 to 24 carbon atoms, wherein the substituent can be any of those which may be had by $RED_{11}$.

When $L_{11}$ represents a group of the formula —$CR_{C1}R_{C2}R_{C3}$, each of $R_{C1}$, $R_{C2}$ and $R_{C3}$ independently represents any of a hydrogen atom, alkyl group, aryl group, heterocyclic group, alkylthio group, arylthio group, alkylamino group, arylamino group, heterocyclic amino group, alkoxy group, aryloxy group and hydroxyl group. These may be bonded with each other to thereby form a cyclic structure. Each of these may further have a substituent. The substituent can be any of those which may be had by $RED_{11}$. Provided however that, when one of $R_{C1}$, $R_{C2}$ and $R_{C3}$ represents a hydrogen atom or alkyl group, the remaining two do not represent a hydrogen atom or alkyl group. It is preferred that each of $R_{C1}$, $R_{C2}$ and $R_{C3}$ independently represent an alkyl group, aryl group (especially, phenyl), alkylthio group, arylthio group, alkylamino group, arylamino group, heterocyclic group, alkoxy group or hydroxyl group. Specific examples thereof include phenyl, p-dimethylaminophenyl, p-methoxyphenyl, 2,4-dimethoxyphenyl, p-hydroxyphenyl, methylthio, phenylthio, phenoxy, methoxy, ethoxy, dimethylamino, N-methylanilino, diphenylamino, morpholino, thiomorpholino and hydroxyl. Examples of groups having a cyclic structure formed by mutual bonding of these include 1,3-dithiolan-2-yl, 1,3-dithian-2-yl, N-methyl-1,3-thiazolidin-2-yl and N-benzylbenzothiazolidin-2-yl.

Preferred groups of the formula —$CR_{C1}R_{C2}R_{C3}$ can be, for example, trityl, tri(p-hydroxyphenyl)methyl, 1,1-diphenyl-1-(p-dimethylaminophenyl)methyl, 1,1-diphenyl-1-(methylthio)methyl, 1-phenyl-1,1-(dimethylthio)methyl, 1,3-dithiolan-2-yl, 2-phenyl-1,3-dithiolan-2-yl, 1,3-dithian-2-yl, 2-phenyl-1,3-dithian-2-yl, 2-methyl-1,3-dithian-2-yl, N-methyl-1,3-thiazolidin-2-yl, 2-methyl-3-methyl-1,3-thiazolidin-2-yl, N-benzylbenzothiazolidin-2-yl, 1,1-diphenyl-1-dimethylaminomethyl and 1,1-diphenyl-1-morpholinomethyl group. It is also preferred that the group of the formula —$CR_{C1}R_{C2}R_{C3}$ be the same group as the residue resulting from removal of $L_{11}$ from the general formula (A) as a consequence of selection within the above scopes with respect of the $R_{C1}$, $R_{C2}$ and $R_{C3}$.

In the general formula (A), $R_{112}$ represents a hydrogen atom or substituent capable of substituting on the carbon atom. When $R_{112}$ represents a substituent capable of substituting on the carbon atom, the substituent can be, for example, any of those mentioned as substituent examples with respect to the $RED_{11}$ having a substituent. Provided, however, that $R_{112}$ and $L_{11}$ do not represent the same group.

In the general formula (A), $R_{111}$ represents a group of nonmetallic atoms capable of forming a specific 5-membered or 6-membered cyclic structure together with the carbon atom (C) and $RED_{11}$. Herein, the expression "specific 5-membered or 6-membered cyclic structure" formed by $R_{111}$ means a cyclic structure corresponding to a tetrahydro form, hexahydro form or octahydro form of 5-membered or 6-membered aromatic ring (including an aromatic heterocycle). Herein, the terminology "hydro form" means a cyclic structure resulting from partial hydrogenation of an internal carbon to carbon double bond (or a carbon to nitrogen double bond) of an aromatic ring (including an aromatic heterocycle). The tetrahydro form refers to a structure resulting from hydrogenation of two carbon to carbon double bonds (or carbon to nitrogen double bonds). The hexahydro form refers to a structure resulting from hydrogenation of three carbon to carbon double bonds (or carbon to nitrogen double bonds). The octahydro form refers to a structure resulting from hydrogenation of four carbon to carbon double bonds (or carbon to nitrogen double bonds). As a result of hydrogenation, the aromatic ring becomes a partially hydrogenated nonaromatic cyclic structure.

Specifically, as examples of 5-membered monocycles, there can be mentioned a pyrrolidine ring, imidazolidine ring, thiazolidine ring, pyrazolidine ring and oxazolidine ring which correspond to tetrahydro forms of aromatic rings including a pyrrole ring, imidazole ring, thiazole ring, pyrazole ring and oxazole ring, respectively. As examples of 6-membered monocycles, there can be mentioned tetrahydro or hexahydro forms of aromatic rings such as a pyridine ring, pyridazine ring, pyrimidine ring and pyrazine ring. Particular examples thereof include a piperidine ring, tetrahydropyridine ring, tetrahydropyrimidine ring and piperazine ring. As examples of 6-membered condensed rings, there can be mentioned a tetralin ring, tetrahydroquinoline ring, tetrahydroisoquinoline ring, tetrahydroquinazoline ring and tetrahydroquinoxaline ring which correspond to tetrahydro forms of aromatic rings including a naphthalene ring, quinoline ring, isoquinoline ring, quinazoline ring and quinoxaline ring, respectively. As examples of tricyclic compounds, there can be mentioned a tetrahydrocarbazole ring, which is a tetrahydro form of a carbazole ring, and an octahydrophenanthridine ring, which is an octahydro form of a phenanthridine ring.

These cyclic structures may further be substituted. As examples of suitable substituents, there can be mentioned those described above with respect to substituents which may be had by the $RED_{11}$. Substituents of these cyclic structures may be further bonded with each other to thereby form a ring. The thus newly formed ring is a nonaromatic carbon ring or heterocycle.

Preferred range of compounds represented by the general formula (A) of the present invention will be described below.

In the general formula (A), $L_{11}$ preferably represents a carboxyl group or a salt thereof, or hydrogen atom. More preferably, $L_{11}$ is a carboxyl group or a salt thereof.

As a counter ion of the salt, there can preferably be mentioned an alkali metal ion or an ammonium ion. An alkali metal ion (especially $Li^+$, $Na^+$ or $K^+$ ion) is most preferred.

When $L_{11}$ represents a hydrogen atom, it is preferred that the compound represented by the general formula (A) has an intramolecular base moiety. By virtue of the action of the base moiety, the compound represented by the general formula (A) is oxidized, and thereafter the hydrogen atom represented by $L_{11}$ is deprotonized to thereby enable further release of an electron therefrom.

Herein, the base refers to, for example, a conjugated base of acid exhibiting a pKa value of about 1 to about 10. As the base, there can be mentioned, for example, any of nitrogen-containing heterocycles (pyridines, imidazoles, benzimidazoles, thiazoles, etc.), anilines, trialkylamines, an amino group, carbon acids (active methylene anion, etc.), a thioacetate anion, carboxylate (—COO⁻), sulfate (—$SO_3^-$) and an amine oxide (>$N^+(O^-)$—). Preferred base is a conjugated base of acid exhibiting a pKa value of about 1 to about 8. Carboxylate, sulfate and an amine oxide are more preferred. Carboxylate is most preferred. When these bases have an anion, a counter cation may be had thereby. The counter cation can be, for example, an alkali metal ion, an alkaline earth metal ion, a heavy metal ion, an ammonium ion or a phosphonium ion.

These bases are linked at an arbitrary position thereof to the compound represented by the general formula (A). The position at which the base moiety is bonded may be any of $RED_{11}$, $R_{111}$ and $R_{112}$ of the general formula (A). Also, the bases may be linked at substituents of these groups.

When $L_{11}$ represents a hydrogen atom, it is preferred that the hydrogen atom and the base moiety be linked to each other through an atomic group consisting of 8 or less atoms. More preferably, the linkage is made by an atomic group consisting of 5 to 8 atoms. Herein, what is counted as a linking atomic group refers to an atomic group which links the hydrogen atom to the central atom of base moiety (namely, an atom having an anion, or an atom having a lone electron pair) by a covalent bond. For example, with respect to carboxylate, two atoms of —C—O⁻ are counted. With respect to sulfate, two atoms of S—O⁻ are counted. Also, the carbon atom represented by C in the general formula (A) is included in the count.

In the general formula (A), when $L_{11}$ represents a hydrogen atom and when $RED_{11}$ represents an aniline whose nitrogen atom forms a 6-membered monocyclic saturated ring structure (for example, a piperidine ring, piperazine ring, morpholine ring, thiomorpholine ring or selenomorpholine ring) together with $R_{111}$, it is preferred that the compound have an adsorptive group acting on silver halides in its molecule. It is more preferred that the compound simultaneously have an intramolecular base moiety, the base moiety and the hydrogen atom linked to each other through an atomic group consisting of 8 or less atoms.

In the general formula (A), it is preferred that $RED_{11}$ represents an alkylamino group, arylamino group, heterocyclic amino group, aryl group, or aromatic or nonaromatic heterocyclic group. As the heterocyclic group, preferred group is, for example, tetrahydroquinolinyl, tetrahydroquinoxalinyl, tetrahydroquinazolinyl, indolyl, indolenyl, carbazolyl, phenoxazinyl, phenothiazinyl, benzothiazolinyl, pyrrolyl, imidazolyl, thiazolidinyl, benzimidazolyl, benzimidazolinyl or 3,4-methylenedioxyphenyl-1-yl. More preferred group is an arylamino group (especially an anilino) or aryl group (especially an phenyl). When $RED_{11}$ represents an aryl group, it is preferred that the aryl group has at least one electron-donating group (the number of electron-donating groups is preferably 4 or less, more preferably 1 to 3). Herein, the electron-donating group specifically refers to a hydroxyl group, alkoxy group, mercapto group, sulfonamido group, acylamino group, alkylamino group, arylamino group, heterocyclic amino group, active methine group, electron-excessive aromatic heterocyclic group (e.g., indolyl, pyrrolyl, imidazolyl, benzimidazolyl, thiazolyl, benzthiazolyl or indazolyl), or a nonaromatic nitrogen-containing heterocyclic group that is bonded to the carbon atom of the general formula (A) via its nitrogen atom (e.g., pyrrolidinyl, indolinyl, piperidinyl, piperazinyl or morpholino). Herein, the active methine group refers to a methine group substituted with two electron-withdrawing groups. Herein, the electron-withdrawing groups refer to an acyl group, alkoxycarbonyl group, aryloxycarbonyl group, carbamoyl group, alkylsulfonyl group, arylsulfonyl group, sulfamoyl group, trifluoromethyl group, cyano group, nitro group and carbonimidoyl group. These two electron-withdrawing groups may be bonded with each other to thereby form a circular structure. When $RED_{11}$ represents an aryl group, the substituent of the aryl group is preferably an alkylamino group, hydroxyl group, alkoxy group, mercapto group, sulfonamido group, active methine group, or nonaromatic nitrogen-containing heterocyclic group that is bonded to the carbon atom of the general formula (A) via its nitrogen atom. More preferably, the substituent is an alkylamino group, hydroxyl group, active methine group, or nonaromatic nitrogen-containing heterocyclic group that is bonded to the carbon atom of the general formula (A) via its nitrogen atom. Most preferably, the substituent is an alkylamino group, or nonaromatic nitrogen-containing heterocyclic group that is bonded to the carbon atom of the general formula (A) via its nitrogen atom.

In the general formula (A), $R_{112}$ preferably represents any of a hydrogen atom, alkyl group, aryl group (e.g., phenyl), alkoxy group (e.g., methoxy, ethoxy or benzyloxy), hydroxyl group, alkylthio group (e.g., methylthio or butylthio), amino group, alkylamino group, arylamino group and heterocyclic amino group. More preferably, $R_{112}$ represents any of a hydrogen atom, alkyl group, alkoxy group, hydroxy group, phenyl group, or alkylamino group.

In the general formula (A), $R_{111}$ preferably represents a group of nonmetallic atoms capable of forming the following specific 5- or 6-membered cyclic structure together with the carbon atom (C) and $RED_{11}$. Specifically, the cyclic structure formed by $R_{111}$ may be, for example, either of a pyrrolidine ring and an imidazolidine ring which correspond to tetrahydro forms of monocyclic 5-membered aromatic rings including a pyrrole ring and imidazole ring, respectively. Also, the cyclic structure may be a tetrahydro or hexahydro form of monocyclic 6-membered aromatic ring such as a pyridine ring, pyridazine ring, pyrimidine ring or pyrazine ring. For example, the cyclic structure may be a piperidine ring, tetrahydropyridine ring, tetrahydropyrimidine ring or piperazine ring. Further, the cyclic structure may be any of a tetralin ring, tetrahydroquinoline ring, tetrahydroisoquinoline ring, tetrahydroquinazoline ring and tetrahydroquinoxaline ring which correspond to tetrahydro forms of condensed-ring of 6-membered aromatic rings including a naphthalene ring, a quinoline ring, isoquinoline ring, quinazoline ring and quinoxaline ring, respectively. Still further, the cyclic structure may be a tetrahydrocarbazole ring which is a tetrahydro form of a tricyclic aromatic carbazole ring, or octahydrophenanthridine ring which is an octahydro form of a phenanthridine ring. The cyclic structure formed by $R_{111}$ is more preferably selected from a pyrrolidine ring, imidazolidine ring, piperidine ring, tetrahydropyridine ring, tetrahydropyrimidine ring, piperazine ring, tetrahydroquinoline ring, tetrahydroquinazoline ring, tetrahydroquinoxaline ring and tetrahydrocarbazole ring. Most preferably, the cyclic structure formed by $R_{111}$ is selected from a pyrrolidine ring, piperidine ring, piperazine ring, tetrahydroquinoline ring, tetrahydroquinazoline ring, tetrahydroquinoxaline ring and tetrahydrocarbazole ring optimally, the cyclic structure formed by $R_{111}$ is selected from a pyrrolidine ring, piperidine ring and tetrahydroquinoline ring.

Now, the general formula (B) will be described in detail.

With respect to the $RED_{12}$ and $L_{12}$ of the general formula (B), not only the meanings but also the preferred ranges thereof are the same as those of the $RED_{11}$ and $L_{11}$ of the general formula (A), respectively. Provided, however, that $RED_{12}$ represents a monovalent group unless the following cyclic structure is formed thereby. For example, the monovalent group can be any of those mentioned with respect to $RED_{11}$. With respect to $R_{121}$ and $R_{122}$, not only the meanings but also the preferred ranges thereof are the same as those of the $R_{112}$ of the general formula (A). $ED_{12}$ represents an electron-donating group. $R_{121}$ and $RED_{12}$; $R_{121}$ and $R_{122}$; or $ED_{12}$ and $RED_{12}$ may be bonded with each other to thereby form a cyclic structure.

In the general formula (B), the electron-donating group represented by $ED_{12}$ refers to a hydroxyl group, alkoxy group, mercapto group, alkylthio group, arylthio group, heterocyclic thio group, sulfonamido group, acylamino group, alkylamino group, arylamino group, heterocyclic amino group, active methine group, electron-excessive aromatic heterocyclic group (e.g., indolyl, pyrrolyl or indazolyl), a nonaromatic nitrogen-containing heterocyclic group that is bonded to the carbon atom of the general formula (B) via its nitrogen atom (e.g., pyrrolidinyl, piperidinyl, indolinyl, piperazinyl or morpholino), or an aryl group substituted with any of these electron-donating groups (e.g., p-hydroxyphenyl, p-dialkylaminophenyl, an o,p-dialkoxyphenyl or 4-hydroxynaphthyl). Herein, the active methine group is the same as described above as a substituent when $RED_{11}$ represents an aryl group. $ED_{12}$ preferably represents a hydroxyl group, alkoxy group, mercapto group, sulfonamido group, alkylamino group, arylamino group, active methine group, electron-excessive aromatic heterocyclic group, nonaromatic nitrogen-containing heterocyclic group that is bonded to the carbon atom of the general formula (B) via its nitrogen atom, or phenyl group substituted with any of these electron-donating groups. More preferably, $ED_{12}$ represents a hydroxyl group, mercapto group, sulfonamido group, alkylamino group, arylamino group, active methine group, nonaromatic nitrogen-containing heterocyclic group that is bonded to the carbon atom of the general formula (B) via its nitrogen atom, or phenyl group substituted with any of these electron-donating groups (e.g., p-hydroxyphenyl, p-dialkylaminophenyl or o,p-dialkoxyphenyl).

In the general formula (B), $R_{121}$ and $RED_{12}$; $R_{122}$ and $R_{121}$; or $ED_{12}$ and $RED_{12}$ may be bonded with each other to thereby form a cyclic structure. The thus formed cyclic structure is a substituted or unsubstituted cyclic structure of a 5- to 7-membered monocyclic or condensed-ring nonaromatic carbon ring or heterocycle. When $R_{121}$ and $RED_{12}$ form a cyclic structure, the thus formed cyclic structure can be, for example, a pyrrolidine ring, pyrroline ring, imidazolidine ring, imidazoline ring, thiazolidine ring, thiazoline ring, pyrazolidine ring, pyrazoline ring, oxazolidine ring, oxazoline ring, indane ring, piperidine ring, piperazine ring, morpholine ring, tetrahydropyridine ring, tetrahydropyrimidine ring, indoline ring, tetralin ring, tetrahydroquinoline ring, tetrahydroisoquinoline ring, tetrahydroquinoxaline ring, tetrahydro-1,4-oxazine ring, 2,3-dihydrobenzo-1,4-oxazine ring, tetrahydro-1,4-thiazine ring, 2,3-dihydrobenzo-1,4-thiazine ring, 2,3-dihydrobenzofuran ring or 2,3-dihydrobenzothiophene ring. When $ED_{12}$ and $RED_{12}$ form a cyclic structure, $ED_{12}$ preferably represents an amino group, alkylamino group or arylamino group. The cyclic structure formed thereby can be, for example, a tetrahydropyrazine ring, piperazine ring, tetrahydroquinoxaline ring or tetrahydroisoquinoline ring. When $R_{122}$ and $R_{121}$ form a cyclic structure, the thus formed cyclic structure can be, for example, a cyclohexane ring or cyclopentane ring.

Those which are more preferred among the compounds of the general formula (A) of the present invention are represented by the following general formulae (10) to (12). Those which are more preferred among the compounds of the general formula (B) are represented by the following general formulae (13) and (14):

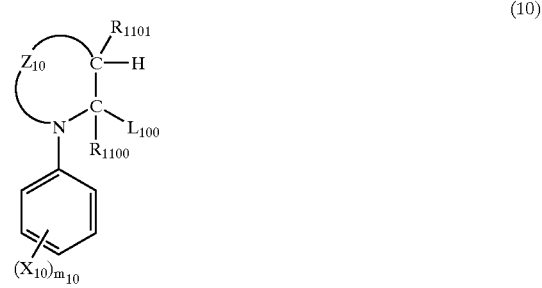

(10)

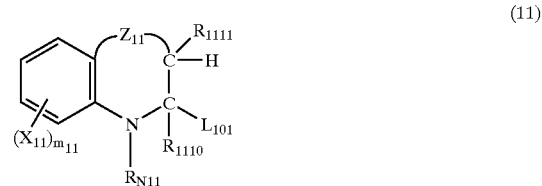

(11)

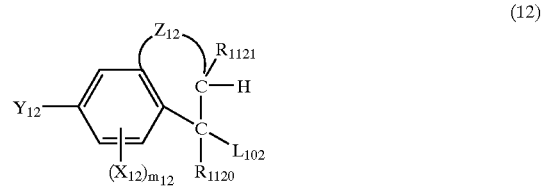

(12)

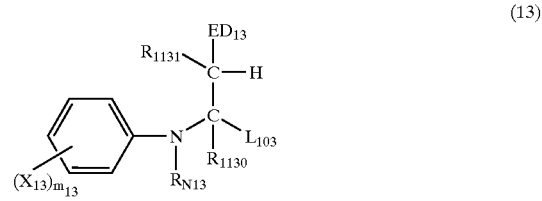

(13)

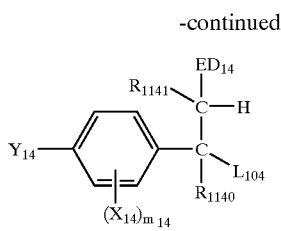

(14)

With respect to the $L_{100}$, $L_{101}$, $L_{102}$, $L_{103}$ and $L_{104}$ of the general formulae (10) to (14), not only the meanings but also the preferred ranges thereof are the same as those of the $L_{11}$ of the general formula (A). With respect to $R_{1100}$ and $R_{1101}$; $R_{1110}$ and $R_{1111}$; $R_{1120}$ and $R_{1121}$; $R_{1130}$ and $R_{1131}$; and $R_{1140}$ and $R_{1141}$; not only the meanings but also the preferred ranges thereof are the same as those of the $R_{122}$ and $R_{121}$, respectively of the general formula (B). With respect to the $ED_{13}$ and $ED_{14}$, not only the meanings but also the preferred ranges thereof are the same as those of the $ED_{12}$ of the general formula (B). Each of $X_{10}$, $X_{11}$, $X_{12}$, $X_{13}$ and $X_{14}$ represents a substituent capable of substituting on the benzene ring. Each of $m_{10}$, $m_{11}$, $m_{12}$, $m_{13}$ and $m_{14}$ is an integer of 0 to 3. When it is 2 or more, a plurality of $X_{10}$, $X_{11}$, $X_{12}$, $X_{13}$ or $X_{14}$ groups may be the same or different. Each of $Y_{12}$ and $Y_{14}$ represents an amino group, alkylamino group, arylamino group, nonaromatic nitrogen-containing heterocyclic group that is bonded to the benzene ring of the general formula (12) or (14) via its nitrogen atom (e.g., pyrrolyl, piperidinyl, indolinyl, piperazino or morpholino), hydroxyl group or alkoxy group.

Each of $Z_{10}$, $Z_{11}$ and $Z_{12}$ represents a nonmetallic atomic group capable of forming a specific cyclic structure. The specific cyclic structure formed by $Z_{10}$ means a cyclic structure corresponding to a tetrahydro form or hexahydro form of 5- or 6-membered, monocyclic or condensed-ring, nitrogen-containing aromatic heterocycle. As such a cyclic structure, there can be mentioned, for example, a pyrrolidine ring, imidazolidine ring, thiazolidine ring, pyrazolidine ring, piperidine ring, tetrahydropyridine ring, tetrahydropyrimidine ring, piperazine ring, tetrahydroquinoline ring, tetrahydroisoquinoline ring, tetrahydroquinazoline ring or tetrahydroquinoxaline ring. The specific cyclic structure formed by $Z_{11}$ refers to a tetrahydroquinoline ring or tetrahydroquinoxaline ring. The specific cyclic structure formed by $Z_{12}$ refers to a tetralin ring, tetrahydroquinoline ring or tetrahydroisoquinoline ring.

Each of $R_{N11}$ and $R_{N13}$ represents a hydrogen atom or substituent capable of substituting on the nitrogen atom. The substituent can be, for example, any of an alkyl group, alkenyl group, alkynyl group, aryl group, heterocyclic group and acyl group, preferably an alkyl group or aryl group.

The substituents capable of substituting on the benzene ring, represented by $X_{10}$, $X_{11}$, $X_{12}$, $X_{13}$ or $X_{14}$, can be, for example, those which may be had by the $RED_{11}$ of the general formula (A). Preferably, the substituents can be a halogen atom, alkyl group, aryl group, heterocyclic group, acyl group, alkoxycarbonyl group, aryloxycarbonyl group, carbamoyl group, cyano group, alkoxy group (including a group containing ethyleneoxy or propyleneoxy repeating units), alkyl-, aryl- or heterocyclic-amino group, an acylamino group, sulfonamido group, ureido group, thioureido group, imido group, alkoxy- or aryloxy-carbonylamino group, nitro group, alkyl-, aryl- or heterocyclic-thio group, alkyl- or aryl-sulfonyl group, a sulfamoyl group, etc. Each of $m_{10}$, $m_{11}$, $m_{12}$, $m_{13}$ and $m_{14}$ is preferably an integer of 0 to 2, more preferably 0 or 1.

Each of $Y_{12}$ and $Y_{14}$ preferably represents an alkylamino group, arylamino group, nonaromatic nitrogen-containing heterocyclic group that is bonded to the benzene ring of the general formula (12) or (14) via its nitrogen atom, hydroxyl group or alkoxy group. More preferably, each of $Y_{12}$ and $Y_{14}$ represents an alkylamino group, 5- or 6-membered nonaromatic nitrogen-containing heterocyclic group that is bonded to the benzene ring of the general formula (12) or (14) via its nitrogen atom, or hydroxyl group. Most preferably, each of $Y_{12}$ and $Y_{14}$ represents an alkylamino group (especially, dialkylamino) or a 5- or 6-membered nonaromatic nitrogen-containing heterocyclic group that is bonded to the benzene ring of the general formula (12) or (14) via its nitrogen atom.

In the general formula (13), $R_{1131}$ and $X_{13}$; $R_{1131}$ and $R_{N13}$; $R_{1130}$ and $X_{13}$; or $R_{1130}$ and $R_{N13}$ may be bonded with each other to thereby form a cyclic structure. In the general formula (14), $R_{1141}$ and $X_{14}$; or $R_{1141}$ and $R_{1140}$; $ED_{14}$ and $X_{14}$; or $R_{1140}$ and $X_{14}$ may be bonded with each other to thereby form a cyclic structure. The thus formed cyclic structure is a substituted or unsubstituted cyclic structure consisting of a 5- to 7-membered monocyclic or condensed-ring nonaromatic carbon ring or heterocycle. When, in the general formula (13), $R_{1131}$ and $X_{13}$ are bonded with each other to thereby form a cyclic structure, or $R_{1131}$ and $R_{N13}$ are bonded with each other to thereby form a cyclic structure, the resultant compound, like that wherein no cyclic structure is formed, is a preferred example of the compounds of the general formula (13). As the cyclic structure formed by $R_{1131}$ and $X_{13}$ in the general formula (13), there can be mentioned, for example, any of an indoline ring (in which case, $R_{1131}$ represents a single bond), tetrahydroquinoline ring, tetrahydroquinoxaline ring, 2,3-dihydrobenzo-1,4-oxazine ring and 2,3-dihydrobenzo-1,4-thiazine ring. Of these, an indoline ring, tetrahydroquinoline ring and tetrahydroquinoxaline ring are especially preferred. As the cyclic structure formed by $R_{1131}$ and $R_{N13}$ in the general formula (13), there can be mentioned, for example, any of a pyrrolidine ring, pyrroline ring, imidazolidine ring, imidazoline ring, thiazolidine ring, thiazoline ring, pyrazolidine ring, pyrazoline ring, oxazolidine ring, oxazoline ring, piperidine ring, piperazine ring, morpholine ring, tetrahydropyridine ring, tetrahydropyrimidine ring, indoline ring, tetrahydroquinoline ring, tetrahydroisoquinoline ring, tetrahydroquinoxaline ring, tetrahydro-1,4-oxazine ring, 2,3-dihydrobenzo-1,4-oxazine ring, tetrahydro-1,4-thiazine ring, 2,3-dihydrobenzo-1,4-thiazine ring, 2,3-dihydrobenzofuran ring and 2,3-dihydrobenzothiophene ring. Of these, a pyrrolidine ring, piperidine ring, tetrahydroquinoline ring and tetrahydroquinoxaline ring are especially preferred.

When, in the general formula (14), $R_{1141}$ and $X_{14}$ are bonded with each other to thereby form a cyclic structure, or $ED_{14}$ and $X_{14}$ are bonded with each other to thereby form a cyclic structure, the resultant compound, like that wherein no cyclic structure is formed, is a preferred example of the compounds of the general formula (14). As the cyclic structure formed by the bonding of $R_{1141}$ and $X_{14}$ in the general formula (14), there can be mentioned, for example, an indane ring, tetralin ring, tetrahydroquinoline ring, tetrahydroisoquinoline ring or indoline ring. As the cyclic structure formed by the bonding of $ED_{14}$ and $X_{14}$, there can be mentioned, for example, a tetrahydroisoquinoline ring or tetrahydrocinnoline ring.

Now, the general formulae (1) to (3) will be described.

In the general formulae (1) to (3), each of $R_1$, $R_2$, $R_{11}$, $R_{12}$ and $R_{31}$ independently represents a hydrogen atom or substituent. With respect to these, not only the meanings but also the preferred ranges thereof are the same as those of the $R_{112}$ of the general formula (A). Each of $L_1$, $L_{21}$ and $L_{31}$ independently represents a split-off group, which can be any of those mentioned as examples in the above description of the $L_{11}$ of the general formula (A). The preferred ranges thereof are also the same as mentioned there. Each of $X_1$ and $X_{21}$ represents a substituent capable of substituting on the benzene ring. Each thereof independently represents any of those mentioned as the substituent examples with respect to substituted $RED_{11}$ of the general formula (A). Each of $m_1$ and $m_{21}$ is an integer of 0 to 3, preferably 0 to 2, and more preferably 0 or 1.

Each of $R_{N1}$, $R_{N21}$ and $R_{N31}$ represents a hydrogen atom or substituent capable of substituting on the nitrogen atom. The substituent can preferably be any of an alkyl group, aryl group and heterocyclic group. These groups may further have a substituent. This substituent can be any of those which may be had by the $RED_{11}$ of the general formula (A). Each of $R_{N1}$, $R_{N21}$ and $R_{N31}$ preferably represents a hydrogen atom, alkyl group or aryl group, more preferably a hydrogen atom or alkyl group.

Each of $R_{13}$, $R_{14}$, $R_{32}$, $R_{33}$, $R_a$ and $R_b$ independently represents a hydrogen atom or substituent capable of substituting on the carbon atom. The substituent can be any of those that may be had by the $RED_{11}$ of the general formula (A). The substituent can preferably be, for example, an alkyl group, aryl group, acyl group, alkoxycarbonyl group, carbamoyl group, cyano group, alkoxy group, acylamino group, sulfonamido group, ureido group, thioureido group, alkylthio group, arylthio group, alkylsulfonyl group, arylsulfonyl group or sulfamoyl group.

In the general formula (1), $Z_1$ represents an atomic group capable of forming a 6-membered ring together with the nitrogen atom and the two carbon atoms of the benzene ring. The 6-membered ring formed with $Z_1$ is a nonaromatic carbon ring condensed with the benzene ring of the general formula (1). Specifically, the atomic group can be any of a tetrahydroquinoline ring, tetrahydroquinoxaline ring and tetrahydroquinazoline ring, which ring structures include the benzene ring to which the atomic group condenced. These may have a substituent. The substituent can be any of those mentioned as examples when the $R_{112}$ of the general formula (A) represents a substituent, and the preferred range thereof is also the same as mentioned there.

In the general formula (1), $Z_1$ preferably represents an atomic group capable of forming a tetrahydroquinoline ring or tetrahydroquinoxaline ring together with the nitrogen atom and the two carbon atoms of the benzene ring.

In the general formula (2), $ED_{21}$ represents an electron-donating group. With respect to the $ED_{21}$, not only the meaning but also the preferred range thereof is the same as those of the $ED_{12}$ of the general formula (B).

In the general formula (2), any two of $R_{N21}$, $R_{13}$, $R_{14}$, $X_{21}$ and $ED_{21}$ may be bonded with each other to thereby form a cyclic structure. The cyclic structure formed by $R_{N21}$ and $X_{21}$ is preferably a 5- to 7-membered nonaromatic carbon ring or heterocycle condensed with the benzene ring of the general formula (2). For example, it can be a tetrahydroquinoline ring, tetrahydroquinoxaline ring, indoline ring or 2,3-dihydro-5,6-benzo-1,4-thiazine ring. Preferably, it is a tetrahydroquinoline ring, tetrahydroquinoxaline ring or indoline ring.

In the general formula (3), when $R_{N31}$ represents a group other than aryl group, $R_a$ and $R_b$ are bonded with each other to thereby form an aromatic ring. Herein, this aromatic ring is an aryl group. Herein, the aromatic group is an aryl group (e.g., phenyl or naphthyl) or an aromatic heterocyclic group (e.g., a pyridine ring, pyrrole ring, quinoline ring or indole ring). An aryl group is preferred. The aromatic ring group may have a substituent. The substituent can be any of those mentioned when $X_1$ of the general formula (1) represents a substituent, and the preferred range thereof is also the same as mentioned there.

In the general formula (3), it is preferred that $R_a$ and $R_b$ be bonded with each other to thereby form an aromatic ring (especially a phenyl group).

In the general formula (3), $R_{32}$ preferably represents, for example, a hydrogen atom, alkyl group, aryl group, hydroxyl group, alkoxy group, mercapto group or amino group. When $R_{32}$ represents a hydroxyl group, it is a preferred mode that simultaneously $R_{33}$ represents an electron-withdrawing group. This electron-withdrawing group refers to any of an acyl group, alkoxycarbonyl group, aryloxycarbonyl group, carbamoyl group, alkylsulfonyl group, arylsulfonyl group, sulfamoyl group, trifluoromethyl group, cyano group, nitro group and carbonimidoyl group. Of these, an acyl group, alkoxycarbonyl group, carbamoyl group and cyano group are preferred.

The compound of type 2 will be described below.

The compound of type 2 is a compound capable of undergoing a one-electron oxidation to thereby form a one-electron oxidation product and capable of, only thereafter, undergoing a bond cleavage reaction to thereby further release another electron. That is, the one-electron oxidation product of the compound of type 2 is capable of being oxidized with a further one-electron oxidation. Herein, the expression "bond cleavage reaction" refers to the cleavage of a carbon-carbon bond, carbon-silicon bond, carbon-hydrogen bond, carbon-boron bond, carbon-tin bond, or carbon-germanium bond. Cleavage of carbon-hydrogen bond may accompany the above bond cleavage.

Provided that the compound of type 2 has, in its molecule, two or more (preferably two to six, more preferably two to four) groups adsorptive to silver halide. More preferably, the compound of type 2 has a nitrogen-containing heterocyclic group substituted with two or more mercapto groups, as its adsorptive group. The adsorptive group will be described later.

Among the compounds of type 2, those preferred are represented by general formula (C):

(C)

Herein, the compound of the general formula (C) is, after the one-electron oxidation of the reducing group represented by $RED_2$, $L_2$ is spontaneously split off through a bond cleavage reaction, namely, the C (carbon atom)— to —$L_2$ bond is cleaved, so that further another electron can be released.

With respect to $RED_2$ of the general formula (C), not only the meaning but also the preferred range thereof is the same as those of the $RED_{12}$ of the general formula (B). $L_2$ has the same meaning as described for $L_{11}$ of the general formula (A). The preferable range of $L_2$ is also the same as that of $L_{11}$. When $L_2$ represents a silyl group, the compound of the general formula (C) has, in its molecule, a nitrogen-containing heterocyclic group that is substituted by two or more mercapto groups, as an adsorptive group. Each of $R_{21}$ and $R_{22}$ represents a hydrogen atom or substituent. With respect to these, not only the meanings but also the preferred ranges thereof are the same as those of the $R_{112}$ of the general formula (A). $RED_2$ and $R_{21}$ may be bonded with each other to thereby form a cyclic structure.

The thus formed cyclic structure is preferably a 5- to 7-membered monocyclic or condensed-ring nonaromatic carbon ring or heterocycle, which may have a substituent. Provided, however, that the cyclic structure is not one corresponding to a tetrahydro form, hexahydro form or octahydro form of an aromatic ring or aromatic heterocycle. The substituent can be any of those mentioned as substituent examples with respect to substituted $RED_{11}$ of the general formula (A). The cyclic structure is preferably a cyclic structure corresponding to a dihydro form of an aromatic or aromatic heterocycle. Preferable example of the cyclic structure, for example, is a 2-pyrroline ring, 2-imidazoline ring, 2-thiazoline ring, 1,2-dihydropyridine ring, 1,4-dihydropyridine ring, indoline ring, benzimidazoline ring, benzothiazoline ring, benzoxazoline ring, 2,3-dihydrobenzothiophene ring, 2,3-dihydrobenzofuran ring, benzo-α-pyran ring, 1,2-dihydroquinoline ring, 1,2-dihydroquinazoline ring and 1,2-dihydroquinoxaline ring.

Of these, a 2-imidazoline ring, 2-thiazoline ring, indoline ring, benzimidazoline ring, benzothiazoline ring, benzoxazoline ring, 1,2-dihydropyridine ring, 1,2-dihydroquinoline ring, 1,2-dihydroquinazoline ring and 1,2-dihydroquinoxaline ring are preferred. An indoline ring, benzimidazoline ring, benzothiazoline ring and 1,2-dihydroquinoline ring are more preferred. An indoline ring is most preferred.

The compound of type 3 will be described below.

The compound of type 3 is a compound characterized in that it can undergo a one-electron oxidation to thereby form a one-electron oxidation product, the one-electron oxidation product being capable of releasing further one or more electrons after going through a subsequent bond-forming reaction. The bond-forming process refers to the formation of bond between atoms, for example, of carbon-carbon bond, carbon-nitrogen bond, carbon-sulfur bond or carbon-oxygen bond.

The compound of type 3 is preferably a compound characterized in that it can undergo a one-electron oxidation to thereby form a one-electron oxidation product, the one-electron oxidation product subsequently reacting with a reactive group moiety (a carbon to carbon double bond moiety, a carbon to carbon triple bond moiety, an aromatic group moiety or a benzo-condensed nonaromatic heterocyclic group moiety) which coexists in the molecule to thereby form a bond, followed by further release of one or more electrons.

The one-electron oxidation product formed by the one-electron oxidation of the compound of type 3 refers to a cation radical species, which may undergo splitting of a proton to thereby form a neutral radical species. This one-electron oxidation product (cation radical species or neutral radical species) reacts with a carbon to carbon double bond moiety, a carbon to carbon triple bond moiety, an aromatic group moiety and a benzo-condensed nonaromatic heterocyclic group moiety which coexists in the molecule, thereby forming interatomic bonds such as carbon-carbon bond, carbon-nitrogen bond, carbon-sulfur bond and carbon-oxygen bond. Thus, a new intramolecular cyclic structure is formed. Simultaneously or thereafter, further one or more electrons are released. The characteristic of the compound of type 3 resides in this respect.

More specifically, the compound of type 3 is characterized in that the bond-forming reaction after the one-electron oxidation leads to formation of a new radical species of cyclic structure, from which the second electron is further released directly or through splitting of a proton to thereby cause an oxidation thereof.

Furthermore, the compounds of type 3 include one exhibiting such a capability that the thus formed two-electron oxidation product subsequently undergoes a tautomeric reaction accompanying a transfer of proton either by way of a hydrolytic reaction or directly to thereby further release one or more, generally two or more, electrons, resulting in an oxidation thereof. Still further, the compounds of type 3 include one exhibiting such a capability that, without undergoing such a tautomeric reaction, further one or more, generally two or more, electrons are directly released from the two-electron oxidation product, resulting in oxidation thereof.

The compound of type 3 is preferably represented by the general formula (D):

$$RED_3\text{—}L_3\text{—}Y_3 \qquad (D)$$

In the general formula (D), $RED_3$ represents a one-electron oxidizable reducing group, $Y_3$ represents a reactive moiety that reacts with one-electron oxidized $RED_3$. Specifically, $Y_3$ represents an organic group having a carbon-carbon double bond moiety, carbon-carbon triple bond moiety, aromatic moiety or benzo-condensed nonaromatic heterocyclic group. $L_3$ represents a linking group that links between $RED_3$ and $Y_3$.

In the general formula (D), $RED_3$ has the same meaning as $RED_{12}$ of the general formula (B).

In the general formula (D), $RED_3$ preferably represents an arylamino group, heterocyclic amino group, aryloxy group, arylthio group, aryl group, or aromatic or nonaromatic heterocyclic group (especially preferably a nitrogen-containing heterocyclic group). More preferably, $RED_3$ represents an arylamino group, heterocyclic amino group, aryl group, or aromatic or nonaromatic heterocyclic group. With respect to the heterocyclic group, it is preferred to use, for example, a tetrahydroquinoline ring group, tetrahydroquinoxaline ring group, tetrahydroquinazoline ring group, indoline ring group, indole ring group, carbazole ring group, phenoxazine ring group, phenothiazine ring group, benzothiazoline ring group, pyrrole ring group, imidazole ring group, thiazole ring group, benzimidazole ring group, benzimidazoline ring group, benzothiazoline ring group or 3,4-methylenedioxyphenyl-1-yl ring group.

An arylamino group (especially anilino), an aryl group (especially phenyl) or an aromatic or nonaromatic heterocyclic group is most preferred as $RED_3$.

When $RED_3$ represents an aryl group, it is preferred that the aryl group has at least one electron-donating group. Herein, the electron-donating group specifically refers to a hydroxyl group, alkoxy group, mercapto group, alkylthio group, sulfonamido group, acylamino group, alkylamino group, arylamino group, heterocyclic amino group, active methine group, electron-excessive aromatic heterocyclic group (e.g., indolyl, pyrrolyl or indazolyl), or a nonaromatic nitrogen-containing heterocyclic group that is bonded to $L_3$ via its nitrogen atom (e.g., pyrrolidinyl, indolinyl, piperidinyl, piperazinyl, morpholino or thiomorpholino). Herein, the active methine group refers to a methine group substituted with two electron-withdrawing groups. Herein, the electron-withdrawing groups refer to an acyl group, alkoxycarbonyl group, aryloxycarbonyl group, carbamoyl group, alkylsulfonyl group, arylsulfonyl group, sulfamoyl group, trifluoromethyl group, cyano group, nitro group and carbonimidoyl group. These two electron-withdrawing groups may be bonded with each other to thereby form a cyclic structure.

When $RED_3$ represents an aryl group, the substituent of the aryl group is preferably an alkylamino group, hydroxyl group, alkoxy group, mercapto group, sulfonamido group, active methine group, or nonaromatic nitrogen-containing heterocyclic group that is bonded to $L_3$ via its nitrogen atom. More preferably, the substituent is an alkylamino group, hydroxyl group, active methine group, or nonaromatic nitrogen-containing heterocyclic group that is bonded to $L_3$ via its nitrogen atom. Most preferably, the substituent is an alkylamino group, or nonaromatic nitrogen-containing heterocyclic group that is bonded to $L_3$ via its nitrogen atom.

When the reactive group represented by $Y_3$ is an organic substituted group having a carbon to carbon double bond or a carbon to carbon triple bond moiety, the substituent of the substituted organic group can preferably be any of, for example, an alkyl group (preferably having 1 to 8 carbon atoms), aryl group (preferably having 6 to 12 carbon atoms), alkoxycarbonyl group (preferably having 2 to 8 carbon atoms), carbamoyl group, acyl group and electron-donating group. Herein, the electron-donating group refers to any of an alkoxy group (preferably having 1 to 8 carbon atoms), hydroxyl group, amino group, alkylamino group (preferably having 1 to 8 carbon atoms), arylamino group (preferably having 6 to 12 carbon atoms), heterocyclic amino group (preferably having 2 to 6 carbon atoms), sulfonamido group, acylamino group, active methine group, mercapto group, an alkylthio group (preferably having 1 to 8 carbon atoms), arylthio group (preferably having 6 to 12 carbon atoms) and aryl group having any of these groups as a substituent (the number of carbon atoms of the aryl moiety is preferably in the range of 6 to 12). The hydroxyl group may be protected with a silyl group, for example, a trimethylsilyloxy group, t-butyldimethylsilyloxy group, triphenylsilyloxy group, triethylsilyloxy group or phenyldimethylsilyloxy group. Examples of the carbon to carbon double bond moiety and carbon to carbon triple bond moiety are vinyl group and ethynyl group, respectively.

When $Y_3$ represents an organic group comprising a carbon to carbon double bond moiety having a substituent, the substituent thereof is more preferably, for example, an alkyl group, phenyl group, acyl group, cyano group, alkoxycarbonyl group, carbamoyl group or electron-donating group. Herein, the electron-donating group preferably refers to any of an alkoxy group, hydroxyl group (which may be protected with a silyl group), amino group, alkylamino group, arylamino group, sulfonamido group, active methine group, mercapto group, alkylthio group and phenyl group having any of these electron-donating groups as a substituent, among the substituents mentioned above.

When the carbon to carbon double bond moiety has a hydroxyl group as a substituent, $Y_3$ contains a partial structure of the formula $>C_1=C_2(-OH)-$. This may be tautomerized into a partial structure of the formula $>C_1H-C_2(=O)-$. Further, in this structure, it is preferred that the substituent on $C_1$ carbon be an electron-withdrawing group. In this instance, $Y_3$ has a partial structure of "active methylene group" or "active methine group". The electron-withdrawing groups capable of providing this partial structure of active methylene group or active methine group are the same as mentioned in the above description of "active methine groups".

When $Y_3$ represents an organic group having a carbon to carbon triple bond moiety having a substituent, the substituent is preferably, for example, an alkyl group, phenyl group, alkoxycarbonyl group, carbamoyl group or electron-donating group. Herein, the electron-donating group preferably refers to any of an alkoxy group, amino group, alkylamino group, arylamino group, heterocyclic amino group, sulfonamido group, acylamino group, active methine group, mercapto group, alkylthio group and phenyl group having any of these electron-donating groups as a substituent.

When $Y_3$ represents an organic group having an aromatic group moiety, the aromatic group is preferably an indole ring group or an aryl group (especially preferably a phenyl group) having an electron-donating group as a substituent. Herein, the electron-donating group preferably refers to a hydroxyl group (the hydroxyl group may be protected with a silyl group), alkoxy group, amino group, alkylamino group, active methine group, sulfonamido group or mercapto group.

When $Y_3$ represents a benzo-condensed organic group having a nonaromatic heterocyclic moiety, the benzo-condensed nonaromatic heterocyclic group is preferably one having an aniline structure as an internal partial structure, which can be, for example, an indoline ring group, 1,2,3,4-tetrahydroquinoline ring group, 1,2,3,4-tetrahydroquinoxaline ring group or 4-quinolone ring group.

In the general formula (D), the reactive group represented by $Y_3$ is more preferably an organic group containing a carbon to carbon double bond moiety, aromatic group moiety or benzo-condensed nonaromatic heterocyclic group. Still more preferably, the reactive group is an organic group having a carbon to carbon double bond moiety, phenyl group having an electron-donating group as a substituent, indole ring group, or benzo-condensed nonaromatic heterocyclic group having an aniline structure as an internal partial structure. Herein, it is more preferred that the carbon to carbon double bond moiety have at least one electron-donating group as a substituent.

When the reactive group represented by $Y_3$ of the general formula (D) has the same partial structure as that of the reducing group represented by $RED_3$ of the general formula (D) as a result of selection within the range described hereinbefore, also, preferred examples of the compounds of the general formula (D) are provided thereby.

In the general formula (D), $L_3$ represents a linking group which links between $RED_3$ and $Y_3$. For example, $L_3$ represents a group consisting of each of, or each of combinations of, a single bond, alkylene group, arylene group, heterocyclic group, $-O-$, $-S-$, $-NR_N-$, $-C(=O)-$, $-SO_2-$, $-SO-$ and $-P(=O)-$. Herein, $R_N$ represents a hydrogen atom, alkyl group, aryl group or heterocyclic group. The linking group represented by $L_3$ may have a substituent. The substituent can be any of those mentioned hereinbefore as substituents which may be had by $RED_{11}$ of the general formula (A). The linking group represented by $L_3$ can engage in linkage by replacing one arbitrary hydrogen atom of each of the groups represented by $RED_3$ and $L_3$ at an arbitrary position thereof.

The linking group represented by $L_3$ of the general formula (D) is preferably such that, when the cationic radical species ($X^+$.) formed as a result of oxidation of $RED_3$ of the general formula (D) or radical species (X.) formed through splitting of proton therefrom reacts with the reactive group represented by $Y_3$ of the general formula (D) to thereby form a bond, the relevant atomic groups engaging therein can form a 3- to 7-membered cyclic structure including $L_3$. From this viewpoint, it is preferred that the radical species ($X^+$. or X.), the reactive group represented by $Y_3$ and the group $L_3$ be linked to each other by a group of 3 to 7 atoms.

As a preferred example of $L_3$, there can be mentioned a divalent linking group selected from a single bond, alkylene group (especially methylene, ethylene or propylene), an arylene group (especially phenylene), $-C(=O)-$ group, $-O-$ group, $-NH-$ group, $-N$(alkyl group)- group and combinations thereof.

Among the compounds of the general formula (D), preferred compounds are represented by the following general formulae (D-1) to (D-4):

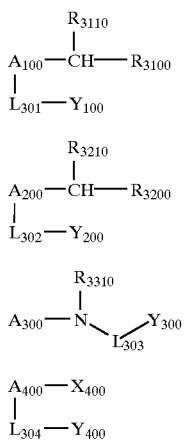

(D-1)
(D-2)
(D-3)
(D-4)

In the general formulae (D-1) to (D-4), each of $A_{100}$, $A_{200}$ and $A_{400}$ represents an arylene group or divalent heterocyclic group, and $A_{300}$ represents an aryl group or a heterocyclic group. The preferred range thereof is the same as that of $RED_3$ of the general formula (D). Each of $L_{301}$, $L_{302}$, $L_{303}$ and $L_{304}$ represents a linking group. With respect to these, not only the meanings but also the preferred ranges thereof are the same as those of $L_3$ of the general formula (D). Each of $Y_{100}$, $Y_{200}$, $Y_{300}$ and $Y_{400}$ represents a reactive group. With respect to these, not only the meanings but also the preferred ranges thereof are the same as those of $Y_3$ of the general formula (D). Each of $R_{3100}$, $R_{3110}$, $R_{3200}$, $R_{3210}$ and $R_{3310}$ represents a hydrogen atom or substituent. Each of $R_{3100}$ and $R_{3110}$ preferably represents a hydrogen atom, alkyl group or aryl group. Each of $R_{3200}$ and $R_{3310}$ preferably represents a hydrogen atom. $R_{3210}$ preferably represents a substituent. This substituent is preferably an alkyl group or aryl group. $R_{3110}$ and $A_{100}$; $R_{3210}$ and $A_{200}$; and $R_{3310}$ and $A_{300}$ may be bonded with each other to thereby form a cyclic structure. The thus formed cyclic structure is preferably, for example, a tetralin ring, indane ring, tetrahydroquinoline ring or indoline ring. $X_{400}$ represents a hydroxyl group, mercapto group or alkylthio group, preferably represents a hydroxyl group or mercapto group, and more preferably represents a mercapto group.

Among the compounds of the general formulae (D-1) to (D-4), the compounds of the general formulae (D-2), (D-3) and (D-4) are preferred. The compounds of the general formulae (D-2) and (D-3) are more preferred.

The compound of type 4 will be described below.

The compound of type 4 is a compound having a circular structure substituted with a reducing group, which compound can undergo a one-electron oxidation of the reducing group and thereafter a cleavage reaction of the circular structure to thereby further release one or more electrons.

In the compound of type 4, the cyclic structure is cleaved after a one-electron oxidation. Herein, the cyclic cleavage reaction refers to the following scheme of reaction:

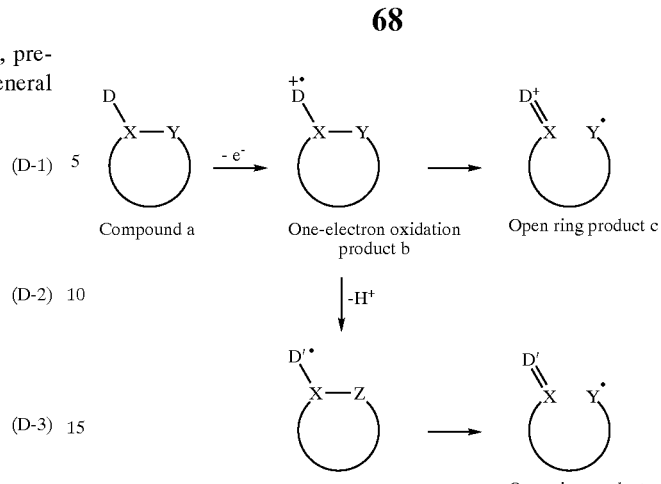

Compound a    One-electron oxidation product b    Open ring product c

Radical intermediate d    Open ring product e

In the formulae, the compound a represents a compound of type 4. In the compound a, D represents a reducing group, and X and Y represent atoms forming a bond of the circular structure which is cleaved after a one-electron oxidation. First, the compound a undergoes a one-electron oxidation to thereby form a one-electron oxidation product b. Then, the D—X single bond is converted to a double bond, and simultaneously the X—Y bond is cleaved to thereby form an open-ring product c. An alternative route wherein a proton is split from the one-electron oxidation product b to thereby form a radical intermediate d, from which an open-ring product e is similarly formed, may be taken. One or more electrons are further released from the thus formed open-ring product c or e. The characteristic of this compound of the present invention resides in this respect.

The cyclic structure of the compound of type 4 refers to a nonaromatic, saturated or unsaturated, monocyclic or condensed-ring, 3- to 7-membered carbon ring or heterocycle. A saturated cyclic structure is preferred, and a 3- or 4-membered ring is more preferred. As preferred cyclic structures, there can be mentioned a cyclopropane ring, cyclobutane ring, oxirane ring, oxetane ring, aziridine ring, azetidine ring, episulfide ring and thietane ring. Of these, a cyclopropane ring, cyclobutane ring, oxirane ring, oxetane ring and azetidine ring are preferred. A cyclopropane ring, cyclobutane ring and azetidine ring are more preferred. The cyclic structure may have a substituent.

The compound of type 4 is preferably represented by the general formula (E) or (F):

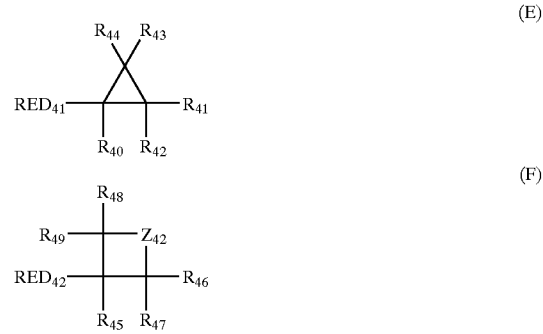

(E)
(F)

With respect to $RED_{41}$ and $RED_{42}$ of the general formulae (E) and (F), not only the meanings but also the preferred ranges thereof are the same as those of $RED_{12}$ of the general formula (B). Each of $R_{40}$ to $R_{44}$ and $R_{45}$ to $R_{49}$ represents a hydrogen atom or substituent. The substituent can be any of those which may be had by $RED_{12}$. In the general formula (F), $Z_{42}$ represents $—CR_{420}R_{421}—$, $—NR_{423}—$ or $—O—$. Each of $R_{420}$ and $R_{421}$ represents a hydrogen atom or substituent, and $R_{423}$ represents a hydrogen atom, alkyl group, aryl group or heterocyclic group.

In the general formula (E), $R_{40}$ preferably represents any of a hydrogen atom, alkyl group, alkenyl group, alkynyl group, aryl group, heterocyclic group, alkoxy group, amino group, alkylamino group, arylamino group, heterocyclic amino group, alkoxycarbonyl group, acyl group, carbamoyl group, cyano group and sulfamoyl group. Of these, a hydrogen atom, alkyl group, aryl group, heterocyclic group, alkoxy group, alkoxycarbonyl group, acyl group and carbamoyl group are more preferred. A hydrogen atom, alkyl group, aryl group, heterocyclic group, alkoxycarbonyl group and carbamoyl group are most preferred.

With respect to $R_{41}$ to $R_{44}$, it is preferred that a case wherein at least one thereof be a donating group. It is also preferred that a case wherein $R_{41}$ and $R_{42}$; or $R_{43}$ and $R_{44}$ be simultaneously electron-withdrawing groups. The electron-withdrawing groups are the same as those mentioned in the above description of active methine group. More preferably, at least one of $R_{41}$ to $R_{44}$ is a donating group. Most preferably, at least one of $R_{41}$ to $R_{44}$ is a donating group while, a group(s) that is not a donating group among $R_{41}$ to $R_{44}$, is (are) a hydrogen atom or alkyl group. The electron-withdrawing groups are the same as those already described with regard to an active methine group.

Herein, the donating group refers to a hydroxyl group, alkoxy group, aryloxy group, mercapto group, acylamino group, sulfonylamino group, active methine group, or group selected from preferred examples of the $RED_{41}$ and $RED_{42}$ groups. As the donating group, there can preferably be used any of an alkylamino group, arylamino group, heterocyclic amino group, 5-membered aromatic heterocyclic group having one nitrogen atom in its ring (the 5-membered aromatic ring may be monocyclic or in the form of condensed rings), a nonaromatic nitrogen-containing heterocyclic group that is bonded to the carbon atom of the general formula (E) via its nitrogen atom and phenyl group substituted with at least one electron-donating group (wherein the electron-donating group refers to a hydroxyl group, alkoxy group, aryloxy group, amino group, alkylamino group, arylamino group, heterocyclic amino group or nonaromatic nitrogen-containing heterocyclic group that is bonded to the carbon atom of the phenyl group via its nitrogen atom). Of these, an alkylamino group, arylamino group, 5-membered aromatic heterocyclic group having one nitrogen atom in its ring (wherein the aromatic heterocycle refers to an indole ring, pyrrole ring or carbazole ring), and a phenyl group substituted with at least one electron-donating group (in particular, a phenyl group substituted with three or more alkoxy groups or a phenyl group substituted with a hydroxyl group, alkylamino group or arylamino group), are more preferred. An arylamino group, 5-membered aromatic heterocyclic group having one nitrogen atom in its ring (wherein the 5-membered aromatic heterocyclic group represents a 3-indolyl group), and a phenyl group substituted with at least one electron-donating group (in particular, a trialkoxyphenyl group or a phenyl group substituted with an alkylamino group or arylamino group), are most preferred.

In the general formula (F), the preferred range of $R_{45}$ is the same as described above with respect to $R_{40}$ of the general formula (E). Each of $R_{46}$ to $R_{49}$ preferably represents any of a hydrogen atom, alkyl group, alkenyl group, alkynyl group, aryl group, heterocyclic group, hydroxyl group, alkoxy group, amino group, alkylamino group, arylamino group, heterocyclic amino group, mercapto group, arylthio group, alkylthio group, acylamino group and sulfonamino group. Of these, a hydrogen atom, alkyl group, aryl group, heterocyclic group, alkoxy group, alkylamino group, arylamino group and heterocyclic amino group are more preferred. Most preferably, each of $R_{46}$ to $R_{49}$ represents a hydrogen atom, alkyl group, aryl group, heterocyclic group, alkylamino group or arylamino group when $Z_{42}$ represents a group of the formula $—CR_{420}R_{421}—$; represents a hydrogen atom, alkyl group, aryl group or heterocyclic group when $Z_{42}$ represents a $—NR_{423}—$; and represents a hydrogen atom, alkyl group, aryl group or heterocyclic group when $Z_{42}$ represents $—O—$.

$Z_{42}$ preferably represents $—CR_{420}R_{421}—$ or $—NR_{423}—$, and more preferably represents $—NR_{423}—$. Each of $R_{420}$ and $R_{421}$ preferably represents any of a hydrogen atom, alkyl group, alkenyl group, alkynyl group, aryl group, heterocyclic group, hydroxyl group, alkoxy group, amino group, mercapto group, acylamino group and sulfonamino group. Of these, a hydrogen atom, alkyl group, aryl group, heterocyclic group, alkoxy group and amino group are more preferred. $R_{423}$ preferably represents a hydrogen atom, alkyl group, aryl group or aromatic heterocyclic group, and more preferably represents methyl, ethyl, isopropyl, t-butyl, t-amyl, benzyl, diphenylmethyl, allyl, phenyl, naphthyl, 2-pyridyl, 4-pyridyl or 2-thiazolyl.

When each of $R_{40}$ to $R_{49}$, $R_{420}$, $R_{421}$ and $R_{423}$ represents a substituent, the total number of carbon atoms of each thereof is preferably 40 or less, more preferably 30 or less, and most preferably 15 or less. These substituents may be bonded with each other or bonded with other moieties (e.g., $RED_{41}$, $RED_{42}$ or $Z_{42}$) of the molecule to thereby form rings.

It is preferred that the compounds of types 1, 3 and 4 according to the present invention be "compounds each having, in its molecule, a group adsorptive to silver halides" or "compounds each having, in its molecule, a partial structure of spectral sensitizing dye". More preferably, the compounds of types 1, 3 and 4 according to the present invention are "compounds each having, in its molecule, a group adsorptive to silver halides". The compound of type 2 is a "compound having, in its molecule, two or more groups adsorptive to silver halides". The compounds of types 1 to 4 are more preferably "compounds each having a nitrogen-containing heterocyclic group substituted with two or more mercapto groups as an adsorptive group."

With respect to the compounds of types 1 to 4 according to the present invention, the adsorptive group to silver halides refers to a group directly adsorbed onto silver halides or a group capable of promoting the adsorption onto silver halides. For example, the adsorptive group is a mercapto group (or a salt thereof), thione group (—C(=S)—), heterocyclic group containing at least one atom selected from a nitrogen atom, sulfur atom, selenium atom and tellurium atom, sulfido group, cationic group or ethynyl group. Provided however that, with respect to the compound of type 2 according to the present invention, a sulfido group is not included in the adsorptive groups thereof.

The terminology "mercapto group (or a salt thereof)" as the adsorptive group means not only a mercapto group (or a salt thereof) per se but also, preferably, a heterocyclic, aryl or alkyl group substituted with at least one mercapto group (or a salt thereof). Herein, the heterocyclic group refers to a 5- to 7-membered, monocyclic or condensed-ring, aromatic or nonaromatic heterocycle. As the heterocyclic group, there can be mentioned, for example, an imidazole ring group, thiazole ring group, oxazole ring group, benzimidazole ring group, benzothiazole ring group, benzoxazole ring group, triazole ring group, thiadiazole ring group, oxadiazole ring group, tetrazole ring group, purine ring group, pyridine ring group, quinoline ring group, isoquinoline ring group, pyrimidine ring group or triazine ring group. The heterocyclic group may be one containing a quaternary nitrogen atom, which may become a mesoion as a result of dissociation of a substituted mercapto group. This heterocyclic group can be, for example, any of an imidazolium ring group, pyrazolium ring group, thiazolium ring group, triazolium ring group, tetrazolium ring group, thiadiazolium ring group, pyridinium ring group, pyrimidinium ring group and triazinium ring group. Of these groups, a triazolium ring group (e.g., 1,2,4-triazolium-3-thiolate ring group) is preferred. The aryl group can be, for example, a phenyl group or naphthyl group. The alkyl group can be a linear, or branched, or cyclic alkyl group having 1 to 30 carbon atoms. When the mercapto group forms a salt, as the counter ion, there can be mentioned, for example, a cation of alkali metal, alkaline earth metal or heavy metal (e.g., $Li^+$, $Na^+$, $K^+$, $Mg^{2+}$, $Ag^+$ or $Zn^{2+}$), an ammonium ion, a heterocyclic group containing a quaternary nitrogen atom, or a phosphonium ion.

The mercapto group as the adsorptive group may further be tautomerized into a thione group. As such, there can be mentioned, for example, a thioamido group (herein a —C(=S)—NH— group) or a group containing a partial structure of the thioamido group, namely, a linear or cyclic thioamido group, thioureido group, thiourethane group or dithiocarbamic acid ester group. As examples of suitable cyclic groups, there can be mentioned, for example, a thiazolidine-2-thione group, oxazolidine-2-thione group, 2-thiohydantoin group, rhodanine group, isorhodanine group, thiobarbituric acid group and 2-thioxo-oxazolidin-4-one group.

The thione groups as the adsorptive group include not only the above thione groups resulting from tautomerization of mercapto groups but also a linear or cyclic thioamido group, thioureido group, thiourethane group and dithiocarbamic acid ester group which cannot be tautomerized into mercapto groups, i.e., not having any hydrogen atom at the a-position of thione group.

The heterocyclic group containing at least one atom selected from a nitrogen atom, sulfur atom, selenium atom and tellurium atom as the adsorptive group is a nitrogen-containing heterocyclic group having an —NH— group capable of forming an iminosilver (>NAg) as a partial structure of the heterocycle, or a heterocyclic group having an "—S—" group or "—Se—" group or "—Te—" group or "=N—" group capable of coordinating to silver ion by coordinate bond as a partial structure of the heterocycle. The former heterocyclic group can be, for example, a benzotriazole group, triazole group, indazole group, pyrazole group, tetrazole group, benzimidazole group, imidazole group or purine group. The latter heterocyclic group can be, for example, a thiophene group, thiazole group, oxazole group, benzothiazole group, benzoxazole group, thiadiazole group, oxadiazole group, triazine group, selenoazole group, benzoselenoazole group, tellurazole group or benzotellurazole group. The former heterocyclic group is preferred.

As the sulfido group as the adsorptive group, there can be mentioned all the groups having a partial structure of "—S—". Preferably, the sulfido group is a group having a partial structure of alkyl (or alkylene) —S— alkyl (or alkylene), aryl (or arylene) —S— alkyl (or alkylene), or aryl (or arylene) —S— aryl (or arylene). This sulfido group may be in the form of a cyclic structure or —S—S— group. As examples of sulfido groups forming a cyclic structure, there can be mentioned groups containing a thiolane ring, 1,3-dithiolane ring, 1,2-dithiolane ring, thiane ring, dithiane ring, tetrahydro-1,4-thiazine ring (thiomorpholine ring) or the like. Among the sulfido groups, groups having a partial structure of alkyl (or alkylene) —S-alkyl (or alkylene) are especially preferred.

The cationic group as the adsorptive group refers to a group containing a quaternary nitrogen atom. For example, it is a group containing an ammonio group or a nitrogen-containing heterocyclic group containing a quaternary nitrogen atom. However, the cationic group does not become part of an atomic group forming a dye structure (for example, cyanine chromophore). Herein, the ammonio group is, for example, a trialkylammonio group, dialkylarylammonio group or alkyldiarylammonio group. For example, as such, there can be mentioned benzyldimethylammonio group, trihexylammonio group or phenyldiethylammonio group. The nitrogen-containing heterocyclic group containing a quaternary nitrogen atom can be, for example, any of pyridinio group, quinolinio group, isoquinolinio group and imidazolio group. Of these, pyridinio group and imidazolio group are preferred. A pyridinio group is most preferred. The nitrogen-containing heterocyclic group containing a quaternary nitrogen atom may have an arbitrary substituent. However, when the nitrogen-containing heterocyclic group is a pyridinio group or imidazolio group, the substituent is preferably selected from, for example, an alkyl group, aryl group, acylamino group, chlorine atom, alkoxycarbonyl group and carbamoyl group. When the nitrogen-containing heterocyclic group is a pyridinio group, the substituent is most preferably a phenyl group.

The ethynyl group as the adsorptive group refers to a —C≡CH group, whose hydrogen atom may be replaced by a substituent.

The above adsorptive groups may have an arbitrary substituent.

Furthermore, examples of suitable adsorptive groups include those listed on pages 4 to 7 of JP-A-11-95355.

In the present invention, it is preferred that the adsorptive group be a nitrogen-containing heterocyclic group substituted with mercapto (e.g., a 2-mercaptothiadiazole group, 3-mercapto-1,2,4-triazole group, 5-mercaptotetrazole group, 2-mercapto-1,3,4-oxadiazole group, 2-mercaptobenzoxazole group, 2-mercaptobenzothiazole group or 1,5-dimethyl-1,2,4-triazolium-3-thiolate group), or a nitrogen-containing heterocyclic group having an —NH— group capable of forming an iminosilver (>NAg) as a partial structure of the heterocycle (e.g., a benzotriazole group, benzimidazole group or indazole group). More preferably, the adsorptive group is a 5-mercaptotetrazole group, 3-mercapto-1,2,4-triazole group or benzotriazole group. Most preferably, the adsorptive group is a 3-mercapto-1,2, 4-triazole group or 5-mercaptotetrazole group.

Among the compounds of the present invention, those having, in its molecule, two or more mercapto groups as partial structures are also especially preferred. Herein, the mercapto group (—SH) may become a thione group when it can be tautomerized. Examples of such compounds may include a compound possessing in its molecule two or more adsorptive groups having the above mercapto group or thione group as a partial structure (e.g., a ring forming thioamido group, alkylmercapto group, arylmercapto group or heterocyclic mercapto group), and a compound possessing at least one adsorptive group having, in the adsorptive group per se, two or more mercapto groups or thione groups as a partial structure (e.g., a dimercapto-substituted nitrogen-containing heterocyclic group).

As examples of adsorptive groups having two or more mercapto groups as a partial structure (e.g., dimercapto-substituted nitrogen-containing heterocyclic groups), there can be mentioned a 2,4-dimercaptopyrimidine group, 2,4-dimercaptotriazine group, 3,5-dimercapto-1,2,4-triazole group, 2,5-dimercapto-1,3-thiazole group, 2,5-dimercapto-1,3-oxazole group, 2,7-dimercapto-5-methyl-s-triazolo[1,5-a]pyrimidine group, 2,6,8-trimercaptopurine group, 6,8-dimercaptopurine group, 3,5,7-trimercapto-s-triazolotriazine group, 4,6-dimercaptopyrazolopyrimidine group and 2,5-dimercaptoimidazole group. Of these, a 2,4-dimercaptopyrimidine group, 2,4-dimercaptotriazine group and 3,5-dimercapto-1,2,4-triazole group are especially preferred.

Although substitution with the adsorptive group may be effected at any position of the general formulae (A) to (F) and general formulae (1) to (3), it is preferred that the substitution be effected at $RED_{11}$, $RED_{12}$, $RED_2$ and $RED_3$ in the general formulae (A) to (D); at $RED_{41}$, $R_{41}$, $RED_{42}$ and $R_{46}$ to $R_{48}$ in the general formulae (E) and (F); and at any arbitrary position except $R_1$, $R_2$, $R_{11}$, $R_{12}$, $R_{31}$, $L_1$, $L_{21}$ and $L_{31}$ in the general formulae (1) to (3). It is more preferred that, in all the general formulae (A) to (F), the substitution be effected at $RED_{11}$ to $RED_{42}$.

The partial structure of spectral sensitizing dye refers to a group containing a chromophore of spectral sensitizing dye, and refers to a residue resulting from removal of an arbitrary hydrogen atom or substituent from a spectral sensitizing dye compound. Although substitution with the partial structure of spectral sensitizing dye may be effected at any position of the general formulae (A) to (F) and general formulae (1) to (3), it is preferred that the substitution be effected at $RED_{11}$, $RED_{12}$, $RED_2$ and $RED_3$ in the general formulae (A) to (D); at $RED_{41}$, $R_{41}$, $RED_{42}$ and $R_{46}$ to $R_{48}$ in the general formulae (E) and (F); and at any arbitrary position except $R_1$, $R_2$, $R_{11}$, $R_{12}$, $R_{31}$, $L_1$, $L_{21}$ and $L_{31}$ in the general formulae (1) to (3). It is more preferred that, in all the general formulae (A) to (F), the substitution be effected at $RED_{11}$ to $RED_{42}$. Preferred spectral sensitizing dyes are those typically employed in color sensitization techniques, which include, for example, cyanine dyes, composite cyanine dyes, merocyanine dyes, composite merocyanine dyes, homopolar cyanine dyes, styryl dyes and hemicyanine dyes. Representative spectral sensitizing dyes are disclosed in Research Disclosure, item 36544, September 1994, the entire contents of which are incorporated herein by reference. These spectral sensitizing dyes can be synthesized by persons skilled in the art to which the invention pertains in accordance with the procedure described in the above Research Disclosure or F. M. Hamer "The Cyanine Dyes and Related Compounds", Interscience Publishers, New York, 1964. Further, all the dyes described on pages 7 to 14 of JP-A-11-95355 (U.S. Pat. No. 6,054,260, the entire contents of which are incorporated herein by reference) per se are applicable.

With respect to the compounds of types 1 to 4 according to the present invention, the total number of carbon atoms is preferably in the range of 10 to 60, more preferably 10 to 50, most preferably 11 to 40, and optimally 12 to 30.

With respect to the compounds of types 1 to 4 according to the present invention, a one-electron oxidation of the compounds is induced upon exposure of the silver halide photographic photosensitive material using the compounds. After the subsequent reaction, another electron, or two or more electrons depending on the type of compound are released to thereby cause further oxidation. The oxidation potential with respect to the first electron is preferably about 1.4 V or below, more preferably 1.0 V or below. This oxidation potential is preferably higher than 0 V, more preferably higher than 0.3 V. Thus, the oxidation potential is preferably in the range of about 0 to about 1.4 V, more preferably about 0.3 to about 1.0 V.

Herein, the oxidation potential can be measured in accordance with the cyclic voltammetry technique. Specifically, a sample compound is dissolved in a solution consisting of a 80%:20% (vol. %) mixture of acetonitrile and water (containing 0.1 M lithium perchlorate), and nitrogen gas is passed through the solution for 10 min. Thereafter, the oxidation potential is measured at 25° C. and at a potential scanning rate of 0.1 V/sec with the use of a glassy carbon disk as a working electrode, a platinum wire as a counter electrode and a calomel electrode (SCE) as a reference electrode. The oxidation potential vs. SCE is determined at the peak potential of cyclic voltammetry wave.

With respect to, among the compounds of types 1 to 4 according to the present invention, those which undergo a one-electron oxidation and, after a subsequent reaction, further release another electron, the oxidation potential at the latter stage is preferably in the range of −0.5 to −2 V, more preferably −0.7 to −2 V, and most preferably −0.9 to −1.6 V.

With respect to, among the compounds of types 1 to 4 according to the present invention, those which undergo a one-electron oxidation and, after a subsequent reaction, further release two or more electrons to thereby effect oxidation, the oxidation potential at the latter stage is not particularly limited. The reason is that the oxidation potential with respect to the second electron cannot be clearly distinguished from the oxidation potential with respect to the third electron et seqq., so that it is often difficult to practically accomplish accurate measuring and distinguishing thereof.

Specific examples of the compounds of types 1 to 4 according to the present invention will be listed below, which however in no way limit the scope of the present invention.

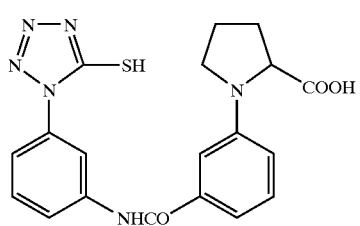

PE 1

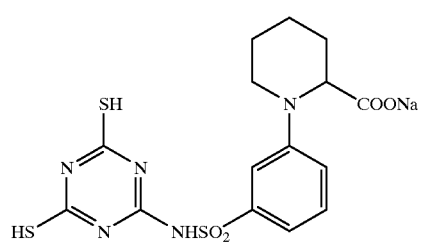

PE 2

PE 3
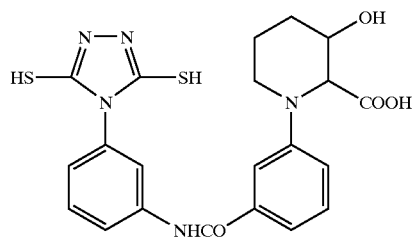
PE 4
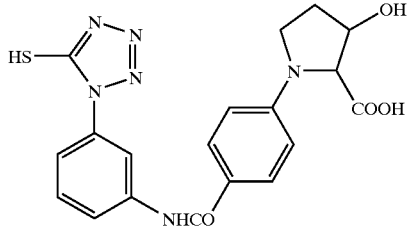
PE 5
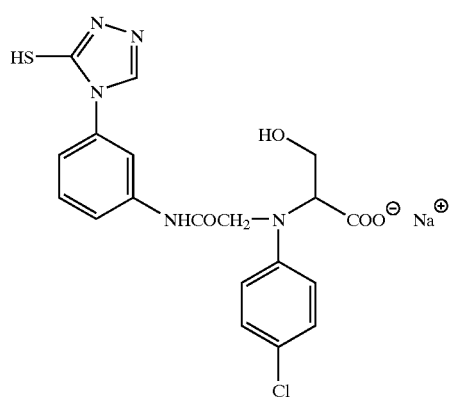
PE 6
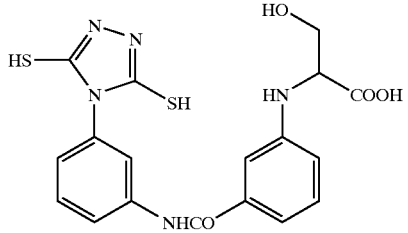
PE 7
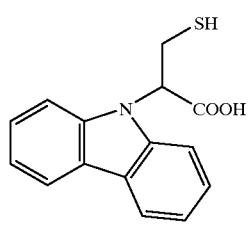
PE 8
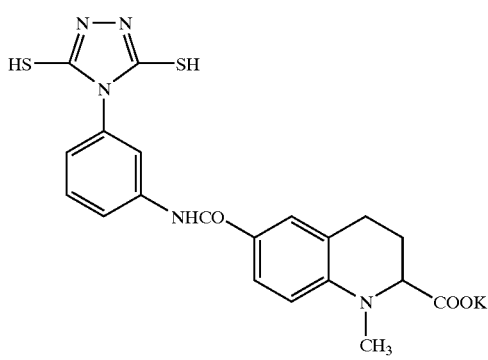
PE 9
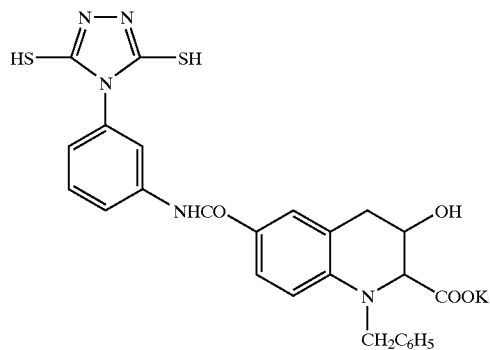
PE 10
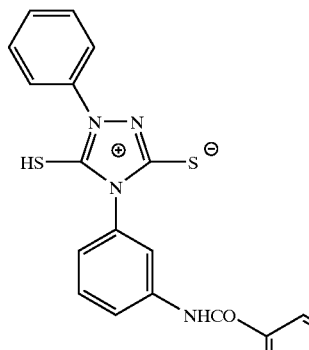
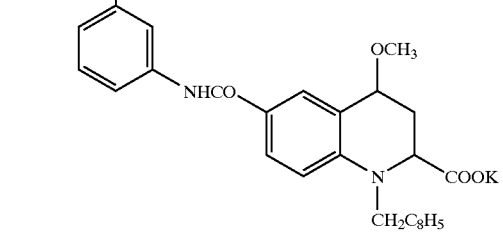

PE 11
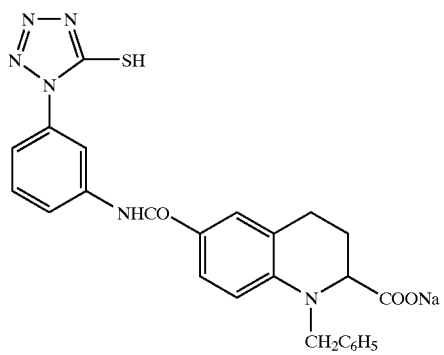
PE 12
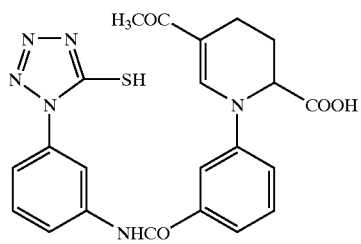
PE 13
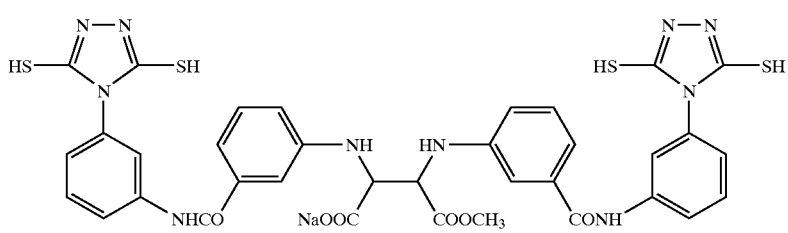
PE 14
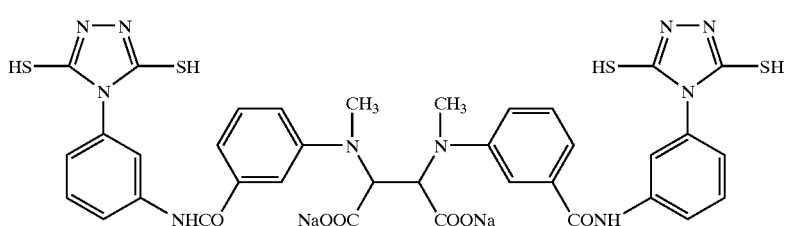
PE 15
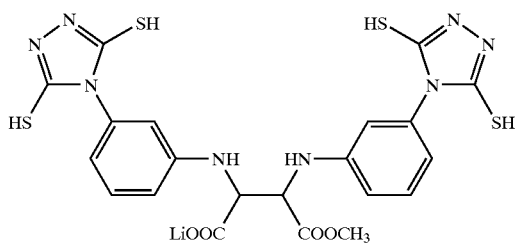
PE 16
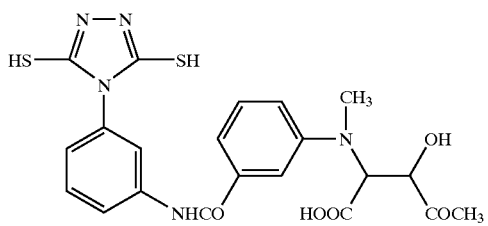
PE 17
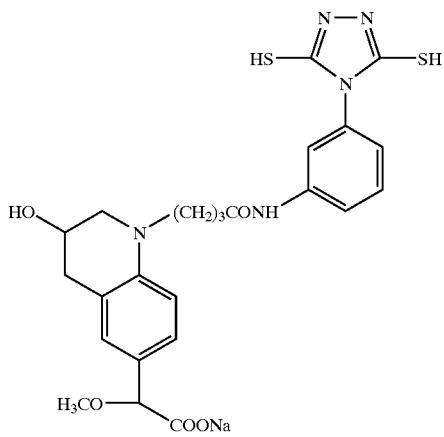
PE 18
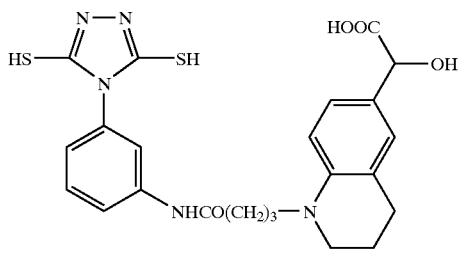

PE 19
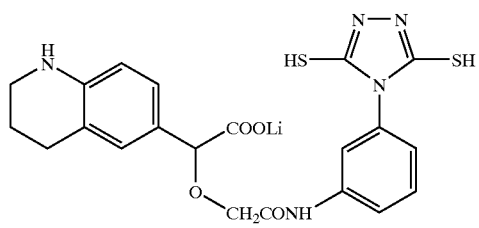
PE 20
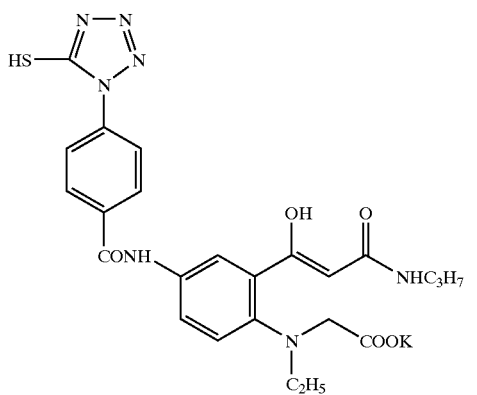
PE 21
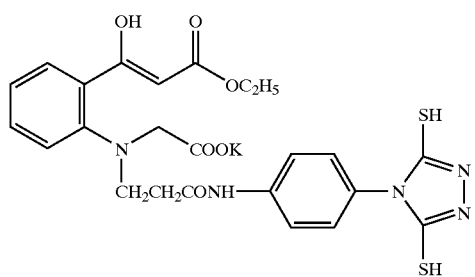
PE 22
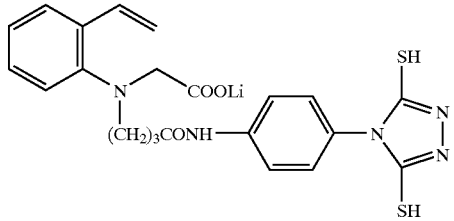
PE 23
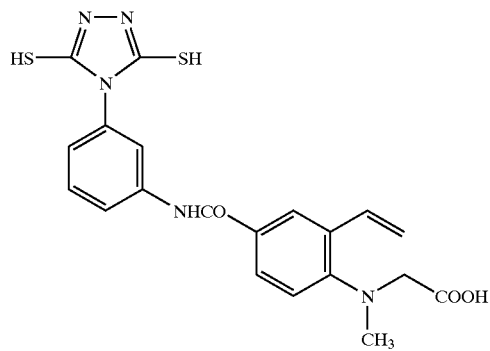
PE 24
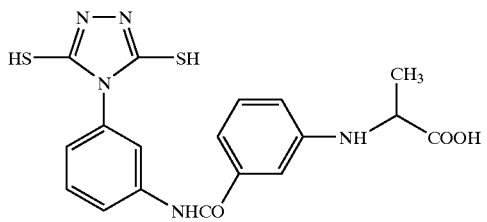
PE 25
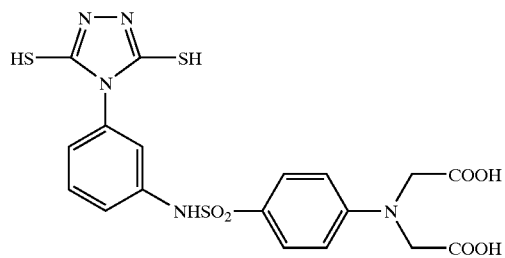
PE 26
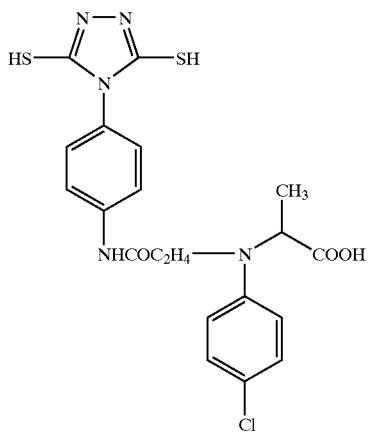

-continued
PE 27
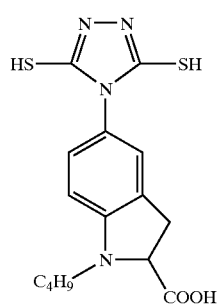
PE 28
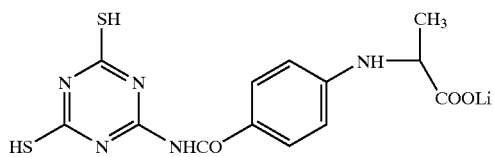
PE 29
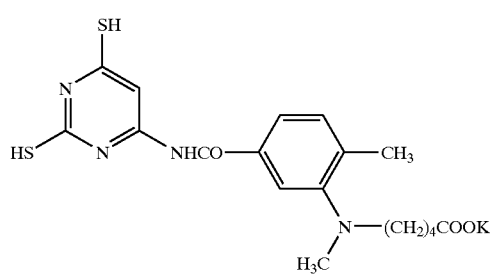
PE 30
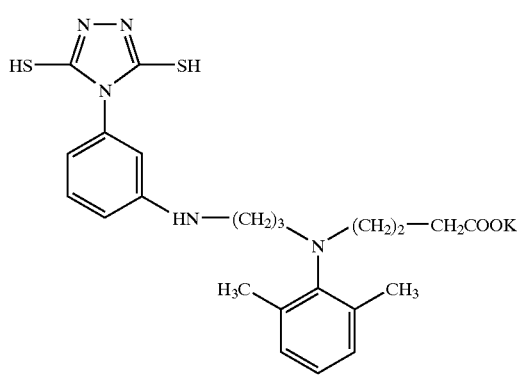
PE 31
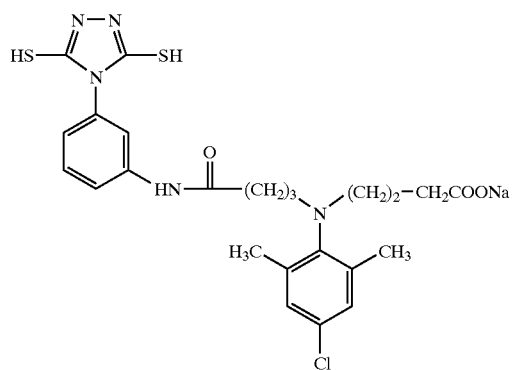
PE 32
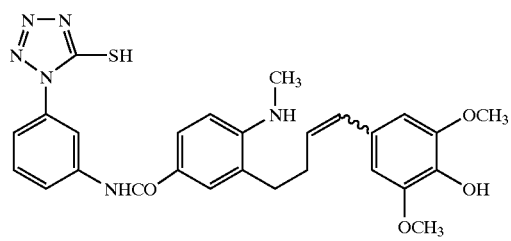
(cis or trans)
PE 33
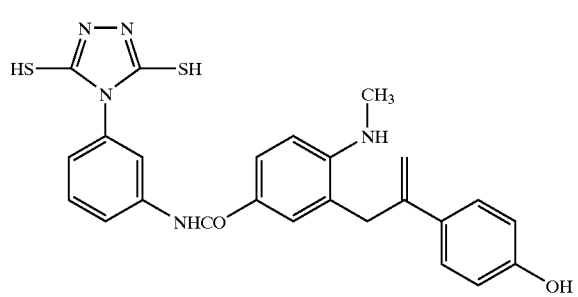

PE 34
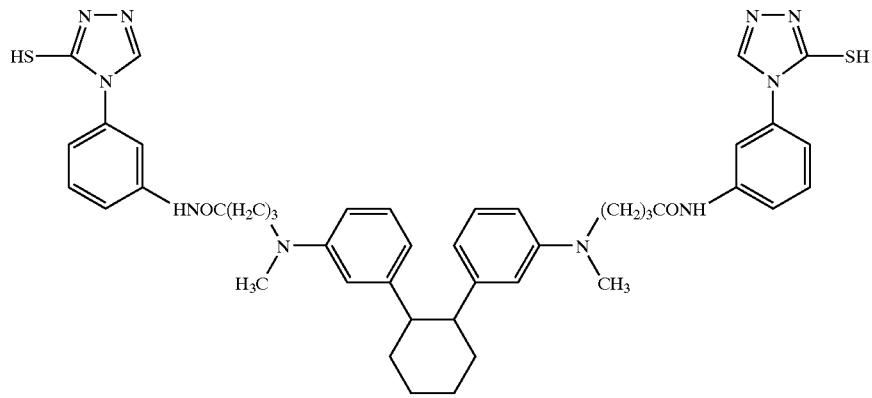
PE 35
PE 36
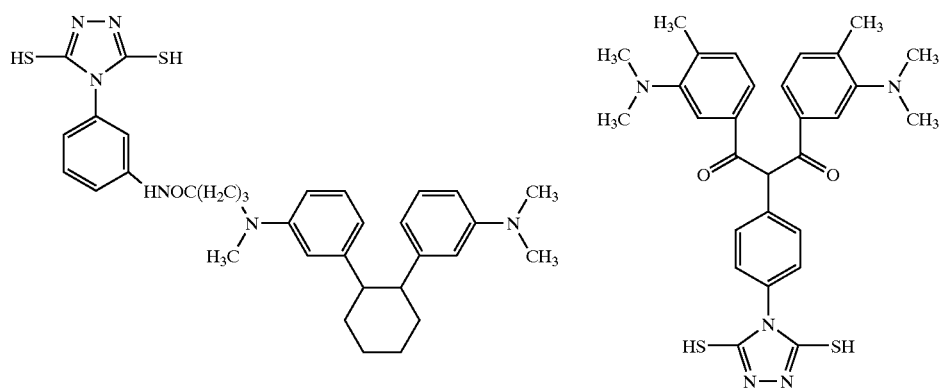
PE 37
PE 38
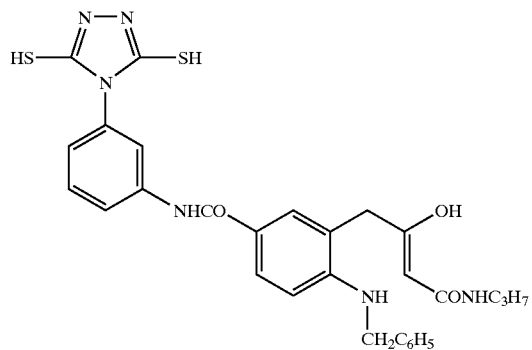
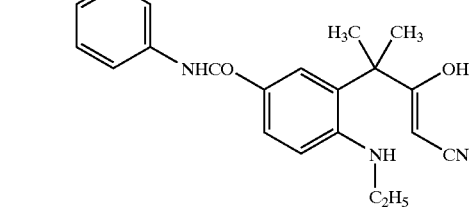
PE 39
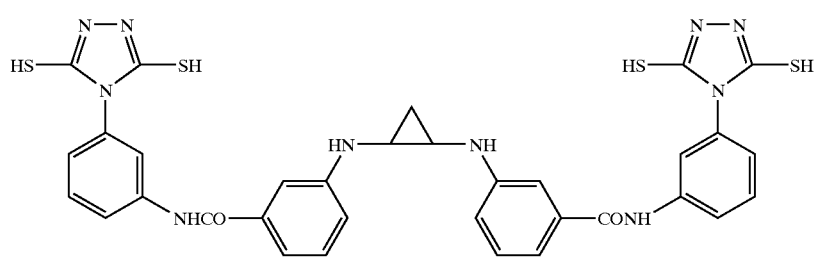

-continued
PE 40
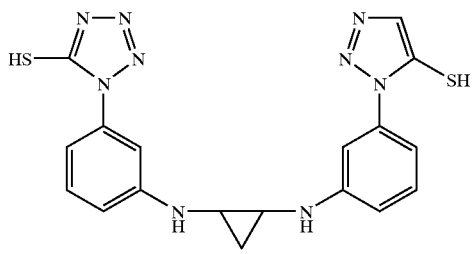
PE 41
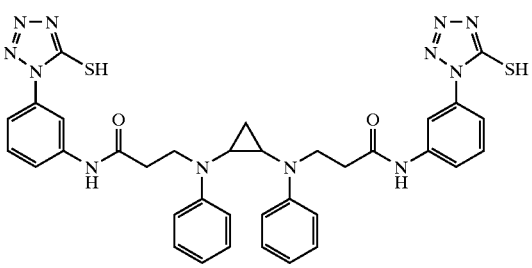
PE 42
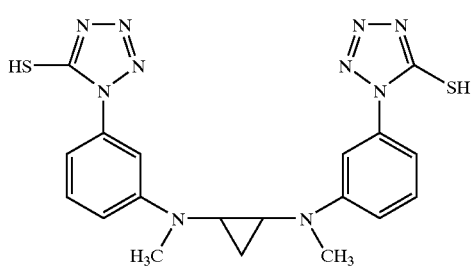
PE 43
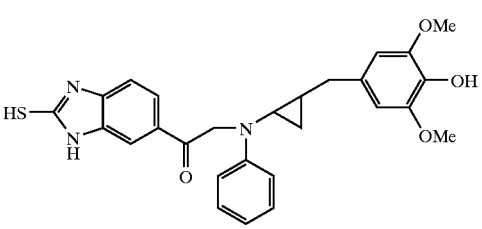
PE 44
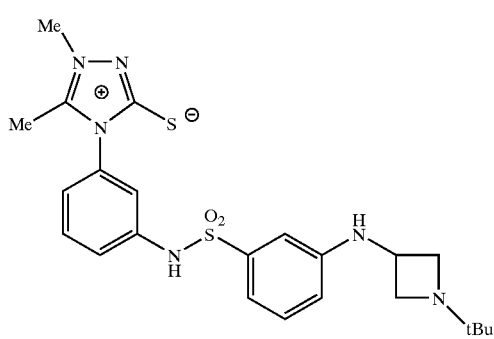
PE 45
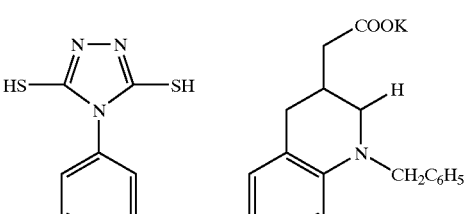
PE 46
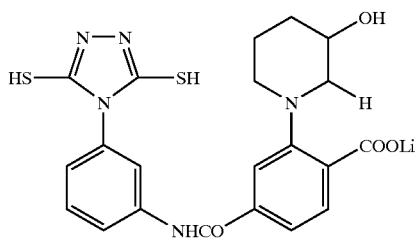
PE 47
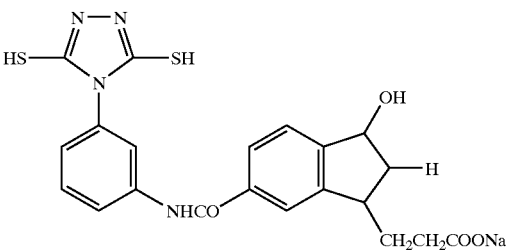
PE 48
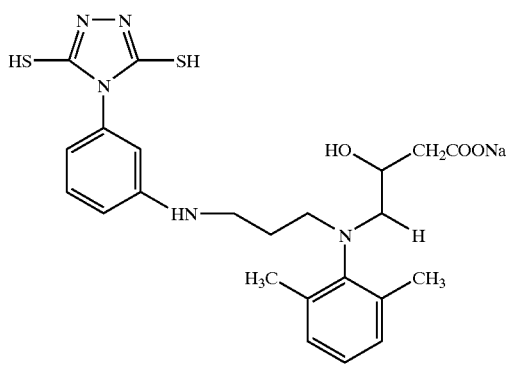
PE 49
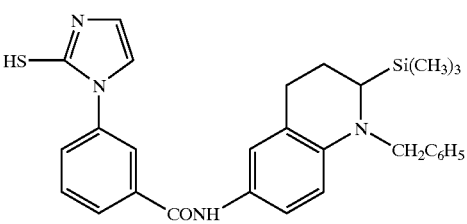

-continued
PE 50
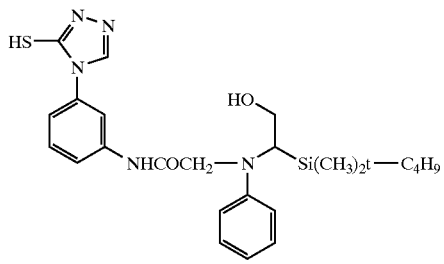
PE 51
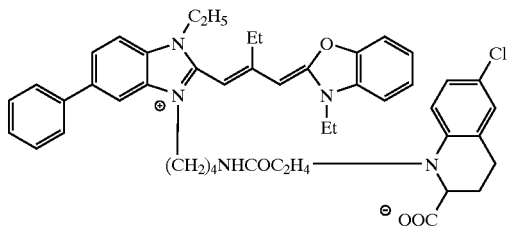
PE 52
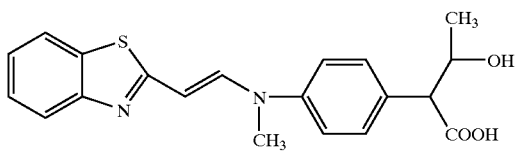
PE 53
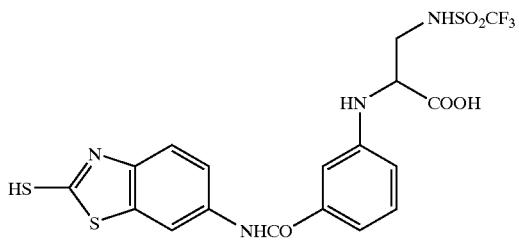
PE 54
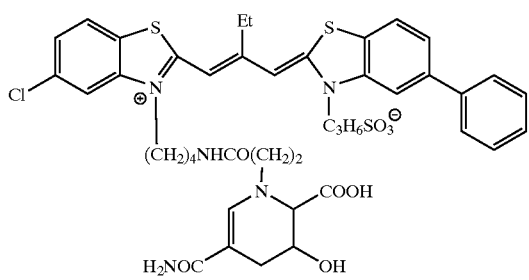
PE 55
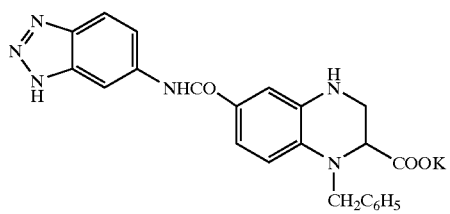
PE 56
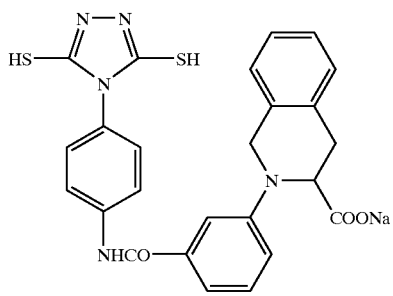
PE 58
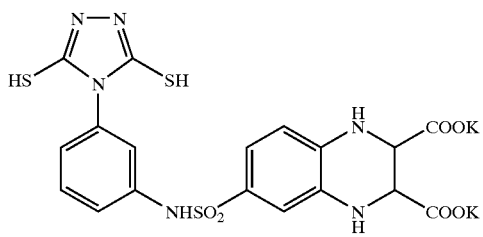
PE 59
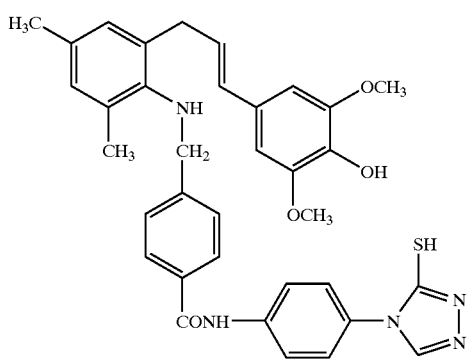
The compounds of types 1 to 4 according to the present invention are the same as those described in detail in JP-A-2003-114487, 2003-114486, 2003-140287 and JP-A-2003-75950, the entire contents of which are incorporated herein by reference. The specific compounds disclosed in the specifications of these patent applications can also be mentioned as specific examples of the compounds of types 1 to 4 according to the present invention. Further, examples of synthesis of the compounds of types 1 to 4 according to the present invention are also the same as those described in these patent applications.

The compound of type 5 will be described below.

The compound of type 5 is represented by X—Y, wherein X represents a reducing group and Y represents a split-off group. The compound of type 5 is such a compound that the reducing group represented by X is capable of undergoing a one-electron oxidation to thereby form a one-electron oxidation product thereof, from which Y is split accompanying a subsequent cleavage reaction of X—Y bond to thereby form an X radical, the X radical capable of further releasing another electron. The reaction when such compound as type 5 is oxidized may be represented by the following formulae:

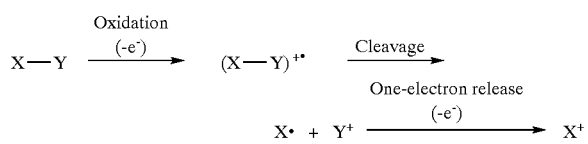

The oxidation potential of the compound of type 5 is preferably in the range of 0 to 1.4 V, more preferably 0.3 to 1.0 V. The oxidation potential of the radical X. formed according to the above reaction formula is preferably in the range of −0.7 to −2.0 V, more preferably −0.9 to −1.6 V.

The compound of type 5 is preferably represented by the general formula (G):

(G)

In the general formula (G), $RED_0$ represents a reducing group. $L_0$ represents a split-off group, and each of $R_0$ and $R_{00}$ represents a hydrogen atom or substituent. $RED_0$ and $R_0$, and also $R_0$ and $R_{00}$ may be bonded with each other to thereby form a ring structure. $RED_0$ represents the same groups as those represented by $RED_2$ of the general formula (C), and the preferred ranges thereof are also the same. $R_0$ and $R_{00}$ respectively represent the same groups as those represented by $R_{21}$ and $R_{22}$ of the general formula (C), and the preferred ranges thereof are also the same. Provided, however, that each of $R_0$ and $R_{00}$ does not represent the same groups as those represented by $L_0$, except for a hydrogen atom. $RED_0$ and $R_0$ may be bonded with each other to thereby form a ring structure. This ring structure can be, for example, any of those formed by bonding between $RED_2$ and $R_{21}$ of the general formula (C), and the preferred ranges thereof are also the same. Examples of the ring structures formed by bonding between $R_0$ and $R_{00}$ include a cyclopentane ring and a tetrahydrofuran ring. $L_0$ of the general formula (G) represents the same groups as those represented by $L_2$ of the general formula (C), and the preferred ranges thereof are also the same.

Each of the compounds of the general formula (G), although preferably having, in its molecule, an adsorptive group to silver halides or a partial structure of spectral sensitizing dye, does not simultaneously have two or more adsorptive groups in its molecule when $L_0$ represents a group other than a silyl group. Provided, however, that with respect to the sulfide group as an adsorptive group, two or more thereof may be had, irrespective of $L_0$.

The adsorptive groups to silver halides possessed by the compounds of the general formula (G) can be, for example, those which may be had by the compounds of types 1 to 4 according to the present invention. Furthermore, the adsorptive groups include a selenoxo group (—C=Se—), a telluroxo group (—C=Te—), a seleno group (—Se—), a telluro group (—Te—) and an active methine group. Herein, the selenoxo group (—C=Se—) and telluroxo group (—C=Te—) respectively refer to Se and Te derivatives of a compound having a thione group (—C=S—) and, as mentioned above with respect to thione groups, may be groups containing a selenoamido group (—C=Se—NH—) and a telluramido group (—C=Te—NH—), respectively. The seleno group (—Se—) and telluro group (—Te—) also respectively refer to Se and Te derivatives of a compound having a sulfido group (—S—), and can be, for example, any of Se and Te substitution products of compounds having a sulfido group. The active methine group refers to a methine group substituted with two electron-withdrawing groups. Herein, the electron-withdrawing group refers to an acyl group, alkoxycarbonyl group, aryloxycarbonyl group, carbamoyl group, alkylsulfonyl group, arylsulfonyl group, sulfamoyl group, trifluoromethyl group, cyano group, nitro group or carbonimidoyl group. The above two electron-withdrawing groups may be bonded with each other to thereby form a ring structure.

The adsorptive groups possessed by the compounds of the general formula (G) are preferably a mercapto group (or its salt), thione group (—C=S—), heterocyclic group containing at least one atom selected from a nitrogen atom, sulfur atom, selenium atom and tellurium atom, and sulfido group. More preferably, the adsorptive groups are a nitrogen-containing heterocyclic group substituted with mercapto, and a nitrogen-containing heterocyclic group having a —NH— group capable of forming iminosilver (>NAg) as a partial structure of the heterocycle. These are the same as those described with respect to the preferred range of adsorptive groups which may be possessed by the compounds of types 1 to 4. Although the site of adsorptive group substitution in the general formula (G) is not limited, the substitution is preferably effected at $RED_0$ or $R_0$, more preferably $RED_0$.

The partial structure of spectral sensitizing dye which may be had by the compounds of the general formula (G) is the same as the partial structure of spectral sensitizing dye which may be had by the compounds of types 1 to 4 according to the present invention.

Specific examples of the compounds of the general formula (G) will be set out below, to which however the present invention is in no way limited.

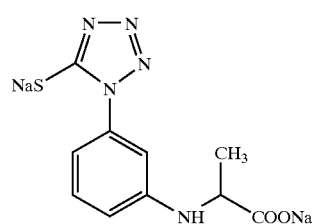

G-1

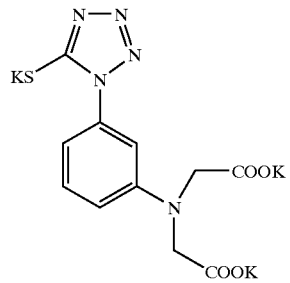
G-2
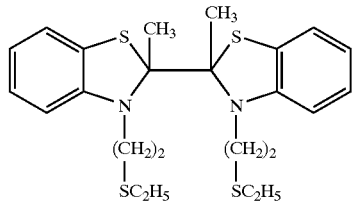
G-7
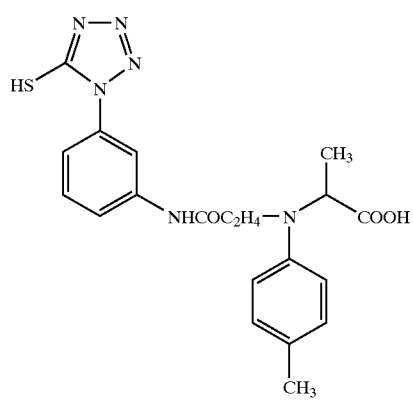
G-3
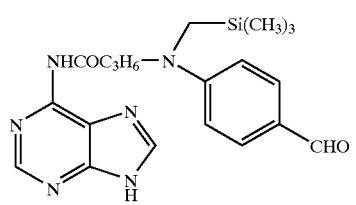
G-8
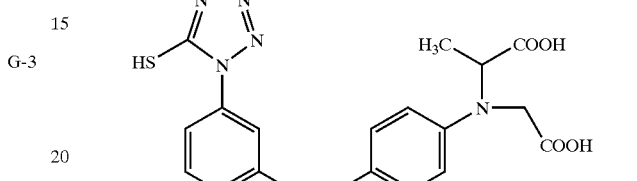
G-9
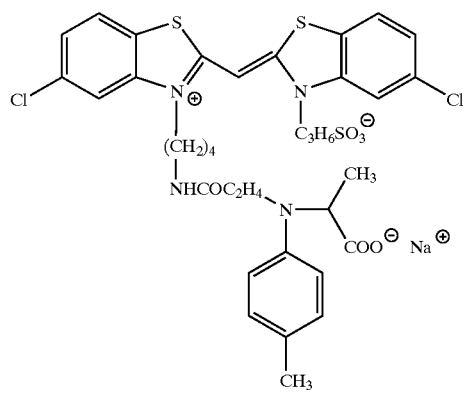
G-4
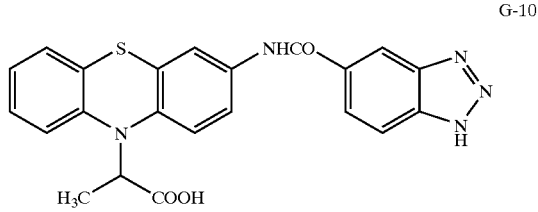
G-10
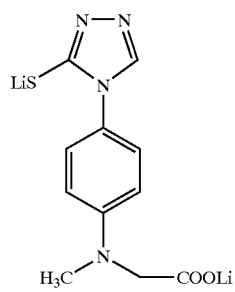
G-5
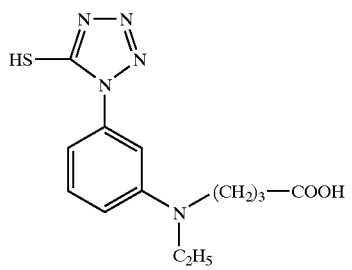
G-11
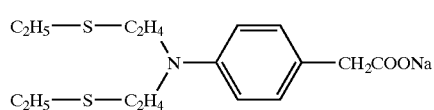
G-6
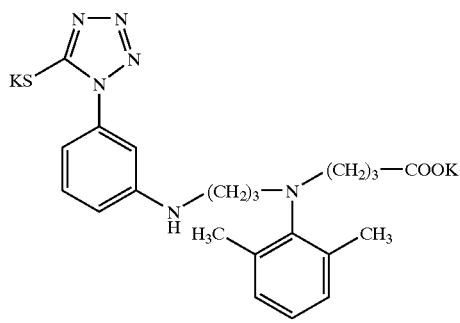
G-12

G-13
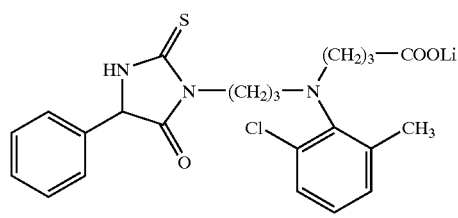
G-14
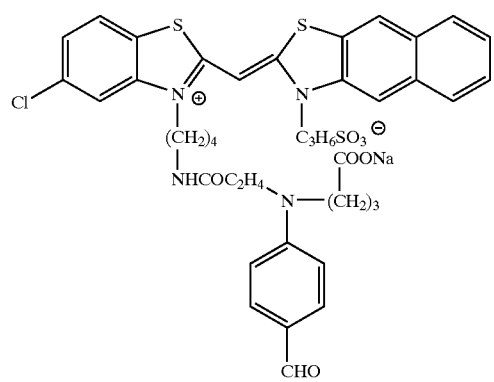
G-15
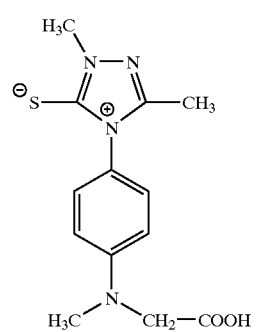
G-16
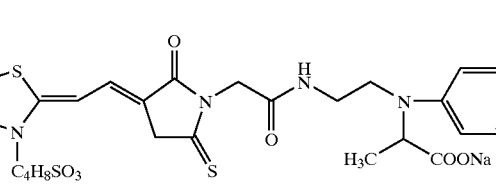
G-17
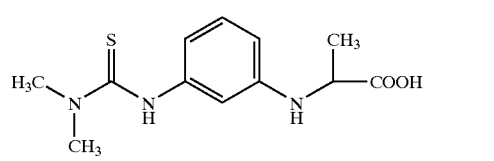
G-18
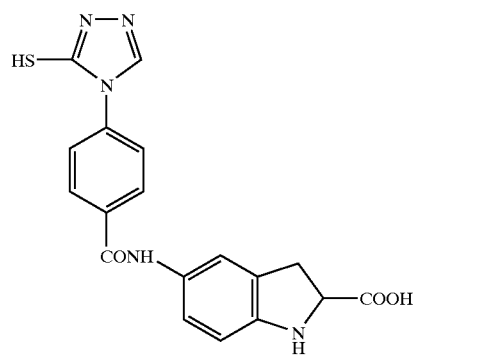
G-19
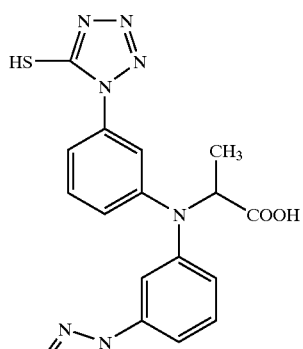
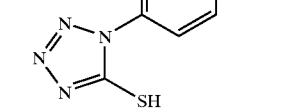
G-20
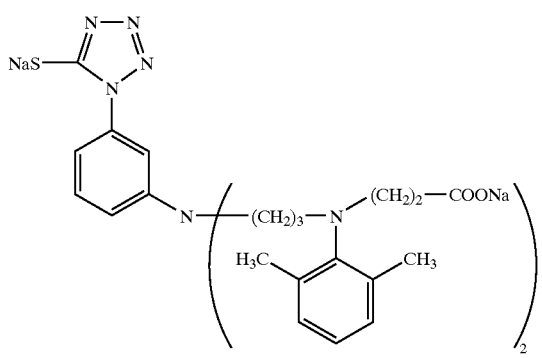
G-21
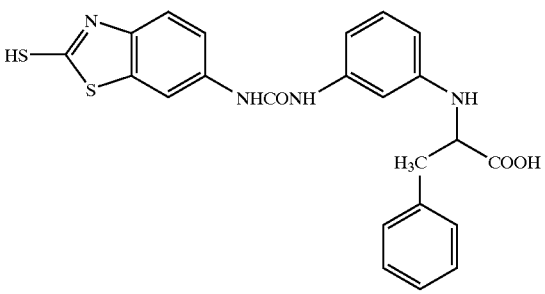
G-22
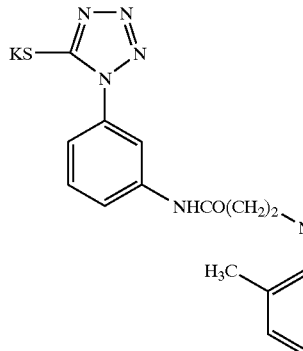
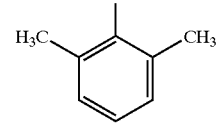

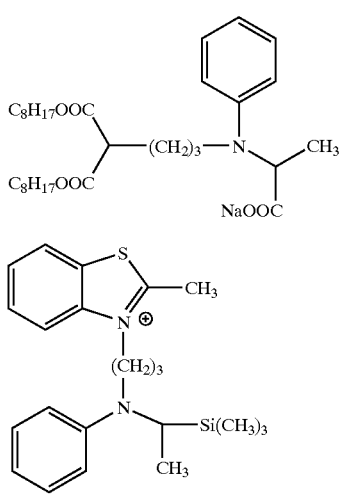

G-23

G-24

Specific examples of the compounds of the general formula (G) further include examples of compounds described as "one photon two electrons sensitizers" or "deprotonating electron-donating sensitizers" in the patent publications and specifications of, for example, JP-A-9-211769 (compounds PMT-1 to S-37 listed in Tables E and F on pages 28 to 32), JP-A's-9-211774 and 11-95355 (compounds INV 1 to 36), Japanese Patent Application KOHYO Publication 2001-500996 (compounds 1 to 74, 80 to 87 and 92 to 122), U.S. Pat. Nos. 5,747,235 and 5,747,236, EP 786692A1 (compounds INV 1 to 35), EP 893732A1 and U.S. Pat. Nos. 6,054,260 and 5,994,051, the entire contents of all of which is incorporated herein by reference.

The compound of types 1 to 5 may be used at any time during emulsion preparation or in photosensitive material manufacturing step, for example, during grain formation, at desalting step, at the time of chemical sensitization, or before coating. The compound may be added separately in a plurality of times during the steps. Preferable addition timing is from the completion of grain formation to before a desalting step, at the time of chemical sensitization (immediately before the initiation of chemical sensitization to immediately after the completion thereof), or before coating. More preferable addition timing is at chemical sensitization or before coating.

The compound of types 1 to 5 according to the present invention may preferably be added by dissolving it to a water or water-soluble solvent such as methanol, ethanol or a mixture of solvents. When the compound is added to water, if the solubility of the compound increases in a case where pH is raised or lowered, the compound may be added to the solvent by raising or lowering the pH thereof.

It is preferable that the compound of types 1 to 5 according to the present invention is used in an emulsion layer, but the compound may be added in a protective layer or interlayer together with the emulsion layer, thereby making the compound diffuse during coating. The addition time of the compound of the invention is irrespective of before or after the addition time of a sensitizing dye. Each of the compounds is preferably contained in a silver halide emulsion layer in an amount of $1 \times 10^{-9}$ to $5 \times 10^{-2}$ mol, more preferably $1 \times 10^{-8}$ to $2 \times 10^{-3}$ mol pre mol of silver halide.

In the silver halide photosensitive material of the present invention, it is preferable to use a compound represented by the general formula (M) or (U). The use of the compound enables to attain further speed enhancement, in addition to the advantage of speed enhancement of the present invention.

The compound weakens the adsorption of a spectral sensitizing dye to the emulsion surface during development to activate latent images that are not usually developed, thereby the advantage of speed enhancement is exhibited. Since the number of development initiating point increases, the advantage of improvement in graininess is also exhibited.

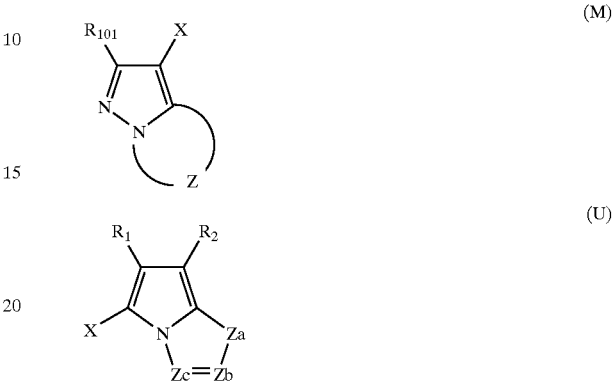

In the general formula (M), $R_{101}$ represents a hydrogen atom or substituent. Z represents a nonmetallic atom group required to form a 5-membered azole ring containing 2 to 4 nitrogen atoms wherein the azole ring may have a substituent (including a condensed ring). X represents a hydrogen atom or substituent.

In the general formula (U), Za represents —NH— or —CH($R_3$)—, each of Zb and Zc independently represents —C($R_4$)= or —N=. Each of $R_1$, $R_2$ and $R_3$ independently represents an electron-withdrawing group having a Hammett substituent constant σp of 0.2 to 1.0. $R_4$ represents a hydrogen atom or substituent. When there are two or more $R_4$s in the general formula (U), these may be the same or different to each other. X represents a hydrogen atom or substituent.

The compound of the present invention will be described in detail below. Of the skeletons represented by formula (M), preferable skeletons are 1H-pyrazolo[1,5-b][1,2,4]triazole and 1H-pyrazolo[5,1-c][1,2,4]triazole, which are represented by formula (M-1) and (M-2), respectively.

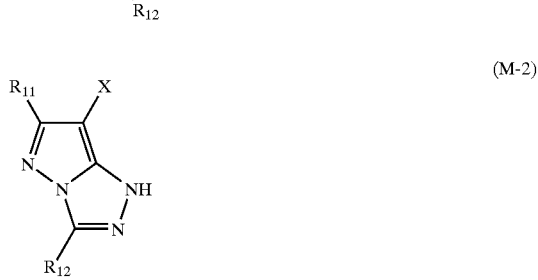

In the formula, $R_{11}$ and $R_{12}$ represent a substituent. X represents a hydrogen atom or substituent.

The substituents $R_{11}$, $R_{12}$ and X in formula (M-1) or (M-2) will be described in detail.

$R_{11}$ preferably represents a halogen atom (e.g., chlorine atom, bromine atom, and fluorine atom), alkyl group (having 1 to 60 carbon atoms, e.g., methyl, ethyl, propyl, iso-butyl, t-butyl, t-octyl, 1-ethylhexyl, nonyl, undecyl, pentadecyl, n-hexadecyl, and 3-decanamidepropyl), alkenyl group (having 2 to 60 carbon atoms, e.g., vinyl, allyl, and oleyl), cycloalkyl group (having 5 to 60 carbon atoms, e.g., cyclopentyl, cyclohexyl, 4-t-butylcyclohexyl, 1-indanyl, and cyclododecyl), aryl group (having 6 to 60 carbon atoms, e.g., phenyl, p-tolyl, and naphthyl), acylamino group (having 2 to 60 carbon atoms, e.g., acetylamino, n-butanamide, octanoylamino, 2-hexyldecanamide, 2-(2',4'-di-t-amylphenoxy)butanamide, benzoylamino, and nicotinamide), sulfonamide group (having 1 to 60 carbon atoms, e.g., methanesulfonamide, octanesulfonamide, and benzenesulfonamide), ureide group (having 2 to 60 carbon atoms, e.g., decylaminocarbonylamino, and di-n-octylaminocarbonylamino), urethane group (having 2 to 60 carbon atoms, e.g., dodecyloxycarbonylamino, phenoxycarbonylamino, and 2-ethylhexyloxycarbonylamino), alkoxy group (having 1 to 60 carbon atoms, e.g., methoxy, ethoxy, butoxy, n-octyloxy, hexadecyloxy, and methoxyethoxy), aryloxy group (having 6 to 60 carbon atoms, e.g., phenoxy, 2,4-di-t-amylphenoxy, 4-t-octylphenoxy, and naphthoxy), alkylthio group (having 1 to 60 carbon atoms, e.g., methylthio, ethylthio, butylthio, and hexadecylthio), arylthio group (having 6 to 60 carbon atoms, e.g., phenylthio, and 4-dodecyloxyphenylthio), acyl group (having 1 to 60 carbon atoms, e.g., acetyl, benzoyl, butanoyl, and dodecanoyl), sulfonyl group (having 1 to 60 carbon atoms, e.g., methanesulfonyl, butanesulfonyl, and toluenesulfonyl), cyano group, carbamoyl group (having 1 to 60 carbon atoms, e.g., N,N-dicyclohexylcarbamoyl), sulfamoyl group (having 0 to 60 carbon atoms, e.g., N,N-dimethylsulfamoyl), hydroxy group, sulfo group, carboxyl group, nitro group, alkylamino group (having 1 to 60 carbon atoms, e.g., methylamino, diethylamino, octylamino, and octadecylamino), arylamino group (having 6 to 60 carbon atoms, e.g., phenylamino, naphthylamino, and N-methyl-N-phenylamino), heterocyclic group (having 0 to 60 carbon atoms, preferably 3- to 8-membered, and more preferably, 5- to 6-membered heterocyclic group including a hetero atom, which forms a ring, selected from the group consisting of a nitrogen atom, oxygen atom, and sulfur atom, and more preferably, including a carbon atom as the ring-forming atoms in addition to the hetero atoms, 3- to 8-ring member, more preferably 5- to 6-rign member, e.g., a group indicated as an example of term X described later), and an acyloxy group (having 1 to 60 carbon atoms, e.g., formyloxy, acetyloxy, myristoyloxy, and benzoyloxy).

Of the above, the alkyl group, cycloalkyl group, aryl group, acylamino group, ureide group, urethane group, alkoxy group, aryloxy group, alkylthio group, arylthio group, acyl group, sulfonyl group, cyano group, carbamoyl group, and sulfamoyl group include those having a substituent Examples of the substituent are an alkyl group, cycloalkyl group, aryl group, acylamino group, ureide group, urethane group, alkoxy group, aryloxy group, alkylthio group, arylthio group, acyl group, sulfonyl group, cyano group, carbamoyl group and sulfamoyl group.

Of these substituents, preferable examples of $R_{11}$ are an alkyl group, aryl group, alkoxy group, and aryloxy group. An alkyl group, alkoxy group and aryloxy group are more preferably. A branched alkyl group is especially preferable.

$R_{12}$ preferably represents the substituents as indicated for $R_{11}$. More preferable examples of the substituents are an alkyl group, aryl group, heterocyclic group, alkoxy group, and aryloxy group. $R_{12}$ still more preferably represents an alkyl group and substituted aryl group, and most preferably, a substituted aryl group. Compounds represented by general formulas (M-3) and (M-4) are preferable. In general formulas (M-3) and (M-4), the substitution position of —NHSO$_2$R$_{13}$ is not particularly limited, but m- and p-positions are preferable, and p-position is more preferable.

The sum of the carbon atoms of the substituent including $R_{101}$, X and Z on the azole ring is not particularly limited but 13 to 60 is preferable, and 20 to 50 is more preferable in order to enhance adsorptivity to emulsion grains, and enhance the improving effect of speed/graininess ratio.

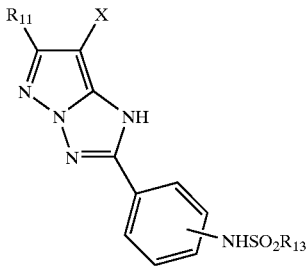

(M-3)

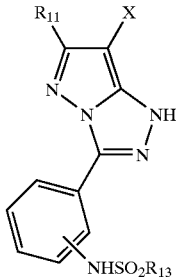

(M-4)

In the formula, $R_{11}$ and X have the same meanings as those defined in general formulae (M-1) and (M-2). $R_{13}$ represents a substituent. Examples of preferable substituents represented by $R_{13}$ are the substituents enumerated above for $R_{11}$. Examples of more preferable substituents are a substituted aryl group, and a substituted or unsubstituted alkyl group. As the substituent in this case, the substituents enumerated above as examples of $R_{11}$ are preferable.

X represents a hydrogen atom or substituent. Preferable examples of the substituents are those enumerated as examples of $R_{11}$. More preferable examples of the substituents represented by X are an alkyl group, alkoxycarbonyl group, carbamoyl group or a group which leaves by reaction with an oxidized developing agent. Examples of the leaving group are a halogen atom (fluorine, chlorine, bromine, etc.), alkoxy group (ethoxy, methoxycarbonylmethoxy, carboxypropyloxy, methanesulfonylethoxy, perfluoropropoxy, etc.), aryloxy group (4-carboxyphenoxy, 4-(4-hydroxyphenylsulfonyl)phenoxy, 4-methanesulfonyl-3-carboxyphenoxy, 2-methanesulfonyl-4-acetylsulfamoylphenoxy, etc.), acyloxy group (acetoxy, benzoyloxy, etc.), sulfonyloxy group (methanesulfonyloxy, benzenesulfonyloxy, etc.), acylamino group (heptafluorobutyrylamino, etc.), sulfonamide group (methanesulfonamide, etc.), alkoxycarbonyloxy group (ethoxycarbonyloxy, etc.), carbamoyloxy group (diethylcarbamoyloxy, piperidinocarbonyloxy, morpholinocarbonyloxy, etc.), alkylthio group (2-carboxyethylthio, etc.), arylthio group (2-octyloxy-5-t-octylphenylthio, 2-(2,4-di-t-amylphenoxy)butyrylaminophenylthio, etc.), heterocyclic thio group (1-phenyltetrazolylthio, 2-benzimidazolylthio, etc.), heterocyclic oxy group (2-pyridyloxy, 5-nitro-2-pyridyloxy, etc.), 5- or 6-membered, nitrogen-containing heterocyclic group (1-triazolyl, 1-imidazolyl, 1-pyrazolyl, 5-chloro-1-tetrazolyl, 1-benzotriazolyl, 2-phenylcarbamoyl-1-imidazolyl, 5,5-dimethylhydantoin-3-yl, 1-benzylhydantoin-3-yl, 5,5-dimethyloxazolidine-2,4-dione-3-yl, purine, etc.), azo group (4-methoxyphenylazo, 4-pivaloylaminophenylazo, etc.), etc.

The substituent represented by X is preferably an alkyl group, alkoxycarbonyl group, carbamoyl group, halogen atom, alkoxy group, aryloxy group, alkylthio group, arylthio group, or a 5- or 6-membered, nitrogen-containing heterocyclic group which bonds to the coupling active position with a nitrogen atom, and more preferably an alkyl group, carbamoyl group, halogen atom, substituted aryloxy group, substituted arylthio group, alkylthio group, or 1-pyrazolyl group.

The compound preferably used in the present invention which is represented by general formulae (M-1) and (M-2) may form a polymer which is greater than or equal to a dimer through $R_{11}$ and $R_{12}$, or may bond to a macromolecular chain. In the present invention, formula (M-1) is preferable and formula (M-3) is more preferable.

Next, general formula (U) will be described. The formula (U) of the present invention is specifically expressed by the following formulae (U3) to (U10):

(U3)
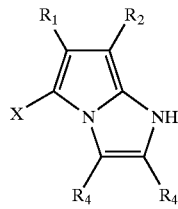

(U4)
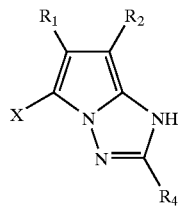

(U5)
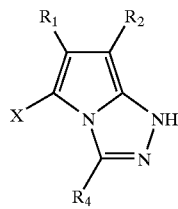

(U6)
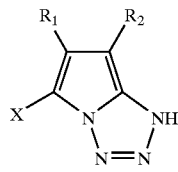

(U7)
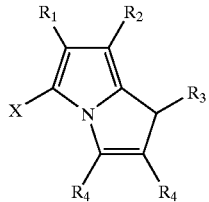

(U8)
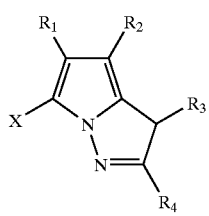

(U9)
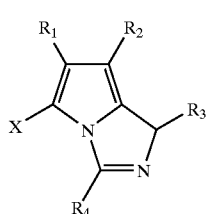

(U10)
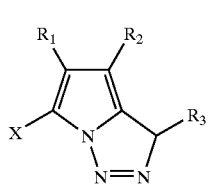

In the formulae, $R_1$ to $R_4$ and X have the same meanings as those defined in formula (U).

In the present invention, the compounds represented by formulae (U3), (U4), (U5) and (U8) are preferable, and the compound represented by (U4) is especially preferable.

In formula (U), the substituent represented by $R_1$, $R_2$ and $R_3$ is an electron attractive group having a Hammett constant σp value of 0.20 to 1.0, preferably an electron attractive group having a σp value of 0.20 to 0.8. Hammett's rule is an empirical rule proposed by L. P. Hammett in 1935 in order to quantitatively argue the effects of substituents on reaction or equilibrium of benzene derivatives. The rule is widely regarded as appropriate these days. The substituent constants obtained by the Hammett rule include a σp value and a σm value, and these values are described in a large amount of general literature. For example, the values are described in detail in J. A. Dean ed., "Lange's Handbook of Chemistry," the 12th edition, 1979 (McGraw-Hill), "The Extra Number of The Domain of Chemistry (KAGAKUNO RYOIKI ZOUKAN)," Vol. 122, pages 96 to 103, 1979 (Nanko Do) and Chemical Reviews, Vol. 91, pp. 165–195 (1991).

In the present invention, $R_1$, $R_2$, and $R_3$ are defined by the Hammett constant σp value. However, this does not mean that $R_1$, $R_2$, and $R_3$ are limited to substituents having the known values stated in the above literature. That is, the present invention includes, of course, substituents having values that fall within the above range when measured on the basis of Hammett's rule even if they are unknown in literature.

Examples of $R_1$, $R_2$, and $R_3$, as the electron attractive group having a σp value of 0.2 to 1.0, are an acyl group, alkoxycarbonyl group, aryloxycarbonyl group, carbamoyl group, cyano group, nitro group, dialkylphosphono group, diarylphosphono group, diarylphosphinyl group, alkylsulfinyl group, arylsulfinyl group, alkylsulfonyl group, arylsulfonyl group, etc. Of these substituents, those capable of further having substituents can further have substituents to be enumerated later for $R_4$.

$R_1$, $R_2$, and $R_3$ preferably represent an acyl group, alkoxycarbonyl group, aryloxycarbonyl group, carbamoyl group, cyano group, and sulfonyl group, and more preferably, an cyano group, acyl group, alkoxycarbonyl group, aryloxycarbonyl group, and carbamoyl group.

A preferable example of the combination of $R_1$ and $R_2$, is one wherein $R_1$ represents a cyano group and $R_2$ represents an alkoxycarbonyl group.

$R_4$ represents a hydrogen atom or substituent. Examples of the substituent are those enumerated above for $R_{11}$.

Preferable examples of the substituents represented by $R_4$ are an alkyl group, aryl group, heterocyclic group, alkoxy group, aryloxy group, and acylamino group. An alkyl group and substituted aryl group are more preferable, and a substituted aryl group is most preferable. Examples of the substituent in this case are those mentioned above. X has the same meaning as that defined in formula (M).

Representative examples of the compounds represented by the general formula (M) and general formula (U) preferably used in the present invention are shown below, but the present invention is not limited to these examples.

DA(1)

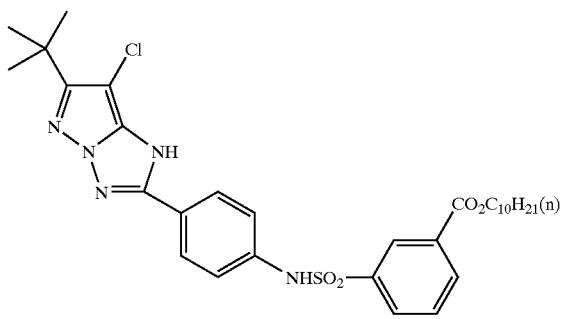

DA(2)

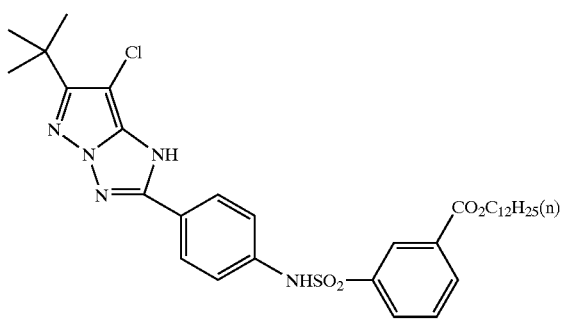

DA(3)

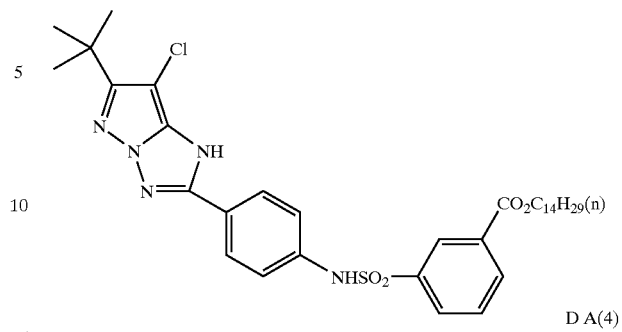

DA(4)

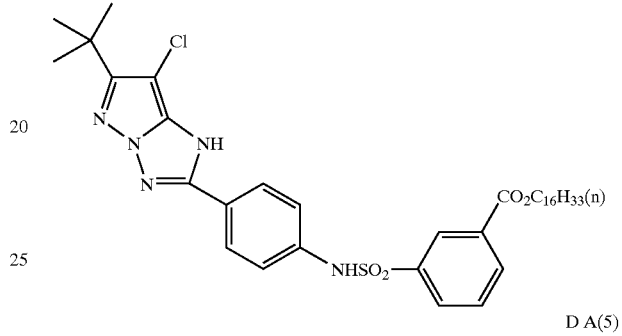

DA(5)

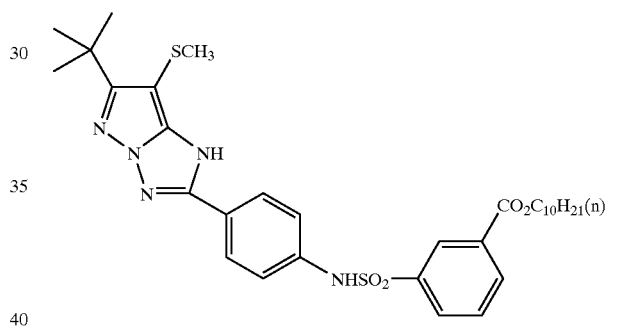

DA(6)

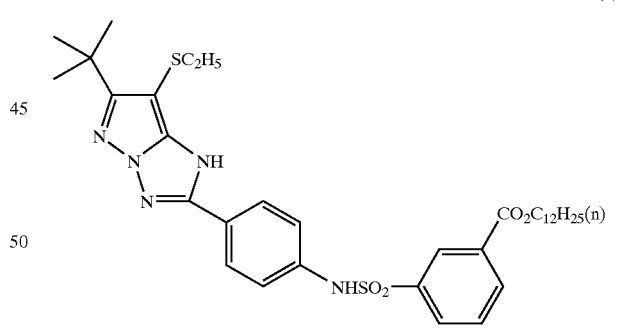

DA(7)

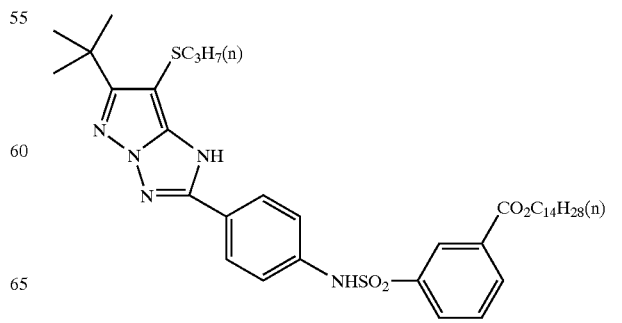

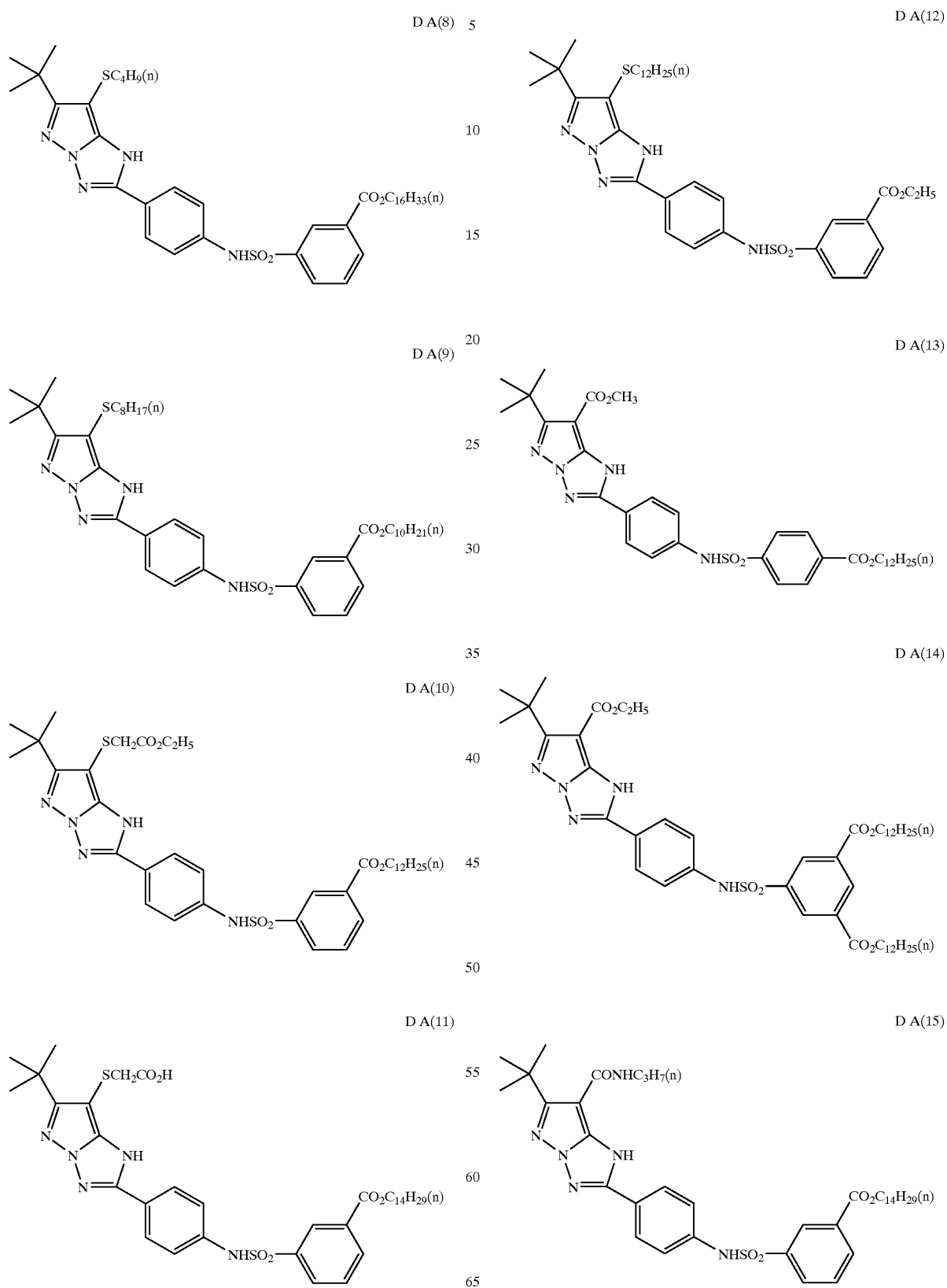

D A(16)
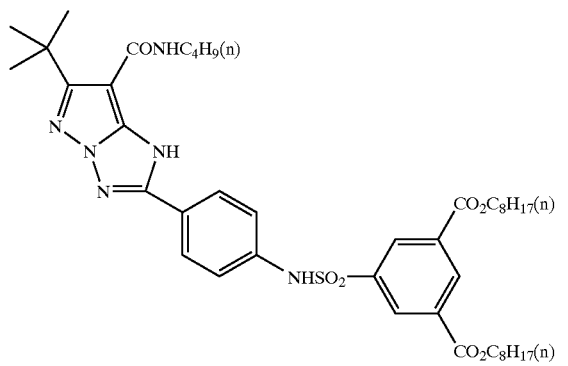
D A(17)
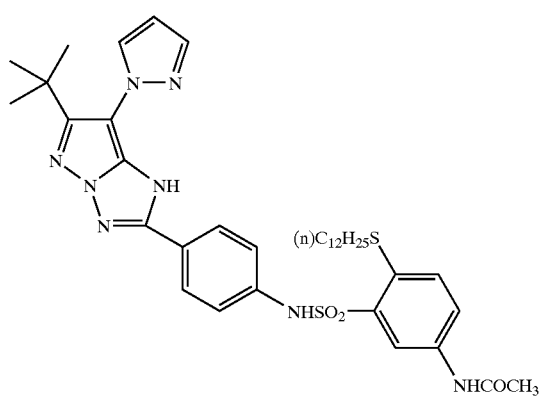
D A(18)
D A(19)
D A(20)
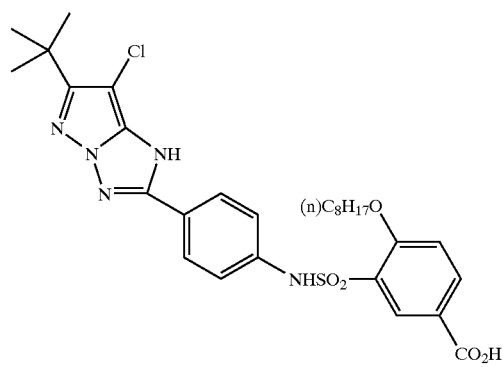
D A(21)
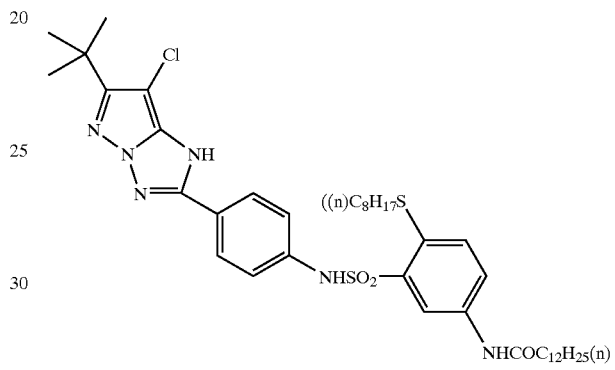
D A(22)
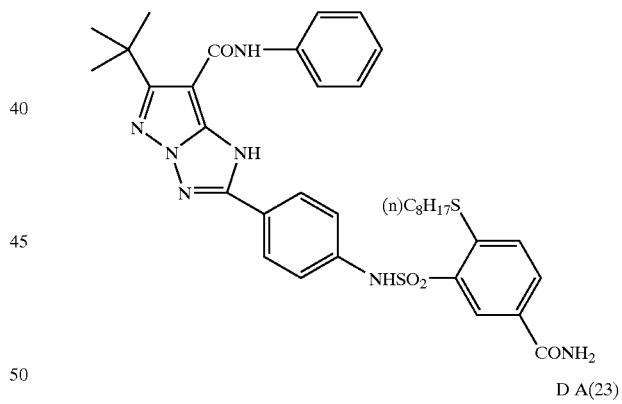
D A(23)
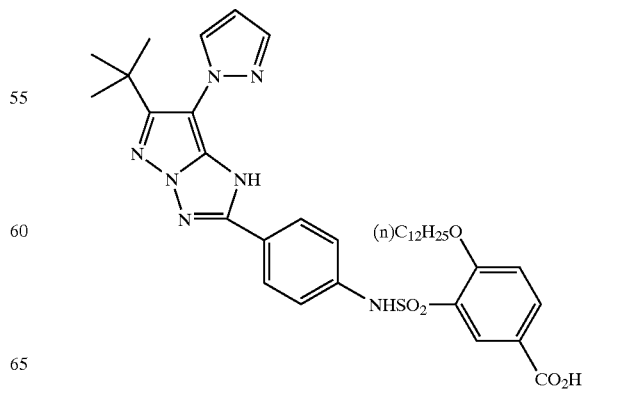

DA(24)
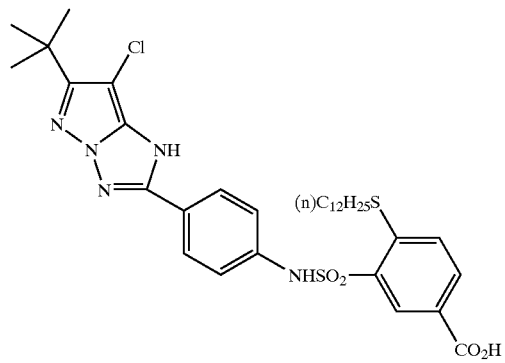
DA(25)
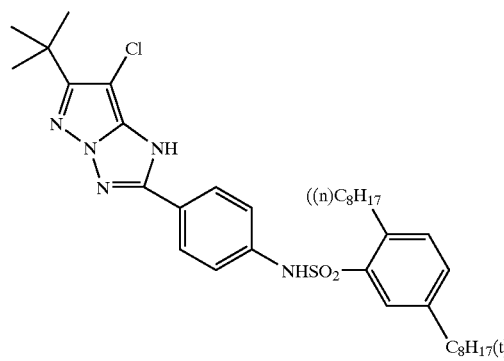
DA(26)
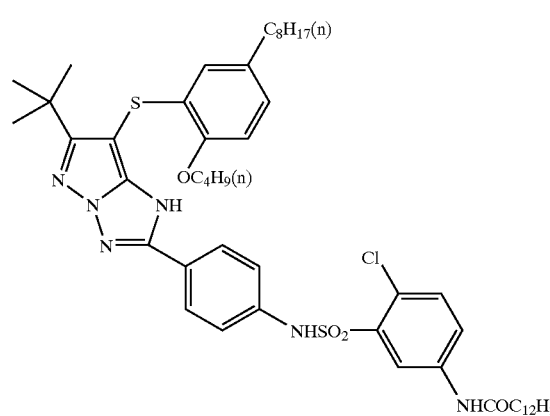
DA(27)
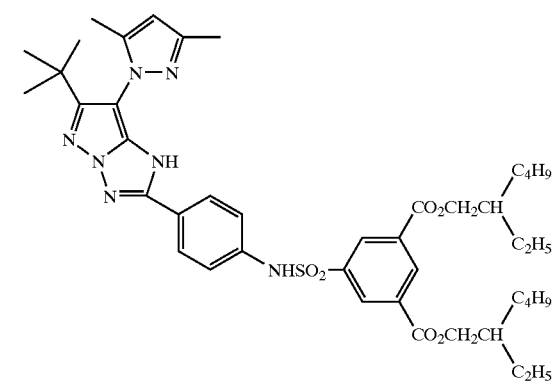
DA(28)
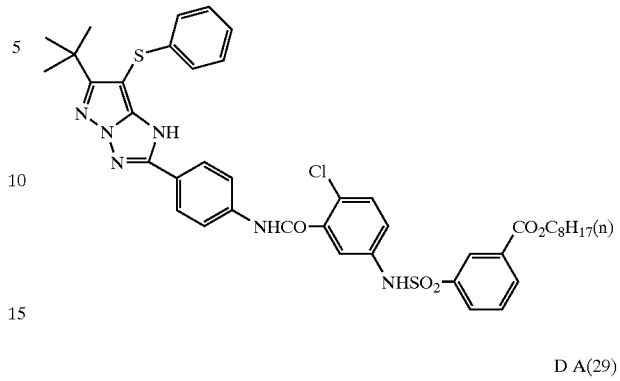
DA(29)
DA(30)
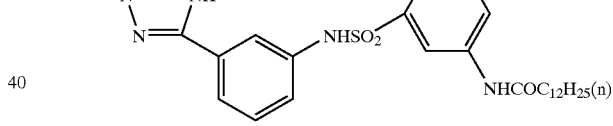
DA(31)
DA(32)
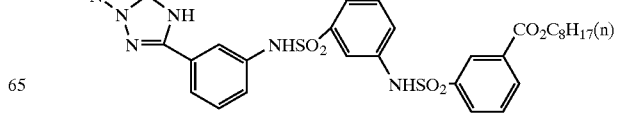

DA(33)
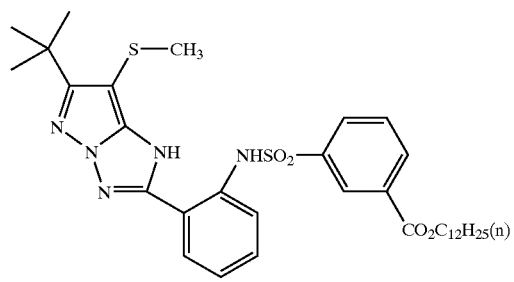
DA(34)
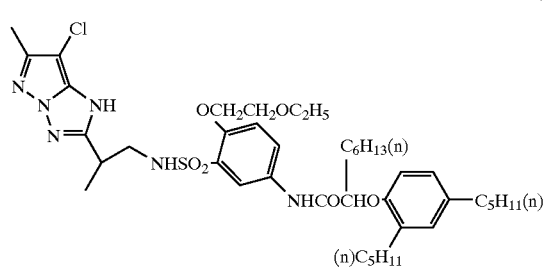
DA(35)
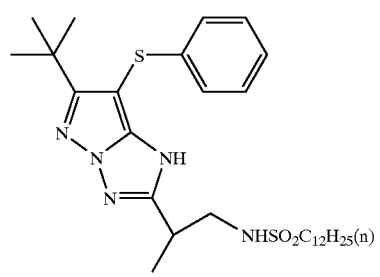
DA(36)
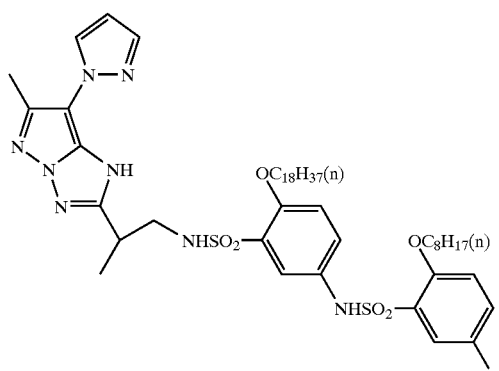
DA(37)
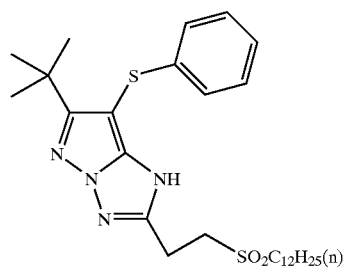
DA(38)
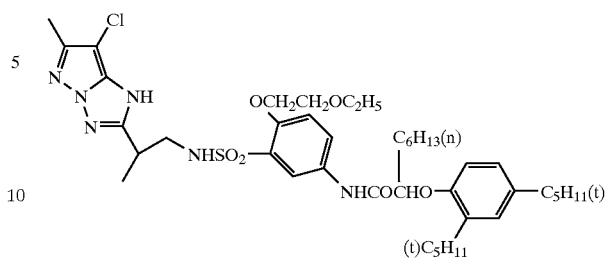
DA(39)
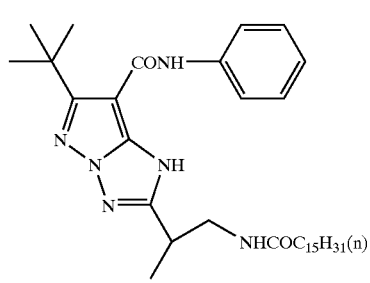
DA(40)
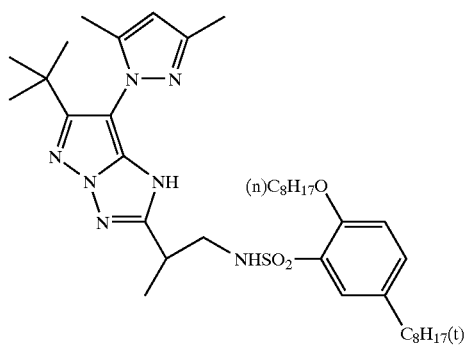
DA(41)
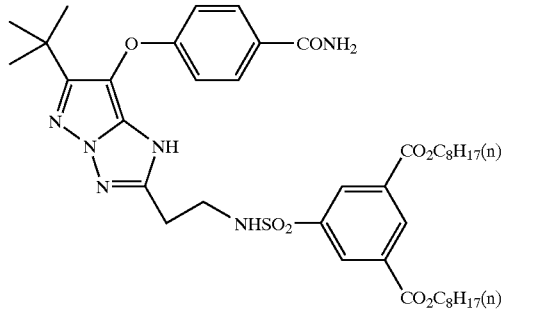
DA(42)
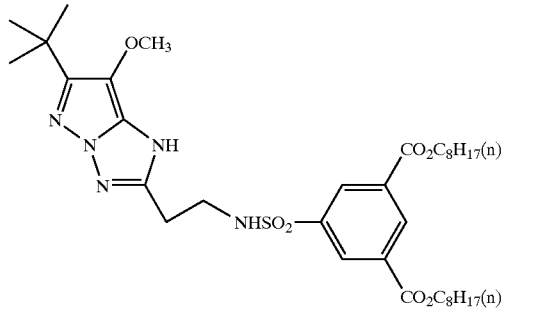

-continued
D A(43)
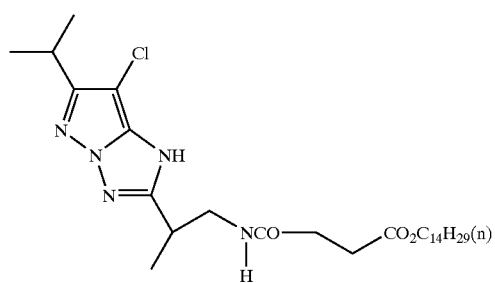
D A(44)
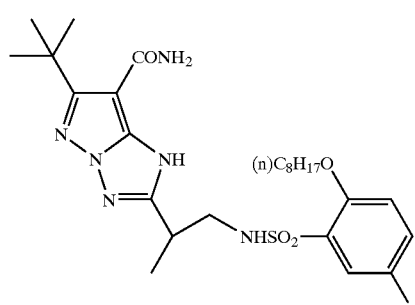
D A(45)
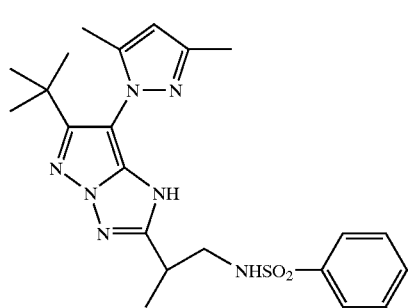
D A(46)
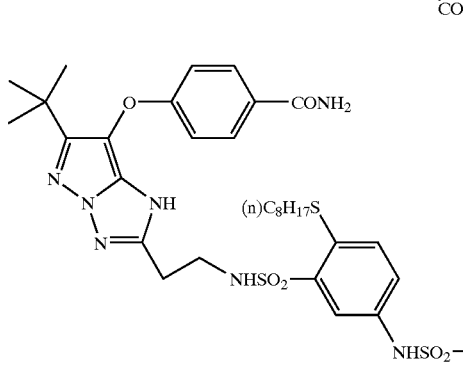
D A(47)
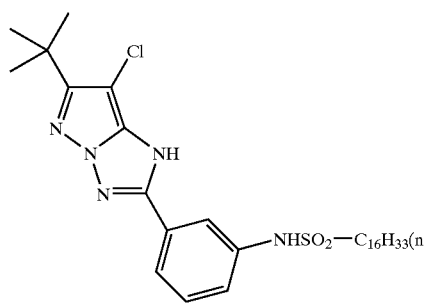
-continued
D A(48)
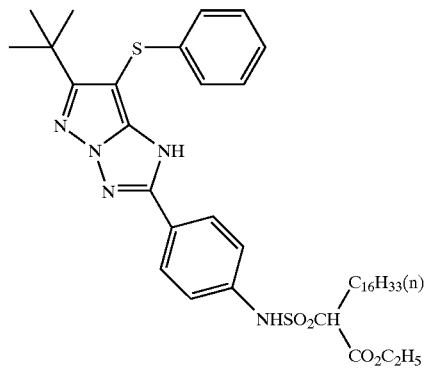
D A(49)
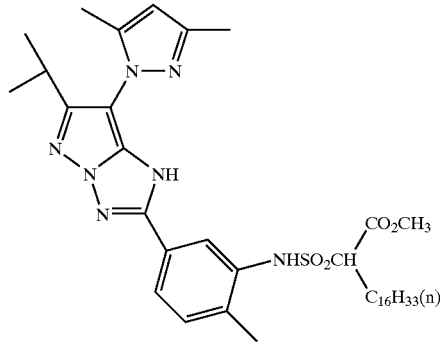
D A(50)
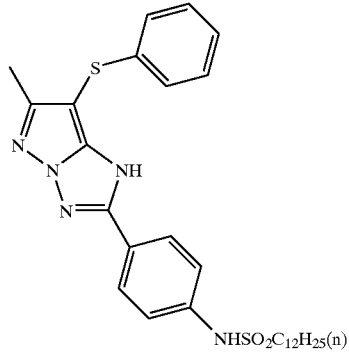
D A(51)
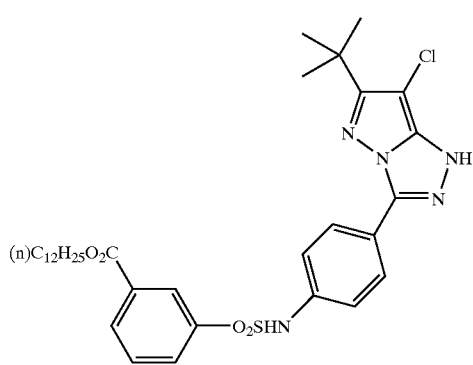

D A(52)
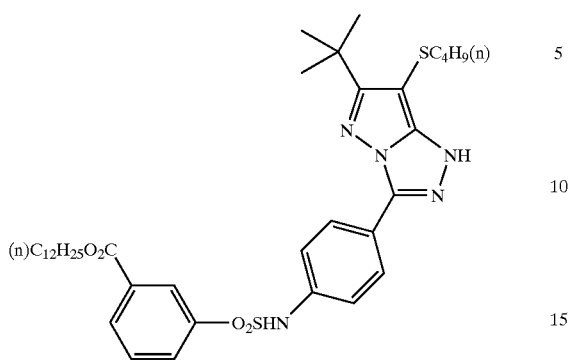
D A(53)
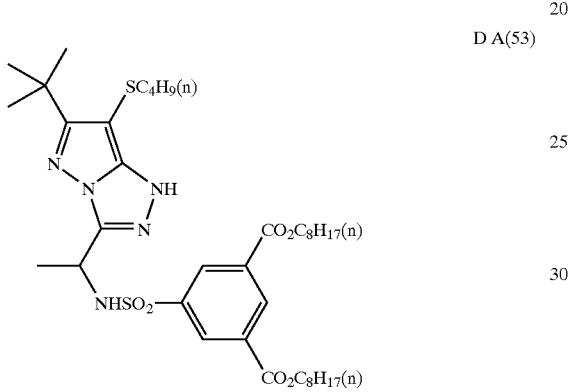
D A(54)
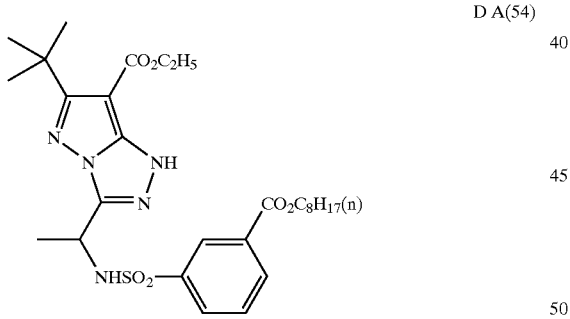
D A(55)
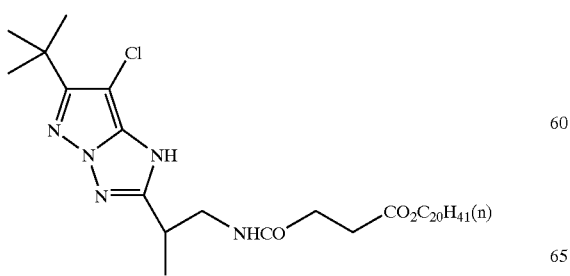
D A(56)
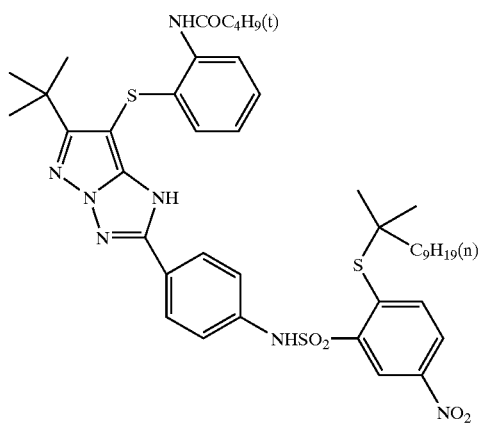
D A(57)
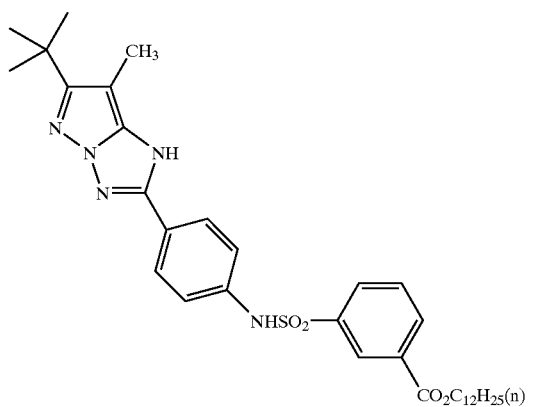
D A(58)
D A(59)
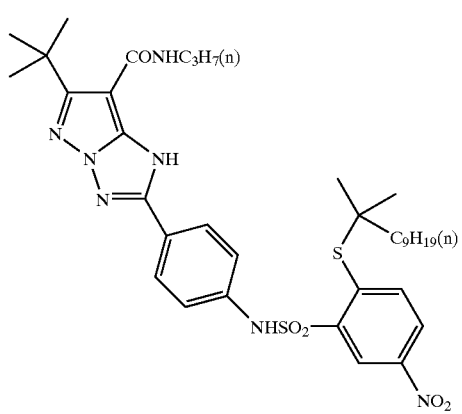

-continued
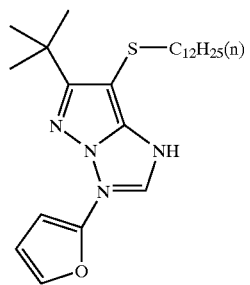
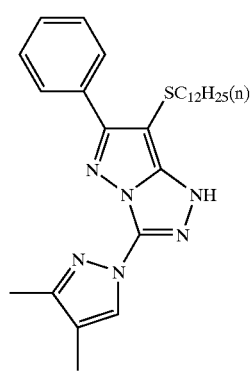
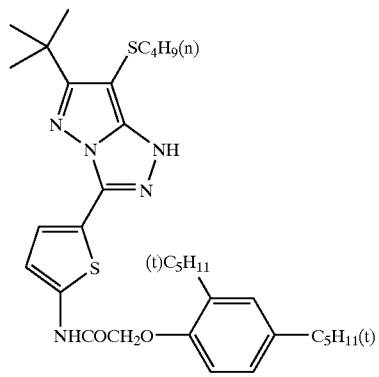
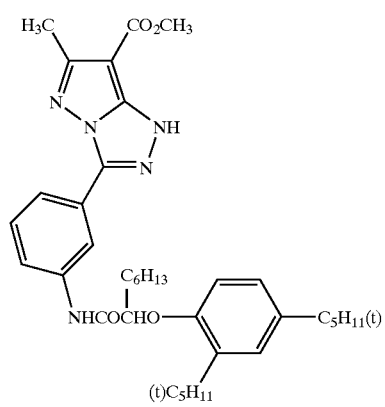
-continued
DA(60)
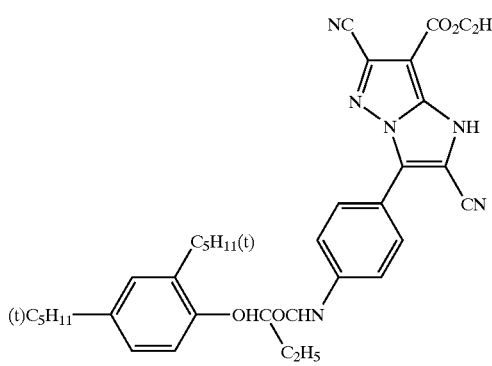
DA(61)
DA(65)
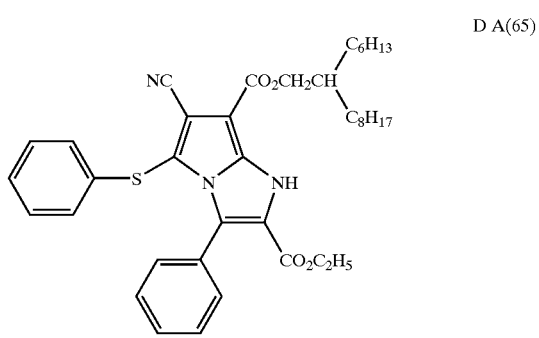
DA(66)
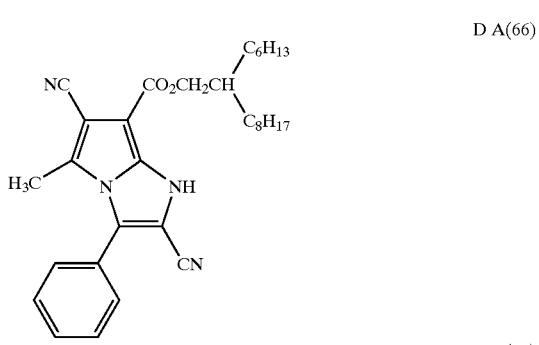
DA(67)
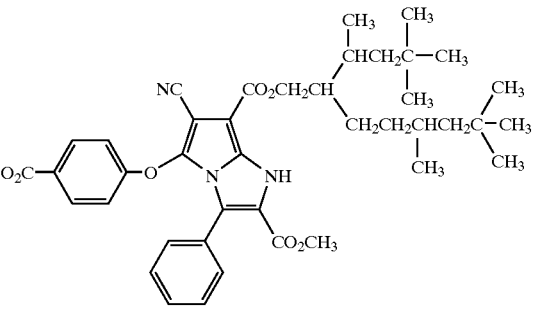
DA(68)
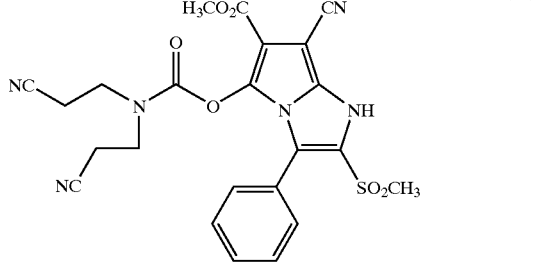

DA(69)
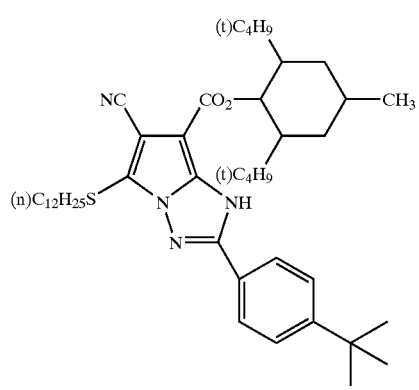
DA(70)
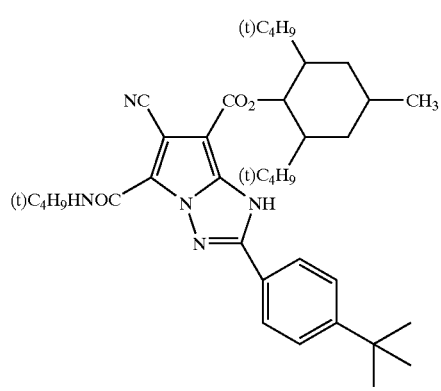
DA(71)
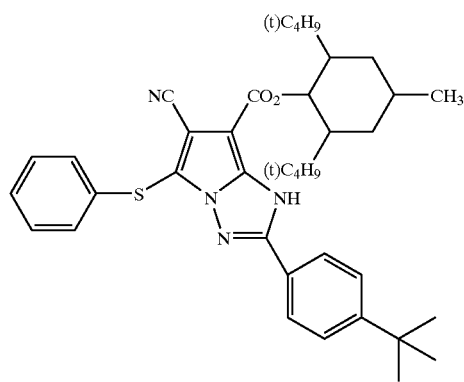
DA(72)
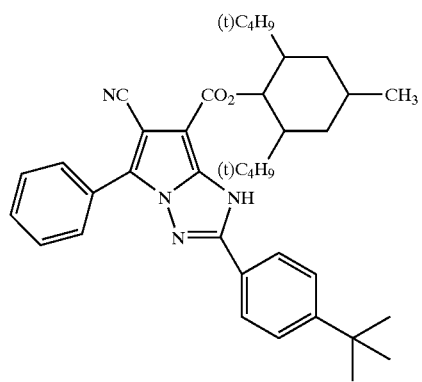
DA(73)
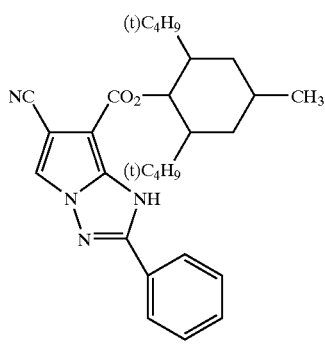
DA(74)
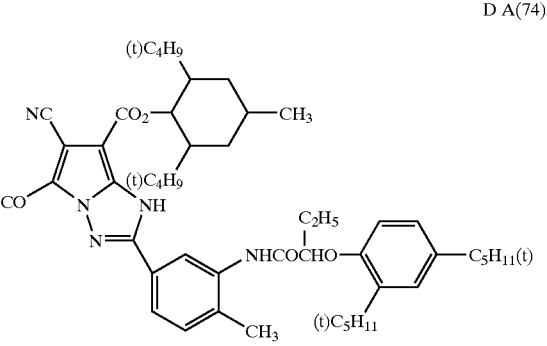
DA(75)
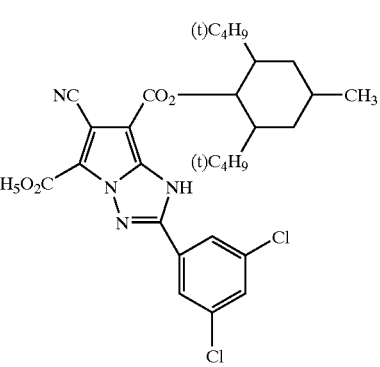
DA(76)
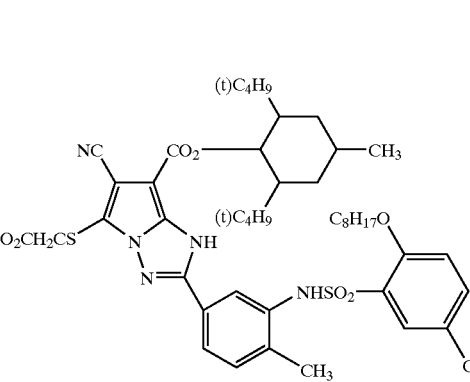

D A(77)
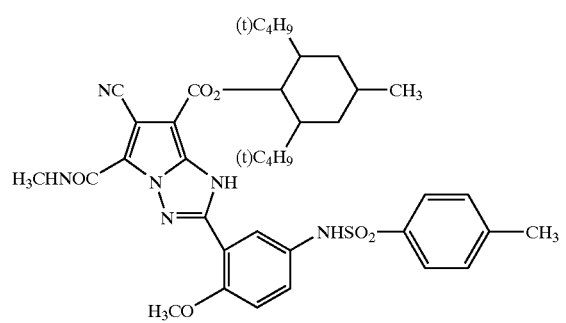
D A(78)
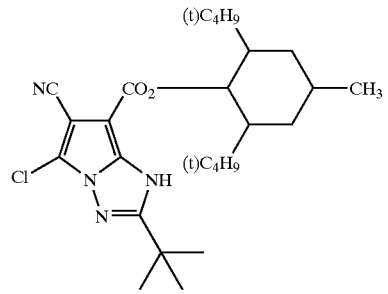
D A(79)
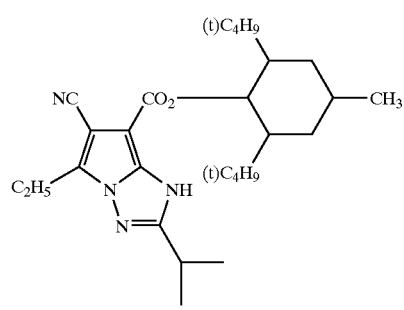
D A(80)
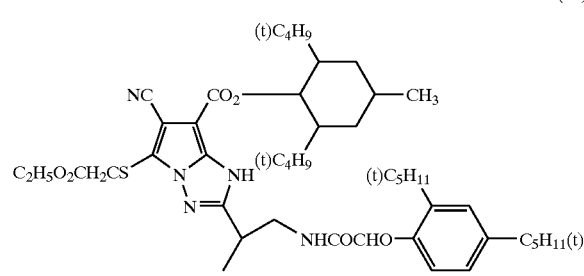
D A(81)
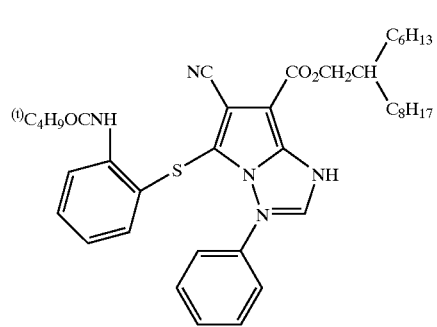
D A(82)
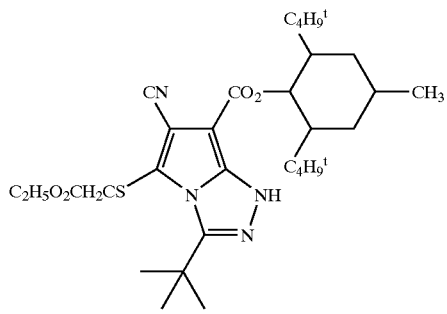
D A(83)
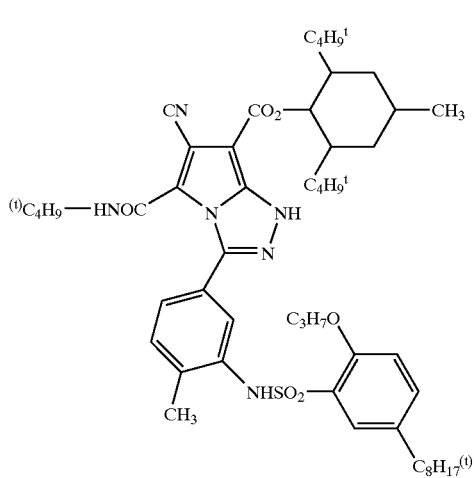
D A(84)
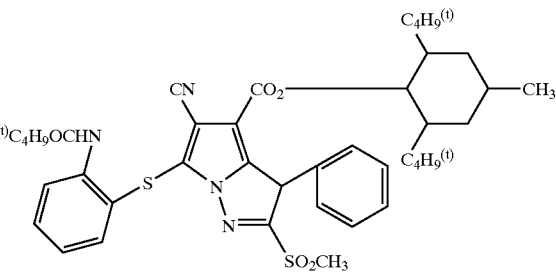
D A(85)
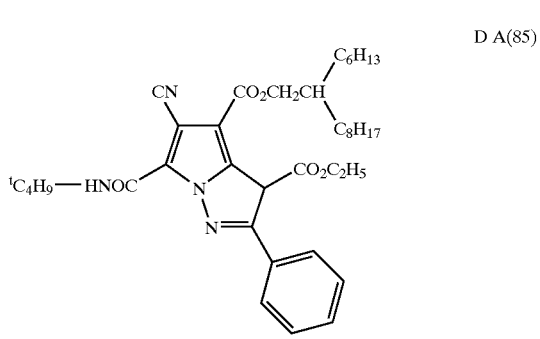

DA(86)
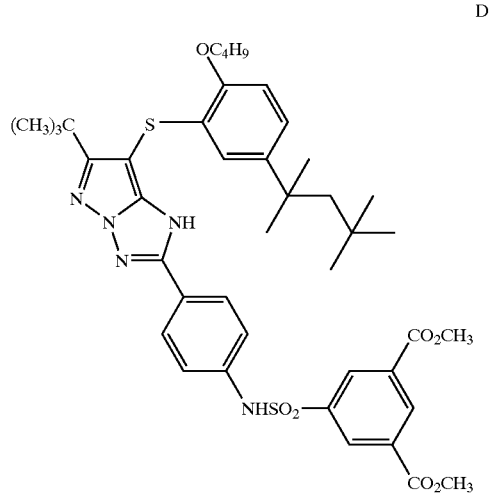
DA(87)
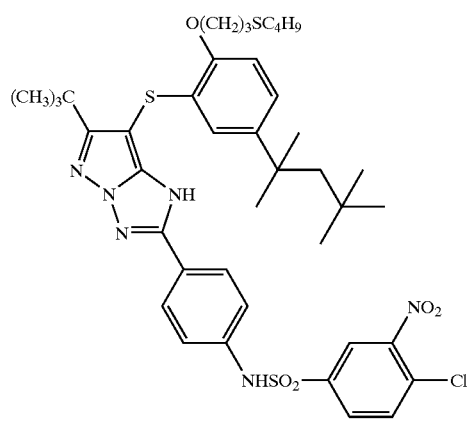
DA(88)
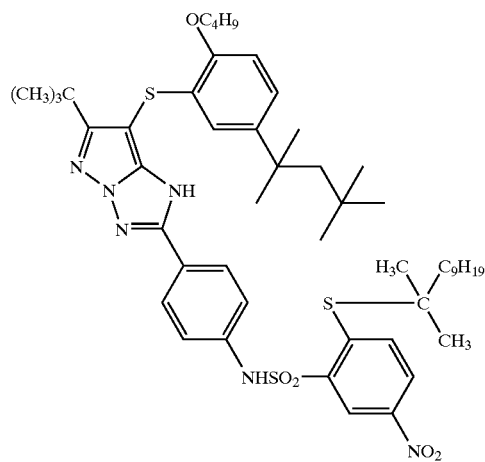
DA(89)
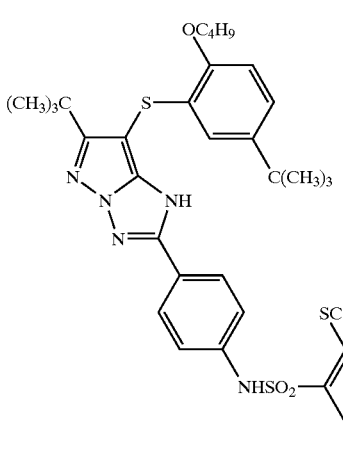
DA(90)
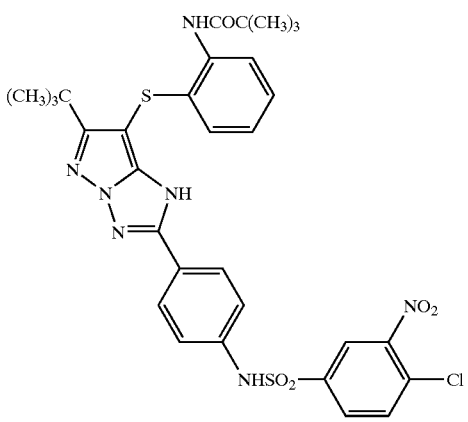
DA(91)
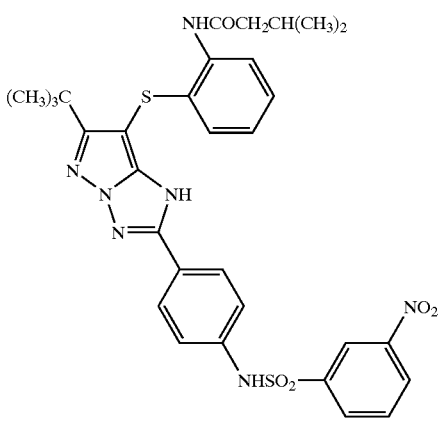

-continued
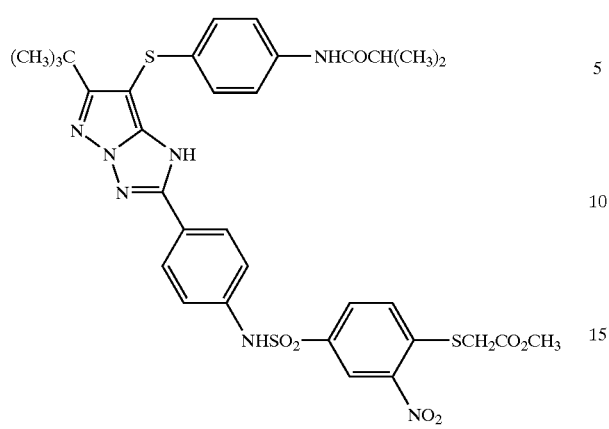
D A(92)
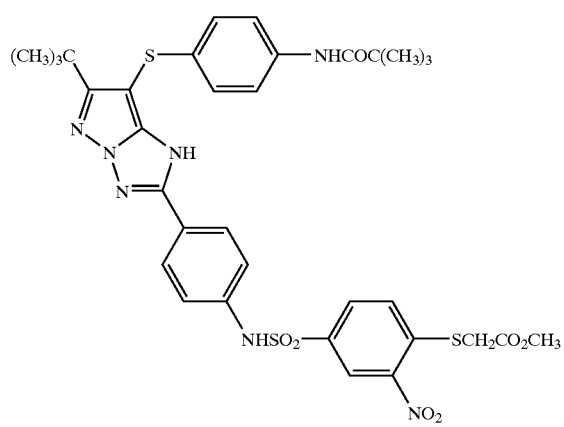
D A(93)
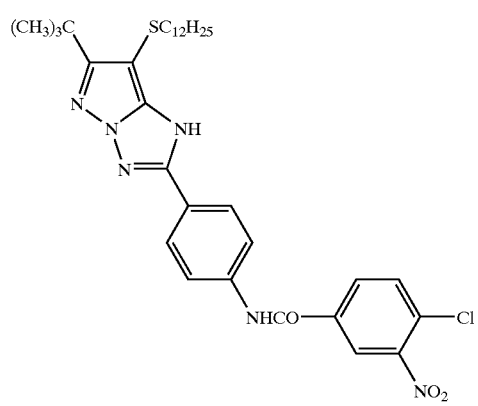
D A(94)
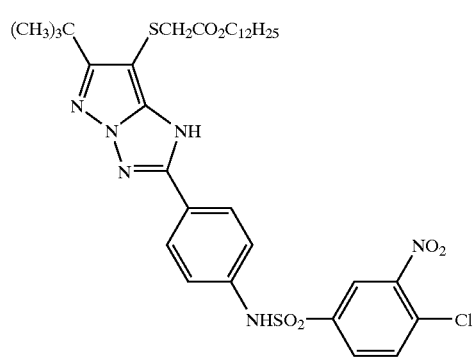
D A(95)
-continued
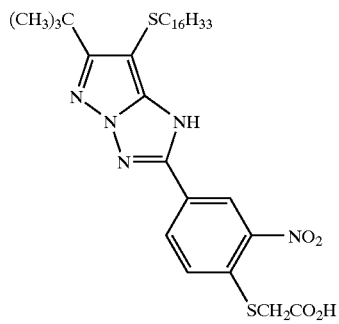
D A(96)
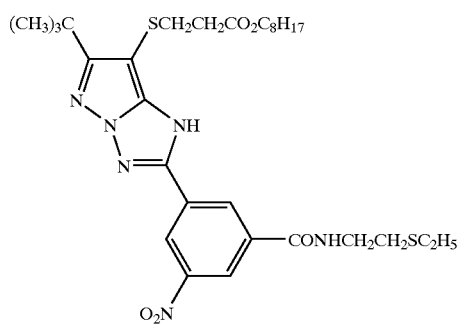
D A(97)
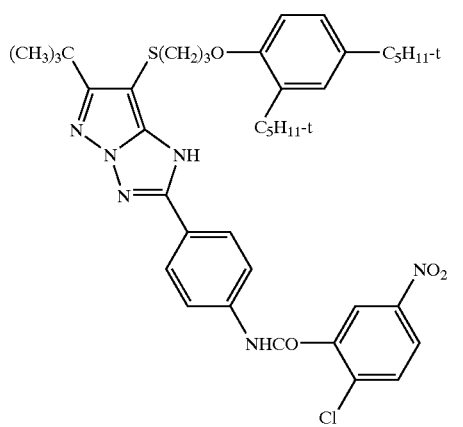
D A(98)
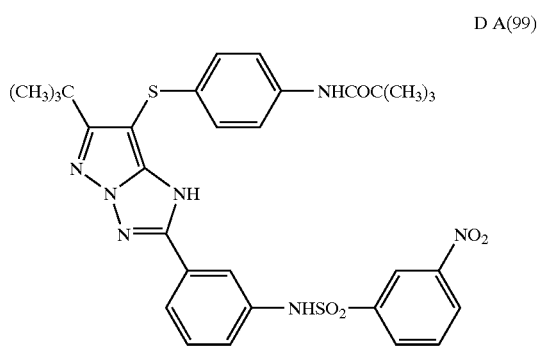
D A(99)

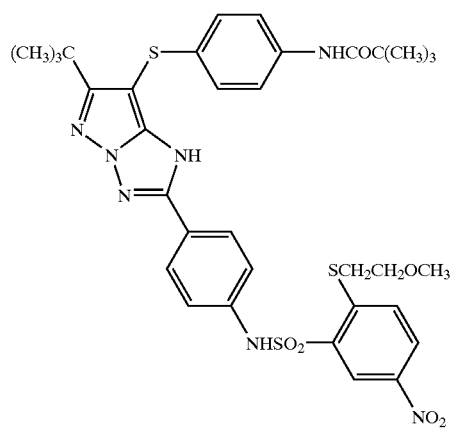
DA(100)
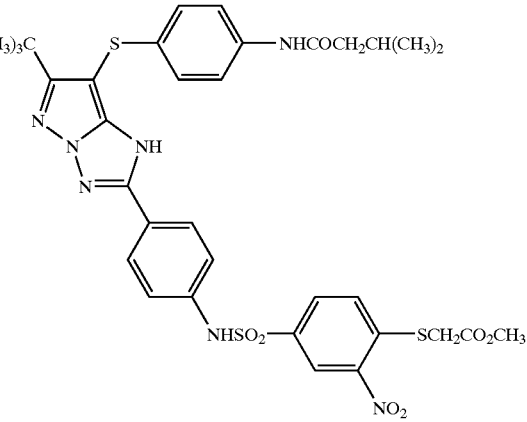
DA(101)
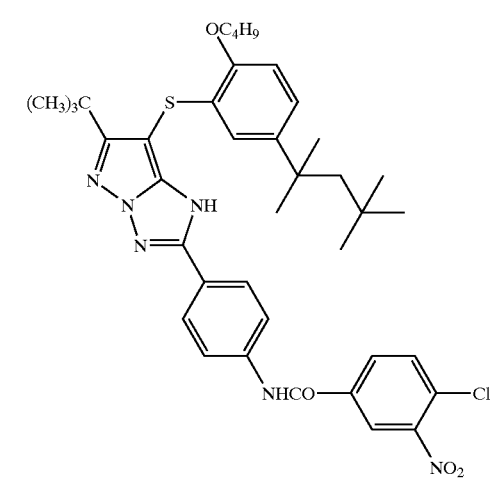
DA(102)
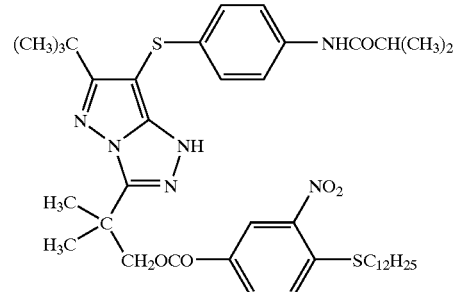
DA(103)
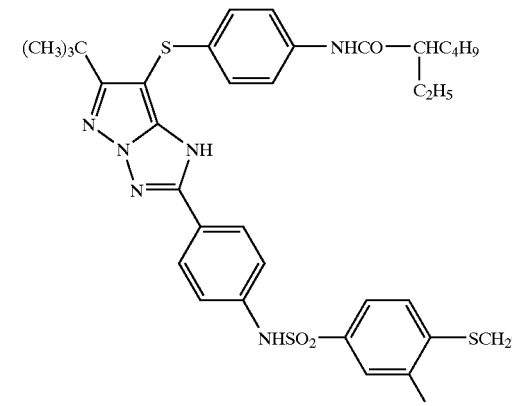
DA(104)
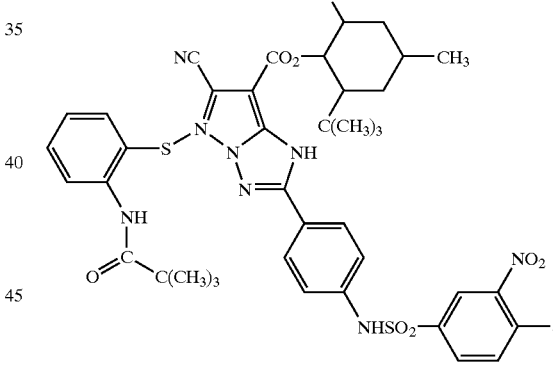
DA(105)
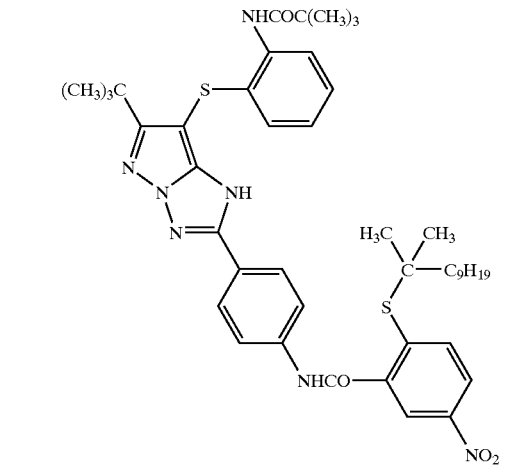
DA(106)

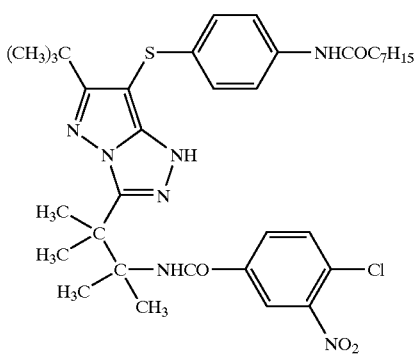

DA(107)

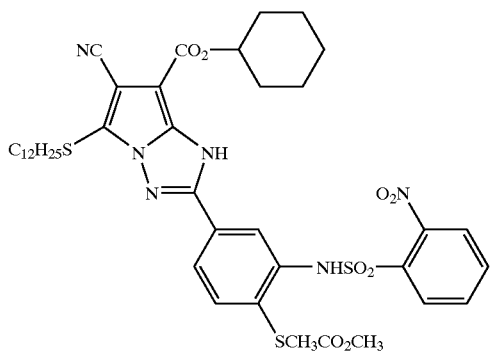

DA(108)

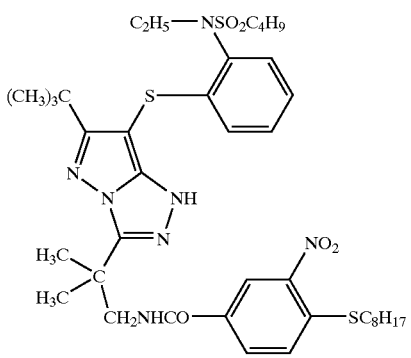

DA(109)

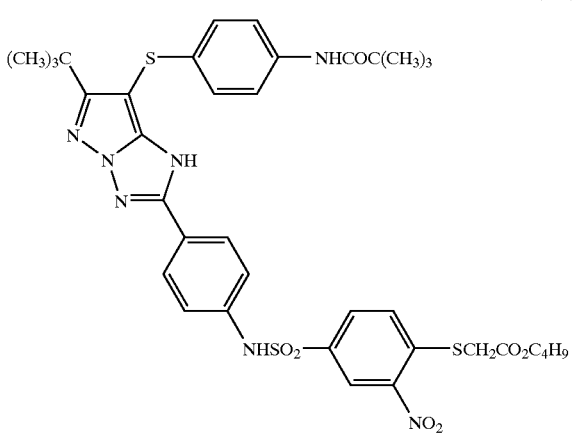

DA(110)

DA(111)

The compound of the present invention can easily be prepared according to the synthesis methods described in JP-A's-61-65245, 61-65246, 61-147254 and 8-122984, etc.

The addition place of the compound represented by the general formula (M) or (U) of the present invention is not limited as long as the compound is able to act on the silver halide color photosensitive material of the present invention. The compound is preferably added to the silver halide photosensitive material.

When the compound represented by the general formula (M) or (U) is to be added in the silver halide color photosensitive material, it may be used either in a silver halide light-sensitive layer or non light-sensitive layer.

When the compound is to be used in a silver halide light-sensitive layer, the light-sensitive layer containing the silver halide emulsion of the present invention is preferable. When the light-sensitive layer is divided into a plurality of layers having different speeds, the compounds may be added to any one of the layers, but a highest-speed layer is preferable.

When the compound is to be used in a non light-sensitive layer, a non light-sensitive layer between a red-sensitive layer and a green-sensitive layer, or between a green-sensitive layer and a blue-sensitive layer is preferable. The non light-sensitive layer includes all the layers except for a silver halide emulsion layer, for example, an antihalation layer, interlayer, yellow filter layer, and protective layer.

There is no particular limitation of a method for adding a compound represented by the general formula (M) or (U), for example, a method of adding the compound together with a high-boiling organic solvent, solid dispersion, a method of adding the compound to a coating solution by dissolving the compound to an organic solvent such as methanol, a method of adding the compound during preparation of the silver halide emulsion. It is preferable to introduce the compound into a photosensitive material by emulsified dispersion The addition amount of the compound represented by the general formula (M) or general formula (U) is preferably 0.1 to 1000 mg/m$^2$, more preferably 1 to 500 mg/m$^2$, and especially preferably 5 to 100 mg/m$^2$.

When the compound is used in a light-sensitive silver halide emulsion layer, the amount of $1\times10^{-4}$ to $1\times10^{-1}$ mol per mol of silver contained in the same layer is preferable, and $1\times10^{-3}$ to $5\times10^{-2}$ g/m$^2$ per mol of silver contained in the same layer is more preferable.

In the silver halide photosensitive material of the present invention, a light-sensitive silver halide emulsion other than the light-sensitive silver halide emulsion of the present invention may be used in combination. The combination use may be such that the emulsions are used in separate emulsion layers or in the same emulsion layer.

These emulsions are usually spectrally sensitized with methine dyes or others. Although the dyes used in case where mutilayer dye chromophores are adsorbed on silver halide grains was already described, the silver halide emulsions including those other than the adsorbed emulsions used in the silver halide photosensitive material of the present invention may use the following dyes: cyanine dyes, merocyanine dyes, composite cyanine dyes, composite merocyanine dyes, holopolar cyanine dyes, hemicyanine dyes, styryl dyes and hemioxonol dyes. Particularly useful dyes are those belonging to cyanine dyes, merocyanine dyes and composite merocyanine dyes. Any of nuclei commonly used in cyanine dyes as basic heterocyclic nuclei can be applied to these dyes. Examples of such applicable nuclei include a pyrroline nucleus, an oxazoline nucleus, a thiozoline nucleus, a pyrrole nucleus, an oxazole nucleus, a thiazole nucleus, a selenazole nucleus, an imidazole nucleus, a tetrazole nucleus and a pyridine nucleus; nuclei comprising these nuclei fused with alicyclic hydrocarbon rings; and nuclei comprising these nuclei fused with aromatic hydrocarbon rings, such as an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus. These nuclei may have a carbon atom being substituted.

In the merocyanine dyes and composite merocyanine dyes, any of 5 or 6-membered heterocyclic nuclei such as a pyrazolin-5-one nucleus, a thiohydantoin nucleus, a 2-thioxazolidine-2,4-dione nucleus, a thiazolidine-2,4-dione nucleus, a rhodanine nucleus and a thiobarbituric acid nucleus can be applied as a nucleus having a ketomethylene structure.

These spectral sensitizing dyes may be used either individually or in combination. The spectral sensitizing dyes are often used in combination for the purpose of attaining supersensitization. Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, GB's 1,344,281 and 1,507,803, JP-B-43-4936 and 53-12375 and JP-A-52-110618 and 52-109925.

The emulsion used in the present invention may contain a dye which itself exerts no spectral sensitizing effect or a substance which absorbs substantially none of visible radiation and exhibits supersensitization, together with the above spectral sensitizing dye.

The addition timing of the spectral sensitizing dye to the emulsion may be performed at any stage of the process for preparing the emulsion which is known as being useful. Although the doping is most usually conducted at a stage between the completion of the chemical sensitization and the coating, the spectral sensitizing dye can be added simultaneously with the chemical sensitizer to thereby simultaneously effect the spectral sensitization and the chemical sensitization as described in U.S. Pat. Nos. 3,628,969 and 4,225,666. Alternatively, the spectral sensitization can be conducted prior to the chemical sensitization and, also, the spectral sensitizing dye can be added prior to the completion of silver halide grain precipitation to thereby initiate the spectral sensitization as described in JP-A-58-113928. Further, the above sensitizing dye can be divided prior to addition, that is, part of the sensitizing dye can be added prior to the chemical sensitization with the rest of the sensitizing dye added after the chemical sensitization as taught in U.S. Pat. No. 4,225,666. Still further, the spectral sensitizing dye can be added at any stage during the formation of silver halide grains according to the method disclosed in U.S. Pat. No. 4,183,756 and other methods.

When a plurality of sensitizing dyes are added a suitable method may be selected depending on the selected type of the sensitizing dye and desired spectral sensitivity, for example, from a method of adding each one separately with intervals, a method of adding them as a mixture, a method of adding one kind of sensitizing dye from a group of sensitizing dyes precedentially and adding the remaining dyes as a mixture with other sensitizing dyes.

The addition amount of the sensitizing dye may be from $4 \times 10^{-6}$ to $8 \times 10^{-3}$ mol per mol of silver halide. For preferable silver halide grains having a size of 0.2 to 1.2 $\mu$m, about $5 \times 10^{-5}$ to $2 \times 10^{-3}$ mol per mol of silver is preferable.

With respect to a plurality of silver halide emulsion layers constituting each unit light-sensitive layer, it is preferred that two layers consisting of a high-speed emulsion layer and a low-speed emulsion layer be arranged so that the speed is sequentially decreased toward a support as described in DE 1,121,470 or GB 923,045. Also, as described in JP-A's-57-112751, 62-200350, 62-206541 and 62-206543, layers can be arranged so that a low-speed emulsion layer is formed on a side remote from a support while a high-speed emulsion layer is formed on a side close to the support.

Specifically, layers can be arranged, from the farthest side from a support, in the order of low-speed blue-sensitive layer (BL)/high-speed blue-sensitive layer (BH)/high-speed green-sensitive layer (GH)/low-speed green-sensitive layer (GL)/high-speed red-sensitive layer (RH)/low-speed red-sensitive layer (RL), or the order of BH/BL/GL/GH/RH/RL, or the order of BH/BL/GH/GL/RL/RH, or the like.

In addition, as described in JP-B-55-34932, layers can be arranged, from the farthest side from a support, in the order of blue-sensitive layer/GH/RH/GL/RL. Furthermore, as described in JP-A's-56-25738 and 62-63936, layers can be arranged, from the farthest side from a support, in the order of blue-sensitive layer/GL/RL/GH/RH.

As described in JP-B-49-15495, three layers can be arranged so that a silver halide emulsion layer having the highest speed is arranged as an upper layer, a silver halide emulsion layer having a speed lower than that of the upper layer is arranged as an inter layer, and a silver halide emulsion layer having a speed lower than that of the inter layer is arranged as a lower layer; i.e., three layers having different sensitivities can be arranged so that the speed is sequentially decreased toward the support. Even when a layer structure is constituted by three layers having different sensitivities as mentioned above, these layers can be arranged in the order of medium-speed emulsion layer/high-speed emulsion layer/low-speed emulsion layer from the farthest side from a support in layers of the same color sensitivity as described in JP-A-59-202464.

In addition, the layer arrangement can be made in the order of high-speed emulsion layer/low-speed emulsion layer/medium-speed emulsion layer, or in the order of low-speed emulsion layer/medium-speed emulsion layer/high-speed emulsion layer.

Furthermore, the layer arrangement can be changed as mentioned above even when four or more layers are formed.

It is preferable to utilize an inter layer inhibitory effect as means for improving a color reproduction.

With respect to the silver halide grains for use in interlayer effect-donating layer to a red-sensitive layer, although, for example, the size and configuration thereof are not particularly limited, it is preferred to use so-called tabular grains of high aspect ratio, a monodisperse emulsion having uniform grain size, or silver iodobromide grains having a layer structure of iodide. Further, for expanding an exposure latitude, it is preferred to mix a plurality of emulsions whose grain sizes are different from each other.

Although an inter layer effect-donating layer to a red-sensitive layer may be provided by coating on any position on a support, it is preferred that the interlayer-donating layer be provided by coating at a position which is closer to the support than the blue-sensitive layer and which is more remote from the support than the red-sensitive layer. It is further preferred that the interlayer-donating layer be positioned closer to the support than the yellow filter layer.

It is more preferred that the interlayer effect-donating layer to a red-sensitive layer be provided at a position which is closer to the support than the green-sensitive layer and which is more remote from the support than the red-sensitive layer. The interlayer-donating layer is most preferably arranged at a position adjacent to a side of the green-sensitive layer close to the support. The terminology "adjacent" used herein means that an inter layer or the like is not interposed therebetween.

There may be a plurality of interlayer effect-donating layers to a red-sensitive layer. These layers may be positioned so that they are adjacent to each other or are apart from each other.

In the present invention, use can be made of solid disperse dyes described in JP-A-11-305396.

The emulsions for use in the photosensitive material of the present invention may be any of the surface latent image type in which latent images are mainly formed in the surface, the internal latent image type in which latent images are formed in the internal portion of grains and the type in which latent images exist in both the surface and the internal portion of grains. However, it is requisite that the emulsion be a negative type. The emulsion of the internal latent image type may specifically be, for example, a core/shell internal-latent-image type emulsion described in JP-A-63-264740, whose preparation method is described in JP-A-59-133542. The thickness of the shell of this emulsion, although varied depending on development processing, etc., is preferably in the range of 3 to 40 nm, more preferably 5 to 20 nm.

The silver halide emulsions are generally subjected to physical ripening, chemical sensitization and spectral sensitization before use. Additives employed in these steps are described in RD Nos. 17643, 18716 and 307105. Positions where the description is made are listed in the following table.

In the photosensitive material of the present invention, two or more emulsions which are different from each other in at least one of the characteristics, specifically the grain size, grain size distribution, halogen composition, grain configuration and speed of light-sensitive silver halide emulsion, can be mixed together and used in the same layer.

It is preferred that silver halide grains having a grain surface fogged as described in U.S. Pat. No. 4,082,553 and silver halide grains or colloidal silver having a grain internal portion fogged as described in U.S. Pat. No. 4,626,498 and JP-A-59-214852 be used in light-sensitive silver halide emulsion layers and/or substantially nonlight-sensitive hydrophilic colloid layers. The expression "silver halide grains having a grain surface or grain internal portion fogged" refers to silver halide grains which can be developed uniformly (nonimagewise) irrespective of the nonexposed or exposed zone of photosensitive material. The process for producing them is described in U.S. Pat. No. 4,626,498 and JP-A-59-214852. The silver halides constituting internal nuclei of core/shell silver halide grains having a grain internal portion fogged may have different halogen composition. Any of silver chloride, silver chlorobromide, silver iodobromide and silver chloroiodobromide can be used as the silver halide having a grain surface or grain internal portion fogged. The average grain size of these fogged silver halide grains is preferably in the range of 0.01 to 0.75 µm, more preferably 0.05 to 0.6 µm. With respect to the grain configuration, although both regular grains and a polydisperse emulsion can be used, monodispersity (at least 95% of the weight or number of silver halide grains have grain diameters falling within ±40% of the average grain diameter) is preferred.

In the present invention, it is preferred to use nonlight-sensitive fine-grain silver halides. The expression "nonlight-sensitive fine-grain silver halides" refers to silver halide fine grains which are not sensitive to light at the time of imagewise exposure for obtaining dye images and which are substantially not developed at the time of development processing thereof. Those not having been fogged in advance are preferred. The fine-grain silver halides have a silver bromide content of 0 to 100 mol %, and, if necessary, may contain silver chloride and/or silver iodide. Preferably, silver iodide is contained in an amount of 0.5 to 10 mol %. The average grain diameter (average of equivalent circular diameters of projected areas) of fine-grain silver halides is preferably in the range of 0.01 to 0.5 µm, more preferably 0.02 to 0.2 µm.

The fine-grain silver halides can be prepared by the same process as used in the preparation of common light-sensitive silver halides. It is not needed to optically sensitize the surface of silver halide grains. Further, any spectral sensitization thereof is also not needed. However, it is preferred to add known stabilizers, such as triazole-type, azaindene-type, benzothiazolium-type and mercapto-type compounds or zinc compounds, thereto prior to the addition of fine-grain silver halides to a coating liquid. Colloidal silver can be incorporated in layers containing fine-grain silver halides.

Various additives mentioned above are used in the photosensitive material regarding the technique of the invention, and other various additives may be used depending on purposes.

The additives are described in detail in Research Disclosure Item 17643 (December 1978), Item 18716 (November 1979) and Item 308119 (December 1989). A summary of the locations where they are described will be listed in the following table.

| Types of additives | | RD17643 | RD18716 | RD308119 |
|---|---|---|---|---|
| 1 | Chemical sensitizing dyes | page 23 | page 648 right column | page 996 |
| 2 | Sensitivity-increasing agents | | page 648 right column | |
| 3 | Spectral sensitizing dye, super-sensitizers | pages 23–24 | page 648, right column to page 649, right column | page 996, right column to page 998, right column |
| 4 | Brighteners | page 24 | | page 998 right column |
| 5 | Antifoggants, stabilizers | pages 24–25 | page 649 right column | page 998, right column to page 1000, right column |

-continued

| Types of additives | RD17643 | RD18716 | RD308119 |
|---|---|---|---|
| 6 Light absorbents, filter dyes, ultraviolet absorbents | pages 25–26 | page 649, right column to page 650, left column | page 1003, left column to page 1003, right column |
| 7 Stain preventing agents | page 25, right column | page 650, left to right columns | page 1002, right column |
| 8 Dye image stabilizers | page 25 | | page 1002, right column |
| 9 Film hardeners | page 26 | page 651, left column | page 1004, right column page 1005, left column |
| 10 Binders | page 26 | page 651, left column | page 1003, right column to page 1004, right column |
| 11 Plasticizers, lubricants | page 27 | page 650, right column | page 1006, left to right columns |
| 12 Coating aids, surfactants | pages 26–27 | page 650, right column | page 1005, left column to page 1006, left column |
| 13 Antistatic agents | page 27 | page 650, right column | page 1006, right column to page 1007, left column |
| 14 Matting agents | | | page 1008, left column to page 1009, left column |

With respect to the photosensitive material of the present invention and the emulsion suitable for use in the photosensitive material and also with respect to layer arrangement and related techniques, silver halide emulsions, dye forming couplers, DIR couplers and other functional couplers, various additives and development processing which can be used in the photographic photosensitive material, reference can be made to EP 0565096A1 (published on Oct. 13, 1993) and patents cited therein. Individual particulars and the locations where they are described will be listed below.

1. Layer arrangement: page 61 lines 23 to 35, page 61 line 41 to page 62 line 14,
2. Interlayers: page 61 lines 36 to 40,
3. Interlayer effect-donating layers: page 62 lines 15 to 18,
4. Silver halide halogen compositions: page 62 lines 21 to 25,
5. Silver halide grain crystal habits: page 62 lines 26 to 30,
6. Silver halide grain sizes: page 62 lines 31 to 34,
7. Emulsion preparation methods: page 62 lines 35 to 40,
8. Silver halide grain size distributions: page 62 lines 41 to 42,
9. Tabular grains: page 62 lines 43 to 46,
10. Internal structures of grains: page 62 lines 47 to 53,
11. Latent image forming types of emulsions: page 62 line 54 to page 63 to line 5,
12. Physical ripening and chemical sensitization of emulsion: page 63 lines 6 to 9,
13. Emulsion mixing: page 63 lines 10 to 13,
14. Fogged emulsions: page 63 lines 14 to 31,
15. Non light-sensitive emulsions: page 63 lines 32 to 43,
16. Silver coating amounts: page 63 lines 49 to 50,
17. Formaldehyde scavengers: page 64 lines 54 to 57,
18. Mercapto antifoggants: page 65 lines 1 to 2,
19. Fogging agent, etc.-releasing agents: page 65 lines 3 to 7,
20. Dyes: page 65, lines 7 to 10,
21. Color coupler summary: page 65 lines 11 to 13,
22. Yellow, magenta and cyan couplers: page 65 lines 14 to 25,
23. Polymer couplers: page 65 lines 26 to 28,
24. Diffusive dye forming couplers: page 65 lines 29 to 31,
25. Colored couplers: page 65 lines 32 to 38,
26. Functional coupler summary: page 65 lines 39 to 44,
27. Bleaching accelerator-releasing couplers: page 65 lines 45 to 48,
28. Development accelerator-releasing couplers: page 65 lines 49 to 53,
29. Other DIR couplers: page 65 line 54 to page 66 to line 4,
30. Method of dispersing couplers: page 66 lines 5 to 28,
31. Antiseptic and mildewproofing agents: page 66 lines 29 to 33,
32. Types of photosensitive materials: page 66 lines 34 to 36,
33. Thickness of light-sensitive layer and swelling speed: page 66 line 40 to page 67 line 1,
34. Back layers: page 67 lines 3 to 8,
35. Development processing summary: page 67 lines 9 to 11,
36. Developing solutions and developing agents: page 67 lines 12 to 30,
37. Developing solution additives: page 67 lines 31 to 44,
38. Reversal processing: page 67 lines 45 to 56,
39. Processing solution open ratio: page 67 line 57 to page 68 line 12,
40. Development time: page 68 lines 13 to 15,
41. Bleach-fix, bleaching and fixing: page 68 line 16 to page 69 line 31,
42. Automatic processor: page 69 lines 32 to 40,
43. Washing, rinse and stabilization: page 69 line 41 to page 70 line 18,
44. Processing solution replenishment and reuse: page 70 lines 19 to 23,
45. Developing agent built-in sensitive material: page 70 lines 24 to 33,
46. Development processing temperature: page 70 lines 34 to 38, and
47. Application to film with lens: page 70 lines 39 to 41.

Moreover, preferred use can be made of a bleaching solution containing 2-pyridinecarboxylic acid or 2,6-pyridinedicarboxylic acid, a ferric salt such as ferric nitrate and a persulfate as described in EP 602,600. When this bleaching solution is used, it is preferred that the steps of stop and water washing be conducted between the steps of color development and bleaching. An organic acid such as acetic acid, succinic acid or maleic acid is preferably used as a stop solution. For pH adjustment and bleaching fog, it is preferred that the bleaching solution contains an organic acid such as acetic acid, succinic acid, maleic acid, glutaric acid or adipic acid in an amount of 0.1 to 2 mol/liter (hereinafter liter-is referred to as "L", and milliliter is referred to as "mL".).

A magnetic recording layer usable in the present invention will be described below.

This magnetic recording layer is formed by coating the surface of a support with an aqueous or organic solvent-based coating solution which is prepared by dispersing magnetic grains in a binder.

As the magnetic grains, it is possible to use grains of, e.g., ferromagnetic iron oxide such as $\gamma Fe_2O_3$, Co-deposited $\gamma Fe_2O_3$, Co-deposited magnetite, Co-containing magnetite, ferromagnetic chromium dioxide, a ferromagnetic metal, ferromagnetic alloy, Ba ferrite of a hexagonal system, Sr ferrite, Pb ferrite, and Ca ferrite. Co-deposited ferromagnetic iron oxide such as Co-deposited $\gamma Fe_2O_3$ is preferable. The grain can take the shape of any of, e.g., a needle, rice grain, sphere, cube, and plate. The specific area is preferably 20 m$^2$/g or more, and more preferably 30 m$^2$/g or more as $S_{BET}$.

The saturation magnetization ($\sigma$s) of the ferromagnetic substance is preferably $3.0 \times 10^4$ to $3.0 \times 10^5$ A/m, and especially preferably $4.0 \times 10^4$ to $2.5 \times 10^5$ A/m. A surface treatment can be performed for the ferromagnetic grains by using silica and/or alumina or an organic material. Also, the surface of the ferromagnetic grain can be treated with a silane coupling agent or a titanium coupling agent as described in JP-A-6-161032. A ferromagnetic grain whose surface is coated with an inorganic or organic substance described in JP-A-4-259911 or 5-81652 can also be used.

As a binder used together with the magnetic grains, it is possible to use a thermoplastic resin described in JP-A-4-219569, thermosetting resin, radiation-curing resin, reactive resin, acidic, alkaline, or biodegradable polymer, natural polymer (e.g., a cellulose derivative and sugar derivative), and their mixtures. The Tg of the resin is $-40°$ C. to 300° C., and its weight average molecular weight is 2,000 to 1,000,000. Examples are a vinyl-based copolymer, cellulose derivatives such as cellulosediacetate, cellulosetriacetate, celluloseacetatepropionate, celluloseacetatebutylate, and cellulosetripropionate, acrylic resin, and polyvinylacetal resin. Gelatin is also preferable. Cellulosedi(tri)acetate is particularly preferable. This binder can be hardened by the addition of an epoxy-, aziridine-, or isocyanate-based crosslinking agent. Examples of the isocyanate-based crosslinking agent are isocyanates such as tolylenediisocyanate, 4,4'-diphenylmethanediisocyanate, hexamethylenediisocyanate, and xylylenediisocyanate, reaction products of these isocyanates and polyalcohol (e.g., a reaction product of 3 mols of tolylenediisocyanate and 1 mol of trimethylolpropane), and polyisocyanate produced by condensation of any of these isocyanates. These examples are described in JP-A-6-59357.

As a method of dispersing the magnetic substance in the binder, as described in JP-A-6-35092, a kneader, pin type mill, and annular mill are preferably used singly or together. Dispersants described in JP-A-5-088283 and other known dispersants can be used. The thickness of the magnetic recording layer is 0.1 to 10 μm, preferably 0.2 to 5 μm, and more preferably 0.3 to 3 μm.

The weight ratio of the magnetic grains to the binder is preferably 0.5:100 to 60:100, and more preferably 1:100 to 30:100. The coating amount of the magnetic grains is 0.005 to 3 g/m$^2$, preferably 0.01 to 2 g/m$^2$, and more preferably 0.02 to 0.5 g/m$^2$. The transmitting yellow density of the magnetic recording layer is preferably 0.01 to 0.50, more preferably 0.03 to 0.20, and especially preferably 0.04 to 0.15. The magnetic recording layer can be formed in the whole area of, or into the shape of stripes on, the back surface of a photographic support by coating or printing. As a method of coating the magnetic recording layer, it is possible to use any of an air doctor, blade, air knife, squeegee, impregnation, reverse roll, transfer roll, gravure, kiss, cast, spray, dip, bar, and extrusion. A coating solution described in JP-A-5-341436 is preferable.

The magnetic recording layer can be given a lubricating property improving function, curling adjusting function, antistatic function, adhesion preventing function, and head polishing function. Alternatively, another functional layer can be formed and these functions can be given to that layer. A polishing agent in which at least one type of grains are aspherical inorganic grains having a Mohs hardness of 5 or more is preferable. The composition of this aspherical inorganic grain is preferably an oxide such as aluminum oxide, chromium oxide, silicon dioxide, titanium dioxide, and silicon carbide, a carbide such as silicon carbide and titanium carbide, or a fine powder of diamond. The surfaces of the grains constituting these polishing agents can be treated with a silane coupling agent or titanium coupling agent. These grains can be added to the magnetic recording layer or overcoated (as, e.g., a protective layer or lubricant layer) on the magnetic recording layer. A binder used together with the grains can be any of those described above and is preferably the same binder as in the magnetic recording layer. Sensitive materials having the magnetic recording layer are described in U.S. Pat. Nos. 5,336,589, 5,250,404, 5,229,259, and 5,215,874, and EP 466,130.

A polyester support used in the present invention will be described below. Details of the polyester support and sensitive materials, processing, cartridges, and examples (to be described later) are described in Journal of Technical Disclosure No. 94-6023 (JIII; 1994, Mar. 15). Polyester used in the present invention is formed by using diol and aromatic dicarboxylic acid as essential components. Examples of the aromatic dicarboxylic acid are 2,6-, 1,5-, 1,4-, and 2,7-naphthalenedicarboxylic acids, terephthalic acid, isophthalic acid, and phthalic acid. Examples of the diol are diethyleneglycol, triethyleneglycol, cyclohexanedimethanol, bisphenol A, and bisphenol. Examples of the polymer are homopolymers such as polyethyleneterephthalate, polyethylenenaphthalate, and polycyclohexanedimethanolterephthalate. Polyester containing 50 to 100 mol % of 2,6-naphthalenedicarboxylic acid is particularly preferable. Polyethylene-2,6-naphthalate is especially preferable among other polymers.

The weight-average molecular weight ranges between about 5,000 and 200,000. The Tg of the polyester of the present invention is 50° C. or higher, preferably 90° C. or higher.

To give the polyester support a resistance to curling, the polyester support is heat-treated at a temperature of 40° C. to less than Tg, more preferably Tg $-20°$ C. to less than Tg. The heat treatment can be performed at a fixed temperature within this range or can be performed together with cooling. The heat treatment time is 0.1 to 1500 hrs, more preferably 0.5 to 200 hrs. The heat treatment can be performed for a roll-like support or while a support is conveyed in the form of a web. The surface shape can also be improved by roughening the surface (e.g., coating the surface with conductive inorganic fine grains such as $SnO_2$ or $Sb_2O_5$). It is desirable to knurl and slightly raise the end portion, thereby preventing the cut portion of the core from being photographed. These heat treatments can be performed in any stage after support film formation, after surface treatment, after back layer coating (e.g., an antistatic agent or lubricating agent), and after undercoating. A preferable timing is after the antistatic agent is coated.

An ultraviolet absorbent can be incorporated into this polyester. Also, to prevent light piping, dyes or pigments such as Diaresin manufactured by Mitsubishi Kasei Corp. or Kayaset manufactured by NIPPON KAYAKU CO. LTD. commercially available for polyester can be incorporated.

In the present invention, it is preferable to perform a surface treatment in order to adhere the support and the sensitive material constituting layers. Examples of the surface treatment are surface activation treatments such as a chemical treatment, mechanical treatment, corona discharge treatment, flame treatment, ultraviolet treatment, high-frequency treatment, glow discharge treatment, active plasma treatment, laser treatment, mixed acid treatment, and ozone oxidation treatment. Among other surface treatments, the ultraviolet radiation treatment, flame treatment, corona treatment, and glow treatment are preferable.

An undercoating layer can include a single layer or two or more layers. Examples of an undercoating layer binder are copolymers formed by using, as a starting material, a monomer selected from vinylchloride, vinylidenechloride, butadiene, methacrylic acid, acrylic acid, itaconic acid, and maleic anhydride. Other examples are polyethyleneimine, an epoxy resin, grafted gelatin, nitrocellulose, and gelatin. Resorcin and p-chlorophenol are examples of a compound which swells a support. Examples of a gelatin hardener added to the undercoating layer are chromium salt (e.g., chromium alum), aldehydes (e.g., formaldehyde and glutaraldehyde), isocyanates, an active halogen compound (e.g., 2,4-dichloro-6-hydroxy-s-triazine), epichlorohydrin resin, and active vinylsulfone compound. $SiO_2$, $TiO_2$, inorganic fine grains, or polymethylmethacrylate copolymer fine grains (0.01 to 10 $\mu$m) can also be contained as a matting agent.

In the present invention, an antistatic agent is preferably used. Examples of this antistatic agent are carboxylic acid, carboxylate, a macromolecule containing sulfonate, cationic macromolecule, and ionic surfactant compound.

As the antistatic agent, it is especially preferable to use fine grains of at least one crystalline metal oxide selected from ZnO, $TiO_2$, $SnO_2$, $Al_2O_3$, $In_2O_3$, $SiO_2$, MgO, BaO, $MoO_3$, and $V_2O_5$, and having a volume resistivity of $10^7$ $\Omega\cdot$cm or less, more preferably $10^5$ $\Omega\cdot$cm or less and a grain size of 0.001 to 1.0 $\mu$m, fine grains of composite oxides (e.g., Sb, P, B, In, S, Si, and C) of these metal oxides, fine grains of sol metal oxides, or fine grains of composite oxides of these sol metal oxides.

The content in a sensitive material is preferably 5 to 500 mg/m$^2$, and especially preferably 10 to 350 mg/m$^2$. The ratio of a conductive crystalline oxide or its composite oxide to the binder is preferably 1/300 to 100/1, and more preferably 1/100 to 100/5.

A sensitive material of the present invention preferably has a slip property. Slip agent-containing layers are preferably formed on the surfaces of both a sensitive layer and back layer. A preferable slip property is 0.01 to 0.25 as a coefficient of kinetic friction. This represents a value obtained when a stainless steel sphere 5 mm in diameter is conveyed at a speed of 60 cm/min (25° C., 60% RH). In this evaluation, a value of nearly the same level is obtained when the surface of a sensitive layer is used as a sample to be measured.

Examples of a slip agent usable in the present invention are polyorganocyloxane, higher fatty acid amide, higher fatty acid metal salt, and ester of higher fatty acid and higher alcohol. As the polyorganocyloxane, it is possible to use, e.g., polydimethylcyloxane, polydiethylcyloxane, polystyrylmethylcyloxane, or polymethylphenylcyloxane. A layer to which the slip agent is added is preferably the outermost emulsion layer or back layer. Polydimethylcyloxane or ester having a long-chain alkyl group is particularly preferable.

A sensitive material of the present invention preferably contains a matting agent. This matting agent can be added to either the emulsion surface or back surface and is especially preferably added to the outermost emulsion layer. The matting agent can be either soluble or insoluble in processing solutions, and the use of both types of matting agents is preferable. Preferable examples are polymethylmethacrylate grains, poly(methylmethacrylate/methacrylic acid)=9/1 or 5/5 (molar ratio)) grains, and polystyrene grains. The grain size is preferably 0.8 to 10 $\mu$m, and a narrow grain size distribution is preferable. It is preferable that 90% or more of all grains have grain sizes 0.9 to 1.1 times the average grain size. To increase the matting property, it is preferable to simultaneously add fine grains with a grain size of 0.8 $\mu$m or smaller. Examples are polymethylmethacrylate grains (0.2 $\mu$m), poly(methylmethacrylate/methacrylic acid)=9/1 (molar ratio, 0.3 $\mu$m) grains, polystyrene grains (0.25 $\mu$m), and colloidal silica grains (0.03 $\mu$m).

EXAMPLE

Examples of the present invention will be described below, which however in no way limit the scope of the present invention.

Example 1

(Measurement of the Amount of Dye Adsorbed on Silver Halide Grains)

The amount of dye adsorbed was determined by carrying out centrifugal sedimentation of an obtained liquid emulsion at 4000 rpm for 10 min, subsequently effecting freeze drying of the thus obtained deposit, thereafter adding 25 mL of a 10% aqueous sodium thiosulfate solution, 12.5 mL of DMF and methanol to 0.02 g of dried deposit so that the total volume became 50 mL and finally analyzing the resultant solution by high-performance liquid chromatography, thereby identifying the concentration of dye.

The monolayered saturated adsorption amount of dye on silver halide grains was estimated through determining of the adsorption isotherm of each dye as described herein in the section "DETAILED DESCRIPTION OF THE INVENTION".

(Measurement of Light Absorption by Microspectroscopy)

In the measurement of the light absorptivity and intensity of light absorption of each individual silver halide grain, a thin coating of obtained emulsion was provided on a slide glass, and the transmission spectrum and reflection spectrum of each grain were measured by means of microspectrophotometer MSP65 manufactured by Carl Zeiss in the following manner, thereby obtaining the absorption spectrum thereof. Part devoid of grains was used as the reference of transmission spectrum, while with respect to reflection spectrum, silicon carbide whose reflectance was known was measured and used as the reference thereof. Measured part consisted of circular aperture part of 1 $\mu$m diameter, and while making position adjustment so as to avoid overlapping of aperture part with grain contour, the transmission spectrum and reflection spectrum were measured in the wavenumber region from 14000 cm$^{-1}$ (714 nm) to 28000 cm$^{-1}$ (357 nm). Considering the value of 1−T (transmission factor)−R (reflectance) as absorptivity A, the absorption spectrum was determined.

The remainder resulting from deduction of the absorption of silver halides therefrom was designated absorptivity A'. The value resulting from integration of −Log(1−A') over wavenumber (cm$^{-1}$) and halving (½) of the integral value was designated intensity of light absorption per unit surface area. The integration ranged from 14000 cm$^{-1}$ to 28000 cm$^{-1}$. In the measurement of light absorption, a tungsten lamp was used as the light source, and the voltage of light source was 8 V. For minimizing the damage of dye by light irradiation, use was made of a primary-side monochrometer, and the wavelength interval and slit width were set for 2 nm and 2.5 nm, respectively.

(Gelatin for Use in Preparation of Silver Halide Emulsion and Process for Producing the Same)

Gelatin-1 to -6 used as protective colloid dispersing medium used in the emulsion preparation of the following examples are those having the following property.

Gelatin-1: Common alkali-processed ossein gelatin made from bovine bones.

Gelatin-2: Gelatin formed by decreasing the molecular weight of gelatin-1 by allowing enzyme to act on it such that the average molecular weight was 15,000, deactivating the enzyme, and drying the resultant material.

Gelatin-3: Gelatin formed by adding phthalic anhydride to an aqueous solution of gelatin-1 at 50° C. and pH 9.0 to cause chemical reaction, removing the residual phthalic acid, and drying the resultant material. The ratio of the number of chemically modified —$NH_2$ groups in the gelatin was 95%.

Gelatin-4: Gelatin formed by adding anhydrous succinic acid to a solution of gelatin-1 at 50° C. and pH 9.0 to cause chemical reaction, removing the residual succinic acid, and drying the resultant material. The ratio of the number of chemically modified —$NH_2$ groups in the gelatin was 98%.

Gelatin-5: Gelatin formed by adding anhydrous trimellitic acid to an aqueous solution of gelatin-1 at 50° C. and pH 9.0 to cause chemical reaction, removing the residual trimellitic acid, and drying the resultant material. The ratio of the number of chemically modified —$NH_2$ groups in the gelatin was 95%.

Gelatin-6: Gelatin formed by adding anhydrous pyromellitic acid to an aqueous solution of gelatin-1 at 50° C. and pH 9.0 to cause chemical reaction, removing the residual pyromellitic acid, and drying the resultant material. The ratio of the number of chemically modified —$NH_2$ groups in the gelatin was 93%.

(Water Base Dispersion of Sensitizing Dye for Use in Preparation of Silver Halide Emulsion and Process for Producing the Same)

(Preparation of Dye Despersion a-1 of First Layer)

11.1 g of sensitizing dye Exs-3, 3.4 g of sensitizing dye Exs-6 and 4.0 g of sensitizing dye Exs-7 were added to 1000 mL of water under agitation by means of a dissolver blade. Agitation was further continued at 50° C. for 2 hr. $H_2O$ and 80 g of gelatin were added so that the whole amount became 1500 g.

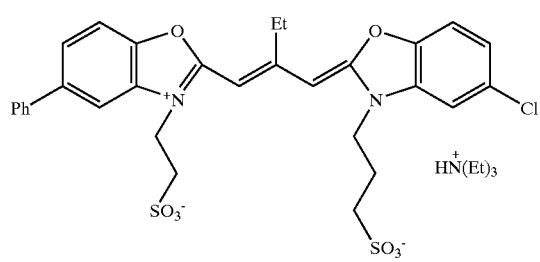

ExS-3

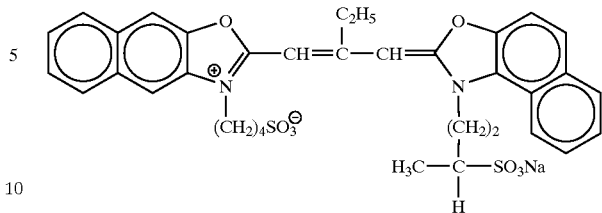

ExS-6

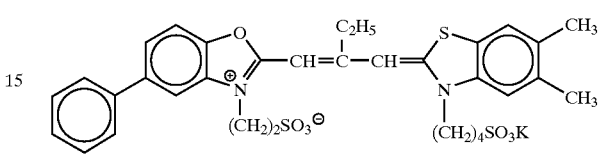

ExS-7

(Preparation of Dye Dispersion b-1 of Second Layer or the Rest of the Layers)

1.0 g of sensitizing dye Exs-12 and 2.0 g of sodium sulfate were added to 96 mL of water. 200 g of zirconia beads of 0.2 mm diameter were further added, and dispersion was performed by means of a sand grinder mill at 45° C. for 2 hr. The zirconia beads were separated, thereby obtaining dye dispersion b-1.

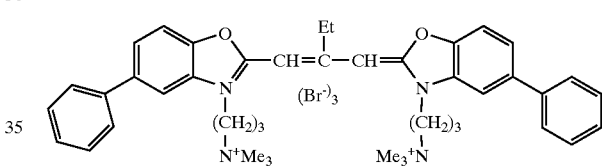

Exs-12

(Preparation of Dye Dispersion c-1 of Second Layer or the Rest of the Layers)

1.2 g of sensitizing dye Exs-13 was added to 85 mL of water. Agitation was performed by means of a dissolver blade at 55° C. for 1 hr. 5 g of gelatin was further added, and agitation was continued for 20 min. Thus, dye dispersion c-1 was obtained.

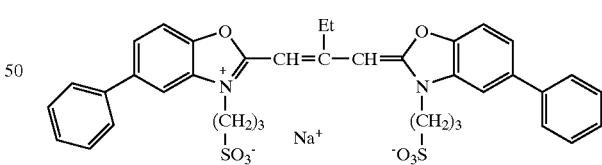

Exs-13

With respect to the preparation of emulsions of comparative examples and the present invention, embodiments will be described below.

(Preparation of Emulsion EGA-1 of Comparative Example)

1200 mL of an aqueous solution containing 0.38 g of gelatin-2 and 0.9 g of KBr was vigorously agitated at a pH value adjusted to 2.0 while maintaining the temperature thereof at 60° C. An aqueous solution containing 0.7 g of $AgNO_3$ and an aqueous solution containing 0.6 g of KBr and 0.06 g of KI were added by the double jet method over a period of 30 sec, and ripened. After the completion of ripening, 13.5 g of gelatin-1 was added. The pH was adjusted to 5.7, and 2.0 g of KBr was added. An aqueous solution of KBr and 60.7 mL of an aqueous solution containing 27.3 g of AgNO$_3$ were added by the double jet method over a period of 41 min. During this period, the pAg of bulk emulsion solution in the reaction vessel was maintained at 8.7. Further, an aqueous solution containing 65.6 g of AgNO$_3$ and an aqueous solution of KBr were added by the double jet method over a period of 50 min while increasing the flow rate so that the final flow rate was 2.1 times the initial flow rate. During this period, a silver iodide fine grain emulsion of 0.032 μm grain size was simultaneously added while conducting a flow rate increase so that the silver iodide content became 6.5 mol %, and the pAg of bulk emulsion solution in the reaction vessel was maintained at 8.7.

Subsequently, an aqueous solution of KBr and 132 mL of an aqueous solution containing 41.8 g of AgNO$_3$ were added by the double jet method over a period of 19 min. The addition of the aqueous solution of KBr was regulated so that the pAg of bulk emulsion solution in the reaction vessel at the completion of addition became 7.70. 2 mg of sodium benzenethiosulfonate was added, and KBr was added so that the pAg of bulk emulsion solution in the reaction vessel was adjusted to 9.80. Further, 6.2 g, in terms of the weight of KI, of silver iodide fine grain emulsion of 0.032 μm grain size was added. Immediately upon the completion of addition, 300 mL of an aqueous solution containing 88.5 g of AgNO$_3$ was added over a period of 10 min. The addition of KBr aqueous solution was regulated so that the pAg of bulk emulsion solution in the reaction vessel at the completion of addition became 7.40. Just prior to subjecting the mixture to desalting washing, 13.5 g of gelatin-1 was added.

Thereafter, desalting washing was carried out according to the dialytic method using a semipermeable membrane. Then, under agitation, water, NaOH and the above gelatin-1 were added so as to attain adjustment to pH 5.8 and pAg 8.8 at 50° C.

TAZ-1 was added, and the mixture was heated to 58° C. The above prepared dye dispersion a-1 was added, and potassium thiocyanate, chloroauric acid, sodium thiosulfate and N,N-dimethylselenourea were sequentially added to thereby effect the optimum chemical sensitization. At the completion of chemical sensitization, MER-1 and MER-2 were added.

With respect to the amount of sensitizing dyes added by the above addition of dye dispersion a-1, the total addition amount of sensitizing dyes Exs-3, Exs-6 and Exs-7 was 6.08×10$^{-4}$ mol per mol of silver.

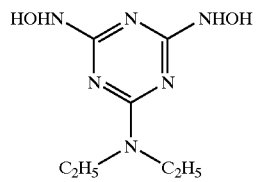

TAZ-1

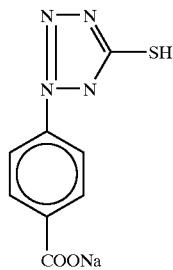

MER-1

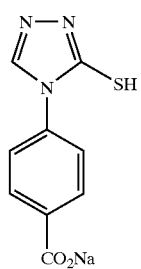

MER-2

The thus obtained emulsion was composed of silver halide tabular grains of 1.20 μm equivalent sphere diameter, 2.40 μm average equivalent circle diameter of main surfaces and 0.20 μm average grain thickness wherein mutually parallel main surfaces consisted of (111) planes. The variation coefficient of equivalent circle diameter was 25%.

The ratio of adsorption of sensitizing dyes was 99% based on the addition amount, and the dye adsorption amount was estimated at 82% based on the monolayered saturated adsorption amount.

The measuring of light absorption by microspectroscopy with respect to randomly chosen silver halide grains was carried out in the aforementioned manner. As a result, it was found that in the intensity of light absorption per unit area, substantially no difference existe7611d between grains, and that the sensitizing dyes were in the form of monolayer adsorption with respect to substantially all the grains.

(Preparation of Emulsion EGA-2 of Comparative Example)

The above emulsion EGA-1 was converted to dissolved form at 40° C., and the above prepared dye dispersion b-1 was added thereto and ripened for 5 min. Further, the above prepared dye dispersion c-1 was added thereto and ripened for 20 min. Thus, emulsion EGA-2 was obtained.

With respect to the amount of sensitizing dyes added by the above addition of dye dispersions b-1 and c-1, the addition amounts of sensitizing dyes Exs-12 and Exs-13 were both 2.00×10$^{-4}$ mol per mol of silver.

The ratio of adsorption of sensitizing dye was 99% based on the addition amount with respect to sensitizing dye Exs-12 and 91% based on the addition amount with respect to sensitizing dye Exs-13. The dye adsorption amount was estimated at 134% based on the monolayered saturated adsorption amount.

The measuring of light absorption by microspectroscopy with respect to randomly chosen silver halide grains was carried out in the aforementioned manner. As a result, it was found that with respect to substantially all the grains, the intensity of light absorption per unit area exceeded that exhibited at monolayered saturated adsorption, and hence that substantially all the grains were in the state of multilayer adsorption of dye chromophores mentioned in the present invention.

(Preparation of Emulsion EGA-3 of Comparative Example)

Emulsion EGA-3 was prepared under the same conditions as in the above preparation of emulsion EGA-2, except that the addition amounts of sensitizing dyes Exs-12 and Exs-13 were both $6.08\times10^{-4}$ mol per mol of silver.

The ratio of adsorption of sensitizing dye was 99% based on the addition amount with respect to sensitizing dye Exs-12 and 88% based on the addition amount with respect to sensitizing dye Exs-13. The dye adsorption amount was estimated at 237% based on the monolayered saturated adsorption amount.

The measuring of light absorption by microspectroscopy with respect to randomly chosen silver halide grains was carried out in the aforementioned manner. As a result, it was found that with respect to substantially all the grains, the intensity of light absorption per unit area exceeded that exhibited at monolayered saturated adsorption, and hence that substantially all the grains were in the state of multilayer adsorption of dye chromophores mentioned in the present invention.

(Preparation of Emulsion EGA-4 of Comparative Example and Emulsions EGA-5 and -6 of Present Invention)

Emulsions EGA-4 to -6 were prepared under the same conditions as in the above preparation of emulsions EGA-1 to -3, except that the gelatin-1 added just before desalting washing was replaced by an equal weight of gelatin-3 being phthalated gelatin having its —$NH_2$ group chemically modified.

Whilst the emulsions EGA-1 to -3 contained none of gelatin having its —$NH_2$ group chemically modified, the ratio of gelatin having its —$NH_2$ group chemically modified to all the dispersion mediums with respect to the emulsions EGA-4 to -6 was 11%.

The adsorption ratio and light absorption by microspectroscopy of sensitizing dyes were substantially unchanged despite the above gelatin replacement.

(Preparation of Emulsion EGB-1 of Comparative Example)

1200 mL of an aqueous solution containing 0.38 g of gelatin-2 and 0.9 g of KBr was vigorously agitated at a pH value adjusted to 2.0 while maintaining the temperature thereof at 60° C. An aqueous solution containing 0.7 g of $AgNO_3$ and an aqueous solution containing 0.6 g of KBr and 0.06 g of KI were added by the double jet method over a period of 30 sec, and ripened. After the completion of ripening, 13.5 g of gelatin-3 was added. The pH was adjusted to 5.7, and 2.0 g of KBr was added. An aqueous solution of KBr and 60.7 mL of an aqueous solution containing 27.3 g of $AgNO_3$ were added by the double jet method over a period of 41 min. During this period, the pAg of bulk emulsion solution in the reaction vessel was maintained at 9.0. Further, an aqueous solution containing 65.6 g of $AgNO_3$ and an aqueous solution of KBr were added by the double jet method over a period of 50 min while increasing the flow rate so that the final flow rate was 2.1 times the initial flow rate. During this period, a silver iodide fine grain emulsion of 0.032 μm grain size was simultaneously added while conducting a flow rate increase so that the silver iodide content became 6.5 mol %, and the pAg of bulk emulsion solution in the reaction vessel was maintained at 9.0.

Subsequently, an aqueous solution of KBr and 132 mL of an aqueous solution containing 41.8 g of $AgNO_3$ were added by the double jet method over a period of 19 min. The addition of the aqueous solution of KBr was regulated so that the pAg of bulk emulsion solution in the reaction vessel at the completion of addition became 7.70. 2 mg of sodium benzenethiosulfonate was added, and KBr was added so that the pAg of bulk emulsion solution in the reaction vessel was adjusted to 9.80. Further, 6.2 g, in terms of the weight of KI, of silver iodide fine grain emulsion of 0.032 μm grain size was added. Immediately upon the completion of addition, 300 mL of an aqueous solution containing 88.5 g of $AgNO_3$ were added over a period of 10 min. The addition of KBr aqueous solution was regulated so that the pAg of bulk emulsion solution in the reaction vessel at the completion of addition became 7.40. Just prior to subjecting the mixture to desalting washing, 13.5 g of gelatin-1 was added.

Thereafter, desalting washing was carried out according to the dialytic method using a semipermeable membrane. Then, under agitation, water, NaOH and the aforementioned gelatin-1 were added so as to attain adjustment to pH 5.8 and pAg 8.8 at 50° C.

The aforementioned TAZ-1 was added, and the mixture was heated to 58° C. The above prepared dye dispersion a-1 was added, and potassium thiocyanate, chloroauric acid, sodium thiosulfate and N,N-dimethylselenourea were sequentially added to thereby effect the optimum chemical sensitization. At the completion of chemical sensitization, the aforementioned MER-1 and MER-2 were added.

With respect to the amount of sensitizing dyes added by the above addition of dye dispersion a-1, the total addition amount of sensitizing dyes Exs-3, Exs-6 and Exs-7 was $1.01\times10^{-3}$ mol per mol of silver.

The thus obtained emulsion was composed of silver halide tabular grains of 1.20 μm equivalent sphere diameter, 3.10 μm average equivalent circle diameter of main surfaces and 0.12 μm average grain thickness wherein mutually parallel main surfaces consisted of (111) planes. The variation coefficient of equivalent circle diameter was 33%.

The ratio of adsorption of sensitizing dyes was 98% based on the addition amount, and the dye adsorption amount was estimated at 81% based on the monolayered saturated adsorption amount.

The measuring of light absorption by microspectroscopy with respect to randomly chosen silver halide grains was carried out in the aforementioned manner. As a result, it was found that in the intensity of light absorption per unit area, substantially no difference existed between grains, and that the sensitizing dyes were in the form of monolayer adsorption with respect to substantially all the grains.

(Preparation of Emulsion EGB-2 of Present Invention)

The above emulsion EGB-1 was converted to dissolved form at 40° C., and the above prepared dye dispersion b-1 was added thereto and ripened for 5 min. Further, the above prepared dye dispersion c-1 was added thereto and ripened for 20 min. Thus, emulsion EGB-2 was obtained.

With respect to the amount of sensitizing dyes added by the above addition of dye dispersions b-1 and c-1, the addition amounts of sensitizing dyes Exs-12 and Exs-13 were $5.55\times10^{-4}$ mol and $4.54\times10^{-4}$ mol, respectively, per mol of silver.

The ratio of adsorption of sensitizing dye was 98% based on the addition amount with respect to sensitizing dye Exs-12 and also 98% based on the addition amount with respect to sensitizing dye Exs-13. The dye adsorption amount was estimated at 162% based on the monolayered saturated adsorption amount.

The measuring of light absorption by microspectroscopy with respect to randomly chosen silver halide grains was carried out in the aforementioned manner. As a result, it was found that with respect to substantially all the grains, the intensity of light absorption per unit area exceeded that exhibited at monolayered saturated adsorption, and hence that substantially all the grains were in the state of multilayer adsorption of dye chromophores mentioned in the present invention.

(Preparation of Emulsion EGB-3 of Present Invention)

Emulsion EGB-3 was prepared under the same conditions as in the above preparation of emulsion EGB-2, except that the addition amounts of sensitizing dyes Exs-12 and Exs-13 were both changed to $5.04 \times 10^{-4}$ mol per mol of silver.

The ratio of adsorption of sensitizing dye was 99% based on the addition amount with respect to sensitizing dye Exs-12 and 91% based on the addition amount with respect to sensitizing dye Exs-13. The dye adsorption amount was estimated at 159% based on the monolayered saturated adsorption amount.

The measuring of light absorption by microspectroscopy with respect to randomly chosen silver halide grains was carried out in the aforementioned manner. As a result, it was found that with respect to substantially all the grains, the intensity of light absorption per unit area exceeded that exhibited at monolayered saturated adsorption, and hence that substantially all the grains were in the state of multilayer adsorption of dye chromophores mentioned in the present invention.

(Preparation of Emulsion EGB-4 of Present Invention)

Emulsion EGB-4 was prepared under the same conditions as in the above preparation of emulsion EGB-2, except that the addition amounts of sensitizing dyes Exs-12 and Exs-13 were changed to $4.54 \times 10^{-4}$ mol and $5.55 \times 10^{-4}$ mol, respectively, per mol of silver.

The ratio of adsorption of sensitizing dye was 99% based on the addition amount with respect to sensitizing dye Exs-12 and 89% based on the addition amount with respect to sensitizing dye Exs-13. The dye adsorption amount was estimated at 158% based on the monolayered saturated adsorption amount.

The measuring of light absorption by microspectroscopy with respect to randomly chosen silver halide grains was carried out in the aforementioned manner. As a result, it was found that with respect to substantially all the grains, the intensity of light absorption per unit area exceeded that exhibited at monolayered saturated adsorption, and hence that substantially all the grains were in the state of multilayer adsorption of dye chromophores mentioned in the present invention.

The above emulsions EGA-1 to -6 and EGB-1 to -4 were observed through 400 kV transmission electron microscope at liquid nitrogen temperature. With respect to all the emulsions, grains amounting to 50% or more of the total projected area had 10 or more dislocation lines per grain at peripheral regions of the grains.

Undercoated cellulose triacetate film supports were coated with the above emulsions EGA-1 to -6 and EGB-1 to -4 under the coating conditions specified in Table 1 below.

TABLE 1

Emulsion coating condition (1) Emulsion layer

| | |
|---|---|
| Emulsion: Each emulsion | (silver $9.3 \times 10^{-3}$ mol/m$^2$) |
| Coupler | ($1.29 \times 10^{-3}$ mol/m$^2$) |

TABLE 1-continued

Emulsion coating condition

[Chemical structure: a coupler compound with $^tC_5H_{11}$ groups, $OCHCONH$ with $C_2H_5$ substituent, pyrazolone ring with CONH linker, and 2,4,6-trichlorophenyl group]

| | |
|---|---|
| Tricresyl phosphate | (0.75 g/m$^2$) |
| Gelatin | (3.24 g/m$^2$) |

(2) Protective layer

| | |
|---|---|
| 2,4-Dichloro-6-hydroxy-s-triazine sodium salt | (0.08 g/m$^2$) |
| Gelatin | (1.80 g/m$^2$) |

These samples were subjected to film hardening for 14 hr at 40° C. and a relative humidity of 70%. After that, the samples were exposed for 1/100 sec through a gelatin filter SC-50 (a long-wavelength light transmitting filter having a cutoff wavelength of 500 nm) manufactured by Fuji Photo Film Co., Ltd. and a continuous wedge. The exposed samples were processed with the processing to be described later and the density was measured with a green filter to conduct evaluation of photographic speed.

For the evaluation of storability, the above coated samples were subjected to the film hardening, kept under an ambience of 60° C. and 60% RH for four days. The extent in the increment of fog density was compared to evaluate the storability. When the extent in increment of fog density of the sample is smaller, the sample was evaluated as better in storability.

The development was done as follows by using an automatic processor FP-350 manufactured by Fuji Photo Film Co., Ltd (until the accumulated replenishing amount becomes three times the mother tank solution).

(Processing Steps)

| Step | Time | Temperature | Replenishing amount* |
|---|---|---|---|
| Color development | 2 min 45 sec | 38° C. | 45 mL |
| Bleaching | 1 min 00 sec | 38° C. | 20 mL All of the overflow of the bleach solution was flown to the tank of bleach-fix |
| Bleach-fix | 3 min 15 sec | 38° C. | 30 mL |
| Washing (1) | 40 sec | 35° C. | Counter current flow from (2) to (1) |
| Washing (2) | 1 min 00 sec | 35° C. | 30 mL |
| Stabilization | 40 sec | 38° C. | 20 mL |
| Drying | 1 min 15 sec | 55° C. | |

*The replenishment rate is a value per 1.1 m of a 35- mm wide lightsensitive material (equivalent to one role of 24 Ex. film).

The composition of each processing solution was as follows.

| (Color developer) | Tank solution (g) | Replenisher (g) |
|---|---|---|
| Diethylenetriaminepentaacetic acid | 1.0 | 1.1 |
| 1-Hydroxyethylidene-1,1-diphosphonic acid | 2.0 | 2.0 |
| Sodium sulfite | 4.0 | 4.4 |
| Potassium carbonate | 30.0 | 37.0 |
| Potassium bromide | 1.4 | 0.7 |
| Potassium iodide | 1.5 mg | — |
| Hydroxylamine sulfate | 2.4 | 2.8 |
| 4-[N-ethyl-N-(β-hydroxyethyl)amino]-2-methylaniline sulfate | 4.5 | 5.5 |
| Water to make | 1.0 L | 1.0 L |
| pH (adjusted by the use of potassium hydroxide and sulfuric acid) | 10.05 | 10.10 |
| (Bleach solution) | Common to tank solution and replenisher (unit: g) | |
| Fe (III) ammonium ethylenediaminetetraacetate dihydrate | 120.0 | |
| Disodium ethylenediaminetetraacetate | 10.0 | |
| Ammonium bromide | 100.0 | |
| Ammonium nitrate | 10.0 | |
| Bleach accelerator $(CH_3)_2N-CH_2-CH_2-S-S-CH_2-CH_2-N(CH_3)_2 \cdot 2HCl$ | 0.005 mol | |
| Aqueous ammonia (27%) | 15.0 ml | |
| Water to make | 1.0 L | |
| pH (adjusted by the use of aqueous ammonia and nitric acid) | 6.3 | |

| (Bleach-fix sol) | Tank solution (g) | Replenisher (g) |
|---|---|---|
| Fe (III) ammonium ethylenediaminetetraacetate Dihydrate | 50.0 | — |
| Disodium ethylenediaminetetraacetate | 5.0 | 2.0 |
| Sodium sulfite | 12.0 | 20.0 |
| Aqueous solution of ammonium thiosulfate (700 g/L) | 240.0 mL | 400.0 mL |
| Aqueous ammonia (27%) | 6.0 ml | — |
| Water to make | 1.0 L | 1.0 L |
| pH (adjusted by aqueous ammonia and acetic acid) | 7.2 | 7.3 |
| (Washing water) Common to the tank solution and replenisher | | |

Tap water was passed through a mixed-bed column filled with H-type strongly acidic cation exchange resin (Amberlite IR-120B produced by Rohm & Haas Co.) and OH-type strongly basic anion exchange resin (Amberlite IR-400 produced by the same maker) so as to set the concentration of calcium and magnesium ions at 3 mg/L or less. Subsequently, 20 mg/L of sodium dichloroisocyanurate and 0.15 g/L of sodium sulfate were added. The pH of the solution ranged from 6.5 to 7.5.

| (Stabilizer) | Common to tank solution and replenisher (unit: g) |
|---|---|
| Sodium p-toluenesulfinate | 0.03 |
| Polyoxyethylene-p-monononylphenyl ether (av. polymerization degree: 10) | 0.2 |
| Disodium Ethylenediaminetetraacetic acid | 0.05 |
| 1,2,4-Triazole | 1.3 |
| 1,4-Bis(1,2,4-triazol-1-ylmethyl)piperazine | 0.75 |
| Water to make | 1.0 L |
| pH | 8.5 |

The properties and performance of emulsions used in coating were assessed, and the results thereof are listed in Table 2 below. The speed was expressed by a relative value of inverse number of exposure amount required for reaching a density of fog density ±0.2.

The storability was expressed by an increment of fog density during the storage of the coating samples.

TABLE 2

| Emulsion No. | Av. grain ECD ($\mu$m) | Av. Grain thickness ($\mu$m) | Amount of the first dye (mol/Ag mol) | Amount of the second dye (mol/Ag mol) | Amount of the third dye (mol/Ag mol) | Ration of amino group modified gelatin (%) | Relative speed[1] | Increment of fog during storage[2] | Remarks |
|---|---|---|---|---|---|---|---|---|---|
| EGA-1 | 2.4 | 0.2 | $6.08 \times 10^{-4}$ | None | None | None | 100 | 0.11 | Comp. |
| EGA-2 | 2.4 | 0.2 | $6.08 \times 10^{-4}$ | $2.00 \times 10^{-4}$ | $2.00 \times 10^{-4}$ | None | 112 | 0.23 | Comp. |
| EGA-3 | 2.4 | 0.2 | $6.08 \times 10^{-4}$ | $6.08 \times 10^{-4}$ | $6.08 \times 10^{-4}$ | None | 126 | 0.31 | Comp. |
| EGA-4 | 2.4 | 0.2 | $6.08 \times 10^{-4}$ | None | None | 11 (Phthalated gelatin) | 100 | 0.12 | Comp. |
| EGA-5 | 2.4 | 0.2 | $6.08 \times 10^{-4}$ | $2.00 \times 10^{-4}$ | $2.00 \times 10^{-4}$ | 11 (Phthalated gelatin) | 142 | 0.10 | Inv. |
| EGA-6 | 2.4 | 0.2 | $6.08 \times 10^{-4}$ | $6.08 \times 10^{-4}$ | $6.08 \times 10^{-4}$ | 11 (Phthalated gelatin) | 192 | 0.10 | Inv. |
| EGB-1 | 3.1 | 0.12 | $1.01 \times 10^{-3}$ | None | None | 11 (Phthalated gelatin) | 126 | 0.19 | Comp. |
| EGB-2 | 3.1 | 0.12 | $1.01 \times 10^{-3}$ | $5.55 \times 10^{-4}$ | $4.54 \times 10^{-4}$ | 11 (Phthalated gelatin) | 215 | 0.18 | Inv. |

TABLE 2-continued

| Emulsion No. | Av. grain ECD (μm) | Av. Grain thickness (μm) | Amount of the first dye (mol/Ag mol) | Amount of the second dye (mol/Ag mol) | Amount of the third dye (mol/Ag mol) | Ration of amino group modified gelatin (%) | Relative speed*1 | Increment of fog during storage*2 | Remarks |
|---|---|---|---|---|---|---|---|---|---|
| EGB-3 | 3.1 | 0.12 | $1.01 \times 10^{-3}$ | $5.04 \times 10^{-4}$ | $5.04 \times 10^{-4}$ | 11 (Phthalated gelatin) | 215 | 0.17 | Inv. |
| EGB-4 | 3.1 | 0.12 | $1.01 \times 10^{-3}$ | $4.54 \times 10^{-4}$ | $5.55 \times 10^{-4}$ | 11 (Phthalated gelatin) | 219 | 0.16 | Inv. |

ECD = Equivalent circle diameter
*1Relative speed when the speed of emulsion EGA-1 is assumed to be 100.
*2In the case where samples coated with emulsions were stored under the ambient at a temperature of 60° C. and a relative humidity of 60% for four days.

From a comparison among the emulsions EGA-1 to -3, it is apparent that although the emulsions having a multilayer adsorption of sensitizing dyes exhibit higher sensitivity than that of the emulsion having a monolayer adsorption of sensitizing dyes, the extent of sensitivity enhancement is far less than expected on the basis of quantitative relationship of sensitizing dyes and a problem of large fog increment during storage is involved. The emulsions EGA-5 and -6 of the present invention wherein a multilayer adsorption of sensitizing dyes was effected on the emulsion containing amino-modified gelatin are preferred from the viewpoint that the extent of sensitivity enhancement is large while the fog increment during storage is slight. Since the effects of use of the above amino-modified gelatin are not exerted in the emulsion having a monolayer adsorption of sensitizing dyes, it is apparent that the effects of the present invention are not a simple sum of the effects of individual factors.

The emulsion EGA-5 of the present invention is preferred from the viewpoint that although the amount of sensitizing dyes thereof is substantially identical with that of the emulsion EGB-1 wherein the amount of sensitizing dyes was increased by reducing the grain thickness, it ultimately realizes high sensitivity and reduction of storage fogging.

In this Example, an anionic sensitizing dye was used as the first dye, a cationic sensitizing dye as the second dye and an anionic sensitizing dye as the third dye, and a multilayer adsorption thereof was accomplished by the use of Coulomb's force. Fundamentally the effects of the present invention can be attained as long as the amount of second dye and third dye for the formation of the second layer or the rest of the layers is not larger than that of first dye for the formation of the first layer. Further, although the ratio of second dye and third dye was basically set for about 1:1 in this Example, slight deviation of the ratio from 1:1 would have substantially no influence on the advantages of the present invention.

Example 2

(Preparation of Emulsion EGA-7 of Comparative Example and Emulsions EGA-8 to -15 of Present Invention)

Emulsions EGA-7 to -10 were prepared in the same manner as in the preparation of emulsion EGA-6 of Example 1 except that the amount of gelatin-3 added to just before desalting washing was changed. Further, emulsions EGA-11 to -13 were prepared in the same manner as in the preparation of emulsion EGA-6 of Example 1 except that gelatin-4 to -6 were substituted for the gelatin-3.

Still further, emulsions EGA-14 and -15 were prepared in the same manner as in the preparation of emulsion EGA-6 of Example 1 except that the addition of gelatin-3 was performed after desalting washing in place of performing before desalting washing and that the amount thereof was changed in two ways. These emulsions are emulsions wherein the proportion, type and addition timing of gelatin having its —NH$_2$ group chemically modified were changed from those of emulsions EGA-3 and -6.

In this connection, with respect to the light absorption by microspectroscopy and adsorption ratio of sensitizing dyes, there was substantially no change attributed to changes of the proportion, type and addition timing of the above gelatin.

Coating with these emulsions, together with the emulsions EGA-1 and -3 of comparative examples and emulsion EGA-6 of the present invention, was performed under the same conditions as in Example 1, and performance estimation was carried out. Table 3 lists the proportion, type and addition timing of gelatin having its —NH$_2$ group chemically modified with respect to each of the emulsions and further lists performance thereof.

TABLE 3

| Emulsion No. | Amount of the first dye (mol/Ag mol) | Amount of the second dye (mol/Ag mol) | Amount of the third dye (mol/Ag mol) | Ration of amino group modified gelatin (%) | Type of amino group modified gelatin | Addition time of amino group modified gelatin | Relative speed*1 | Increment of fog during storage*2 | Remarks |
|---|---|---|---|---|---|---|---|---|---|
| EGA-1 | $6.08 \times 10^{-4}$ | None | None | None | — | — | 100 | 0.11 | Comp. |
| EGA-3 | $6.08 \times 10^{-4}$ | $6.08 \times 10^{-4}$ | $6.08 \times 10^{-4}$ | None | — | — | 126 | 0.31 | Comp. |
| EGA-7 | $6.08 \times 10^{-4}$ | $6.08 \times 10^{-4}$ | $6.08 \times 10^{-4}$ | 1 | Phthalated gelatin | Immediately before desalting washing | 129 | 0.29 | Comp. |

TABLE 3-continued

| Emulsion No. | Amount of the first dye (mol/ Ag mol) | Amount of the second dye (mol/ Ag mol) | Amount of the third dye (mol/ Ag mol) | Ration of amino group modified gelatin (%) | Type of amino group modified gelatin | Addition time of amino group modified gelatin | Relative speed*1 | Increment of fog during storage*2 | Remarks |
|---|---|---|---|---|---|---|---|---|---|
| EGA-8 | $6.08 \times 10^{-4}$ | $6.08 \times 10^{-4}$ | $6.08 \times 10^{-4}$ | 2 | Phthalated gelatin | Immediately before desalting washing | 141 | 0.22 | Inv. |
| EGA-9 | $6.08 \times 10^{-4}$ | $6.08 \times 10^{-4}$ | $6.08 \times 10^{-4}$ | 5 | Phthalated gelatin | Immediately before desalting washing | 169 | 0.15 | Inv. |
| EGA-6 | $6.08 \times 10^{-4}$ | $6.08 \times 10^{-4}$ | $6.08 \times 10^{-4}$ | 11 | Phthalated gelatin | Immediately before desalting washing | 192 | 0.10 | Inv. |
| EGA-10 | $6.08 \times 10^{-4}$ | $6.08 \times 10^{-4}$ | $6.08 \times 10^{-4}$ | 22 | Phthalated gelatin | Immediately before desalting washing | 194 | 0.11 | Inv. |
| EGA-11 | $6.08 \times 10^{-4}$ | $6.08 \times 10^{-4}$ | $6.08 \times 10^{-4}$ | 11 | Succinated gelatin | Immediately before desalting washing | 188 | 0.10 | Inv. |
| EGA-12 | $6.08 \times 10^{-4}$ | $6.08 \times 10^{-4}$ | $6.08 \times 10^{-4}$ | 11 | Trimellitated gelatin | Immediately before desalting washing | 180 | 0.13 | Inv. |
| EGA-13 | $6.08 \times 10^{-4}$ | $6.08 \times 10^{-4}$ | $6.08 \times 10^{-4}$ | 11 | Pyromellitated gelatin | Immediately before desalting washing | 174 | 0.15 | Inv. |
| EGA-14 | $6.08 \times 10^{-4}$ | $6.08 \times 10^{-4}$ | $6.08 \times 10^{-4}$ | 5 | Phthalated gelatin | Redispersin after desalting washing | 158 | 0.15 | Inv. |
| EGA-15 | $6.08 \times 10^{-4}$ | $6.08 \times 10^{-4}$ | $6.08 \times 10^{-4}$ | 22 | Phthalated gelatin | Redispersin after desalting washing | 182 | 0.12 | Inv. |

*1Relative speed when the speed of emulsion EGA-1 is assumed to be 100.
*2In the case where samples coated with emulsions were stored under the ambient at a temperature of 60° C. and a relative humidity of 60% for four days.

It is apparent from the results of Table 3 that in the emulsion EGA-7 of comparative example wherein the ratio of gelatin having its —NH$_2$ group chemically modified was 1% based on the total amount of dispersion mediums, the effects of the present invention were as slight as being indescribable as having been exerted. However, when the ratio was 2% or higher, the effects of the present invention were exerted to such an extent as being recognizable as a substantial advantage. Further, when the ratio was 5% or higher, it is apparent that the effects of the present invention were favorably exerted.

With respect to the type of gelatin having its —NH$_2$ group chemically modified, the effects of the present invention are more striking in the use of succinated gelatin or phthalated gelatin having one —COOH group introduced at every modification of one —NH$_2$ group than in the use of trimellitated gelatin having two —COOH groups introduced at every modification of one —NH$_2$ group or pyromellitated gelatin having three —COOH groups introduced at every modification of one —NH$_2$ group.

Example 3

(Preparation of Emulsions EGB-5 to -7 and EGB-8 to -12 wherein the Method of Desalting Washing and the Content of Anionic Surfactant were Changed from those of Emulsion EGB-1 of Comparative Example and Emulsion EGB-3 of Present Invention)

Emulsions EGB-5 to -7 and EGB-8 to -12 were prepared in the same manner as in the preparation of emulsions EGB-1 and EGB-3 of Example 1 except that the method of desalting washing and the content of anionic surfactant were changed.

With respect to the method of desalting washing in the preparation of emulsions, the dialytic method using a semi-permeable membrane conducted in Example 1 was changed to three ways, namely, to the coagulation sedimentation method wherein no anionic surfactant was employed and the coagulation sedimentation methods wherein respective use was made of anionic surfactants SA-40 and SA-41 mentioned as examples herein in the section "DETAILED DESCRIPTION OF THE INVENTION."

In the performing of the coagulation sedimentation method wherein no anionic surfactant was employed, desalting washing was repeated while regulating the pH at coagulation sedimentation within the range of 3.5 to 3.95.

In the performing of the coagulation sedimentation methods wherein respective use was made of anionic surfactants SA-40 and SA-41, 0.6 to 6 g of anionic surfactant SA-40 or SA-41 was added and desalting washing was repeated while regulating the pH at coagulation sedimentation within the range of 3.85 to 4.25.

Coating with these emulsions together with the emulsions EGB-1 and EGB-3 was performed under the same conditions as in Example 1, and performance estimation was carried out. Table 4 lists, with respect to each of the emulsions, the amounts of first, second and third dyes, the method of desalting washing and the amount of anionic surfactant just after the completion of addition of all the sensitizing dyes and further lists the performance thereof.

Example 4

(Preparation of Emulsions Wherein the Content of Ca or Mg in Emulsion was Changed from those of Emulsion EGB-1 of Comparative Example and Emulsion EGB-4 of Present Invention)

Emulsions EGB-5 and EGB-14 were prepared in the same manner as in the preparation of emulsions EGB-1 and EGB-4 of Example 1 except that the method of desalting washing was changed to the coagulation sedimentation method performed in the absence of any anionic surfactant under the same conditions as in Example 3.

TABLE 4

| Emulsion No. | Amount of the first dye (mol/ Ag mol) | Amount of the second dye (mol/ Ag mol) | Amount of the third dye (mol/ Ag mol) | Method of desalting washing | Content of anionic surfactant*1 (g/Ag mol) | Relative speed*2 | Increment of fog during storage*3 | Remarks |
|---|---|---|---|---|---|---|---|---|
| EGB-1 | $1.01 \times 10^{-3}$ | None | None | Dialysis | None | 100 | 0.19 | Comp. |
| EGB-5 | $1.01 \times 10^{-3}$ | None | None | Coagulation sedimentation without anionic surfactant | None | 100 | 0.19 | Comp. |
| EGB-6 | $1.01 \times 10^{-3}$ | None | None | Coagulation sedimentation with SA-40*4 | 4.5 (SA-40) | 101 | 0.20 | Comp. |
| EGB-7 | $1.01 \times 10^{-3}$ | None | None | Coagulation sedimentation with SA-41*4 | 4.5 (SA-41) | 101 | 0.19 | Comp. |
| EGB-3 | $1.01 \times 10^{-3}$ | $5.04 \times 10^{-4}$ | $5.04 \times 10^{-4}$ | None | Dialysis | 171 | 0.17 | Inv. |
| EGB-8 | $1.01 \times 10^{-3}$ | $5.04 \times 10^{-4}$ | $5.04 \times 10^{-4}$ | Coagulation sedimentation without anionic surfactant | None | 174 | 0.16 | Inv. |
| EGB-9 | $1.01 \times 10^{-3}$ | $5.04 \times 10^{-4}$ | $5.04 \times 10^{-4}$ | Coagulation sedimentation with SA-40*4 | 0.45 (SA-40) | 168 | 0.17 | Inv. |
| EGB-10 | $1.01 \times 10^{-3}$ | $5.04 \times 10^{-4}$ | $5.04 \times 10^{-4}$ | Coagulation sedimentation with SA-40*4 | 1.5 (SA-40) | 153 | 0.18 | Inv. |
| EGB-11 | $1.01 \times 10^{-3}$ | $5.04 \times 10^{-4}$ | $5.04 \times 10^{-4}$ | Coagulation sedimentation with SA-40*4 | 4.5 (SA-40) | 133 | 0.19 | Inv. |
| EGB-12 | $1.01 \times 10^{-3}$ | $5.04 \times 10^{-4}$ | $5.04 \times 10^{-4}$ | Coagulation sedimentation with SA-41*4 | 4.5 (SA-41) | 138 | 0.18 | Inv. |

*1Content of anionic surfactant immdiately after the completion of the addition of all the sensitizing dye in the emulsion preparation steps.
*2Relative speed when the speed of emulsion EGB-1 is assumed to be 100.
*3In the case where samples coated with emulsions were stored under the ambient at a temperature of 60° C. and a relative humidity of 60% for four days.
*4Exemplified compound of anionic surfactant set forth in the text of the present application It is seen from the results of Table 4 that in the present invention it is recommendable to prepare emulsions under such conditions that use of anionic surfactants at the desalting washing is avoided to the utmost and that the amount of anionic surfactant at the adsorption of sensitizing dyes is minimized. The advantages of the present invention can be desirably exerted by preparing emulsions while limiting the amount of anionic surfactant at the adsorption of sensitizing dyes to 0.45 g or less per mol of silver.

It is also seen that this consideration about the anionic surfactant at emulsion production is not needed for the ordinary monolayer adsorption emulsions.

Emulsions EGB-13 and EGB-15 to -20 were prepared in the same manner as in the preparation of emulsions EGB-5 and EGB-14 except that the step of intentionally adding calcium nitrate or magnesium nitrate was additionally implemented after the addition of first dye.

Coating with these emulsions EGB-5 and EGB-13 to -20 was performed under the same conditions as in Example 1, and performance estimation was carried out. Table 5 lists, with respect to each of the emulsions, the amounts of first, second and third dyes and the content of Ca or Mg and further lists the performance thereof.

TABLE 5

| Emulsion No. | Amount of the first dye (mol/ Ag mol) | Amount of the second dye (mol/ Ag mol) | Amount of the third dye (mol/ Ag mol) | Content of Ca or Mg (mol/Ag mol) | Relative speed*1 | Increment of fog during storage*2 | Remarks |
|---|---|---|---|---|---|---|---|
| EGB-5  | $1.01 \times 10^{-3}$ | None | None | None | 100 | 0.19 | Comp. |
| EGB-13 | $1.01 \times 10^{-3}$ | None | None | Ca $8.0 \times 10^{-3}$ | 100 | 0.18 | Comp. |
| EGB-14 | $1.01 \times 10^{-3}$ | $4.54 \times 10^{-4}$ | $5.55 \times 10^{-4}$ | None | 173 | 0.18 | Inv. |
| EGB-15 | $1.01 \times 10^{-3}$ | $4.54 \times 10^{-4}$ | $5.55 \times 10^{-4}$ | Ca $5.0 \times 10^{-4}$ | 175 | 0.17 | Inv. |
| EGB-16 | $1.01 \times 10^{-3}$ | $4.54 \times 10^{-4}$ | $5.55 \times 10^{-4}$ | Ca $2.0 \times 10^{-3}$ | 185 | 0.15 | Inv. |
| EGB-17 | $1.01 \times 10^{-3}$ | $4.54 \times 10^{-4}$ | $5.55 \times 10^{-4}$ | Ca $8.0 \times 10^{-3}$ | 189 | 0.15 | Inv. |
| EGB-18 | $1.01 \times 10^{-3}$ | $4.54 \times 10^{-4}$ | $5.55 \times 10^{-4}$ | Ca $3.0 \times 10^{-2}$ | 179 | 0.14 | Inv. |
| EGB-19 | $1.01 \times 10^{-3}$ | $4.54 \times 10^{-4}$ | $5.55 \times 10^{-4}$ | Ca $6.0 \times 10^{-2}$ | 164 | 0.18 | Inv. |
| EGB-20 | $1.01 \times 10^{-3}$ | $4.54 \times 10^{-4}$ | $5.55 \times 10^{-4}$ | Mg $8.0 \times 10^{-3}$ | 185 | 0.15 | Inv. |

*1Relative speed when the speed of emulsion EGB-5 is assumed to be 100.
*2In the case where samples coated with emulsion was stored under the ambient at temperature of 60° C. and a relative humidity of 60% of four days.

It is seen from the results of Table 5 that the advantages of the present invention are enhanced by loading the emulsions with Ca or Mg in the amount recommended in the present invention. However, when Ca or Mg is incorporated in amounts exceeding the amount recommended in the present invention, the advantages of the present invention are contrarily suppressed.

The effect of Ca or Mg is presumed as being exerted as a result of delicate change of condition of adsorption of sensitizing dyes, but the mechanism thereof has not yet been elucidated. The above advantages exerted in the emulsions of the present invention was substantially irrecognizable in the monolayer adsorption emulsion of comparative example.

Example 5

(Water Base Dispersion of Sensitizing Dye for Use in Preparation of Silver Halide Emulsion and Process for Producing the Same)

(Preparation of Dye Dispersion a-1 of First Layer)

The dye dispersion a-1 is the same as prepared in Example 1.

(Preparation of Dye Dispersion b-1 of Second Layer or the Rest of the Layers)

The dye dispersion b-1 is the same as prepared in Example 1, and was prepared under the following conditions. 1 g of sensitizing dye Exs-12 and 2 g of sodium sulfate were added to 96 mL of water. 200 g of zirconia beads of 0.2 mm diameter were further added, and dispersion was performed by means of a sand grinder mill at 45° C. for 2 hr. The zirconia beads were separated, thereby obtaining dye dispersion b-1.

Exs-12

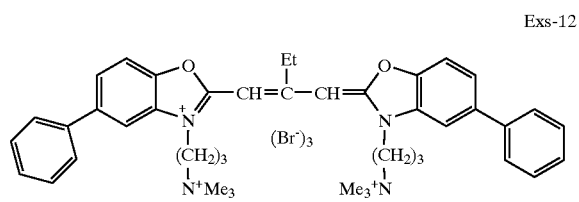

(Preparation of Dye Dispersion b-2 of Second Layer or the Rest of the Layers)

2 g of sensitizing dye Exs-12 and 2 g of sodium sulfate were added to 96 mL of water. 200 g of zirconia beads of 0.2 mm diameter were further added, and dispersion was performed by means of a sand grinder mill at 45° C. for 2 hr. The zirconia beads were separated, thereby obtaining dye dispersion b-2.

(Preparation of Dye Dispersion b-3 of Second Layer or the Rest of the Layers)

0.5 g of sensitizing dye Exs-12 and 2 g of sodium sulfate were added to 96 mL of water. 200 g of zirconia beads of 0.2 mm diameter were further added, and dispersion was performed by means of a sand grinder mill at 45° C. for 2 hr. The zirconia beads were separated, thereby obtaining dye dispersion b-3.

(Preparation of Dye Dispersion b-4 of Second Layer or the Rest of the Layers)

2 g of sensitizing dye Exs-12 was added to 98 mL of water. 200 g of zirconia beads of 0.2 mm diameter were further added, and dispersion was performed by means of a sand grinder mill at 45° C. for 2 hr. The viscosity increase was so intense that the zirconia beads were inseparable to thereby fail to obtain a dye dispersion. The viscosity increase was inhibited by the use of 0.3 g of sensitizing dye, thereby obtaining dye dispersion b-4.

(Preparation of Dye Dispersion b-5 of Second Layer or the Rest of the Layers)

1 g of sensitizing dye Exs-12 was dissolved in 15 mL of phenoxyethanol, and 44 mL of water was added thereto. The thus obtained solution was agitated by means of a dissolver blade of 12,000 revolutions at 50° C. for 25 min. 40 mL of an aqueous solution of gelatin was added to the obtained oil-in-water dispersion, thereby obtaining dye dispersion b-5.

(Preparation of Dye Dispersion b-6 of Second Layer or the Rest of the Layers)

2 g of sensitizing dye Exs-14 and 2 g of sodium sulfate were added to 96 mL of water. 200 g of zirconia beads of 0.2 mm diameter were further added, and dispersion was performed by means of a sand grinder mill at 45° C. for 2 hr. When the zirconia beads were separated, dye precipitation occurred to thereby fail to obtain a dye dispersion.

Exs-14

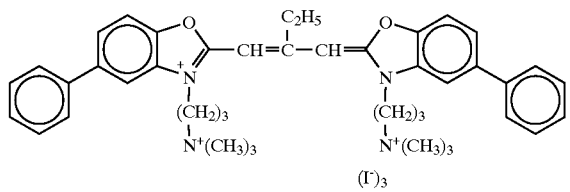

(Preparation of Dye Dispersion c-1 of Second Layer or the Rest of the Layers)

The dye dispersion c-1 is the same as prepared in Example 1.

It is apparent from comparisons between the results of cationic dye dispersions b-1, b-2, b-3 and b-4 that addition of inorganic salts according to the present invention is highly effective in the obtaining of a high-concentration water-based dispersion of cationic dye. It is also apparent from comparison between the results of cationic dye dispersions b-4 and b-5 that the use of an organic solvent enables obtaining a high-concentration water-based dispersion of cationic dye. Further, it is apparent from comparison between the results of cationic dye dispersions b-1 and b-6 that in the present invention the selection of counter ion of cationic sensitizing dye is important for obtaining a dispersion.

(Preparation of Emulsions Em-1 to -5 Having Multilayer Adsorption of Sensitizing Dyes)

Emulsion of silver iodobromide tabular grains of 2.1 μm average equivalent circle diameter, 0.11 μm average thickness and 19 average aspect ratio was prepared under the same conditions as in the preparation of emulsion EGB-1 of Example 1 except that the temperature at the initial stage of grain formation was changed from 60° C. to 40° C. Provided that the conditions for chemical sensitization and thereafter were as follows.

Desalting washing and dispersion were carried out. The obtained emulsion was heated to 60° C., and the above dye dispersion a-1 was added thereto at a ratio of 80% of the amount of monolayered saturated adsorption. Gold-sulfur-selenium sensitization was effected by sequentially adding sodium thiosulfate, N,N-dimethylselenourea, potassium thiocyanate and chloroauric acid. Upon the completion of chemical sensitization, MER-1 was added, and the emulsion was cooled to 40° C.

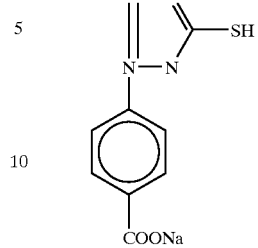

MER-1

The above dye dispersions b-1 to b-5 were added to the emulsion cooled to 40° C. so that the amount of added dye was 50% of the amount of monolayered saturated adsorption, and the obtained emulsions were ripened for 20 min. The above dye dispersion c-1 was added thereto so that the amount of added dye was 55% of the amount of monolayered saturated adsorption, and the obtained emulsions were ripened for 20 min. The resultant emulsions were respectively designated emulsions Em-1 to -5.

Coating with the emulsions Em-1 to -5 was performed under the same conditions as in Example 1, thereby obtaining sample nos. 1 to 5. Further, the emulsions in dissolved form were aged at 40° C. for 24 hr. Coating with the emulsions was performed under the same conditions, thereby obtaining sample nos. 6 to 10. Photographic estimation was conducted in the same manner as in Example 1. The amount of dye adsorption on silver halide grains was measured in the same manner as in Example 1.

The results are listed in Table 6.

TABLE 6

| Sample No. | Emulsion No. | Cationic dye dispersion No. | Whether or not the time was lapsed for emulsion in the dissolved state at 40° C. for 24 hours | Amount of dye adsorption (%)*1 | Relative speed*2 | Fog | Remarks |
|---|---|---|---|---|---|---|---|
| 1 | Em-1 | b-2 | Not lapsed | 178 | 155 | 0.24 | Inv. |
| 2 | Em-2 | b-1 | Not lapsed | 169 | 151 | 0.24 | Inv. |
| 3 | Em-3 | b-3 | Not lapsed | 154 | 131 | 0.25 | Inv. |
| 4 | Em-4 | b-4 | Not lapsed | 120 | 119 | 0.27 | Inv. |
| 5 | Em-5 | b-5 | Not lapsed | 85 | 100 | 0.30 | Inv. |
| 6 | Em-1 | b-2 | Lapsed | 178 | 155 | 0.24 | Inv. |
| 7 | Em-2 | b-1 | Lapsed | 169 | 151 | 0.24 | Inv. |
| 8 | Em-3 | b-3 | Lapsed | 152 | 129 | 0.25 | Inv. |
| 9 | Em-4 | b-4 | Lapsed | 117 | 111 | 0.28 | Inv. |
| 10 | Em-5 | b-5 | Lapsed | 80 | 92 | 0.33 | Inv. |

*1 Adsorption amount of dye when monolayered saturated adsorption amount of the dye is assumed to be 100%
*2 Relative speed when the speed of sample No. 5 is assumed to be 100.

As apparent from the results of Table 6, in the present invention, it is recommended to add cationic sensitizing dyes in the form of a water-based dispersion not containing any organic solvent. It is preferred that the dye concentration of water-based dispersion be 1 wt % or more.

When the concentration of dye dispersion is low, or when an organic solvent is contained, the adsorption amount of sensitizing dyes would be reduced to thereby result in sensitivity decrease.

Furthermore, it is seen that emulsions of high stability whose sensitivity and fog fluctuations upon aging of the emulsions in dissolved form are slight can be obtained by carrying out the addition of cationic sensitizing dyes in the form of a water-based dispersion as recommended in the present invention.

Example 6

The method of obtaining a water-based dispersion of sensitizing dye will be described in greater detail below.

(Preparation of Dye Dispersion d-1 of Second Layer or the Rest of the Layers)

1.2 g of sensitizing dye Exs-15 and 0.7 g of potassium nitrate were added to 86 mL of water. 200 g of zirconia beads of 0.2 mm diameter were further added, and dispersion was performed by means of a sand grinder mill at 45° C. for 2 hr. When the zirconia beads were separated, dye precipitation occurred to thereby fail to obtain a dye dispersion. 0.37 g of surfactant 1 and 1.2 g of organic solvent 1 were added thereto, thereby obtaining dye dispersion d-1.

Exs-15

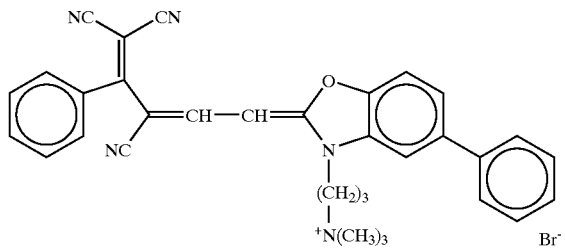

Exs-16

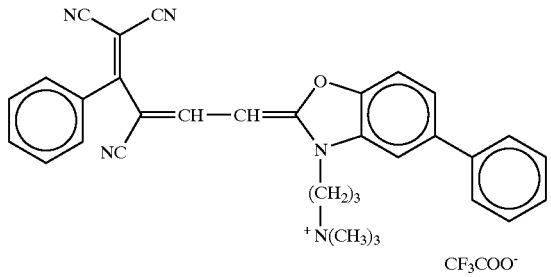

It is seen from comparison between the results of cationic dye dispersions d-1 and d-2 that a high-concentration water-based dispersion of cationic dye can be obtained without the need to use a surfactant and/or an organic solvent by selecting a counter ion of cationic sensitizing dye.

Emulsions 11 and 12 were prepared in the same manner as in Example 5 except that sensitizing dye dispersions d-1 and d-2 were used in place of the sensitizing dye dispersion b-1 of Example 5. Estimation was conducted in the same manner as in Example 1, thereby obtaining results of Table 7.

TABLE 7

| Sample No. | Emulsion No. | Cationic dye dispersion No. | Whether or not the time was lapsed for emulsion in the dissolved state at 40° C. for 24 hours | Amount of dye adsorption (%)*1 | Relative speed*2 | Fog | Remarks |
|---|---|---|---|---|---|---|---|
| 11 | Em-11 | d-1 | Not lapsed | 75 | 100 | 0.31 | Inv. |
| 12 | Em-12 | d-2 | Not lapsed | 171 | 159 | 0.25 | Inv. |
| 13 | Em-11 | d-1 | Lapsed | 68 | 91 | 0.33 | Inv. |
| 14 | Em-12 | d-2 | Lapsed | 168 | 155 | 0.25 | Inv. |

*1Adsorption amount of dye when monolayered saturated adsorption amount of the dye is assumed to be 100%
*2Relative speed when the speed of sample No. 11 is assumed to be 100.

Surfactant 1

CH₂COOCH₂CH(C₂H₅)C₄H₉
|
NaO₃S—CHCOOCH₂CH(C₂H₅)C₄H₉

Organic solvent 1

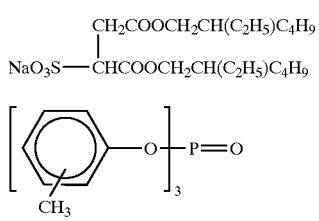

(Preparation of Dye Dispersion d-2 of Second Layer or the Rest of the Layers)

1.2 g of sensitizing dye Exs-16 and 0.7 g of potassium nitrate were added to 86 mL of water. 200 g of zirconia beads of 0.2 mm diameter were further added, and dispersion was performed by means of a sand grinder mill at 45° C. for 2 hr. The zirconia beads were separated, thereby obtaining dye dispersion d-2.

As apparent from the results of Table 7, the use of a water-based dispersion wherein a surfactant and/or an organic solvent is used would cause a decrease of adsorption amount of sensitizing dyes and a decrease of photographic speed gain according to the emulsion of the present invention. Further, it is apparent that emulsions of high stability whose sensitivity and fog fluctuations upon aging of the emulsions in dissolved form are slight can be obtained by carrying out the addition of a water-based dispersion of cationic sensitizing dyes according to the present invention.

Example 7

Emulsions 701 to 705 were prepared in the same manner as in the preparation of emulsion Em-1 of Example 5 except that the amounts of silver and gelatin of silver halide emulsion at the addition of cationic sensitizing dye water-based dispersion b-2 were changed. The obtained emulsions were stored in a refrigerator for one month. Thereafter, the silver halide emulsions were converted to dissolved form at 40° C. Thus, the results of Table 8 were obtained.

TABLE 8

| Emulsion No. | Silver amount (per kg of emulsion) | Gelatin amount (per kg of emulsion) | Change in emulsion after one month storage at 5° C. in a refrigerator |
|---|---|---|---|
| 701 | 160 | 100 | Adsorption amount of sensitizing dye decreased by 4% |
| 702 | 160 | 50 | No change |
| 703 | 160 | 20 | Emulsion grains coagulated |
| 704 | 60 | 50 | Adsorption amount of sensitizing dye decreased by 3% |
| 705 | 30 | 50 | Adsorption amount of sensitizing dye decreased by 3% |

As apparent from the results of Table 8, the amounts of silver and gelatin of silver halide emulsion at the addition of cationic sensitizing dye water-based dispersion greatly influence the storability of emulsions having a multilayer adsorption of sensitizing dyes.

Example 8

(Preparation of Samples Applying Emulsions for Comparison and Emulsions of the Present Invention to Silver Halide Color Negative Multilayer Photosensitive Materials)

Samples 801 to 814 to which each of silver halide emulsions EGA-1 to -6 and EGB-1 to -5, and EGB-13, 14 and 17 which were prepared in the above Examples 1 and 4 was introduced in the 11th layer (high-speed green emulsion layer) of the color negative multilayer photosensitive material set forth below, were prepared to evaluate their performance.

1) Support

A support used in this example was formed as follows.

100 parts by weight of a polyethylene-2,6-naphthalate polymer and 2 parts by weight of Tinuvin P.326 (manufactured by Ciba-Geigy Co.) as an ultraviolet absorbent were dried, melted at 300° C., and extruded from a T-die. The resultant material was longitudinally oriented by 3.3 times at 140° C., laterally oriented by 3.3 times at 130° C., and thermally fixed at 250° C. for 6 sec, thereby obtaining a 90 $\mu$m thick PEN (polyethylenenaphthalate) film. Note that proper amounts of blue, magenta, and yellow dyes (I-1, I-4, I-6, I-24, I-26, I-27, and II-5 described in Journal of Technical Disclosure No. 94-6023) were added to this PEN film. The PEN film was wound around a stainless steel core 20 cm in diameter and given a thermal history of 110° C. and 48 hr, manufacturing a support with a high resistance to curling.

2) Coating of Undercoat Layer

The two surfaces of the above support were subjected to corona discharge, UV discharge, and glow discharge. After that, each surface of the support was coated with an undercoat solution (10 mL/m$^2$, by using a bar coater) consisting of 0.1 g/m$^2$ of gelatin, 0.01 g/m$^2$ of sodium α-sulfodi-2-ethylhexylsuccinate, 0.04 g/m$^2$ of salicylic acid, 0.2 g/m$^2$ of p-chlorophenol, 0.012 g/m$^2$ of ($CH_2$=$CHSO_2CH_2CH_2NHCO)_2CH_2$, and 0.02 g/m$^2$ of a polyamido-epichlorohydrin polycondensation product, thereby forming an undercoat layer on a side at a high temperature upon orientation. Drying was performed at 115° C. for 6 min (all rollers and conveyors in the drying zone were at 115° C.).

3) Coating of Back Layers

One surface of the undercoated support was coated with an antistatic layer, magnetic recording layer, and slip layer having the following compositions as back layers.

3-1) Coating of Antistatic Layer

The surface was coated with 0.2 g/m$^2$ of a dispersion (secondary aggregation grain size=about 0.08 $\mu$m) of a fine-grain powder, having a specific resistance of 5 Ω·cm, of a tin oxide-antimony oxide composite material with an average grain size of 0.005 $\mu$m, together with 0.05 g/m$^2$ of gelatin, 0.02 g/m$^2$ of ($CH_2$=$CHSO_2CH_2CH_2NHCO)_2CH_2$, 0.005 g/m$^2$ of polyoxyethylene-p-nonylphenol (polymerization degree 10), and resorcin.

3-2) Coating of Magnetic Recording Layer

A bar coater was used to coat the surface with 0.06 g/m$^2$ of cobalt-γ-iron oxide (specific area 43 m$^2$/g, major axis 0.14 $\mu$m, minor axis 0.03 $\mu$m, saturation magnetization 89 Am$^2$/kg, $Fe^{+2}/Fe^{+3}$=6/94, the surface was treated with 2 wt % of iron oxide by aluminum oxide silicon oxide) coated with 3-poly(polymerization degree 15)oxyethylene-propyloxytrimethoxysilane (15 wt %), together with 1.2 g/m$^2$ of diacetylcellulose (iron oxide was dispersed by an open kneader and sand mill), by using 0.3 g/m$^2$ of $C_2H_5C$($CH_2OCONH$—$C_6H_3(CH_3)NCO)_3$ as a hardener and acetone, methylethylketone, and cyclohexane as solvents, thereby forming a 1.2-$\mu$m thick magnetic recording layer. 10 mg/m$^2$ of silica grains (0.3 $\mu$m) were added as a matting agent, and 10 mg/m$^2$ of aluminum oxide (0.15 $\mu$m) coated with 3-poly(polymerization degree 15)oxyethylene-propyloxytrimethoxysilane (15 wt %) were added as a polishing agent. Drying was performed at 115° C. for 6 min (all rollers and conveyors in the drying zone were at 115° C.). The color density increase of $D^B$ of the magnetic recording layer measured by an X-light (blue filter) was about 0.1. The saturation magnetization moment, coercive force, and squareness ratio of the magnetic recording layer were 4.2 Am$^2$/kg, 7.3×10$^4$ A/m, and 65%, respectively.

3-3) Preparation of Slip Layer

The surface was then coated with diacetylcellulose (25 mg/m$^2$) and a mixture of $C_6H_{13}CH(OH)C_{10}H_{20}COOC_{40}H_{81}$ (compound a, 6 mg/m$^2$)/$C_{50}H_{101}O(CH_2CH_2O)_{16}H$ (compound b, 9 mg/m$^2$). Note that this mixture was melted in xylene/propylenemonomethylether (1/1) at 105° C. and poured and dispersed in propylenemonomethylether (tenfold amount) at room temperature. After that, the resultant mixture was formed into a dispersion (average grain size 0.01 $\mu$m) in acetone before being added. 15 mg/m$^2$ of silica grains (0.3 $\mu$m) were added as a matting agent, and 15 mg/m$^2$ of aluminum oxide (0.15 $\mu$m) coated with 3-poly (polymerization degree 15)oxyethylene-propyloxytrimethoxysiliane (15 wt %) were added as a polishing agent. Drying was performed at 115° C. for 6 min (all rollers and conveyors in the drying zone were at 115° C.). The resultant slip layer was found to have excellent characteristics; the coefficient of kinetic friction was 0.06 (5 mmø stainless steel hard sphere, load 100 g, speed 6 cm/min), and the coefficient of static friction was 0.07 (clip method). The coefficient of kinetic friction between an emulsion surface (to be described later) and the slip layer also was excellent, 0.12.

4) Coating of Sensitive Layers

Next, the surface of the support on the side away from the back layers formed as above was multi-coated with a plurality of layers having the following compositions to form a sample of a color negative photographic material.

(Compositions of Sensitive Layers)

The main ingredients used in the individual layers are classified as follows, however, the use thereof are not limited to those specified below.

| | | |
|---|---|---|
| ExC: | Cyan coupler | UV: Ultraviolet absorbent |
| ExM: | Magenta coupler | HBS: High-boiling organic solvent |
| ExY: | Yellow coupler | H: Gelatin hardener |

(In the following description, practical compounds have numbers attached to their symbols. Formulas of these compounds will be presented later.)

The number corresponding to each component indicates the coating amount in units of g/m$^2$. The coating amount of a silver halide is indicated by the amount of silver.

First layer (First antihalation layer)

| | | |
|---|---|---|
| Black colloidal silver | silver | 0.10 |
| Gelatin | | 0.66 |
| ExM-1 | | 0.048 |
| Cpd-2 | | 0.001 |
| F-8 | | 0.001 |
| HBS-1 | | 0.090 |
| HBS-2 | | 0.010 |

Second layer (Second antihalation layer)

| | | |
|---|---|---|
| Black colloidal silver | silver | 0.10 |
| Gelatin | | 0.80 |
| ExM-1 | | 0.057 |
| ExF-1 | | 0.002 |
| F-8 | | 0.001 |
| HBS-1 | | 0.090 |
| HBS-2 | | 0.010 |

Third layer (Inter layer)

| | | |
|---|---|---|
| ExC-2 | | 0.010 |
| Cpd-1 | | 0.086 |
| UV-2 | | 0.029 |
| UV-3 | | 0.052 |
| UV-4 | | 0.011 |
| HBS-1 | | 0.100 |
| Gelatin | | 0.60 |

Fourth layer (Low-speed red-sensitive emulsion layer)

| | | |
|---|---|---|
| Em-M | silver | 0.42 |
| Em-N | silver | 0.52 |
| Em-O | silver | 0.10 |
| ExC-1 | | 0.222 |
| ExC-2 | | 0.010 |
| ExC-3 | | 0.072 |
| ExC-4 | | 0.148 |
| ExC-5 | | 0.005 |
| ExC-6 | | 0.008 |
| ExC-8 | | 0.071 |
| ExC-9 | | 0.010 |
| UV-2 | | 0.036 |
| UV-3 | | 0.067 |
| UV-4 | | 0.014 |
| Cpd-2 | | 0.010 |
| Cpd-4 | | 0.012 |
| HBS-1 | | 0.240 |
| HBS-5 | | 0.010 |
| Gelatin | | 1.50 |

Fifth layer (Medium-speed red-sensitive emulsion layer)

| | | |
|---|---|---|
| Em-L | silver | 0.38 |
| Em-M | silver | 0.28 |
| ExC-1 | | 0.111 |
| ExC-2 | | 0.039 |
| ExC-3 | | 0.018 |
| ExC-4 | | 0.074 |
| ExC-5 | | 0.019 |
| ExC-6 | | 0.024 |
| ExC-8 | | 0.010 |
| ExC-9 | | 0.021 |
| Cpd-2 | | 0.020 |
| Cpd-4 | | 0.021 |
| HBS-1 | | 0.129 |
| Gelatin | | 0.85 |

Sixth layer (High-speed red-sensitive emulsion layer)

| | | |
|---|---|---|
| Em-K | silver | 1.40 |
| ExC-1 | | 0.122 |
| ExC-6 | | 0.032 |
| ExC-8 | | 0.110 |
| ExC-9 | | 0.005 |
| ExC-10 | | 0.159 |
| Cpd-2 | | 0.068 |
| Cpd-4 | | 0.015 |
| HBS-1 | | 0.440 |
| Gelatin | | 1.51 |

Seventh layer (Inter layer)

| | | |
|---|---|---|
| Cpd-1 | | 0.081 |
| Cpd-6 | | 0.002 |
| Solid disperse dye ExF-4 | | 0.015 |
| HBS-1 | | 0.049 |
| Polyethylacrylate latex | | 0.088 |
| Gelatin | | 0.80 |

Eighth layer (Interlayer effect-donating layer (Layer donating interlayer effect to red-sensitive layer)

| | | |
|---|---|---|
| Em-E | silver | 0.40 |
| Cpd-4 | | 0.010 |
| ExM-2 | | 0.082 |
| ExM-3 | | 0.006 |
| ExM-4 | | 0.026 |
| ExY-1 | | 0.010 |
| ExY-4 | | 0.040 |
| ExC-7 | | 0.007 |
| HBS-1 | | 0.203 |
| HBS-3 | | 0.003 |
| HBS-5 | | 0.010 |
| Gelatin | | 0.52 |

Ninth layer (Low-speed green-sensitive emulsion layer)

| | | |
|---|---|---|
| Em-H | silver | 0.15 |
| Em-I | silver | 0.23 |
| Em-J | silver | 0.26 |
| ExM-2 | | 0.388 |
| ExM-3 | | 0.040 |
| ExY-1 | | 0.003 |
| ExY-3 | | 0.002 |
| ExC-7 | | 0.009 |
| HBS-1 | | 0.337 |
| HBS-3 | | 0.018 |
| HBS-4 | | 0.260 |
| HBS-5 | | 0.110 |
| Cpd-5 | | 0.010 |
| Gelatin | | 1.45 |

Tenth layer (Medium-speed green-sensitive emulsion layer)

| | | |
|---|---|---|
| Em-G | silver | 0.30 |
| Em-H | silver | 0.12 |
| ExM-4 | | 0.005 |
| ExM-2 | | 0.084 |
| ExM-3 | | 0.012 |
| ExY-3 | | 0.002 |
| ExC-6 | | 0.003 |
| ExC-7 | | 0.007 |
| ExC-8 | | 0.008 |
| HBS-1 | | 0.096 |
| HBS-3 | | 0.002 |
| HBS-5 | | 0.002 |
| Cpd-5 | | 0.004 |
| Gelatin | | 0.42 |

Eleventh layer (High-speed green-sensitive emulsion layer)

| | | |
|---|---|---|
| Each of emulsions described in Tables 2, 4 and 5 | silver | 1.200 |
| ExC-6 | | 0.002 |
| ExC-8 | | 0.010 |
| ExM-1 | | 0.014 |

-continued

| | | |
|---|---|---|
| ExM-2 | | 0.023 |
| ExM-3 | | 0.023 |
| ExM-4 | | 0.005 |
| ExM-5 | | 0.040 |
| ExY-3 | | 0.003 |
| DA (93) | | 0.031 |
| PE11 | | 2.0 × 10$^{-5}$ |
| Cpd-3 | | 0.004 |
| Cpd-4 | | 0.007 |
| Cpd-5 | | 0.010 |
| HBS-1 | | 0.259 |
| HBS-5 | | 0.020 |
| Polyethylacrylate latex | | 0.099 |
| Gelatin | | 1.110 |
| Twelfth layer (Yellow filter layer) | | |
| Cpd-1 | | 0.088 |
| Solid disperse dye ExF-2 | | 0.051 |
| Solid disperse dye ExF-8 | | 0.010 |
| HBS-1 | | 0.049 |
| Gelatin | | 0.54 |
| Thirteenth layer (Low-speed blue-sensitive emulsion layer) | | |
| Em-B | silver | 0.50 |
| Em-C | silver | 0.15 |
| Em-D | silver | 0.10 |
| ExC-1 | | 0.024 |
| ExC-7 | | 0.011 |
| ExY-1 | | 0.002 |
| ExY-2 | | 0.956 |
| ExY-4 | | 0.091 |
| Cpd-2 | | 0.037 |
| Cpd-3 | | 0.004 |
| HBS-1 | | 0.372 |
| HBS-5 | | 0.047 |
| Gelatin | | 2.00 |
| Fourteenth layer (High-speed blue-sensitive emulsion layer) | | |
| Em-A | silver | 1.22 |
| ExY-2 | | 0.235 |

| | | |
|---|---|---|
| ExY-4 | | 0.018 |
| Cpd-2 | | 0.075 |
| Cpd-3 | | 0.001 |
| HBS-1 | | 0.087 |
| Gelatin | | 1.30 |
| Fifteenth layer (First protective layer) | | |
| Silver iodobromide emulsion (av. grain size: equivalent sphere diameter 0.07 μm | silver | 0.25 |
| UV-1 | | 0.358 |
| UV-2 | | 0.179 |
| UV-3 | | 0.254 |
| UV-4 | | 0.025 |
| F-11 | | 0.008 |
| S-1 | | 0.078 |
| ExF-5 | | 0.0024 |
| ExF-6 | | 0.0012 |
| ExF-7 | | 0.0010 |
| HBS-1 | | 0.175 |
| HBS-4 | | 0.050 |
| Gelatin | | 1.80 |
| Sixteenth layer (Second protective layer) | | |
| H-1 | | 0.40 |
| B-1 (diameter 1.7 μm) | | 0.05 |
| B-2 (diameter 1.7 μm) | | 0.15 |
| B-3 | | 0.05 |
| S-1 | | 0.20 |
| Gelatin | | 0.75 |

In addition to the above components, to improve the storage stability, processability, resistance to pressure, antiseptic and mildewproofing properties, antistatic properties, and coating properties, the individual layers contained W-1 to W-6, B-4 to B-6 and F-1 to F-17, iron salt, lead salt, gold salt, platinum salt, palladium salt, iridium salt, and rhodium salt.

The characteristics of silver halide emulsions Em-A to E and G to O are shown in Table 9 below.

TABLE 9

(Grain characteristics of silver halide emulsions Em-A to -G and -G to -O

| Emulsion No. | Layer used | Grain configuration | Av. ESD (μm) | Av. ECD (μm) COV (%) | Av. thickness (μm) COV (%) | Av. aspect ratio | Ratio of tabular grains to the total projected area (%) |
|---|---|---|---|---|---|---|---|
| Em-A | High-speed blue-sensitive layer | (111) main plane tabular grain | 1.6 | 5.2 26 | 0.101 29 | 51 | 97 |
| Em-B | Low-speed blue-sensitive layer | (111) main plane tabular grain | 0.9 | 2.3 19 | 0.092 23 | 25 | 99 |
| Em-C | Low-speed blue-sensitive layer | (111) main plane tabular grain | 0.5 | 0.9 18 | 0.103 19 | 8.7 | 99 |
| Em-D | Low-speed blue-sensitive layer | (100) main plane tabular grain | 0.2 | 0.2 7 | 0.2 7 | 1 | 0 |
| Em-E | Layer donating interlayer effect to red-sensitive layer | (111) main plane tabular grain | 1.1 | 3.0 18 | 0.099 16 | 30 | 96 |
| Em-G | Medium-speed green-sensitive layer | (111) main plane tabular grain | 0.9 | 3.8 23 | 0.034 17 | 112 | 99 |
| Em-H | Low- and Medium-speed green-sensitive layer | (111) main plane tabular grain | 0.6 | 1.8 20 | 0.044 13 | 41 | 99 |
| Em-I | Low-speed green-sensitive layer | (111) main plane tabular grain | 0.5 | 1.2 21 | 0.058 13 | 21 | 97 |
| Em-J | Low-speed green-sensitive layer | (111) main plane tabular grain | 0.4 | 1.0 17 | 0.043 12 | 23 | 96 |
| Em-K | High-speed red-sensitive layer | (111) main plane tabular grain | 1.2 | 5.4 18 | 0.040 15 | 135 | 99 |

TABLE 9-continued (Grain characteristics of silver halide emulsions Em-A to -G and -G to -O)

| | | | | | | | |
|---|---|---|---|---|---|---|---|
| Em-L | Medium-speed red-sensitive layer | (111) main plane tabular grain | 0.9 | 3.6 23 | 0.038 16 | 95 | 99 |
| Em-M | Low- and Medium-speed red-sensitive layer | (111) main plane tabular grain | 0.6 | 1.5 20 | 0.064 12 | 23 | 97 |
| Em-N | Low-speed red-sensitive layer | (111) main plane tabular grain | 0.4 | 0.9 17 | 0.053 11 | 17 | 96 |
| Em-O | Low-speed red-sensitive layer | (111) main plane tabular grain | 0.3 | 0.7 18 | 0.037 10 | 19 | 96 |

| Emulsion No. | Characteristics of grains accounted for 70% or more of the total projected area | Silver amount ratio (%) in grain structure and halide composition (described from grain center); (Epitaxial junction portion) |
|---|---|---|
| Em-A | Having high density dislocation lines at fringe portion | (1%) AgBr/(10%) AgBr$_{90}$I$_{10}$/(60%) AgBr$_{85}$I$_{15}$/(12%) AgBr/(4%) AgI/(13%) AgBr |
| Em-B | Having high density dislocation lines at fringe portion | (1%) AgBr/(20%) AgBr$_{90}$I$_{10}$/(50%) AgBr$_{85}$I$_{15}$/(6%) AgBr/(3%) AgI/(19%) AgBr |
| Em-C | Having high density dislocation lines at fringe portion and on main planes | (15%) AgBr/(40%) AgBr$_{97}$I$_3$/(10%) AgBr/(2%) AgI/(33%) AgBr |
| Em-D | There is no dislocation line | (35%) AgBr/(25%) AgBr$_{90}$I$_{10}$/(1%) AgI/(39%) AgBr |
| Em-E | Having high density dislocation lines at fringe portion | (8%) AgBr/(35%) AgBr$_{97}$I$_3$/(15%) AgBr/(4%) AgI/(38%) AgBr |
| Em-G | Having perfect epitaxial junction at six apexes of hexagonal tabular grain | (15%) AgBr/(67%) AgBr$_{97}$I$_3$/(15%) AgBr$_{93}$I$_7$/(3%) <AgBr$_{70}$Cl$_{25}$I$_5$> |
| Em-H | Having perfect epitaxial junction at six apexes of hexagonal tabular grain | (15%) AgBr/(65%) AgBr$_{99}$I$_1$/(15%) AgBr$_{95}$I$_5$/(5%) <AgBr$_{80}$Cl$_{20}$> |
| Em-I | Having perfect epitaxial junction at six apexes of hexagonal tabular grain | (82%) AgBr/(10%) AgBr$_{95}$I$_5$/(8%) <AgBr$_{75}$Cl$_{20}$I$_5$> |
| Em-J | Having epitaxial junction at one apex of hexagonal tabular grain | (78%) AgBr/(10%) AgBr$_{95}$I$_5$/(12%) <AgBr$_{75}$Cl$_{20}$I$_5$> |
| Em-K | Having perfect epitaxial junction at six apexes of hexagonal tabular grain | (7%) AgBr/(66%) AgBr$_{97}$I$_3$/(25%) AgBr$_{86}$I$_{14}$/(2%) <AgBr$_{60}$Cl$_{30}$I$_{10}$> |
| Em-L | Having perfect epitaxial junction at six apexes of hexagonal tabular grain | (15%) AgBr/(67%) AgBr$_{97}$I$_3$/(15%) AgBr$_{93}$I$_7$/(3%) <AgBr$_{70}$Cl$_{25}$I$_5$> |
| Em-M | Having perfect epitaxial junction at six apexes of hexagonal tabular grain | (15%) AgBr/(65%) AgBr$_{99}$I$_1$/(15%) AgBr$_{95}$I$_5$/(5%) <AgBr$_{80}$Cl$_{20}$> |
| Em-N | Having epitaxial junction at one apex of hexagonal tabular grain | (78%) AgBr/(10%) AgBr$_{95}$I$_5$/(12%) <AgBr$_{75}$Cl$_{20}$I$_5$> |
| Em-O | Having epitaxial junction at one apex of hexagonal tabular grain | (78%) AgBr/(10%) AgBr$_{95}$I$_5$/(12%) <AgBr$_{70}$Cl$_{20}$I$_{10}$> |

| Emulsion No. | Av. silver iodide content (mol %) Coefficient of variation among grains (%) | Surface silver iodide content (mol %)) | Av. silver chloride content (mol %) Coefficient of variation among grains (%) | Surface silver chloride content (mol %) | Distance between twin planes ($\mu$m) Coefficient of variation | (100) plane ratio in side faces (%) |
|---|---|---|---|---|---|---|
| Em-A | 14 17 | 8 | 0 | 0 | 0.013 25 | 21 |
| Em-B | 12.5 22 | 7 | 0 | 0 | 0.011 18 | 32 |
| Em-C | 3.2 15 | 2 | 0 | 0 | 0.011 22 | 18 |
| Em-D | 3.5 8 | 0.9 | 0 | 0 | — | — |
| Em-E | 5.1 9 | 3.5 | 0 | 0 | 0.010 22 | 3 |
| Em-G | 3.2 7 | 6 | 0.8 <10 | 2 | 0.008 18 | 10 |
| Em-H | 1.4 7 | 4 | 1 <10 | 3 | 0.008 18 | 12 |
| Em-I | 0.9 8 | 4 | 1.6 <10 | 5 | 0.008 18 | 25 |

TABLE 9-continued (Grain characteristics of silver halide emulsions Em-A to -G and -G to -O)

| Em-J | 1.1 | 4 | 2.4 | 7 | 0.008 | 17 |
| --- | --- | --- | --- | --- | --- | --- |
| | 8 | | 8 | | 18 | |
| Em-K | 5.7 | 12 | 0.6 | 2 | 0.008 | 8 |
| | 9 | | <10 | | 18 | |
| Em-L | 3.2 | 6 | 0.8 | 2 | 0.008 | 10 |
| | 7 | | <10 | | 18 | |
| Em-M | 1.4 | 4 | 1 | 3 | 0.008 | 12 |
| | 7 | | <10 | | 18 | |
| Em-N | 1.1 | 4 | 2.4 | 7 | 0.008 | 17 |
| | 8 | | 8 | | 18 | |
| Em-O | 1.7 | 4 | 2.4 | 7 | 0.008 | 22 |
| | 8 | | 8 | | 18 | |

| Emulsion No. | Sensitizing dye | Dopant | Chemical sensitization, antifoggant and etc. |
| --- | --- | --- | --- |
| Em-A | ExS-1, 2 | $K_2IrCl_6$ | The contents of the patent publications to be described later were suitably selected and combined |
| Em-B | ExS-1, 2 | $K_2IrCl_6$ | The contents of the patent publications to be described later were suitably selected and combined |
| Em-C | ExS-1, 2 | $K_2RhCl_6$, $K_2IrCl_6$ | The contents of the patent publications to be described later were suitably selected and combined |
| Em-D | ExS-1, 2 | $K_2IrCl_6$ | The contents of the patent publications to be described later were suitably selected and combined |
| Em-E | ExS-3, 4 | $K_2IrCl_6$, $K_2IrCl_5(H_2O)$, $K_4Fe(CN)_6$ | The contents of the patent publications to be described later were suitably selected and combined |
| Em-G | ExS-3, 5, 6, 7, 8 | $K_2IrCl_6$, $K_2IrCl_5(H_2O)$, $K_4Ru(CN)_6$ | The contents of the patent publications to be described later were suitably selected and combined |
| Em-H | ExS-3, 5, 6, 7, 8 | $K_2IrCl_6$, $K_2IrCl_5(H_2O)$, $K_4Ru(CN)_6$ | The contents of the patent publications to be described later were suitably selected and combined |
| Em-I | ExS-3, 5, 6, 7, 8 | $K_2IrCl_6$, $K_2IrCl_5(H_2O)$, $K_4Ru(CN)_6$ | The contents of the patent publications to be described later were suitably selected and combined |
| Em-J | ExS-3, 5, 6, 7, 8 | $K_2IrCl_6$, $K_2IrCl_5(H_2O)$, $K_4Ru(CN)_6$ | The contents of the patent publications to be described later were suitably selected and combined |
| Em-K | ExS-9, 10, 11 | $K_2IrCl_6$, $K_2IrCl_5(H_2O)$, $K_4Ru(CN)_6$ | The contents of the patent publications to be described later were suitably selected and combined |
| Em-L | ExS-9, 10, 11 | $K_2IrCl_6$, $K_2IrCl_5(H_2O)$, $K_4Ru(CN)_6$ | The contents of the patent publications to be described later were suitably selected and combined |
| Em-M | ExS-9, 10, 11 | $K_2IrCl_6$, $K_2IrCl_5(H_2O)$, $K_4Ru(CN)_6$ | The contents of the patent publications to be described later were suitably selected and combined |
| Em-N | ExS-9, 10, 11 | $K_2IrCl_6$, $K_2IrCl_5(H_2O)$, $K_4Ru(CN)_6$ | The contents of the patent publications to be described later were suitably selected and combined |
| Em-O | ExS-9, 10, 11 | $K_2IrCl_6$, $K_2IrCl_5(H_2O)$, $K_4Ru(CN)_6$ | The contents of the patent publications to be described later were suitably selected and combined |

ESD = Equivalent sphere diameter;
ECD = Equivalent circle diameter;
COV = Coefficient of variation These emulsions were prepared based on the contents described in the text and/or examples of the patent publications set forth below and suitably combined and/or changed.

The structure of emulsion, chemical sensitization and spectral sensitization are based on the contents described especially in, e.g., EP 573649B1, Japanese Patent No. 2912768, JP-A's-11-249249, 11-295832 and 11-72860, U.S. Pat. Nos. 5,985,534, 5,965,343 and 3,002,715, Japanese Patent Nos. 3045624 and 3045623, JP-A-2000-275771, U.S. Pat. No. 6,172,110, JP-A's-2000-321702, 2000-321700 and 2000-321698, U.S. Pat. No. 6,153,370, JP-A's-2001-92065, 2001-92064, 2000-92059 and 2001-147501, U.S. Patent Application Publication No. 2001/0006768A1, JP-A's-2001-228572, 2001-255613 and 2001-264911, U.S. Pat. No. 6,2809,20B1, JP-A's-2001-264912 and 2001-281778, and U.S. Patent Application Publication No. 2001/003143A1.

The preparation method is based on the contents described in, e.g., Japanese Patent No. 2878903, JP-A's-11-143002, 11-143003 and 11-174612, U.S. Pat. Nos. 5,925,508 and 5,955,253, JP-A-11-327072, U.S. Pat. No. 5,989,800, Japanese Patent Nos. 3005382 and 3014235, EP 04315858B1, U.S. Pat. No. 6,040,127, Japanese Patent No. 3049647, 3045622 and 3066692, EP 0563708B1, Japanese Patent No. 309104, JP-A's-2000-338620, 2001-83651, 2001-75213 and 2001-100343, U.S. Pat. No. 6,251,577B1, EP 0563701B1, JP-A-2001-281780, and U.S. Patent Application Publication No. 2001/0036606A1.

ExS-1
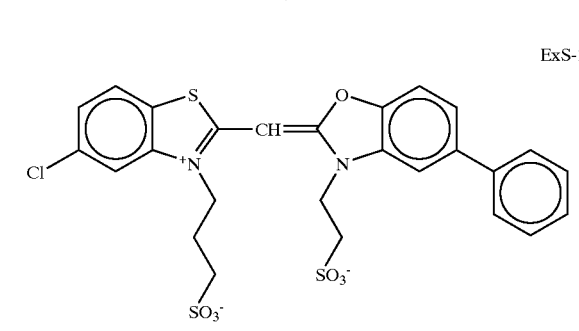

ExS-2
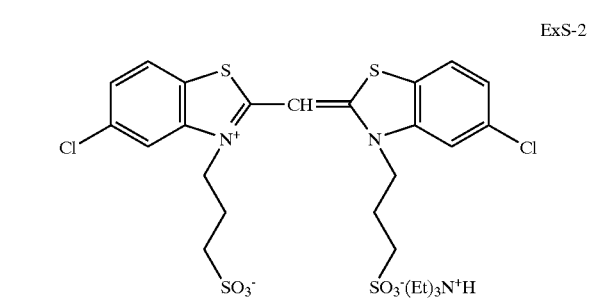

ExS-3
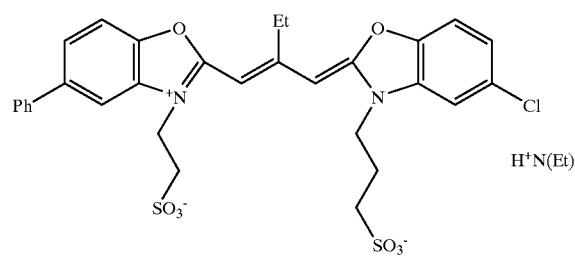

ExS-4
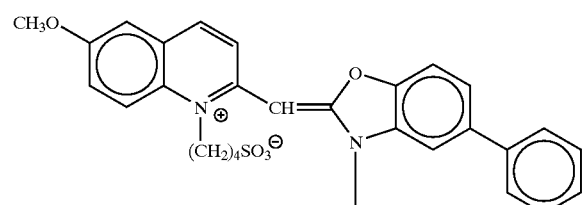

ExS-5
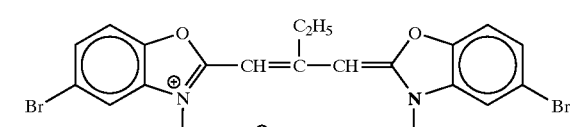

ExS-6
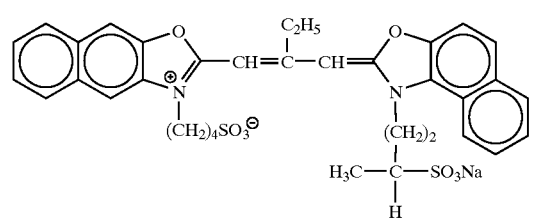

ExS-7
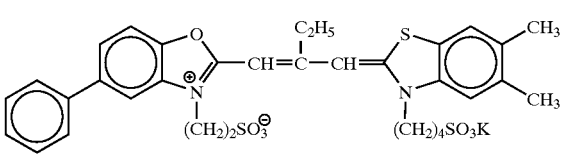

ExS-8
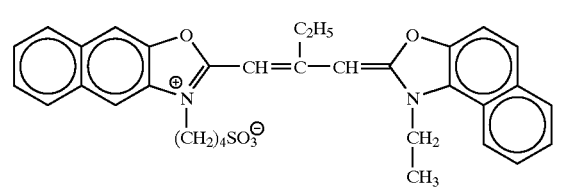

ExS-9
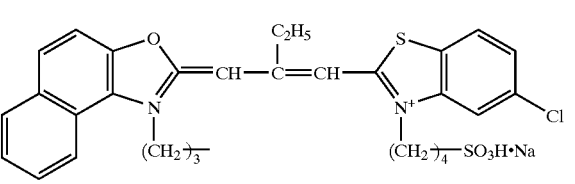

ExS-10
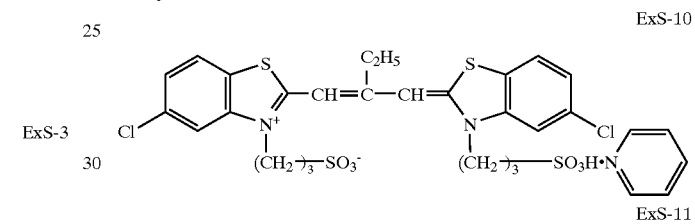

ExS-11
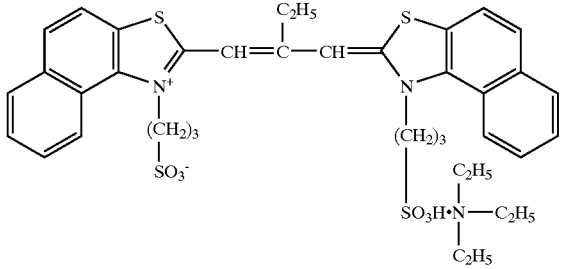

Preparation of Dispersions of Organic Solid Disperse Dyes

ExF-4 was dispersed by the following method. That is, 21.7 mL of water, 3 mL of a 5% aqueous solution of p-octylphenoxyethoxyethanesulfonic acid soda, and 0.5 g of a 5% aqueous solution of p-octylphenoxypolyoxyethyleneether (polymerization degree 10) were placed in a 700-mL pot mill, and 5.0 g of the dye ExF-4 and 500 mL of zirconium oxide beads (diameter 1 mm) were added to the mill. The contents were dispersed for 2 hr. This dispersion was done by using a BO type oscillating ball mill manufactured by Chuo Koki K.K. The dispersion was extracted from the mill and added to 8 g of a 12.5% aqueous solution of gelatin. The beads were filtered away to obtain a gelatin dispersion of the dye. The average grain size of the fine dye grains was 0.44 µm.

Oil-soluble dye ExF-2 was dispersed by a microprecipitation dispersion method described in Example 1 of EP549,489A. The average grain size was found to be 0.06 µm.

A solid dispersion ExF-8 was dispersed by the following method.

4000 g of water and 376 g of a 3% solution of W-2 were added to 2,800 g of a wet cake of ExF-8 containing 18% of water, and the resultant material was stirred to form a slurry of ExF-6 having a concentration of 32%. Next, ULTRA VISCO MILL (UVM-2) manufactured by Imex K.K. was filled with 1,700 mL of zirconia beads having an average grain size of 0.5 mm. The slurry was milled by passing through the mill for 8 hr at a peripheral speed of about 10 m/sec and a discharge amount of 0.5 L/min. The average grain size was 0.45 µm.

Compounds used in each of the above layers are as shown below.

ExC-1

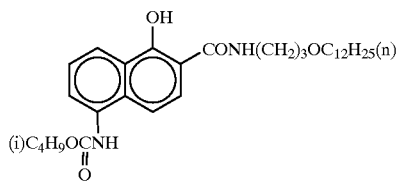

ExC-2

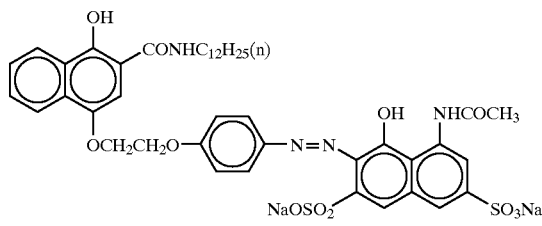

ExC-3

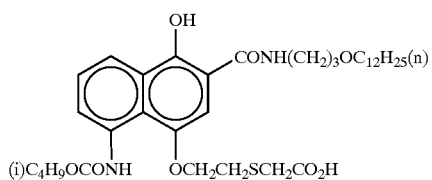

ExC-4

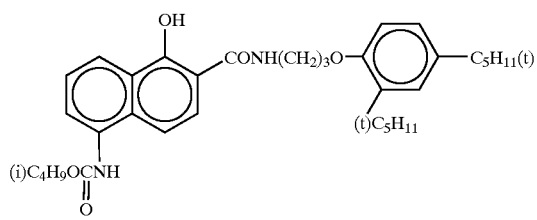

ExC-5

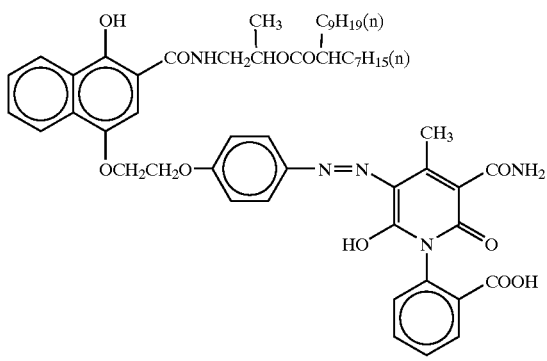

ExC-6

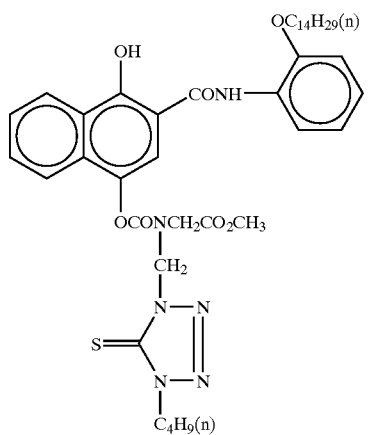

ExC-7

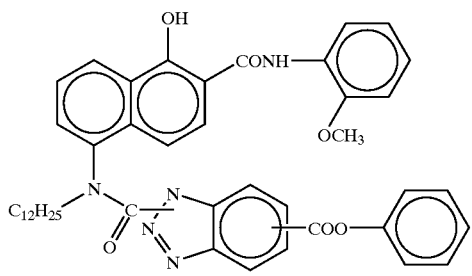

ExC-8

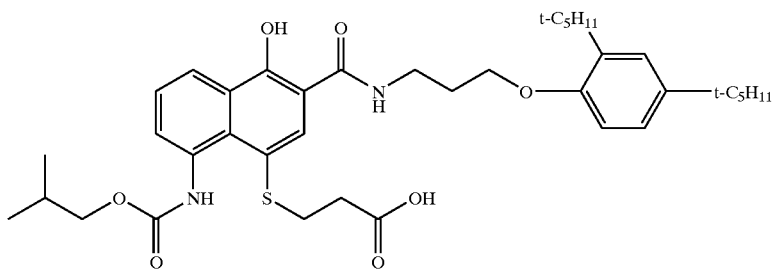

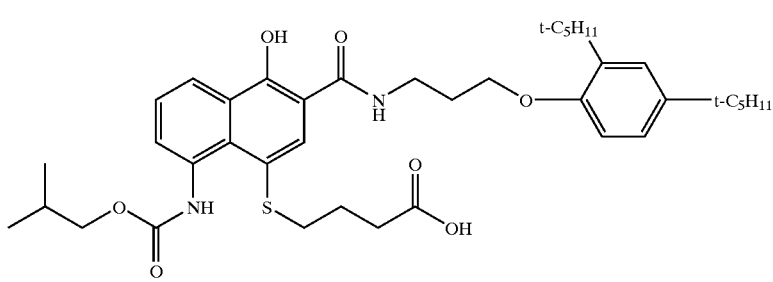
ExC-9
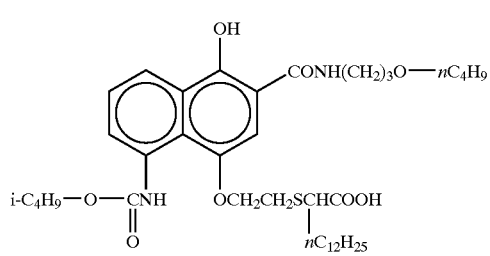
ExC-10
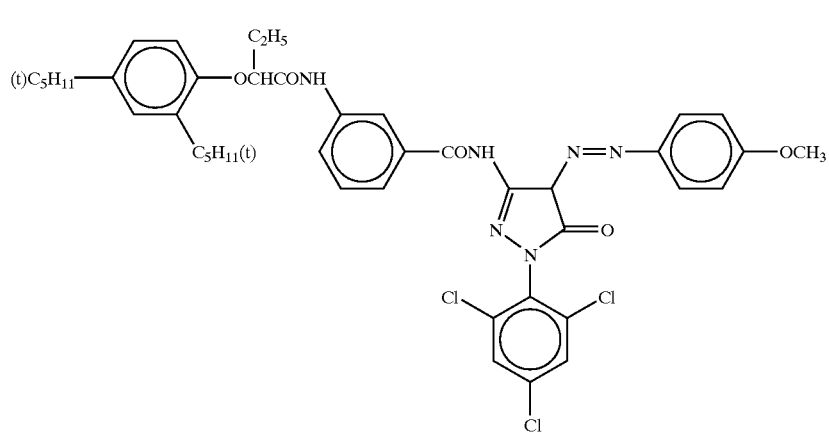
ExM-1
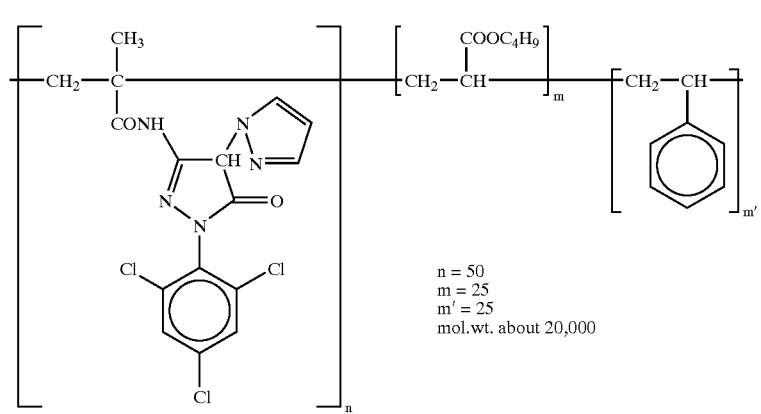
ExM-2
n = 50
m = 25
m' = 25
mol.wt. about 20,000

ExM-3
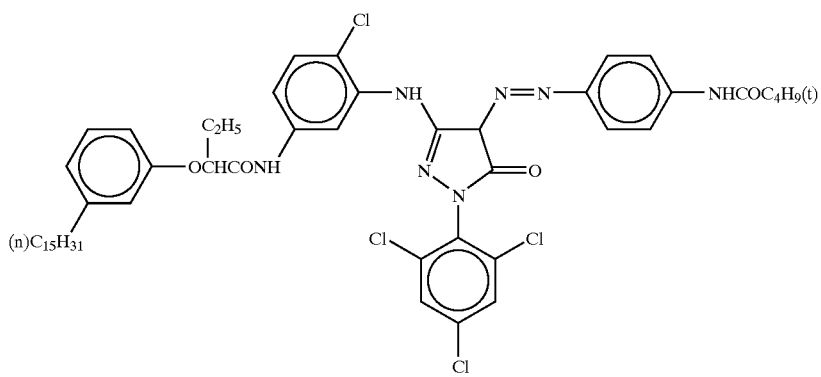
ExM-4  ExM-5
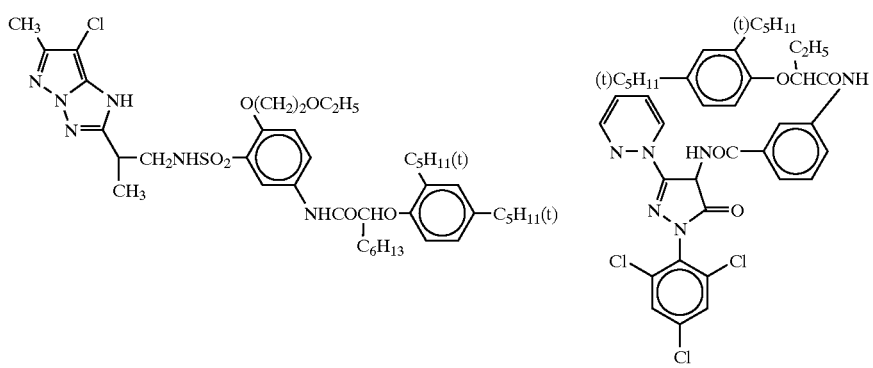
ExY-1
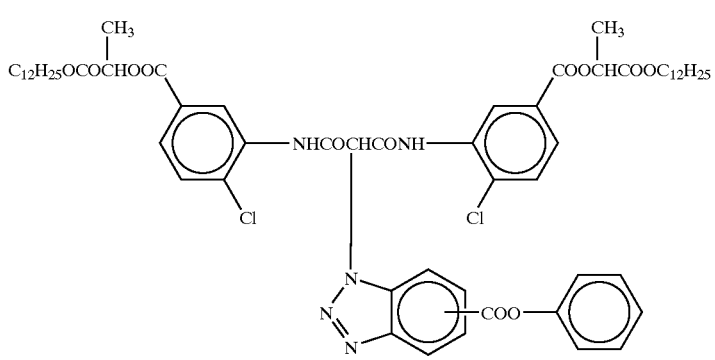
ExY-2
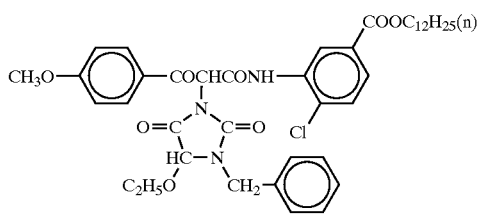
ExY-3
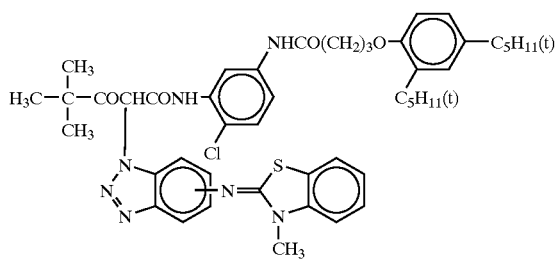
ExY-4
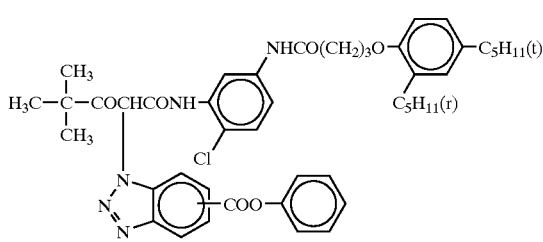
Cpd-1
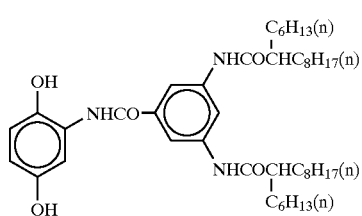

-continued
Cpd-2
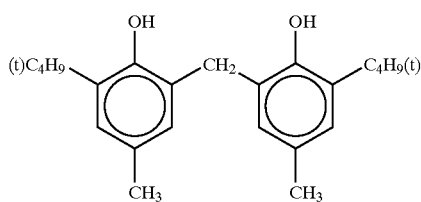
Cpd-3
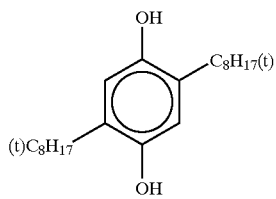
Cpd-4
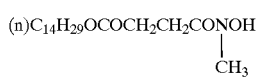
Cpd-5
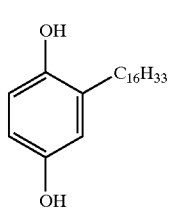
Cpd-6
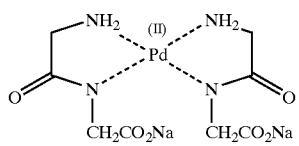
UV-1
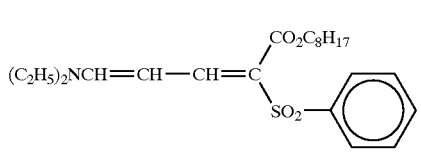
UV-2
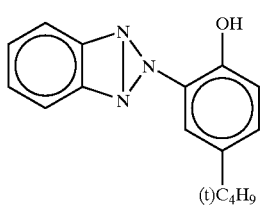
UV-3
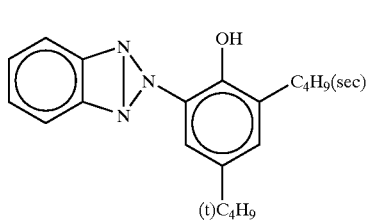
UV-4
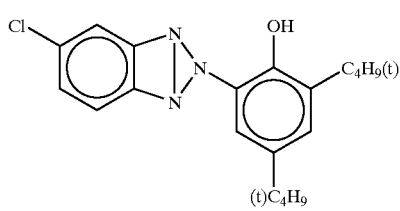
B-1
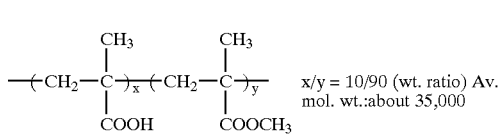 x/y = 10/90 (wt. ratio) Av. mol. wt.:about 35,000
B-2
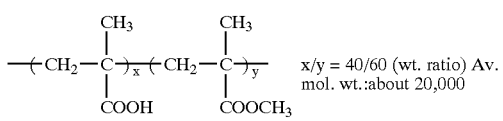 x/y = 40/60 (wt. ratio) Av. mol. wt.:about 20,000
B-3
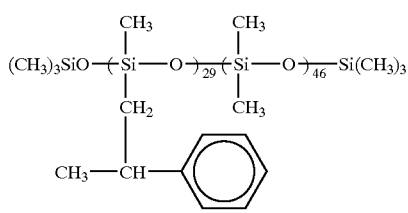
(Molar ratio) Av. mol. wt.:about 8,000
B-4
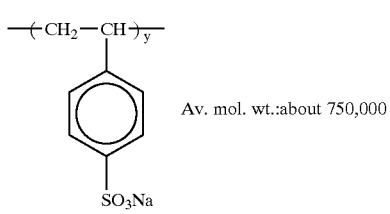 Av. mol. wt.:about 750,000
B-5
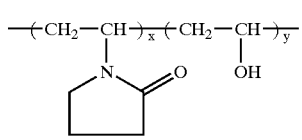
x/y = 70/30 (wt. ratio) Av. mol. wt.:about 17,000
B-6
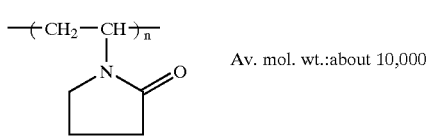 Av. mol. wt.:about 10,000
F-1
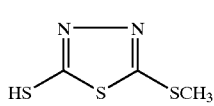

F-2
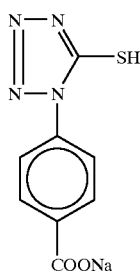
F-3
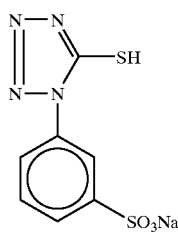
F-4
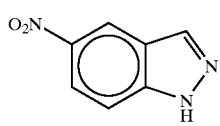
F-5
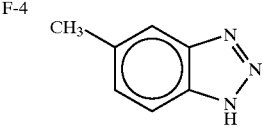
F-6
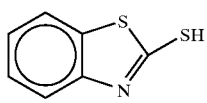
F-7
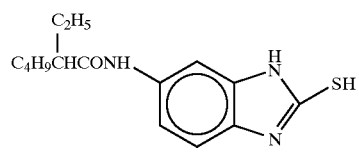
F-8
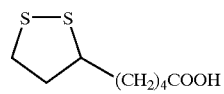
F-9
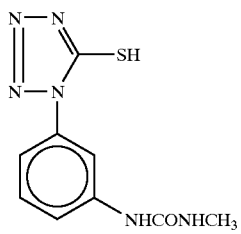
F-10
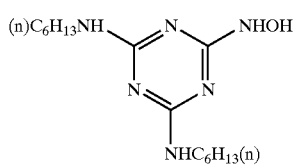
F-11
F-12
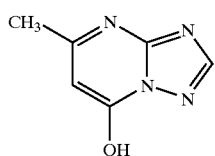
F-13
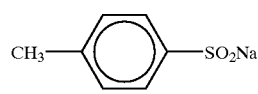
F-14
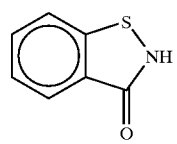
F-15
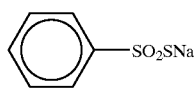
F-16
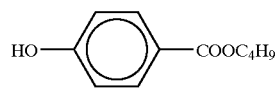
F-17
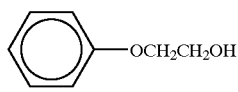
W-1
W-2
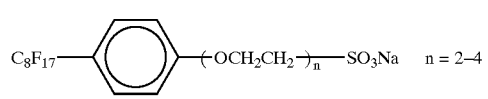

-continued
W-3
W-4
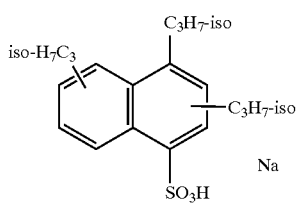
W-5
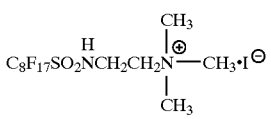
W-6
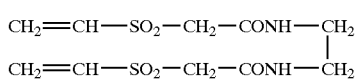
H-1
Tricresyl phosphate
HBS-1
CH₂=CH—SO₂—CH₂—CONH—CH₂
CH₂=CH—SO₂—CH₂—CONH—CH₂
Di-n-butyl phthalate
HBS-2
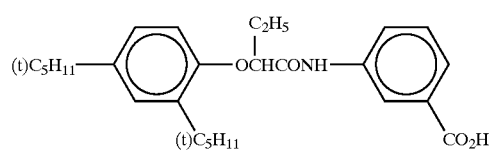
HBS-3
Tri(2-ethylhexyl) phosphate
HBS-4
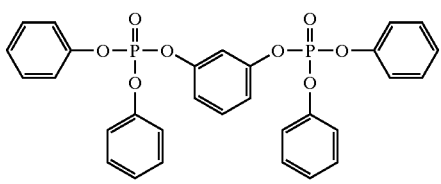
HBS-5
S-1
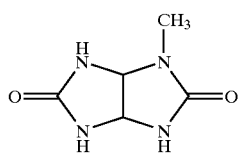
ExF-1
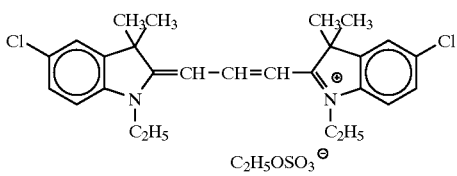
ExF-2
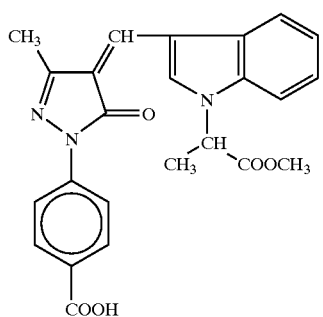
ExF-4
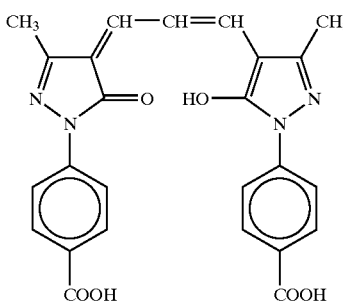
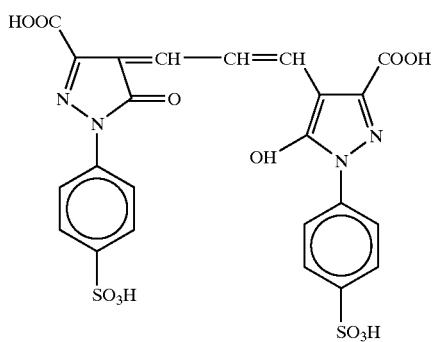
ExF-5

-continued

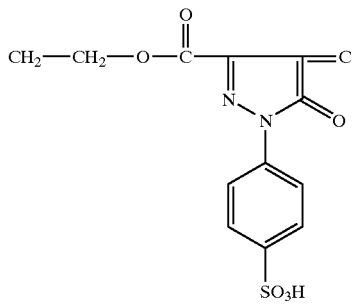
ExF-6

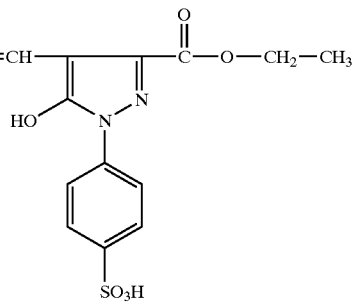

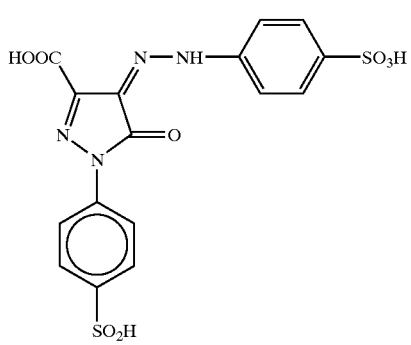
ExF-7

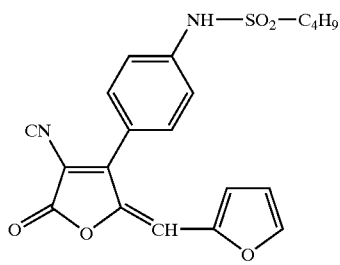
ExF-8

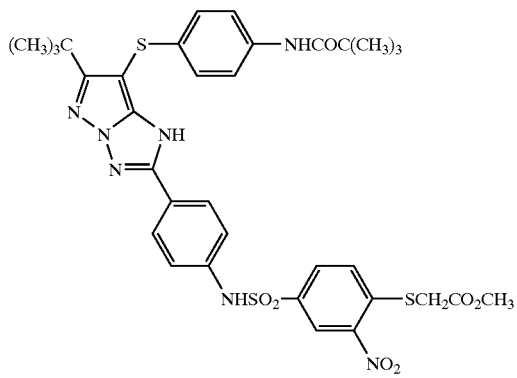
DA(93)

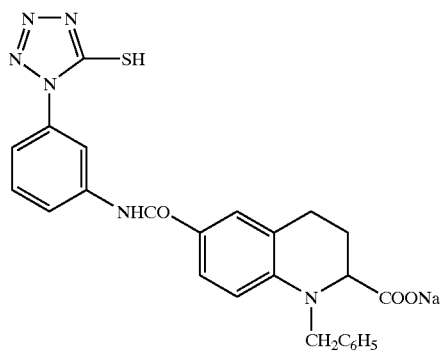
PE11

The specific speed in the present invention is determined in accordance with JIS K 7614-1981, except that the points that the development process is completed within 30 minutes to 6 hours after sensitometric exposure, and the development process is based on the Fuji color standard processing formula CN-16, are different. Others are substantially the same as the method described in JIS.

The same test condition, exposure with light, density measurement, specific photographic speed measurement are the same as those described in JP-A-63-226650, except for the processing method described below.

Development was performed as follows by using an automatic developer FP-360B manufactured by Fuji Photo Film Co., Ltd. Note that FP-360B was modified such that the overflow solution of the bleaching bath was entirely discharged to a waste solution tank without being supplied to the subsequent bath. This FP-360B includes an evaporation correcting means described in JIII Journal of Technical Disclosure No. 94-4992.

The processing steps and the processing solution compositions are presented below.

| (Processing steps) | | | | |
|---|---|---|---|---|
| Step | Time | Temperature | Replenishing rate* | Tank volume |
| Color development | 3 min 5 sec | 37.8° C. | 20 mL | 11.5 L |
| Bleaching | 50 sec | 38.0° C. | 5 mL | 5 L |
| Fixing (1) | 50 sec | 38.0° C. | — | 5 L |
| Fixing (2) | 50 sec | 38.0° C. | 8 mL | 5 L |
| Washing | 30 sec | 38.0° C. | 17 mL | 3 L |
| Stabilization (1) | 20 sec | 38.0° C. | — | 3 L |
| Stabilization (2) | 20 sec | 38.0° C. | 15 mL | 3 L |
| Drying | 1 min 30 sec | 60.0° C. | | |

*The replenishment rate was per 1.1 m of a 35-mm wide sensitized material (equivalent to one 24 Ex. 1)

The stabilizer and fixer were counterflowed from (2) to (1), and the overflow of washing water was entirely introduced to the fixing bath (2). Note that the amounts of the developer, bleaching solution, and fixer carried over to the bleaching step, fixing step, and washing step were 2.5 mL, 2.0 mL, and 2.0 mL, respectively, per 1.1 m of a 35-mm wide sensitized material. Note also that each crossover time was 6 sec, and this time was included in the processing time of each preceding step.

The aperture areas of the processor were 100 cm$^2$ for the color developer, 120 cm$^2$ for the bleaching solution, and about 100 cm$^2$ for the other processing solutions.

The compositions of the processing solutions are presented below.

| (Color developer) | Tank solution (g) | Replenisher (g) |
|---|---|---|
| Diethylenetriamine pentaacetic acid | 3.0 | 3.0 |
| Disodium cathecol-3,5-disulfonate | 0.3 | 0.3 |
| Sodium sulfite | 3.9 | 5.3 |
| Potassium carbonate | 39.0 | 39.0 |
| Disodium-N,N-bis(2-sulfonatoethyl)hydroxylamine | 1.5 | 2.0 |
| Potassium bromide | 1.3 | 0.3 |
| Potassium iodide | 1.3 mg | — |
| 4-hydroxy-6-methyl-1,3,3a,7-tetrazaindene | 0.05 | — |
| Hydroxylamine sulfate | 2.4 | 3.3 |
| 2-methyl-4-[N-ethyl-N-(β-hydroxyethyl) amino] aniline sulfate | 4.5 | 6.5 |
| Water to make | 1.0 L | 1.0 L |
| pH (controlled by potassium hydroxide and sulfuric acid) | 10.05 | 10.18 |

| (Bleaching solution) | Tank solution (g) | Replenisher (g) |
|---|---|---|
| Ferric ammonium 1,3-diaminopropanetetraacetate monohydrate | 113 | 170 |
| Ammonium bromide | 70 | 105 |
| Ammonium nitrate | 14 | 21 |
| Succinic acid | 34 | 51 |
| Maleic acid | 28 | 42 |
| Water to make | 1.0 L | 1.0 L |
| pH (controlled by ammonia water) | 4.6 | 4.0 |
| (Fixing (1) tank solution) | | |

A 5:95 (volume ratio) mixture of the above bleaching tank solution and the following fixing tank solution (pH 6.8).

| (Fixer (2)) | Tank solution (g) | Replenisher (g) |
|---|---|---|
| Aqueous ammonium thiosulfate solution (750 g/L) | 240 mL | 720 mL |
| Imidazole | 7 | 21 |
| Ammonium methane thiosulfonate | 5 | 15 |
| Ammonium methane sulfinate | 10 | 30 |
| Ethylenediamine tetraacetic acid | 13 | 39 |
| Water to make | 1.0 L | 1.0 L |
| pH (controlled by ammonia water and acetic acid) | 7.4 | 7.45 |

(Washing Water) Common to Tank Solution and Replenisher

Tap water was supplied to a mixed-bed column filled with an H type strongly acidic cation exchange resin (Amberlite IR-120B: available from Rohm & Haas Co.) and an OH type strongly basic anion exchange resin (Amberlite IR-400) to set the concentrations of calcium and magnesium to be 3 mg/L or less. Subsequently, 20 mg/L of sodium isocyanuric acid dichloride and 150 mg/L of sodium sulfate were added. The pH of the solution ranged from 6.5 to 7.5.

| (Stabilizer) | common to tank solution and replenisher (g) |
|---|---|
| Sodium p-toluenesulfinate | 0.03 |
| Polyoxyethylene-p-monononylphenylether (average polymerization degree 10) | 0.2 |
| 1,2-benzoisothiazoline-3-one.sodium | 0.10 |
| Disodium ethylenediaminetetraacetate | 0.05 |
| 1,2,4-triazole | 1.3 |
| 1,4-bis(1,2,4-triazole-1-isomethyl) piperazine | 0.75 |
| Water to make | 1.0 L |
| pH | 8.5 |

These samples were exposed for 1/100 sec through a optical wedge. The exposed samples were processed with the processing described above, and the photographic speed was evaluated by measuring the density with a green filter.

For the evaluation of storability, the above coated samples were subjected to the film hardening, kept under an ambience of 60° C. and 60% RH for four days. The extent in the increment of fog density was compared to evaluate the storability.

The speed was expressed by a relative value of inverse number of exposure amount required for reaching a density of fog density +0.2 (The speed of Sample 801 using Emulsion EGA-1 in the 11th layer was assumed to be 100).

The storability was expressed by an increment of fog density during the storage of the coating samples. The results are shown in Table 10.

TABLE 10

| Sample No. | Emulsion No. in 11th layer | Av. grain ECD/ Av. thickness ($\mu$m) | Amount of the first dye (mol/ Ag mol) | Amount of the second dye (mol/ Ag mol) | Amount of the third dye (mol/ Ag mol) | Ratio of amino group modified gelatin (%) | Other conditions | Relative speed*[1] | Increment of fog during storage*[2] | Remarks |
|---|---|---|---|---|---|---|---|---|---|---|
| 801 | EGA-1 | 2.4/0.2 | $6.08 \times 10^{-4}$ | None | None | None | Washing with dialysis without Ca | 100 | 0.18 | Comp. |
| 802 | EGA-2 | 2.4/0.2 | $6.08 \times 10^{-4}$ | $2.00 \times 10^{-4}$ | $2.00 \times 10^{-4}$ | None | Washing with dialysis without Ca | 110 | 0.22 | Comp. |
| 803 | EGA-3 | 2.4/0.2 | $6.08 \times 10^{-4}$ | $6.08 \times 10^{-4}$ | $6.08 \times 10^{-4}$ | None | Washing with dialysis without Ca | 123 | 0.25 | Comp. |
| 804 | EGA-4 | 2.4/0.2 | $6.08 \times 10^{-4}$ | None | None | 11 (Phthalated gelatin) | Washing with dialysis without Ca | 100 | 0.18 | Comp. |
| 805 | EGA-5 | 2.4/0.2 | $6.08 \times 10^{-4}$ | $2.00 \times 10^{-4}$ | $2.00 \times 10^{-4}$ | 11 (Phthalated gelatin) | Washing with dialysis without Ca | 144 | 0.17 | Inv. |
| 806 | EGA-6 | 2.4/0.2 | $6.08 \times 10^{-4}$ | $6.08 \times 10^{-4}$ | $6.08 \times 10^{-4}$ | 11 (Phthalated gelatin) | Washing with dialysis without Ca | 186 | 0.18 | Inv. |
| 807 | EGB-1 | 3.1/0.12 | $1.01 \times 10^{-3}$ | None | None | 11 (Phthalated gelatin) | Washing with dialysis without Ca | 126 | 0.21 | Comp. |
| 808 | EGB-2 | 3.1/0.12 | $1.01 \times 10^{-3}$ | $5.55 \times 10^{-4}$ | $4.54 \times 10^{-4}$ | 11 (Phthalated gelatin) | Washing with dialysis without Ca | 210 | 0.20 | Inv. |
| 809 | EGB-3 | 3.1/0.12 | $1.01 \times 10^{-3}$ | $5.04 \times 10^{-4}$ | $5.04 \times 10^{-4}$ | 11 (Phthalated gelatin) | Washing with dialysis without Ca | 214 | 0.19 | Inv. |
| 810 | EGB-4 | 3.1/0.12 | $1.01 \times 10^{-3}$ | $4.54 \times 10^{-4}$ | $5.55 \times 10^{-4}$ | 11 (Phthalated gelatin) | Washing with dialysis without Ca | 216 | 0.19 | Inv. |
| 811 | EGB-5 | 3.1/0.12 | $1.01 \times 10^{-3}$ | None | None | 11 (Phthalated gelatin) | Washing with coagulation sedimentation without Ca | 126 | 0.21 | Comp. |
| 812 | EGB-13 | 3.1/0.12 | $1.01 \times 10^{-3}$ | None | None | 11 (Phthalated gelatin) | Washing with coagulation sedimentation Ca $8.0 \times 10^{-3}$ mol/Ag mol | 126 | 0.20 | Comp. |
| 813 | EGB-14 | 3.1/0.12 | $1.01 \times 10^{-3}$ | $4.54 \times 10^{-4}$ | $5.55 \times 10^{-4}$ | 11 (Phthalated gelatin) | Washing with coagulation sedimentation without Ca | 218 | 0.20 | Inv. |
| 814 | EGB-17 | 3.1/0.12 | $1.01 \times 10^{-3}$ | $4.54 \times 10^{-4}$ | $5.55 \times 10^{-4}$ | 11 (Phthalated gelatin) | Washing with coagulation sedimentation Ca $8.0 \times 10^{-3}$ mol/Ag mol | 240 | 0.19 | Inv. |

ECD = Equivalent circle diameter
*[1]Relative speed when the speed of sample No. 801 is assumed to be 100.
*[2]In the case where samples coated with emulsion was stored under the ambient at temperature of 60° C. and a relative humidity of 60% of four days.

As seen from the results of Table 10, in the introduction of the silver halide emulsion of the present invention in silver halide color negative multilayer photosensitive materials as well, the effects of the present invention were as striking as in the results of Example 1 or 4.

Example 9

The same comparison as in Example 8 was made through estimation in the systems of color reversal photosensitive material as described in Example 1 of each of JP-A's-7-92601 and 11-160828, the system of instant photosensitive material as described in Example 1 of JP-A-2000-284442, the system of X-ray sensitive material as described in Example 1 of JP-A-8-122954 and the systems of photosensitive material to be processed by thermal development as described in Example 5 of JP-A-2000-122206, Example 1 of JP-A-2001-281785 and Example 1 of JP-A-6-130607. The results thereof showed the same excellent effects of the present invention as in Example 8.

The present invention has enabled obtaining a silver halide emulsion and silver halide photosensitive material which realize high sensitivity and low storage fogging. Further, the employment of conditions recommended in the present invention as those for production of the silver halide emulsion of the present invention has enabled obtaining an emulsion exhibiting high stability at emulsion dissolution and refrigerated storage.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A method of preparing, in a reaction vessel, a silver halide emulsion containing water, dispersion medium and silver halide grains wherein the dispersion medium comprises modified gelatin whose amino group is chemically modified, and the silver halide grains comprise spectrally sensitized silver halide grains each having a multilayer adsorption of dye chromophores on the surface thereof, wherein at least one of the dye chromophores is a cationic sensitizing dye and the method comprises adding, to the reaction vessel, the cationic sensitizing dye in the form of water-based dispersion.

2. The method according to claim 1, wherein the water-based dispersion substantially does not contain an anionic surfactant.

3. The method according to claim 1, wherein the water-based dispersion substantially does not contain an anionic solvent.

4. The method according to claim 1, wherein the concentration of the cationic sensitizing dye in the water-based dispersion is 1 wt % or more.

5. A method of preparing, in a reaction vessel, a silver halide emulsion containing water, dispersion medium and silver halide grains wherein the dispersion medium comprises modified gelatin whose amino group is chemically modified, and the silver halide grains comprise spectrally sensitized silver halide grains each having a multilayer adsorption of dye chromophores on the surface thereof, the method comprising:

adding, to the reaction vessel, the modified gelatin; and desalting a silver halide emulsion to which the modified gelatin is added, wherein said adding the modified gelatin is conducted before said desalting.

6. A method of preparing, in a reaction vessel, a silver halide emulsion containing water, dispersion medium an silver halide grains wherein the dispersion medium comprises modified gelatin whose amino group is chemically modified, and the silver halide grains comprise spectrally sensitized silver halide grains each having a multilayer adsorption of dye chromophores on the surface thereof, wherein a content of an anionic surfactant in the reaction vessel immediately after the completion of adding all the dye chromophores is 0.45 g or less per mole of silver of a silver halide emulsion contained in the reaction vessel.

7. The method according to claim 1, wherein the water-based dispersion contains an inorganic salt.

8. The method according to claim 1, wherein a silver amount of a silver halide emulsion in the reaction vessel at the time of adding the cationic sensitizing dye is 100 g/kg or more, and/or an amount of gelatin of the silver halide emulsion in the reaction vessel at the time of adding the cationic sensitizing dye is 90 g/kg or less.

9. The method according to claim 1, wherein the silver halide emulsion contains Ca or Mg in an amount of $2 \times 10^{-3}$ to $4 \times 10^{-2}$ mol per mol of silver of the silver halide emulsion.

* * * * *